US012534465B2

(12) United States Patent
Maderna et al.

(10) Patent No.: US 12,534,465 B2
(45) Date of Patent: Jan. 27, 2026

(54) 5H-PYRROLO[3,2-D]PYRIMIDINE-2,4-DIAMINO COMPOUNDS AND ANTIBODY CONJUGATES THEREOF

(71) Applicant: SUTRO BIOPHARMA, INC., South San Francisco, CA (US)

(72) Inventors: Andreas Maderna, South San Francisco, CA (US); Adam A. Galan, South San Francisco, CA (US); Krishna Bajjuri, South San Francisco, CA (US)

(73) Assignee: SUTRO BIOPHARMA, INC., South San Francisco, CA (US)

( * ) Notice: Subject to any disclaimer, the term of this patent is extended or adjusted under 35 U.S.C. 154(b) by 987 days.

(21) Appl. No.: 17/617,573

(22) PCT Filed: Jun. 10, 2020

(86) PCT No.: PCT/US2020/037024

§ 371 (c)(1),
(2) Date: Dec. 8, 2021

(87) PCT Pub. No.: WO2020/252043

PCT Pub. Date: Dec. 17, 2020

(65) Prior Publication Data

US 2022/0242871 A1 Aug. 4, 2022

Related U.S. Application Data

(60) Provisional application No. 62/859,638, filed on Jun. 10, 2019.

(51) Int. Cl.
*C07D 487/04* (2006.01)
*A61K 47/68* (2017.01)
*A61P 35/00* (2006.01)

(52) U.S. Cl.
CPC ........ *C07D 487/04* (2013.01); *A61K 47/6803* (2017.08); *A61K 47/6849* (2017.08); *A61P 35/00* (2018.01)

(58) Field of Classification Search
None
See application file for complete search history.

(56) References Cited

U.S. PATENT DOCUMENTS

| | | | |
|---|---|---|---|
| 9,145,410 | B2 | 9/2015 | Hays et al. |
| 9,676,871 | B2 | 6/2017 | Strop et al. |
| 10,596,270 | B2 | 3/2020 | Stafford et al. |
| 10,844,090 | B2 | 11/2020 | Kline et al. |
| 11,708,413 | B2 | 7/2023 | Stafford et al. |
| 11,744,876 | B2 | 9/2023 | Yam et al. |
| 2009/0075980 | A1 | 3/2009 | Hays et al. |
| 2010/0034837 | A1 | 2/2010 | Beria et al. |
| 2015/0105540 | A1 | 4/2015 | Miao et al. |
| 2015/0105541 | A1 | 4/2015 | Kim et al. |
| 2015/0174268 | A1 | 6/2015 | Li |
| 2015/0376161 | A1 | 12/2015 | Johansen et al. |
| 2016/0039920 | A1 | 2/2016 | Casi et al. |
| 2016/0257709 | A1 | 9/2016 | Kline et al. |
| 2017/0158772 | A1 | 6/2017 | Thompson et al. |
| 2017/0224835 | A1 | 8/2017 | Miao et al. |
| 2017/0258934 | A1 | 9/2017 | Van Berkel et al. |
| 2018/0092984 | A1 | 4/2018 | Lewis et al. |
| 2018/0140700 | A1 | 5/2018 | Phillips et al. |
| 2019/0083641 | A1 | 3/2019 | Stafford et al. |
| 2019/0144546 | A1 | 5/2019 | Stafford et al. |
| 2020/0405813 | A1 | 12/2020 | Yam et al. |
| 2022/0242871 | A1 | 8/2022 | Maderna et al. |
| 2022/0259202 | A1 | 8/2022 | Meimetis et al. |
| 2024/0139285 | A1 | 5/2024 | Yam et al. |

FOREIGN PATENT DOCUMENTS

| | | | | |
|---|---|---|---|---|
| WO | WO 2012/000632 A1 | | 1/2012 | |
| WO | WO 2015/168279 A1 | | 11/2015 | |
| WO | WO-2015168269 A1 | * | 11/2015 | ........... A61K 31/519 |
| WO | WO 2017/072662 A1 | | 5/2017 | |
| WO | WO 2018/112027 A1 | | 6/2018 | |
| WO | WO 2018/200812 A1 | | 11/2018 | |
| WO | WO 2019/099412 A1 | | 5/2019 | |
| WO | WO/2020168017 A1 | | 8/2020 | |
| WO | WO 2020/252015 A1 | | 12/2020 | |
| WO | WO 2020/257235 A1 | | 12/2020 | |

OTHER PUBLICATIONS

Golub et al., Science, vol. 286, Oct. 15, 1999, pp. 531-537 (Year: 1999).*

International search report and written opinion of PCT/US2020/037024 mailing date of Oct. 12, 2020.

T. List et al., "A Chemically Defined Trifunctional Antibody-Cytokine-Drug Conjugate with Potent Antitumor Activity", Molecular Cancer Therapeutics, vol. 13, No. 11, Sep. 9, 2014, pp. 2641-2652.

Gang Yin et al., "RF1 attenuation enables efficien non-natural amino acid incorporation for production of homogeneous antibody drug conjugates", Scientific Reports, 7: 3026 | DOI: 10.1038/s41598-017-03192-z.

* cited by examiner

*Primary Examiner* — Sarah Pihonak
*Assistant Examiner* — Donna M Nestor
(74) *Attorney, Agent, or Firm* — SQUIRE PATTON BOGGS (US)

(57) ABSTRACT

The present disclosure relates to 5H-Pyrrolo[3,2-d]pyrimidine-2,4-diamino compounds, and/or antibody conjugates thereof; and pharmaceutical compositions thereof, methods of producing the conjugates, and methods of using the conjugates and compositions for therapy.

59 Claims, 7 Drawing Sheets

Specification includes a Sequence Listing.

A

B

C

5H-PYRROLO[3,2-D]PYRIMIDINE-2,4-DIAMINO COMPOUNDS AND ANTIBODY CONJUGATES THEREOF

CROSS-REFERENCE TO RELATED APPLICATIONS

This application is a filing under 35 U.S.C. § 371 of International Application No. PCT/US20/37024, filed Jun. 10, 2020, which claims the benefit of U.S. Provisional Application No. 62/859,638 filed Jun. 10, 2019. The entirety of each of these applications is herein incorporated by reference.

REFERENCE TO SEQUENCE LISTING SUBMITTED VIA EFS-WEB

This application includes an electronically submitted sequence listing in .txt format. The txt file contains a sequence listing entitled "Sequence_Listing_ST25.txt" created on Dec. 7, 2021, and is 8.63 kilobytes in size. The sequence listing contained in this .txt file is part of the specification and is incorporated herein by reference in its entirety.

FIELD OF THE INVENTION

Provided herein are 5H-Pyrrolo[3,2-d]pyrimidine-2,4-diamino compounds, and/or antibody conjugates thereof; and pharmaceutical compositions comprising the compounds and/or conjugates; methods of producing the compounds and/or conjugates; and methods of using the compounds, conjugates and compositions for therapy. The compounds, conjugates, and compositions are useful in methods of treatment and prevention of cell proliferation and cancer, methods of detection of cell proliferation and cancer, and methods of diagnosis of cell proliferation and cancer. The compounds, conjugates and compositions are also useful in methods of treatment, prevention, detection, and diagnosis of inflammatory diseases or conditions.

BACKGROUND

The innate immune system recognizes structurally conserved pathogen-associated molecular patterns via Toll-like receptors (TLRs), which are usually expressed on immune cells such as macrophages and dendritic cells. Activation of TLRs induces innate (rapid, non-specific) and/or adaptive (slower, more specific) immune responses such as induction of cytokines and/or co-stimulation of phagocytes and/or activation of the T-cell response. Among TLRs, TLR3, 7, 8 and 9 are expressed in the intracellular endosomes, while others (TLR1, 2, 4, 5, 6, 10, and 11) are localized on the plasmalemma. Each TLR elicits specific cellular responses to pathogens owing to differential usage of intracellular adapter proteins. TLR7 is an intracellular receptor expressed on endosomal membranes and is closely related to TLR8. TLR7 recognizes nucleosides and nucleotides from intracellular pathogens. Activation of TLR7 can induce Type 1 interferon and an inflammatory response. Saitoh, S-I et al., *Nature Communications* 2017, 8, Article number: 1592.

Malignant cells exploit the natural immunomodulatory functions of TLRs to foster their survival, invasion, and evasion of anti-tumor immune responses. Current research has demonstrated context-specific roles for TLR activation in different malignancies, promoting disease progression in certain instances while limiting cancer growth in others. Braunstein M. J. et al., *Target Oncol.* 2018, 13(5), 583-598.

Some TLR agonists have been found to induce antitumor activity by indirectly activating the tolerant host immune system to destroy cancer cells. The use of TLR7 agonists such as imiquimod, loxoribine, CL264 (a 9-benzyl-8 hydroxyadenine derivative containing a glycine on the benzyl group), ssRNA40, R848, and SM-276 001, either alone or as vaccine adjuvants, induces potent immunity leading to antitumor therapeutic efficacy in several murine models. TLR7 agonist injection reduces tumor progression and modulates the systemic and intratumoral immune response in colon, renal, and mammary carcinomas. Antitumor effects associated with TLR7 stimulation have been demonstrated in human skin cancers and cervical intraepithelial neoplasia. Dajon, M. et al., *Oncoimmunology.* 2015, 4(3), e991615.

TLR7 targeting may provide new treatment options for both anti-inflammatory, and/or anti-cancer therapies. There is a need in the field for new treatments for inflammatory and/or immunomodulatory diseases, particularly cancer. Antibody conjugates to TLR7 agonists could be used to deliver therapeutic or diagnostic payload moieties to target cells expressing tumor antigens for the treatment and/or diagnosis of such diseases.

SUMMARY

Provided herein are 5H-Pyrrolo[3,2-d]pyrimidine-2,4-diamino compounds of Formula (I-P), Formula (I) and subformulas thereof, compositions comprising the compounds, methods of producing the compounds, and methods of using the compounds, conjugates, and compositions for the treatment of cell proliferation and/or cancer, and/or inflammation. The conjugates are useful in methods of treatment and prevention of cell proliferation and cancer, methods of detection of cell proliferation and cancer, and methods of diagnosis of cell proliferation and cancer. The conjugates are useful in methods of treatment and prevention of inflammatory diseases and conditions.

In one aspect, provided is a Compound of Formula (I):

Formula (I)

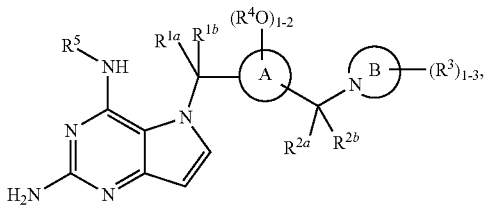

wherein $R^{1a}$, $R^{1b}$, $R^{2a}$, $R^{2b}$, $R^3$, $R^4$, $R^5$, ring A and ring B are as defined herein in the Detailed Description section.

Also provided herein are antibody conjugates comprising residues of the compounds of Formula (I-P), Formula (I) and subformulas thereof. In some or any embodiments, the conjugate is according to Formula (V), $$Ab—[L\text{-}PA]_n \quad (V)$$

wherein Ab is an antibody or an antigen binding fragment thereof, L is a linker; PA is a payload comprising a residue of Formula (I-P), Formula (I), (II), or (III), or an embodiment thereof; and subscript n is an integer from 1 to 30; or a pharmaceutically acceptable salt, solvate, stereoisomer, tautomer, or mixture of regioisomers thereof In another aspect, provided are compositions comprising the compound of Formula (I-P), (I), (II), or (III), or embodiments thereof, or antibody conjugates comprising residues of compounds of Formula (I-P), Formula (I) and subformulas and embodiments thereof. In some or any embodiments, the conjugate is according to Formula (V), $$\text{Ab}—[\text{L-PA}]_n \quad (V)$$

wherein Ab is an antibody or an antigen binding fragment thereof, L is a linker; PA is a payload comprising a residue of Formula (I-P), Formula (I), (II), or (III), or an embodiment thereof; and subscript n is an integer from 1 to 30; or a pharmaceutically acceptable salt, solvate, stereoisomer, tautomer, or mixture of regioisomers thereof. In some embodiments, the compositions are pharmaceutical compositions. Any suitable pharmaceutical composition may be used. In a further aspect, provided herein are kits comprising the compound of Formula (I-P), (I), (II), or (III), or embodiments thereof, the antibody conjugates, e.g. of Formula (V), or pharmaceutical compositions.

In another aspect, provided herein are methods of using the compounds of Formula (I-P), Formula (I), (II), or (III), or an embodiment thereof or the antibody drug conjugates described herein. In some embodiments, the methods are methods of delivering one or more payload moieties to a target cell or tissue. In some embodiments, the methods are methods of treatment. In some embodiments, the methods are diagnostic methods. In some embodiments, the methods are analytical methods. In some embodiments, the compounds and/or antibody drug conjugates are used to treat a disease or condition. In some aspects, the disease or condition is selected from a cancer, and/or an inflammatory disease or condition.

Also provided herein is the use of compounds described herein, and antibody conjugates thereof, for the treatment of cancer, and/or an inflammatory disease or condition.

In a further aspect, provided herein are linker payloads of Formula (IV),

Formula (IV)

$$\begin{array}{c} \qquad\qquad\qquad (\text{HP})_{0\text{-}1} \\ \qquad\qquad\qquad | \\ \text{R}—\text{SG}—(\text{HP})_{0\text{-}1}—\text{W}^6—\text{X}—\text{W}^1—\text{PA} \end{array}$$

wherein R, SG, $W^6$, HP, X, $W^1$ and PA are as defined herein in the Detailed Description section.

BRIEF DESCRIPTION OF THE FIGURES

FIG. 7A shows dose-related minimal body weight loss (<10% of predose). The anti-tumor effect of compound 2 treatment on MC38-hFolRα on tumor growth is illustrated in FIG. 7B.

DETAILED DESCRIPTION

Figure 1:
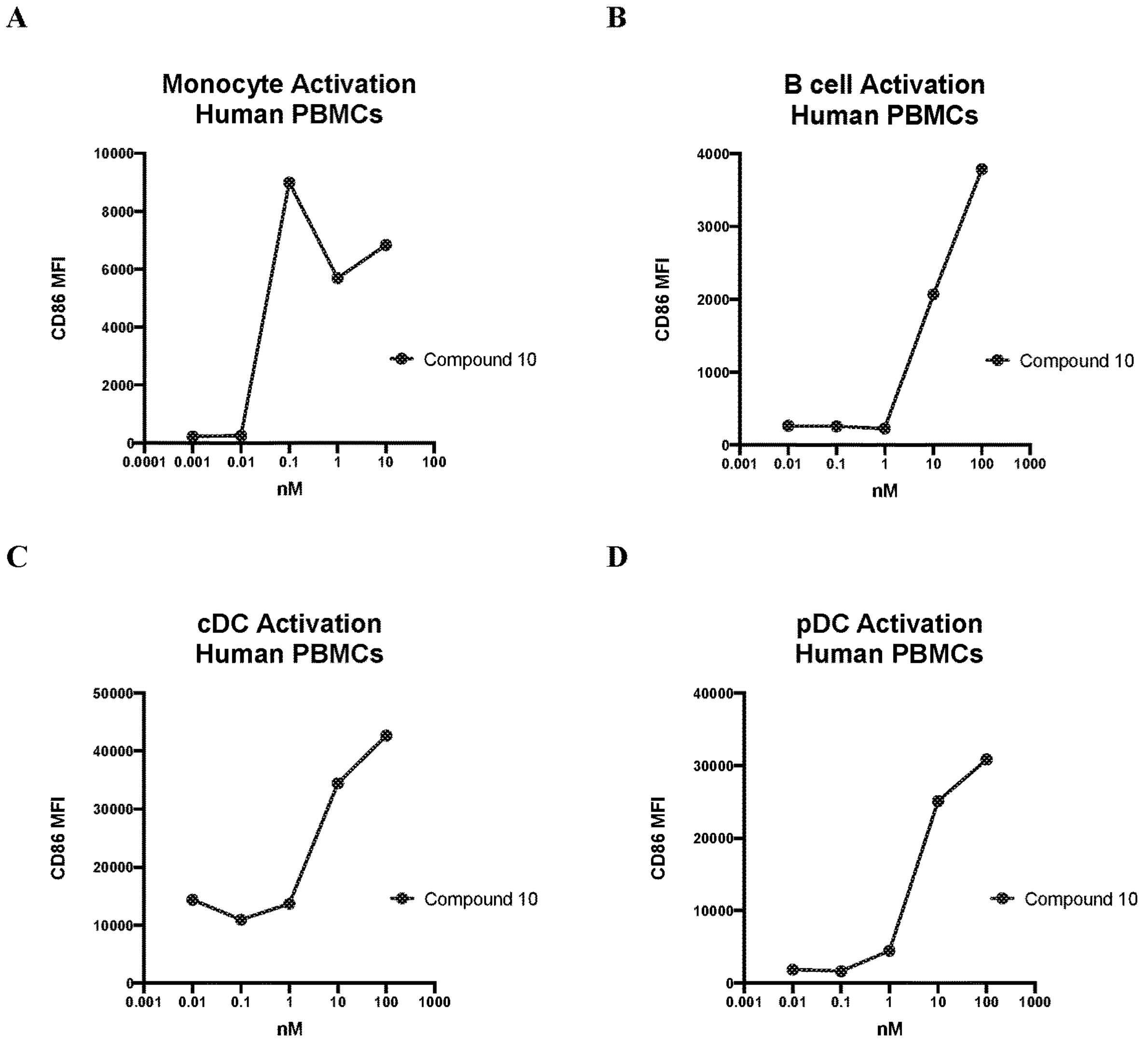
FIG. 1 provides in vitro data demonstrating the ability of Compound 10 to stimulate activation of several immune cell types in human PBMCs (Peripheral blood mononuclear cells)—monocytes (FIG. 1A), B cells (FIG. 1B), cDCs (FIG. 1C), and pDCs (FIG. 1D).

Described herein are Toll-like receptor 7 (TLR7) agonists, and antibody conjugates thereof, for the treatment of cancer, and/or inflammatory conditions. In some instances, the compounds described herein are selective for TLR7 and do not affect TLR8.

I. Definitions

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a difference over what is generally understood in the art. The techniques and procedures described or referenced herein are generally well understood and commonly employed using conventional methodologies by those skilled in the art, such as, for example, the widely utilized molecular cloning methodologies described in Green & Sambrook, *Molecular Cloning: A Laboratory Manual* $4^{th}$ ed. (2012), Cold Spring Harbor Laboratory Press, Cold Spring Harbor, NY; and Ausubel et al., *Current Protocols in Molecular Biology*, John Wiley & Sons. As appropriate, procedures involving the use of commercially available kits and reagents are generally carried out in accordance with manufacturer-defined protocols and conditions unless otherwise noted.

As used herein, the singular forms "a," "an," and "the" include the plural referents unless the context clearly indicates otherwise.

The term "about" indicates and encompasses an indicated value and a range above and below that value. In certain embodiments, the term "about" indicates the designated value±10%, ±5%, or ±10%. In certain embodiments, the term "about" indicates the designated value±one standard deviation of that value. In certain embodiments, e.g., for logarithmic scales (e.g., pH), the term "about" indicates the designated value±0.3, +0.2, or ±0.1.

The term "immunoglobulin" refers to a class of structurally related proteins generally comprising two pairs of polypeptide chains: one pair of light (L) chains and one pair of heavy (H) chains. In an "intact immunoglobulin," all four of these chains are interconnected by disulfide bonds. The structure of immunoglobulins has been well characterized. See, e.g., Paul, *Fundamental Immunology* 7th ed., Ch. 5 (2013) Lippincott Williams & Wilkins, Philadelphia, PA. Briefly, each heavy chain typically comprises a heavy chain variable region ($V_H$ or VH) and a heavy chain constant region ($C_H$ or CH). The heavy chain constant region typically comprises three domains, abbreviated $C_H1$ (or CH1), $C_H2$ (or CH2), and $C_H3$ (or CH3). Each light chain typically comprises a light chain variable region ($V_L$ or VL) and a light chain constant region. The light chain constant region typically comprises one domain, abbreviated $C_L$ or CL.

The term "antibody" is used herein in its broadest sense. An antibody includes intact antibodies (e.g., intact immunoglobulins), and antibody fragments (e.g., antigen binding fragments of antibodies). Antibodies comprise at least one antigen-binding domain. One example of an antigen-binding domain is an antigen binding domain formed by a $V_H$-$V_L$ dimer.

The $V_H$ and $V_L$ regions may be further subdivided into regions of hypervariability ("hypervariable regions (HVRs);" also called "complementarity determining regions" (CDRs)) interspersed with regions that are more conserved. The more conserved regions are called framework regions (FRs). Each $V_H$ and $V_L$ generally comprises three CDRs and four FRs, arranged in the following order (from N-terminus to C-terminus): FR1-CDR1-FR2-CDR2-FR3-CDR3-FR4. The CDRs are involved in antigen binding, and influence antigen specificity and binding affinity of the antibody. See Kabat et al., *Sequences of Proteins of Immunological Interest* 5th ed. (1991) Public Health Service, National Institutes of Health, Bethesda, MD, incorporated by reference in its entirety.

The light chain from any vertebrate species can be assigned to one of two types, called kappa and lambda, based on the sequence of the constant domain.

The heavy chain from any vertebrate species can be assigned to one of five different classes (or isotypes): IgA, IgD, IgE, IgG, and IgM. These classes are also designated α, δ, ε, γ, and μ, respectively. The IgG and IgA classes are further divided into subclasses on the basis of differences in sequence and function. Humans express the following subclasses: IgG1, IgG2, IgG3, IgG4, IgA1, and IgA2.

The amino acid sequence boundaries of a CDR can be determined by one of skill in the art using any of a number of known numbering schemes, including those described by Kabat et al., supra ("Kabat" numbering scheme); Al-Lazikani et al., 1997, *J. Mol. Biol.*, 273:927-948 ("Chothia" numbering scheme); MacCallum et al., 1996, *J. Mol. Biol.* 262:732-745 ("Contact" numbering scheme); Lefranc et al., *Dev. Comp. Immunol.*, 2003, 27:55-77 ("IMGT" numbering scheme); and Honegge and Pluckthun, *J. Mol. Biol.*, 2001, 309:657-70 ("AHo" numbering scheme), each of which is incorporated by reference in its entirety.

CDRs may be assigned, for example, using antibody numbering software, such as Abnum, available at www.bioinf.org.uk/abs/abnum/, and described in Abhinandan and Martin, *Immunology*, 2008, 45:3832-3839, incorporated by reference in its entirety.

The "EU numbering scheme" is generally used when referring to a residue in an antibody heavy chain constant region (e.g., as reported in Kabat et al., supra). Unless stated otherwise, the EU numbering scheme is used to refer to residues in antibody heavy chain constant regions described herein.

An "antibody fragment" comprises a portion of an intact antibody, such as the antigen binding or variable region of an intact antibody. Antibody fragments include, for example, Fv fragments, Fab fragments, $F(ab')_2$ fragments, Fab' fragments, scFv (sFv) fragments, and scFv-Fc fragments.

"Fv" fragments comprise a non-covalently-linked dimer of one heavy chain variable domain and one light chain variable domain.

"Fab" fragments comprise, in addition to the heavy and light chain variable domains, the constant domain of the light chain and the first constant domain ($C_{H1}$) of the heavy chain. Fab fragments may be generated, for example, by recombinant methods or by papain digestion of a full-length antibody.

"$F(ab')_2$" fragments contain two Fab' fragments joined, near the hinge region, by disulfide bonds. $F(ab')_2$ fragments may be generated, for example, by recombinant methods or by pepsin digestion of an intact antibody. The F(ab') fragments can be dissociated, for example, by treatment with β-mercaptoethanol.

"Single-chain Fv" or "sFv" or "scFv" antibody fragments comprise a $V_H$ domain and a $V_L$ domain in a single polypeptide chain. The $V_H$ and $V_L$ are generally linked by a peptide linker. See Plückthun A. (1994). Antibodies from *Escherichia coli*. In Rosenberg M. & Moore G. P. (Eds.), *The Pharmacology of Monoclonal Antibodies* vol. 113 (pp. 269-315). Springer-Verlag, New York, incorporated by reference in its entirety.

"scFv-Fc" fragments comprise an scFv attached to an Fc domain. For example, an Fc domain may be attached to the C-terminus of the scFv. The Fc domain may follow the $V_H$ or $V_L$, depending on the orientation of the variable domains in the scFv (i.e., $V_H$-$V_L$ or $V_L$-$V_H$). Any suitable Fc domain known in the art or described herein may be used. In some cases, the Fc domain comprises an IgG1 Fc domain.

The term "monoclonal antibody" refers to an antibody from a population of substantially homogeneous antibodies. A population of substantially homogeneous antibodies comprises antibodies that are substantially similar and that bind the same epitope(s), except for variants that may normally arise during production of the monoclonal antibody. Such variants are generally present in only minor amounts. A monoclonal antibody is typically obtained by a process that includes the selection of a single antibody from a plurality of antibodies. For example, the selection process can be the selection of a unique clone from a plurality of clones, such as a pool of hybridoma clones, phage clones, yeast clones, bacterial clones, or other recombinant DNA clones. The selected antibody can be further altered, for example, to improve affinity for the target ("affinity maturation"), to humanize the antibody, to improve its production in cell culture, and/or to reduce its immunogenicity in a subject.

The term "chimeric antibody" refers to an antibody in which a portion of the heavy and/or light chain is derived from a particular source or species, while the remainder of the heavy and/or light chain is derived from a different source or species.

"Humanized" forms of non-human antibodies are chimeric antibodies that contain minimal sequence derived from the non-human antibody. A humanized antibody is generally a human immunoglobulin (recipient antibody) in which residues from one or more CDRs are replaced by residues from one or more CDRs of a non-human antibody (donor antibody). The donor antibody can be any suitable non-human antibody, such as a mouse, rat, rabbit, chicken, or non-human primate antibody having a desired specificity, affinity, or biological effect. In some instances, selected framework region residues of the recipient antibody are replaced by the corresponding framework region residues from the donor antibody. Humanized antibodies may also comprise residues that are not found in either the recipient antibody or the donor antibody. Such modifications may be made to further refine antibody function. For further details, see Jones et al., *Nature,* 1986, 321:522-525; Riechmann et al., *Nature,* 1988, 332:323-329; and Presta, *Curr. Op. Struct. Biol.,* 1992, 2:593-596, each of which is incorporated by reference in its entirety.

A "human antibody" is one which possesses an amino acid sequence corresponding to that of an antibody produced by a human or a human cell, or derived from a non-human source that utilizes a human antibody repertoire or human antibody-encoding sequences (e.g., obtained from human sources or designed de novo). Human antibodies specifically exclude humanized antibodies.

An "isolated antibody" is one that has been separated and/or recovered from a component of its natural environment. Components of the natural environment may include enzymes, hormones, and other proteinaceous or nonproteinaceous materials. In some embodiments, an isolated antibody is purified to a degree sufficient to obtain at least 15 residues of N-terminal or internal amino acid sequence, for example by use of a spinning cup sequenator. In some embodiments, an isolated antibody is purified to homogeneity by gel electrophoresis (e.g., SDS-PAGE) under reducing or nonreducing conditions, with detection by Coomassie blue or silver stain. An isolated antibody includes an antibody in situ within recombinant cells, since at least one component of the antibody's natural environment is not present. In some aspects, an isolated antibody is prepared by at least one purification step.

In some embodiments, an isolated antibody is purified to at least 80%, 85%, 90%, 95%, or 99% by weight. In some embodiments, an isolated antibody is purified to at least 80%, 85%, 90%, 95%, or 99% by volume. In some embodiments, an isolated antibody is provided as a solution comprising at least 85%, 90%, 95%, 98%, 99% to 100% by weight. In some embodiments, an isolated antibody is provided as a solution comprising at least 85%, 90%, 95%, 98%, 99% to 100% by volume.

"Affinity" refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity, which reflects a 1:1 interaction between members of a binding pair (e.g., antibody and antigen). The affinity of a molecule X for its partner Y can be represented by the dissociation constant ($K_D$). Affinity can be measured by common methods known in the art, including those described herein. Affinity can be determined, for example, using surface plasmon resonance (SPR) technology, such as a Biacore® instrument. In some embodiments, the affinity is determined at 25° C.

With regard to the binding of an antibody to a target molecule, the terms "specific binding," "specifically binds to," "specific for," "selectively binds," and "selective for" a particular antigen (e.g., a polypeptide target) or an epitope on a particular antigen mean binding that is measurably different from a non-specific or non-selective interaction. Specific binding can be measured, for example, by determining binding of a molecule compared to binding of a control molecule. Specific binding can also be determined by competition with a control molecule that mimics the antibody binding site on the target. In that case, specific binding is indicated if the binding of the antibody to the target is competitively inhibited by the control molecule.

An "affinity matured" antibody is one with one or more alterations in one or more CDRs or FRs that result in an improvement in the affinity of the antibody for its antigen, compared to a parent antibody which does not possess the alteration(s). In one embodiment, an affinity matured antibody has nanomolar or picomolar affinity for the target antigen. Affinity matured antibodies may be produced using a variety of methods known in the art. For example, Marks et al. (Bio/Technology, 1992, 10:779-783, incorporated by reference in its entirety) describes affinity maturation by $V_H$ and $V_L$ domain shuffling. Random mutagenesis of CDR and/or framework residues is described by, for example, Barbas et al. (*Proc. Nat. Acad. Sci. U.S.A.,* 1994, 91:3809-3813); Schier et al., *Gene,* 1995, 169:147-155; Yelton et al., *J. Immunol.,* 1995, 155:1994-2004; Jackson et al., *J. Immunol.,* 1995, 154:3310-33199; and Hawkins et al, *J. Mol. Biol.,* 1992, 226:889-896, each of which is incorporated by reference in its entirety.

The term "amino acid" refers to the twenty common naturally occurring amino acids. Naturally occurring amino acids include alanine (Ala; A), arginine (Arg; R), asparagine (Asn; N), aspartic acid (Asp; D), cysteine (Cys; C); glutamic acid (Glu; E), glutamine (Gln; Q), Glycine (Gly; G); histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V), and the less common pyrrolysine and selenocysteine. Natural amino acids also include citrulline. Naturally encoded amino acids include post-translational variants of the 22 naturally occurring amino acids such as prenylated amino acids, isoprenylated amino acids, myrisoylated amino acids, palmitoylated amino acids, N-linked glycosylated amino acids, O-linked glycosylated amino acids, phosphorylated amino acids and acylated amino acids. The term "amino acid" also includes non-natural (or unnatural) or synthetic α, β γ or δ amino acids, and includes but is not limited to, amino acids found in proteins, i.e. glycine, alanine, valine, leucine, isoleucine, methionine, phenylalanine, tryptophan, proline, serine, threonine, cysteine, tyrosine, asparagine, glutamine, aspartate, glutamate, lysine, arginine and histidine. In certain embodiments, the amino acid is in the L-configuration. Alternatively, the amino acid can be a derivative of alanyl, valinyl, leucinyl, isoleucinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl, histidinyl, β-alanyl, β-valinyl, β-leucinyl, β-isoleuccinyl, β-prolinyl, β-phenylalaninyl, β-tryptophanyl, β-methioninyl, β-glycinyl, β-serinyl, β-threoninyl, β-cysteinyl, β-tyrosinyl, β-asparaginyl, β-glutaminyl, β-aspartoyl, β-glutaroyl, β-lysinyl, β-argininyl or β-histidinyl. Unnatural amino acids are not proteinogenic amino acids, or post-translationally modified variants thereof. In particular, the term unnatural amino acid refers to an amino acid that is not one of the 20 common amino acids or pyrrolysine or selenocysteine, or post-translationally modified variants thereof.

The term "conjugate" or "antibody conjugate" refers to an antibody linked to one or more payload moieties. The antibody can be any antibody described herein. The payload can be any payload described herein. The antibody can be directly linked to the payload via a covalent bond, or the antibody can be linked to the payload indirectly via a linker. Typically, the linker is covalently bonded to the antibody and also covalently bonded to the payload. The term "antibody drug conjugate" or "ADC" refers to a conjugate wherein at least one payload is a therapeutic moiety such as a drug.

"pAMF" mutation refers to a variant phenylalanine residue, i.e., para-azidomethyl-L-phenylalanine, added or substituted into a polypeptide.

The term "payload" refers to a molecular moiety that can be conjugated to an antibody. In particular embodiments, payloads are selected from the group consisting of therapeutic moieties and/or labelling moieties described herein.

The term "linker" refers to a molecular moiety that is capable of forming at least two covalent bonds. Typically, a linker is capable of forming at least one covalent bond to an antibody and at least another covalent bond to a payload. In certain embodiments, a linker can form more than one covalent bond to an antibody. In certain embodiments, a linker can form more than one covalent bond to a payload or can form covalent bonds to more than one payload. After a linker forms a bond to an antibody, or a payload, or both, the remaining structure, i.e. the residue of the linker after one or more covalent bonds are formed, may still be referred to as a "linker" herein. The term "linker precursor" refers to a linker having one or more reactive groups capable of forming a covalent bond with an antibody or payload, or both. In some embodiments, the linker is a cleavable linker. For example, a cleavable linker can be one that is released by a bio-labile function, which may or may not be engineered. In some embodiments, the linker is a non-cleavable linker. For example, a non-cleavable linker can be one that is released upon degradation of the antibody.

When referring to the compounds provided herein, the following terms have the following meanings unless indicated otherwise. Unless defined otherwise, all technical and scientific terms used herein have the same meaning as is commonly understood by one of ordinary skill in the art. In the event that there is a plurality of definitions for a term herein, those in this section prevail unless stated otherwise.

The term "alkyl," as used herein, unless otherwise specified, refers to a saturated straight or branched hydrocarbon. In certain embodiments, the alkyl group is a primary, secondary, or tertiary hydrocarbon. In certain embodiments, the alkyl group includes one to ten carbon atoms, i.e., $C_1$ to $C_{10}$ alkyl. In certain embodiment, the alkyl group includes a saturated straight or branched hydrocarbon having one to six carbon atoms, i.e., $C_1$ to $C_6$ alkyl or lower alkyl. The term includes both substituted and unsubstituted moieties. The term includes both substituted and unsubstituted alkyl groups, including halogenated alkyl groups. In some or any embodiments, the alkyl is unsubstituted. In some or any embodiments, the alkyl is substituted. In certain embodiments, the alkyl group is a fluorinated alkyl group. Non-limiting examples of moieties with which the alkyl group can be substituted are selected from the group consisting of halogen (fluoro, chloro, bromo or iodo), hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., Protective Groups in Organic Synthesis, John Wiley and Sons, Second Edition, 1991, hereby incorporated by reference. In certain embodiments, the alkyl group is selected from the group consisting of methyl, $CF_3$, $CCl_3$, $CFCl_2$, $CF_2Cl$, ethyl, $CH_2CF_3$, $CF_2CF_3$, propyl, isopropyl, butyl, isobutyl, secbutyl, t-butyl, pentyl, isopentyl, neopentyl, hexyl, isohexyl, 3-methylpentyl, 2,2-dimethylbutyl, and 2,3-dimethylbutyl.

The term "alkylene," as used herein, unless otherwise specified, refers to a divalent alkyl group, as defined herein. In some or any embodiments, alkylene is unsubstituted.

"Alkenyl" refers to an olefinically unsaturated hydrocarbon groups, in certain embodiments, having up to about 11 carbon atoms or from 2 to 6 carbon atoms which can be straight-chained or branched and having at least 1 or from 1 to 2 sites of alkenyl unsaturation.

"Alkenylene" refers to a divalent alkenyl as defined herein. Lower alkenylene is $C_2$-$C_6$-alkenylene.

"Alkynyl" refers to acetylenically unsaturated hydrocarbon groups, in certain embodiments, having up to about 11 carbon atoms or from 2 to 6 carbon atoms which can be straight-chained or branched and having at least 1 or from 1 to 2 sites of alkynyl unsaturation. Non-limiting examples of alkynyl groups include acetylenic, ethynyl ($-C\equiv CH$), propargyl ($-CH_2C\equiv CH$), and the like.

"Alkynylene" refers to a divalent alkynyl as defined herein. Lower alkynylene is $C_2$-$C_6$-alkynylene.

The term "aryl," as used herein, and unless otherwise specified, refers to phenyl, biphenyl, or naphthyl. The term includes both substituted and unsubstituted moieties. An aryl group can be substituted with any described moiety, including, but not limited to, one or more moieties selected from the group consisting of halogen (fluoro, chloro, bromo or iodo), alkyl, haloalkyl, hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., *Protective Groups in Organic Synthesis*, John Wiley and Sons, Second Edition, 1991; and wherein the aryl in the arylamino and aryloxy substituents are not further substituted.

The term "arylene," as used herein, and unless otherwise specified refers to a divalent aryl group, as defined herein.

"Alkarylene" refers to an arylene group, as defined herein wherein the aryl ring is substituted with one or two alkyl groups. "Substituted alkarylene" refers to an alkarylene, as defined herein, where the arylene group is further substituted, as defined for aryl.

"Aralkylene" refers to an $-CH_2$-arylene-, -arylene-$CH_2-$, or $-CH_2$-arylene-$CH_2-$ group, where arylene is as defined herein. "Substituted aralkylene" refers to an aralkylene, as defined herein, where the aralkylene group is substituted, as defined for aryl.

"Alkoxy" and "alkoxyl," refer to the group $-OR''$ where R'' is alkyl or cycloalkyl. Alkoxy groups include, by way of example, methoxy, ethoxy, n-propoxy, isopropoxy, n-butoxy, tert-butoxy, sec-butoxy, n-pentoxy, n-hexoxy, 1,2-dimethylbutoxy, and the like.

"Alkoxycarbonyl" refers to a radical $-C(O)$-alkoxy where alkoxy is as defined herein.

"Amino" refers to the radical $-NH_2$.

The term "alkylamino," as used herein, and unless otherwise specified, refers to the group $-NHR''$ where R'' is $C_{1-10}$alkyl, as defined herein. In some or any embodiments, the alkylamino is $C_{1-6}$alkylamino.

The term "cycloalkyl", as used herein, unless otherwise specified, refers to a saturated cyclic hydrocarbon. In certain embodiments, the cycloalkyl group may be a saturated, and/or bridged, and/or non-bridged, and/or a fused bicyclic group. In certain embodiments, the cycloalkyl group includes three to ten carbon atoms, i.e., $C_3$ to $C_{10}$ cycloalkyl. In some embodiments, the cycloalkyl has from 3 to 15 ($C_{3-15}$), from 3 to 10 ($C_{3-10}$), or from 3 to 7 ($C_{3-7}$) carbon atoms. In certain embodiments, the cycloalkyl group is cyclopropyl, cyclobutyl, cyclopentyl, cyclohexyl, cyclohexylmethyl, cycloheptyl, bicyclo[2.1.1]hexyl, bicyclo[2.2.1]heptyl, decalinyl, or adamantyl. In some or any embodiments, cycloalkyl is substituted with 1, 2, or three groups independently selected from halogen (fluoro, chloro, bromo or iodo), alkyl, haloalkyl, hydroxyl, amino, alkylamino, and alkoxy.

The term "cycloalkylene," as used herein refers to a divalent cycloalkyl group, as defined herein. Lower cycloalkylene refers to a $C_3$-$C_6$-cycloalkylene.

The term "dialkylamino," as used herein, and unless otherwise specified, refers to the group —NR"R" where each R" is independently $C_{1-10}$alkyl, as defined herein. In some or any embodiments, the dialkylamino is di-$C_{1-6}$alkylamino.

"Carboxyl" or "carboxy" refers to the radical —C(O)OH.

"Fused bicyclic aryl," as used herein, is naphthyl.

"Lower heteroalkylene," as used herein, refers to a lower alkylene group where 1, 2, or three carbon atoms are replaced with heteroatoms independently selected from N, O, and $S(O)_{0-2}$.

The term "heterocyclyl" and "heterocyclic" refer to a monovalent monocyclic non-aromatic ring system and/or multicyclic ring system that contains at least one non-aromatic ring, wherein one or more of the non-aromatic ring atoms are heteroatoms independently selected from O, S, and N and the remaining ring atoms of the non-aromatic ring are carbon atoms, and wherein any aromatic ring atoms are optionally heteroatoms independently selected from O, S, and N and the remaining ring atoms of the non-aromatic ring are carbon atoms. In certain embodiments, the heterocyclyl or heterocyclic group has from 3 to 20, from 3 to 15, from 3 to 10, from 3 to 8, from 4 to 7, from 4 to 11, or from 5 to 6 ring atoms. Heterocyclyl groups are bonded to the rest of the molecule through the non-aromatic ring. In certain embodiments, the heterocyclyl is a monocyclic, bicyclic, tricyclic, or tetracyclic ring system, which may include a fused or bridged ring system and in which the nitrogen or sulfur atoms may be optionally oxidized, the nitrogen atoms may be optionally quaternized, and some rings may be partially or fully saturated, or aromatic. The heterocyclyl may be attached to the main structure at any heteroatom or carbon atom of its non-aromatic ring which results in the creation of a stable compound. Heterocycloalkyl refers to a heterocycle which is a monovalent, monocyclic or multicyclic, non-aromatic ring system. In some or any embodiments, heterocycloalkyl is a monovalent, monocyclic or multicyclic, fully-saturated ring system. Examples of such heterocyclic and/or heterocycloalkyl radicals include, but are not limited to, 2,5-diazabicyclo[2.2.2]octanyl, 3,9-diazabicyclo[3.3.2]decanyl), azepinyl, benzodioxanyl, benzodioxolyl, benzofuranonyl, benzopyranonyl, benzopyranyl, benzotetrahydrofuranyl, benzotetrahydrothienyl, benzothiopyranyl, benzoxazinyl, β-carbolinyl, chromanyl, chromonyl, cinnolinyl, coumarinyl, decahydroisoquinolinyl, dihydrobenzisothiazinyl, dihydrobenzisoxazinyl, dihydrofuryl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithianyl, furanonyl, imidazolidinyl, imidazolinyl, indolinyl, isobenzotetrahydrofuranyl, isobenzotetrahydrothienyl, isochromanyl, isocoumarinyl, isoindolinyl, isothiazolidinyl, isoxazolidinyl, morpholinyl, octahydroindolyl, octahydroisoindolyl, oxazolidinonyl, oxazolidinyl, oxiranyl, piperazinyl, piperidinyl, 4-piperidonyl, pyrazolidinyl, pyrazolinyl, pyrrolidinyl, pyrrolinyl, quinuclidinyl, tetrahydrofuryl, tetrahydroisoquinolinyl, tetrahydropyranyl, tetrahydrothienyl, thiamorpholinyl, thiazolidinyl, tetrahydroquinolinyl, and 1,3,5-trithianyl. In certain embodiments, heterocyclic may also be optionally substituted as described herein. In some or any embodiments, heterocyclic and heterocycloalkyl are substituted with 1, 2, or 3 groups independently selected from halogen (fluoro, chloro, bromo or iodo), alkyl, haloalkyl, hydroxyl, amino, alkylamino, and alkoxy. In some embodiments, a heterocycloalkyl group may comprise 1, 2, 3, or 4 heteroatoms. Those of skill in the art will recognize that a 4-membered heterocycloalkyl may generally comprise 1 or 2 heteroatoms, a 5-6 membered heterocycloalkyl may generally comprise 1, 2, or 3 heteroatoms, and a 7-10 membered heterocycloalkyl may generally comprise 1, 2, 3 or 4 heteroatoms.

"Heterocycloalkylene" refers to a divalent heterocycloalkyl, as defined herein.

"N-linked heterocycloalkyl" or "N-linked heterocyclyl" refers to a heterocycloalkyl, as defined above, comprising at least one nitrogen and wherein the heterocycloalkyl is attached to the main structure via a nitrogen atom in a non-aromatic ring. In some or any embodiments, the N-linked heterocycloalkyl and/or N-linked heterocyclyl is fully saturated.

The term "heteroaryl" refers to refers to a monovalent monocyclic aromatic group and/or multicyclic aromatic group, wherein at least one aromatic ring contains one or more heteroatoms independently selected from O, S, and N in the ring. Each ring of a heteroaryl group can contain one or two O atoms, one or two S atoms, and/or one to four N atoms, provided that the total number of heteroatoms in each ring is four or less and each ring contains at least one carbon atom. In certain embodiments, the heteroaryl has from 5 to 20, from 5 to 15, or from 5 to 10 ring atoms. A heteroaryl may be attached to the rest of the molecule via a nitrogen or a carbon atom. In some embodiments, monocyclic heteroaryl groups include, but are not limited to, furanyl, imidazolyl, isothiazolyl, isoxazolyl, oxadiazolyl, oxadiazolyl, oxazolyl, pyrazinyl, pyrazolyl, pyridazinyl, pyridyl, pyrimidinyl, pyrrolyl, imidazolyl, triazolyl, thiadiazolyl, thiazolyl, thienyl, tetrazolyl, triazinyl, and triazolyl. Examples of bicyclic heteroaryl groups include, but are not limited to, benzofuranyl, benzimidazolyl, benzoisoxazolyl, benzopyranyl, benzothiadiazolyl, benzothiazolyl, benzothienyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quinazolinyl, thiadiazolopyrimidyl, and thienopyridyl. Examples of tricyclic heteroaryl groups include, but are not limited to, acridinyl, benzindolyl, carbazolyl, dibenzofuranyl, perimidinyl, phenanthrolinyl, phenanthridinyl, phenarsazinyl, phenazinyl, phenothiazinyl, phenoxazinyl, and xanthenyl. In certain embodiments, heteroaryl may also be optionally substituted as described herein. "Substituted heteroaryl" is heteroaryl substituted as defined for aryl.

The term "heteroarylene" refers to a divalent heteroaryl group, as defined herein. "Substituted heteroarylene" is heteroarylene substituted as defined for aryl.

"Partially saturated heteroaryl" refers to a multicyclic (e.g., bicyclic, tricyclic) fused ring system that contains at least one non-aromatic ring and at least one aromatic ring, wherein one or more of the non-aromatic ring atoms and/or one or more of the aromatic ring atoms are heteroatoms independently selected from O, S, and N; and the remaining ring atoms are carbon atoms. Partially saturated heteroaryl groups are bonded to the rest of the molecule through the aromatic ring. In certain embodiments, the partially saturated heteroaryl group has from 6 to 20, from 6 to 15, from 6 to 10, from 6 to 8, or from 8 to 11 ring atoms. In certain embodiments, the partially saturated heteroaryl group has 8, 9, 10, or 11 ring atoms (in some embodiments 9 or 10). The partially saturated heteroaryl may be attached to the main structure at any heteroatom or carbon atom of its aromatic ring which results in the creation of a stable compound. In some or any embodiments, an oxo group may be present as a substituent on one of the ring atoms. A partially saturated heteroaryl radical consists of one of the following or comprises one or more of the following: benzodioxanyl, benzodioxolyl, benzofuranonyl, benzopyranonyl, benzopyranyl, benzotetrahydrofuranyl, benzotetrahydrothienyl, benzothiopyranyl, benzoxazinyl, chromanyl, chromonyl, cinnolinyl, coumarinyl, decahydroisoquinolinyl, dihydrobenzisothiazinyl, dihydrobenzisoxazinyl, dihydrofuryl, dihydroisoindolyl, dihydropyranyl, dihydropyrazolyl, dihydropyrazinyl, tetrahydropyrazinyl, dihydropyrazinonyl, dihydropyridinyl, tetrahydropyridinyl, dihydropyrimidinyl, dihydropyrrolyl, furanonyl, imidazolinyl, indolinyl, tetrahydroindolyl, isoindolinyl, tetrahydroisoindolyl, isobenzotetrahydrofuranyl, isobenzotetrahydrothienyl, isochromanyl, isocoumarinyl, isoindolinyl, dihydroisoxazolyl, oxazinyl, dihydrooxazinyl, oxo-oxazolyl, dihydrooxazolyl, dihydropiperidonyl, dihydro-4-piperidonyl, dihydropyrazolyl, dihydropyrazolinyl, dihydropyrrolyl, azabicyclo[2.2.2]oct-2-enyl, dihydrofuryl, tetrahydroisoquinolinyl, dihydropyranyl, pyranyl, dihydrothienyl, oxathiazinyl, dihydrothiazolyl, tetrahydroquinolinyl, and 5,6,7,8-tetrahydro-[1,2,4]triazolo[4,3-a]pyrazinyl. In certain embodiments, the partially saturated heteroaryl radical is benzodioxanyl, benzodioxolyl, benzofuranonyl, benzopyranonyl, benzopyranyl, benzotetrahydrofuranyl, benzotetrahydrothienyl, benzothiopyranyl, benzoxazinyl, chromanyl, chromonyl, coumarinyl, dihydrobenzisothiazinyl, dihydrobenzisoxazinyl, dihydroisoindolyl, indolinyl, isobenzotetrahydrofuranyl, isobenzotetrahydrothienyl, isochromanyl, isocoumarinyl, isoindolinyl, tetrahydroisoquinolinyl, tetrahydroquinolinyl, or 5,6,7,8-tetrahydro-[1,2,4]triazolo[4,3-a]pyrazinyl. In certain embodiments, partially saturated heteroaryl may also be optionally substituted as described herein.

"Spiro-heterocyclic" or "spiro-heterocycle" or "spiro-heterocycloalkyl" refers to a heterocyclic ring, as defined herein, which comprises two rings which are connected to each other via a common atom. Non-limiting examples of spiro-heterocycles include azetidinyl rings, morpholinyl rings, and/or piperidinyl rings that are attached via a common atom to another ring (e.g., ring B as shown below):

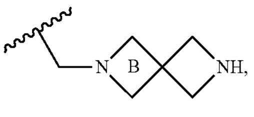
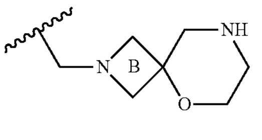
,
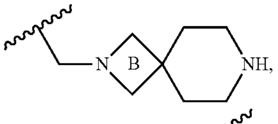
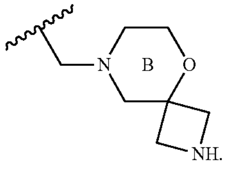
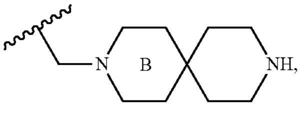

A spiro-heterocycloalkyl may be optionally substituted with, for example, 1-2 $C_{1-3}$alkyl.

The term "protecting group" as used herein and unless otherwise defined refers to a group that is added to an oxygen, nitrogen, or phosphorus atom to prevent its further reaction or for other purposes. A wide variety of oxygen and nitrogen protecting groups are known to those skilled in the art of organic synthesis.

"Pharmaceutically acceptable salt" refers to any salt of a compound provided herein which retains its biological properties and which is not toxic or otherwise undesirable for pharmaceutical use. Such salts may be derived from a variety of organic and inorganic counter-ions well known in the art. Such salts include, but are not limited to: (1) acid addition salts formed with organic or inorganic acids such as hydrochloric, hydrobromic, sulfuric, nitric, phosphoric, sulfamic, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, cyclohexylsulfamic, quinic, muconic acid and the like acids; or (2) salts formed when an acidic proton present in the parent compound either (a) is replaced by a metal ion, e.g., an alkali metal ion, an alkaline earth ion or an aluminum ion, or alkali metal or alkaline earth metal hydroxides, such as sodium, potassium, calcium, magnesium, aluminum, lithium, zinc, and barium hydroxide, ammonia or (b) coordinates with an organic base, such as aliphatic, alicyclic, or aromatic organic amines, such as ammonia, methylamine, dimethylamine, diethylamine, picoline, ethanolamine, diethanolamine, triethanolamine, ethylenediamine, lysine, arginine, ornithine, choline, N,N'-dibenzylethylene-diamine, chloroprocaine, diethanolamine, procaine, N-benzylphenethylamine, N-methylglucamine piperazine, tris(hydroxymethyl)-aminomethane, tetramethylammonium hydroxide, and the like.

Pharmaceutically acceptable salts further include, by way of example only and without limitation, sodium, potassium, calcium, magnesium, ammonium, tetraalkylammonium and the like, and when the compound contains a basic functionality, salts of non-toxic organic or inorganic acids, such as hydrohalides, e.g. hydrochloride and hydrobromide, sulfate, phosphate, sulfamate, nitrate, acetate, trifluoroacetate, trichloroacetate, propionate, hexanoate, cyclopentylpropionate, glycolate, glutarate, pyruvate, lactate, malonate, succinate, sorbate, ascorbate, malate, maleate, fumarate, tartarate, citrate, benzoate, 3-(4-hydroxybenzoyl)benzoate, picrate, cinnamate, mandelate, phthalate, laurate, methanesulfonate (mesylate), ethanesulfonate, 1,2-ethane-disulfonate, 2-hydroxyethanesulfonate, benzenesulfonate (besylate), 4-chlorobenzenesulfonate, 2-naphthalenesulfonate, 4-toluenesulfonate, camphorate, camphorsulfonate, 4-methylbicyclo[2.2.2]-oct-2-ene-1-carboxylate, glucoheptonate, 3-phenylpropionate, trimethylacetate, tert-butylacetate, lauryl sulfate, gluconate, benzoate, glutamate, hydroxynaphthoate, salicylate, stearate, cyclohexylsulfamate, quinate, muconate and the like.

The term "substantially free of" or "substantially in the absence of" with respect to a composition refers to a composition that includes at least 85 or 90% by weight, in certain embodiments 95%, 98%, 99% or 100% by weight, of the designated enantiomer of that compound. In certain embodiments, in the methods and compounds provided herein, the compounds are substantially free of enantiomers.

Similarly, the term "isolated" with respect to a composition refers to a composition that includes at least 85, 90%, 95%, 98%, 99% to 100% by weight, of the compound, the remainder comprising other chemical species or enantiomers.

"Solvate" refers to a compound provided herein or a salt thereof, that further includes a stoichiometric or non-stoichiometric amount of solvent bound by non-covalent intermolecular forces. Where the solvent is water, the solvate is a hydrate.

"Isotopic composition" refers to the amount of each isotope present for a given atom, and "natural isotopic composition" refers to the naturally occurring isotopic composition or abundance for a given atom. Atoms containing their natural isotopic composition may also be referred to herein as "non-enriched" atoms. Unless otherwise designated, the atoms of the compounds recited herein are meant to represent any stable isotope of that atom. For example, unless otherwise stated, when a position is designated specifically as "H" or "hydrogen", the position is understood to have hydrogen at its natural isotopic composition.

"Isotopic enrichment" refers to the percentage of incorporation of an amount of a specific isotope at a given atom in a molecule in the place of that atom's natural isotopic abundance. For example, deuterium enrichment of 10% at a given position means that 10% of the molecules in a given sample contain deuterium at the specified position. Because the naturally occurring distribution of deuterium is about 0.0156%, deuterium enrichment at any position in a compound synthesized using non-enriched starting materials is about 0.0156%. The isotopic enrichment of the compounds provided herein can be determined using conventional analytical methods known to one of ordinary skill in the art, including mass spectrometry and nuclear magnetic resonance spectroscopy.

"Isotopically enriched" refers to an atom having an isotopic composition other than the natural isotopic composition of that atom. "Isotopically enriched" may also refer to a compound containing at least one atom having an isotopic composition other than the natural isotopic composition of that atom.

As used herein, "alkyl," "alkylene," "alkylamino," "dialkylamino," "cycloalkyl," "aryl," "arylene," "alkoxy," "alkoxycarbonyl," "amino," "carboxyl," "heterocyclyl," "heterocycloalkyl," "heteroaryl," "heteroarylene," "partially saturated heteroaryl," "spiro-heterocyclyl," "carboxyl" and "amino acid" groups optionally comprise deuterium at one or more positions where hydrogen atoms are present, and wherein the deuterium composition of the atom or atoms is other than the natural isotopic composition.

Also as used herein, "alkyl," "alkylamino," "dialkylamino," "cycloalkyl," "aryl," "arylene," "alkoxy," "alkoxycarbonyl," "amino," "carboxyl," "heterocyclyl," "heterocycloalkyl," "heteroaryl," "heteroarylene," "partially saturated heteroaryl," "spiro-heterocyclyl," "carboxyl" and "amino acid" groups optionally comprise carbon-13 at an amount other than the natural isotopic composition.

As used herein, $EC_{50}$ refers to a dosage, concentration or amount of a particular test compound that elicits a dose-dependent response at 50% of maximal expression of a particular response that is induced, provoked or potentiated by the particular test compound.

As used herein, the $IC_{50}$ refers to an amount, concentration or dosage of a particular test compound that achieves a 50% inhibition of a maximal response in an assay that measures such response.

As used herein, the terms "subject" and "patient" are used interchangeably herein. The terms "subject" and "subjects" refer to an animal, such as a mammal including a non-primate (e.g., a cow, pig, horse, cat, dog, rat, and mouse) and a primate (e.g., a monkey such as a cynomolgous monkey, a chimpanzee and a human), and for example, a human. In certain embodiments, the subject is refractory or non-responsive to current treatments for hepatitis C infection. In another embodiment, the subject is a farm animal (e.g., a horse, a cow, a pig, etc.) or a pet (e.g., a dog or a cat). In certain embodiments, the subject is a human.

As used herein, the terms "therapeutic agent" and "therapeutic agents" refer to any agent(s) which can be used in the treatment or prevention of a disorder or one or more symptoms thereof. In certain embodiments, the term "therapeutic agent" includes a compound and/or an antibody conjugate provided herein. In certain embodiments, a therapeutic agent is an agent which is known to be useful for, or has been or is currently being used for the treatment or prevention of a disorder or one or more symptoms thereof.

As used herein, the term "therapeutically effective amount" or "effective amount" refers to an amount of an antibody or composition that when administered to a subject is effective to treat a disease or disorder. In some embodiments, a therapeutically effective amount or effective amount refers to an amount of an antibody or composition that when administered to a subject is effective to prevent or ameliorate a disease or the progression of the disease, or result in amelioration of symptoms. A "therapeutically effective amount" can vary depending on, inter alia, the compound, the disease and its severity, and the age, weight, etc., of the subject to be treated.

"Treating" or "treatment" of any disease or disorder refers, in certain embodiments, to ameliorating a disease or disorder that exists in a subject. In another embodiment, "treating" or "treatment" includes ameliorating at least one physical parameter, which may be indiscernible by the subject. In yet another embodiment, "treating" or "treatment" includes modulating the disease or disorder, either physically (e.g., stabilization of a discernible symptom) or physiologically (e.g., stabilization of a physical parameter) or both. In yet another embodiment, "treating" or "treatment" includes delaying or preventing the onset of the disease or disorder, or delaying or preventing recurrence of the disease or disorder. In yet another embodiment, "treating" or "treatment" includes the reduction or elimination of either the disease or disorder, or to retard the progression of the disease or disorder or of one or more symptoms of the disease or disorder, or to reduce the severity of the disease or disorder or of one or more symptoms of the disease or disorder.

As used herein, the term "inhibits growth" (e.g. referring to cells, such as tumor cells) is intended to include any measurable decrease in cell growth (e.g., tumor cell growth) when contacted with an antibody or antibody conjugate, as compared to the growth of the same cells not in contact with the antibody or antibody conjugate. In some embodiments, growth may be inhibited by at least about 10%, 20%, 30%, 40%, 50%, 60%, 70%, 80%, 90%, 99%, or 100%. The decrease in cell growth can occur by a variety of mechanisms, including but not limited to antibody internalization, apoptosis, necrosis, and/or effector function-mediated activity.

As used herein, the terms "prophylactic agent" and "prophylactic agents" as used refer to any agent(s) which can be used in the prevention of a disorder or one or more symptoms thereof. In certain embodiments, the term "prophylactic agent" includes a compound provided herein. In certain other embodiments, the term "prophylactic agent" does not refer a compound provided herein. For example, a prophylactic agent is an agent which is known to be useful for, or has been or is currently being used to prevent or impede the onset, development, progression and/or severity of a disorder.

As used herein, the phrase "prophylactically effective amount" refers to the amount of a therapy (e.g., prophylactic agent) which is sufficient to result in the prevention or reduction of the development, recurrence or onset of one or more symptoms associated with a disorder, or to enhance or improve the prophylactic effect(s) of another therapy (e.g., another prophylactic agent).

In some chemical structures illustrated herein, certain substituents, chemical groups, and atoms are depicted with a curvy/wavy line (e.g., )

that intersects a bond or bonds to indicate the atom through which the substituents, chemical groups, and atoms are bonded. For example, in some structures, such as but not limited to,

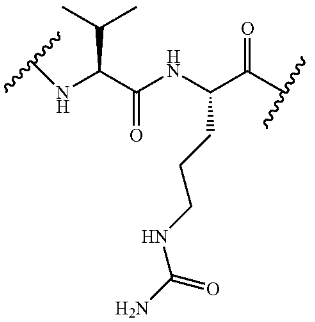

, or

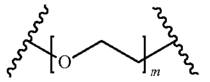

, this curvy/wavy line indicates the atoms in the backbone of a conjugate or linker-payload structure to which the illustrated chemical entity is bonded. In some structures, such as but not limited to

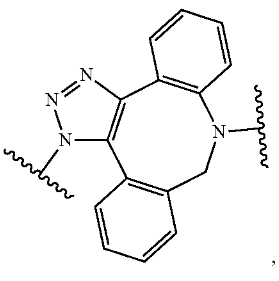 [SMILES: *N1Cc2ccccc2-c2c(nnn2*)-c2ccccc21]

, this curvy/wavy line indicates the atoms in the antibody or antibody fragment as well as the atoms in the backbone of a conjugate or linker-payload structure to which the illustrated chemical entity is bonded.

The term "site-specific" refers to a modification of a polypeptide at a predetermined sequence location in the polypeptide. The modification is at a single, predictable residue of the polypeptide with little or no variation. In particular embodiments, a modified amino acid is introduced at that sequence location, for instance recombinantly or synthetically. Similarly, a moiety can be "site-specifically" linked to a residue at a particular sequence location in the polypeptide. In certain embodiments, a polypeptide can comprise more than one site-specific modification.

2. Payloads—Compounds of Formula (I-P) and (I) and Subformulas Thereof

Provided herein are compounds that can modulate the activity of diseases or disorders associated with Toll-like Receptor 7/8. The pyrazoloquinolines can be formed as described herein and used for the treatment of diseases or disorders associated with diseases or disorders associated with Toll-like Receptor 7/8. In certain embodiments, the disease or disorder is a cancer or an inflammatory disease or condition.

The embodiments described herein include the recited compounds as well as a pharmaceutically acceptable salt, hydrate, solvate, stereoisomer, tautomer, or mixture thereof.

In one aspect, provided herein is a compound of Formula (I-P):

Formula (I-P)

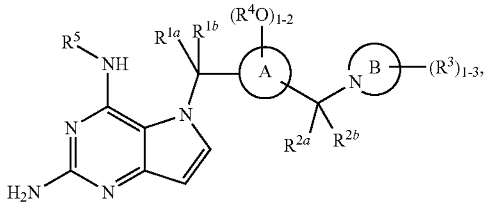

or a pharmaceutically acceptable salt, solvate or N-oxide thereof;

wherein $R^{1a}$, $R^{1b}$, $R^{2a}$, and $R^{2b}$ are independently, at each occurrence, selected from hydrogen, and $C_{1-6}$alkyl;

ring A is cycloalkyl, heterocycloalkyl, monocyclic aryl, monocyclic heteroaryl, fused bicyclic aryl, or fused bicyclic heteroaryl, where heterocycloalkyl and each heteroaryl comprise 1, 2, 3 or 4 heteroatoms selected from N, S, and O;

ring B is a 4-membered N-linked heterocycloalkyl, which is further substituted with 1-2 $R^3$; wherein $R^3$ is, independently, at each occurrence, —$N(R^{3a})_2$, —$OR^{3b}$, —$C(R^{3c})_2NH_2$, $C_{1-6}$alkyl, heterocycloalkyl, heteroaryl, or partially saturated heteroaryl, or two $R^3$ attached to the same carbon, together with the carbon atom to which they are attached, form a spiro-heterocycloalkyl; wherein heterocycloalkyl, spiro-heterocycloalkyl, heteroaryl and partially saturated heteroaryl include 1, 2, 3 or 4 heteroatoms selected from N, S, and O, and are optionally further substituted with 1-2 $C_{1-3}$alkyl;

or ring B is a 5-6 membered N-linked heterocycloalkyl, which is further substituted with 1-3 $R^3$; wherein $R^3$ is, independently, at each occurrence, —$N(R^{3a})_2$, —$OR^{3b}$, —$C(R^{3c})_2NH_2$, heterocycloalkyl, heteroaryl, or partially saturated heteroaryl, or two $R^3$ attached to the same carbon, together with the carbon atom to which they are attached, form a spiro-heterocycloalkyl; wherein heterocycloalkyl, spiro-heterocycloalkyl, heteroaryl and partially saturated heteroaryl include 1, 2, 3 or 4 heteroatoms selected from N, S, and O, and are optionally further substituted with 1-2 $C_{1-3}$alkyl;

or ring B is a 7-10 membered N-linked heterocycloalkyl, which is further substituted with 1-3 R3, or a 5-10 membered N-linked heteroaryl which is further substituted with 1-3 $R^3$; wherein $R^3$ is, independently, at each occurrence, —$N(R^{3a})_2$, —$OR^{3b}$, —$C(R^{3c})_2NH_2$, $C_{1-6}$alkyl, heterocycloalkyl, heteroaryl, or partially saturated heteroaryl, or two $R^3$ attached to the same carbon, together with the carbon atom to which they are attached, form a spiro-heterocycloalkyl; wherein heterocycloalkyl, spiro-heterocycloalkyl, heteroaryl and partially saturated heteroaryl include 1, 2, 3 or 4 heteroatoms selected from N, S, and O, and are optionally further substituted with 1-2 $C_{1-3}$alkyl;

$R^{3a}$ is independently, at each occurrence, selected from hydrogen, $C_{1-6}$alkyl, —C(═O)—$CH_2NH_2$, and cycloalkyl;

$R^{3b}$ is independently, at each occurrence, selected from hydrogen,

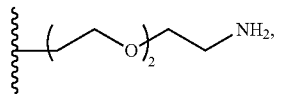

and —$CH_2$-aryl-$CH_2NH_2$;

$R^{3c}$ is independently, at each occurrence, selected from hydrogen, and $C_{1-6}$alkyl, or two $R^{3c}$, together with the carbon atom to which they are attached, form a cycloalkyl;

$R^4$ is $C_{1-6}$alkyl; and $R^5$ is $C_{1-6}$cycloalkyl, or $C_{1-6}$alkyl optionally substituted with halo, hydroxy, alkoxy, amino, $C_{1-6}$alkylamino, $C_{1-6}$dialkylamino, $C_{1-6}$cycloalkyl, aryl or heteroaryl, wherein heteroaryl includes 1, 2, 3 or 4 heteroatoms selected from N, S, and O, and wherein cycloalkyl, aryl and heteroaryl are optionally further substituted with halo, hydroxy, alkyl, or haloalkyl.

In another aspect, provided herein is a compound of Formula (I):

Formula (I)

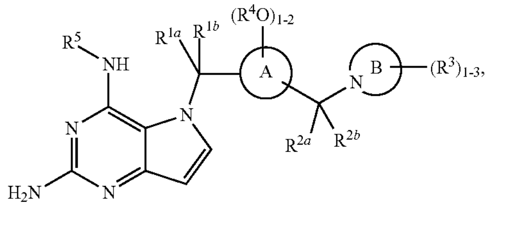

or a pharmaceutically acceptable salt, solvate or N-oxide thereof;

wherein $R^{1a}$, $R^{1b}$, $R^{2a}$, and $R^{2b}$ are independently, at each occurrence, selected from hydrogen, and $C_{1-6}$alkyl;

ring A is cycloalkyl, heterocycloalkyl, monocyclic aryl, monocyclic heteroaryl, fused bicyclic aryl, or fused bicyclic heteroaryl, where heterocycloalkyl and each heteroaryl comprise 1, 2, 3 or 4 heteroatoms independently selected from N, S, and O;

ring B is a 4-membered N-linked heterocycloalkyl, which is substituted with 1-2 $R^3$; wherein $R^3$ is, independently, at each occurrence, —$N(R^{3a})_2$, —$OR^{3b}$, —$C(R^{3c})_2NH_2$, $C_{1-6}$alkyl, heterocycloalkyl, heteroaryl, or partially saturated heteroaryl, or two $R^3$ attached to the same carbon, together with the carbon atom to which they are attached, form a spiro-heterocycloalkyl; wherein heterocycloalkyl, spiro-heterocycloalkyl, heteroaryl, and partially saturated heteroaryl in $R^3$ include 1, 2, 3 or 4 heteroatoms independently selected from N, S, and O, and are optionally substituted with 1-2 $C_{1-3}$alkyl;

or ring B is a 5-6 membered N-linked heterocycloalkyl, which is substituted with 1-3 $R^3$, or a 5-6 membered N-linked heteroaryl, which is substituted with 1-3 $R^3$; wherein $R^3$ is, independently, at each occurrence, —$N(R^{3a})_2$, —$OR^{3b}$, —$C(R^{3c})_2NH_2$, heterocycloalkyl, heteroaryl, or partially saturated heteroaryl, or two $R^3$ attached to the same carbon, together with the carbon atom to which they are attached, form a spiro-heterocycloalkyl; wherein heterocycloalkyl, spiro-heterocycloalkyl, heteroaryl, and partially saturated heteroaryl in $R^3$ include 1, 2, 3 or 4 heteroatoms independently selected from N, S, and O, and are optionally substituted with 1-2 $C_{1-3}$alkyl;

or ring B is a 7-10 membered N-linked heterocycloalkyl, which is substituted with 1-3 $R^3$, or a 5-10 membered N-linked heteroaryl which is substituted with 1-3 $R^3$; wherein $R^3$ is, independently, at each occurrence, —$N(R^{3a})_2$, —$OR^{3b}$, —$C(R^{3c})_2NH_2$, $C_{1-6}$alkyl, heterocycloalkyl, heteroaryl, or partially saturated heteroaryl, or two $R^3$ attached to the same carbon, together with the carbon atom to which they are attached, form a spiro-heterocycloalkyl; wherein heterocycloalkyl, spiro-heterocycloalkyl, heteroaryl, and partially saturated heteroaryl in $R^3$ include 1, 2, 3 or 4 heteroatoms independently selected from N, S, and O, and are optionally substituted with 1-2 $C_{1-3}$alkyl;

$R^{3a}$ is independently, at each occurrence, selected from hydrogen, $C_{1-6}$alkyl, —C(═O)—$CH_2NH_2$, and cycloalkyl;

$R^{3b}$ is independently, at each occurrence, selected from hydrogen,

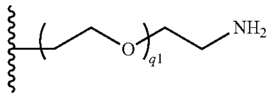

where q1 is 1, 2, or 3, and —$CH_2$-aryl-$CH_2NH_2$;

$R^{3c}$ is independently, at each occurrence, selected from hydrogen, and $C_{1-6}$alkyl, or two $R^{3c}$, together with the carbon atom to which they are attached, form a cycloalkyl;

$R^4$ is $C_{1-6}$alkyl; and $R^5$ is $C_{3-6}$cycloalkyl, or $C_{1-6}$alkyl, each of which is optionally substituted with 1, 2, or 3 $R^{5a}$ groups independently selected from halo, hydroxy, alkoxy, amino, $C_{1-6}$alkylamino, $C_{1-6}$dialkylamino, $C_{3-6}$cycloalkyl, aryl, and heteroaryl, wherein heteroaryl includes 1, 2, 3 or 4 heteroatoms independently selected from N, S, and O, and wherein any of the $R^{5a}$ $C_{3-6}$cycloalkyl, aryl, and heteroaryl groups are optionally substituted with 1, 2, or 3 groups independently selected from halo, hydroxy, alkyl, and haloalkyl.

In a group of embodiments, a compound of Formula I has a structure of Formula (II):

Formula (II)

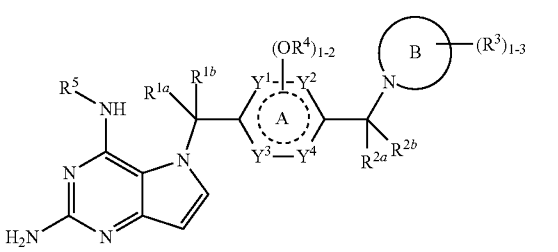

or a pharmaceutically acceptable salt, solvate or N-oxide thereof;

wherein $R^{1a}$, $R^{1b}$, $R^{2a}$, and $R^{2b}$ are independently, at each occurrence, selected from hydrogen, and $C_{1-6}$alkyl;

ring A is a six-membered aryl or six-membered heteroaryl ring, where $Y^1$, $Y^2$, $Y^3$, and $Y^4$ are independently selected from C and N;

ring B is a 4-membered N-linked heterocycloalkyl, which is substituted with 1-2 $R^3$; wherein $R^3$ is, independently, at each occurrence, —$N(R^{3a})_2$, —$OR^{3b}$, —$C(R^{3c})_2NH_2$, $C_{1-6}$alkyl, heterocycloalkyl, heteroaryl, or partially saturated heteroaryl, or two $R^3$ attached to the same carbon, together with the carbon atom to which they are attached, form a spiro-heterocycloalkyl; wherein heterocycloalkyl, spiro-heterocycloalkyl, heteroaryl, and partially saturated heteroaryl in $R^3$ include 1, 2, 3 or 4 heteroatoms independently selected from N, S, and O, and are optionally substituted with 1-2 $C_{1-3}$alkyl;

or ring B is a 5-6 membered N-linked heterocycloalkyl, which is substituted with 1-3 $R^3$, or a 5-6 membered N-linked heteroaryl, which is substituted with 1-3 $R^3$; wherein $R^3$ is, independently, at each occurrence, —$N(R^{3a})_2$, —$OR^{3b}$, —$C(R^{3c})_2NH_2$, heterocycloalkyl, heteroaryl, or partially saturated heteroaryl, or two $R^3$ attached to the same carbon, together with the carbon atom to which they are attached, form a spiro-heterocycloalkyl; wherein heterocycloalkyl, spiro-heterocycloalkyl, heteroaryl, and partially saturated heteroaryl in $R^3$ include 1, 2, 3 or 4 heteroatoms independently selected from N, S, and O, and are optionally substituted with 1-2 $C_{1-3}$alkyl;

or ring B is a 7-10 membered N-linked heterocycloalkyl, which is substituted with 1-3 $R^3$, or a 5-10 membered N-linked heteroaryl which is substituted with 1-3 $R^3$; wherein $R^3$ is, independently, at each occurrence, —$N(R^{3a})_2$, —$OR^{3b}$, —$C(R^{3c})_2NH_2$, $C_{1-6}$alkyl, heterocycloalkyl, heteroaryl, or partially saturated heteroaryl, or two $R^3$ attached to the same carbon, together with the carbon atom to which they are attached, form a spiro-heterocycloalkyl; wherein heterocycloalkyl, spiro-heterocycloalkyl, heteroaryl, and partially saturated heteroaryl in $R^3$ include 1, 2, 3 or 4 heteroatoms independently selected from N, S, and O, and are optionally substituted with 1-2 $C_{1-3}$alkyl;

$R^{3a}$ is independently, at each occurrence, selected from hydrogen, $C_{1-6}$alkyl, —C(═O)—$CH_2NH_2$, and cycloalkyl;

$R^{3b}$ is independently, at each occurrence, selected from hydrogen,

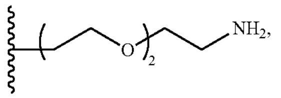

and —$CH_2$-aryl-$CH_2NH_2$;

$R^{3c}$ is independently, at each occurrence, selected from hydrogen, and $C_{1-6}$alkyl, or two $R^{3c}$, together with the carbon atom to which they are attached, form a cycloalkyl;

$R^4$ is $C_{1-6}$alkyl; and $R^5$ is $C_{3-6}$cycloalkyl, or $C_{1-6}$alkyl, each of which is optionally substituted with 1, 2, or 3 $R^{5a}$ groups independently selected from halo, hydroxy, alkoxy, amino, $C_{1-6}$alkylamino, $C_{1-6}$dialkylamino, $C_{3-6}$cycloalkyl, aryl, and heteroaryl, wherein heteroaryl includes 1, 2, 3 or 4 heteroatoms independently selected from N, S, and O, and wherein any of the $R^{5a}$ $C_{3-6}$cycloalkyl, aryl, and heteroaryl groups are optionally substituted with one or two (in some embodiments one) groups independently selected from halo, hydroxy, alkyl, and haloalkyl.

In some embodiments of compounds of Formula (I-P), (I) and/or Formula (II), ring A is a phenyl ring. In some embodiments of compounds of Formula (I-P), (I) and/or Formula (II), ring A is a monocyclic heteroaryl ring. In some embodiments of compounds of Formula (I-P), (I) and/or Formula (II), ring A is pyridinyl. In some embodiments of compounds of Formula (I-P), (I) and/or Formula (II), ring A is a fused bicyclic heteroaryl ring. In some embodiments of compounds of Formula (I-P) and (I), ring A is a cycloalkyl ring. In some embodiments of compounds of Formula (I-P) and (I), ring A is a heterocycloalkyl ring.

In some embodiments of compounds of Formula (I-P), (I) and/or Formula (II), on ring A, at least one —$OR^4$ is in an ortho-position relative to the group,

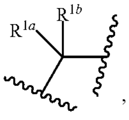

, wherein each

indicates a point of attachment to the rest of the formula.

In a group of embodiments, compounds of Formula (I-P), (I) and/or Formula (II) have the structure of Formula (III):

Formula (III)

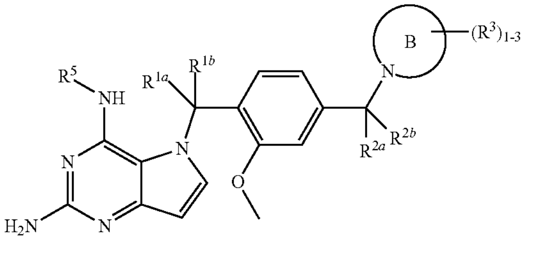

wherein $R^{1a}$, $R^{1b}$, $R^{2a}$, and $R^{2b}$ are independently, at each occurrence, selected from hydrogen, and $C_{1-6}$alkyl;

ring B is an N-linked azetidinyl ring which is substituted with 1-2 $R^3$; wherein $R^3$ is, independently, at each occurrence, —$N(R^{3a})_2$, —$OR^{3b}$, —$C(R^{3c})_2NH_2$, $C_{1-6}$alkyl, heterocycloalkyl, heteroaryl, or partially saturated heteroaryl, or two $R^3$ attached to the same carbon, together with the carbon atom to which they are attached, form a spiro-heterocycloalkyl; wherein heterocycloalkyl, spiro-heterocycloalkyl, heteroaryl, and partially saturated heteroaryl in $R^3$ include 1, 2, 3 or 4 heteroatoms independently selected from N, S, and O, and are optionally substituted with 1-2 $C_{1-3}$alkyl;

or ring B is an N-linked piperidinyl, piperazinyl, morpholinyl, or triazolyl ring which is substituted with 1-3 $R^3$; wherein $R^3$ is, independently, at each occurrence, —$N(R^{3a})_2$, —$OR^{3b}$, —$C(R^{3c})_2NH_2$, heterocycloalkyl, heteroaryl, or partially saturated heteroaryl, or two $R^3$ attached to the same carbon, together with the carbon atom to which they are attached, form a spiro-heterocycloalkyl; wherein heterocycloalkyl, spiro-heterocycloalkyl, heteroaryl and partially saturated heteroaryl in $R^3$ include 1, 2, 3 or 4 heteroatoms independently selected from N, S, and O, and are optionally substituted with 1-2 $C_{1-3}$alkyl;

or ring B is unsubstituted 2,5-diazabicyclo[2.2.2]octanyl, or 3,9-diazabicyclo[3.3.2]decanyl; or ring B is a 5-10 membered N-linked heteroaryl which is substituted with 1-3 $R^3$; wherein the heteroaryl includes 1, 2, 3 or 4 heteroatoms selected from N, S, and O; and wherein $R^3$ is, independently, at each occurrence, —$N(R^{3a})_2$, —$OR^{3b}$, —$C(R^{3c})_2NH_2$, $C_{1-6}$alkyl, heterocycloalkyl, heteroaryl, or partially saturated heteroaryl, or two $R^3$ attached to the same carbon, together with the carbon atom to which they are attached, form a spiro-heterocycloalkyl; wherein heterocycloalkyl, spiro-heterocycloalkyl, heteroaryl, and partially saturated heteroaryl in $R^3$ include 1, 2, 3 or 4 heteroatoms independently selected from N, S, and O, and are optionally substituted with 1-2 $C_{1-3}$alkyl;

$R^{3a}$ is independently, at each occurrence, selected from hydrogen, $C_{1-6}$alkyl, —C(═O)—$CH_2NH_2$, and cycloalkyl;

$R^{3b}$ is independently, at each occurrence, selected from hydrogen,

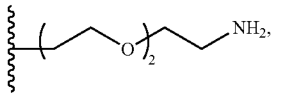

and —$CH_2$-aryl-$CH_2NH_2$;

$R^{3c}$ is independently, at each occurrence, selected from hydrogen and $C_{1-3}$alkyl, or two $R^{3c}$, together with the carbon atom to which they are attached, form a cyclopropyl; and $R^5$ is $C_{3-6}$cycloalkyl, or $C_{1-6}$alkyl, each of which is optionally substituted with 1, 2, or 3 $R^{5a}$ groups independently selected from halo, hydroxy, alkoxy, amino, $C_{1-6}$alkylamino, $C_{1-6}$dialkylamino, $C_{3-6}$cycloalkyl, aryl, and heteroaryl, wherein heteroaryl includes 1, 2, 3 or 4 heteroatoms independently selected from N, S, and O, and wherein any of the $R^{5a}$ $C_{3-6}$cycloalkyl, aryl, and heteroaryl groups are optionally substituted with halo, hydroxy, alkyl, or haloalkyl.

In some embodiments of compounds of Formula (I-P), (I), Formula (II) and/or Formula (III), $R^{1a}$ and $R^{1b}$ are each hydrogen. In some embodiments of compounds of Formula (I-P), (I), Formula (II) and/or Formula (III), $R^{2a}$ and $R^{2b}$ are each hydrogen. In some embodiments of compounds of Formula (I-P), (I), Formula (II) and/or Formula (III), $R^{1a}$, $R^{1b}$, $R^{2a}$, and $R^{2b}$ are each hydrogen.

In some embodiments of compounds of Formula (I-P), (I), Formula (II) and/or Formula (III), $R^4$ is methyl, ethyl, propyl or isopropyl. In some embodiments of compounds of Formula (I-P), (I), Formula (II) and/or Formula (III), $R^4$ is methyl. In some embodiments of compounds of Formula (I-P), (I), Formula (II) and/or Formula (III), $R^4$ is ethyl. In some embodiments of compounds of Formula (I-P), (I), Formula (II) and/or Formula (III), $R^4$ is propyl. In some embodiments of compounds of Formula (I-P), (I), Formula (II) and/or Formula (III), $R^4$ is isopropyl. In some embodiments of compounds of Formula (I-P), (I), Formula (II) and/or Formula (III), $R^4$ is butyl, isobutyl, pentyl, neopentyl, or hexyl.

In some embodiments of compounds of Formula (I-P), (I), Formula (II) and/or Formula (III), $R^5$ is $C_{1-6}$alkyl optionally substituted with 1, 2, or 3 $R^{5a}$ groups independently selected from halo, hydroxy, alkoxy, amino, $C_{1-6}$alkylamino, $C_{1-6}$dialkylamino, $C_{3-6}$cycloalkyl, aryl, and heteroaryl, wherein heteroaryl includes 1, 2, 3 or 4 heteroatoms independently selected from N, S, and O, and wherein any of the $R^{5a}$ $C_{3-6}$cycloalkyl, aryl and heteroaryl groups are optionally substituted with halo, hydroxy, alkyl, or haloalkyl.

In some embodiments of compounds of Formula (I-P), Formula (I), Formula (II) and/or Formula (III), $R^5$ is $C_{1-6}$alkyl optionally substituted with 1, 2, or 3 $R^{5a}$ groups independently selected from halo, hydroxy, alkoxy, amino, $C_{1-6}$alkylamino, and $C_{1-6}$dialkylamino. In some embodiments of compounds of Formula (I-P), Formula (I), Formula (II) and/or Formula (III), $R^5$ is $C_{1-6}$alkyl optionally substituted with one or two hydroxy. In some of such instances, $R^5$ is a branched $C_{1-6}$alkyl optionally substituted with one or two hydroxy.

In some embodiments of compounds of Formula (I-P), Formula (I), Formula (II) and/or Formula (III), $R^5$ is $C_{1-6}$alkyl optionally substituted with hydroxy or alkoxy.

In some embodiments of compounds of Formula (I-P), Formula (I), Formula (II) and/or Formula (III), $R^5$ is

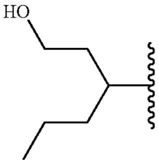

or

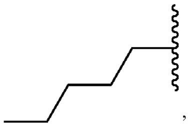

, wherein each

indicates a point of attachment to the rest of the formula.

In some embodiments of compounds of Formula (I-P), Formula (I), Formula (II) and/or Formula (III), $R^5$ is $C_{3-6}$alkyl optionally substituted with $C_{3-6}$cycloalkyl. In some of such instances, $R^5$ is —$CH_2$-cyclopropyl or —$CH_2$-cyclobutyl.

In some embodiments of compounds of Formula (I-P), Formula (I), Formula (II) and/or Formula (III), $R^5$ is $C_{1-6}$alkyl optionally substituted with aryl or heteroaryl, wherein heteroaryl includes 1, 2, 3 or 4 heteroatoms independently selected from N, S, and O, and wherein aryl and heteroaryl are optionally further substituted with halo, alkyl, or haloalkyl.

In some embodiments of compounds of Formula (I-P), Formula (I), Formula (II) and/or Formula (III), $R^5$ is

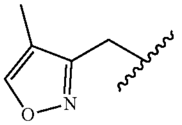

or

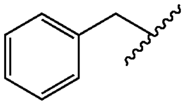

wherein each

indicates a point of attachment to the rest of the formula.

In some embodiments of compounds of Formula (I-P), Formula (I), Formula (II) and/or Formula (III), $R^5$ is $C_{3-6}$cycloalkyl optionally substituted with 1, 2, or 3 $R^{5a}$ groups independently selected from halo, hydroxy, alkoxy, amino, $C_{1-6}$alkylamino, $C_{1-6}$dialkylamino, $C_{3-6}$cycloalkyl, aryl, and heteroaryl, wherein heteroaryl includes 1, 2, 3 or 4 heteroatoms independently selected from N, S, and O, and wherein any of the $R^{5a}$ $C_{3-6}$cycloalkyl, aryl and heteroaryl groups are optionally substituted with halo, hydroxy, alkyl, or haloalkyl.

In some embodiments of compounds of Formula (I-P), Formula (I), Formula (II) and/or Formula (III), $R^5$ is unsubstituted $C_{3-6}$cycloalkyl. In some of such instances, $R^5$ is cyclopropyl or cyclobutyl.

In some or any of the preceding embodiments of compounds of Formula (I-P), Formula (I), Formula (II) and/or Formula (III), ring B is a 4-membered N-linked heterocycloalkyl, which is substituted with 1-2 $R^3$; wherein $R^3$ is, independently, at each occurrence, —$N(R^{3a})_2$, —$OR^{3b}$, —$C(R^{3c})_2NH_2$, $C_{1-6}$alkyl, heterocycloalkyl, heteroaryl, or partially saturated heteroaryl, or two $R^3$ attached to the same carbon, together with the carbon atom to which they are attached, form a spiro-heterocycloalkyl; wherein heterocycloalkyl, spiro-heterocycloalkyl, heteroaryl, and partially saturated heteroaryl in $R^3$ include 1, 2, 3 or 4 heteroatoms independently selected from N, S, and O, and are optionally substituted with 1-2 $C_{1-3}$alkyl.

In some or any of the preceding embodiments of compounds of Formula (I-P), Formula (I), Formula (II) and/or Formula (III), ring B is a 5-6 membered N-linked heterocycloalkyl, which is substituted with 1-3 $R^3$; wherein $R^3$ is, independently, at each occurrence, —$N(R^{3a})_2$, —$OR^{3b}$, —$C(R^{3c})_2NH_2$, heterocycloalkyl, heteroaryl, or partially saturated heteroaryl, or two $R^3$ attached to the same carbon, together with the carbon atom to which they are attached, form a spiro-heterocycloalkyl; wherein heterocycloalkyl, spiro-heterocycloalkyl, heteroaryl, and partially saturated heteroaryl in $R^3$ include 1, 2, 3 or 4 heteroatoms independently selected from N, S, and O, and are optionally substituted with 1-2 $C_{1-3}$alkyl.

In some or any of the preceding embodiments of compounds of Formula (I-P), Formula (I), Formula (II) and/or Formula (III), ring B is a 7-10 membered N-linked heterocycloalkyl, which is substituted with 1-3 $R^3$, or a 5-10 membered N-linked heteroaryl which is substituted with 1-3 $R^3$; wherein $R^3$ is, independently, at each occurrence, —$N(R^{3a})_2$, —$OR^{3b}$, —$C(R^3)_2NH_2$, $C_{1-6}$alkyl, heterocycloalkyl, heteroaryl, or partially saturated heteroaryl, or two $R^3$ attached to the same carbon, together with the carbon atom to which they are attached, form a spiro-heterocycloalkyl; wherein heterocycloalkyl, spiro-heterocycloalkyl, heteroaryl, and partially saturated heteroaryl in $R^3$ include 1, 2, 3 or 4 heteroatoms independently selected from N, S, and O, and are optionally substituted with 1-2 $C_{1-3}$alkyl.

In some or any of the preceding embodiments of compounds of Formula (I-P), Formula (I), Formula (II) and/or Formula (III), ring B is a fully saturated heterocycloalkyl ring substituted with 1-3 $R^3$. In some or any of the preceding embodiments of compounds of Formula (I), Formula (II) and/or Formula (III), ring B is a fully saturated heterocycloalkyl ring substituted with two $R^3$ attached to the same carbon, which together with the carbon atom to which they are attached, form a spiro-heterocycloalkyl; wherein spiro-heterocycloalkyl includes 1, 2, 3 or 4 heteroatoms independently selected from N, S, and O, and is optionally further substituted with 1-2 $C_{1-3}$alkyl.

In some or any of the preceding embodiments of compounds of Formula (I-P), (I), Formula (II) and/or Formula (III), ring B is an N-linked azetidinyl ring substituted with 1-2 $R^3$, an N-linked piperidinyl ring substituted with 1-2 $R^3$, an N-linked triazolyl ring substituted with 1-2 $R^3$, an N-linked morpholinyl ring substituted with 1-2 $R^3$, or an N-linked piperazinyl ring substituted with 1-2 $R^3$. In some or any of the preceding embodiments of compounds of Formula (I-P), Formula (I), Formula (II) and/or Formula (III), ring B is an N-linked azetidinyl ring substituted with 2 $R^3$, an N-linked piperidinyl ring substituted with 2 $R^3$, an N-linked morpholinyl ring substituted with 2 $R^3$, or an N-linked piperazinyl ring substituted with 2 $R^3$; wherein the two $R^3$ are attached to the same carbon, and together with the carbon atom to which they are attached, form a spiro-heterocycloalkyl which is optionally substituted with one or two $C_1$-$C_6$alkyl.

In some or any of the preceding embodiments of compounds of Formula (I-P), Formula (I), Formula (II) and/or Formula (III), ring B is substituted with one or two groups selected from $NH_2$, —$NH(C_1$-$C_6$alkyl), —$NH(C_3$-

$C_6$cycloalkyl), heterocycloalkyl, tetrahydro-[1,2,4]triazolo[4,3-a]pyrazinyl, —C($R^{3c}$)$_2$NH$_2$, OH,

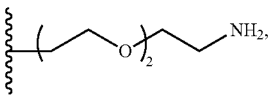

5-membered heteroaryl (optionally substituted with one or two alkyl), and —O—CH$_2$-phenyl-CH$_2$NH$_2$.

In some or any of the preceding embodiments of compounds of Formula (I-P), Formula (I), Formula (II) and/or Formula (III), ring B is an N-linked azetidinyl ring substituted with 1-2 $R^3$. In some or any of the preceding embodiments of compounds of Formula (I-P), Formula (I), Formula (II) and/or Formula (III), ring B is unsubstituted 2,5-diazabicyclo[2.2.2]octanyl, or 3,9-diazabicyclo[3.3.2]decanyl. In some or any of the preceding embodiments of compounds of Formula (I-P), Formula (I), Formula (II) and/or Formula (III), ring B is a piperidine ring or a morpholinyl ring substituted with 1-3 $R^3$. In some or any of the preceding embodiments of compounds of Formula (I-P), Formula (I), Formula (II) and/or Formula (III), ring B is a piperazinyl ring substituted with 1-3 $R^3$. In some or any of the preceding embodiments of compounds of Formula (I-P), Formula (I), Formula (II) and/or Formula (III), ring B is a 5-6 membered heteroaryl substituted with 1-3 $R^3$.

In some or any of the preceding embodiments of compounds of Formula (I-P), Formula (I), Formula (II) and/or Formula (III), ring B in

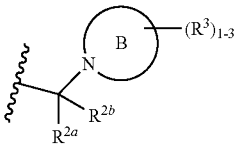

is a 4, 5, or 6-membered fully saturated heterocycloalkyl ring substituted with 1-3 $R^3$. In some or any of the preceding embodiments of compounds of Formula (I-P), Formula (I), Formula (II) and/or Formula (III), ring B in

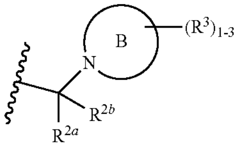

is a 4, 5, or 6-membered fully saturated heterocycloalkyl ring substituted with two $R^3$ attached to the same carbon, which together with the carbon atom to which they are attached, form a spiro-heterocycloalkyl; wherein spiro-heterocycloalkyl includes 1, 2, 3 or 4 heteroatoms independently selected from N, S, and O, and is optionally further substituted with 1-2 $C_{1-3}$alkyl.

In some embodiments of compounds of Formula (I-P), Formula (I), Formula (II) and/or Formula (III)

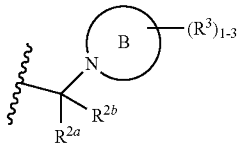

is

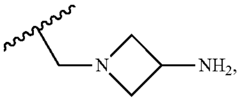 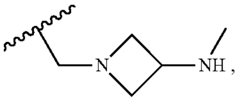

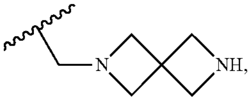 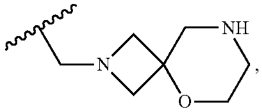

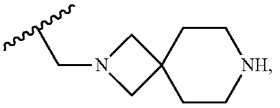

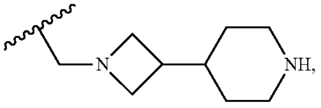

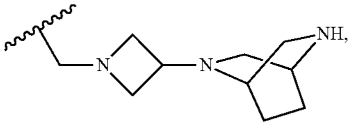

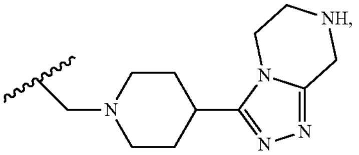

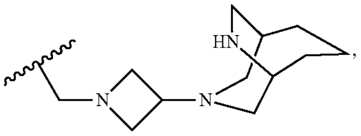

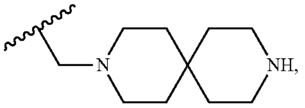 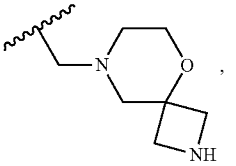

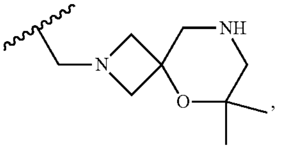 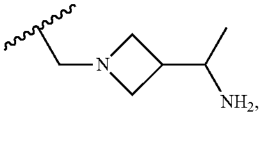

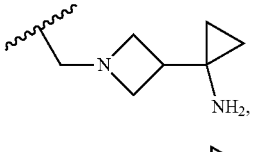 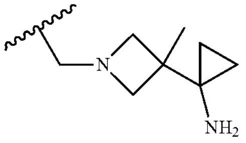

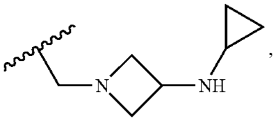 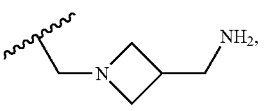

-continued

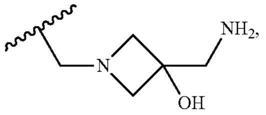

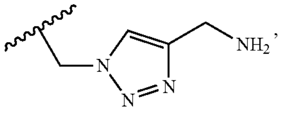

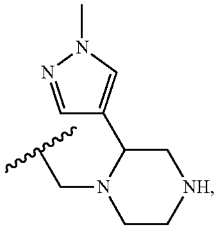

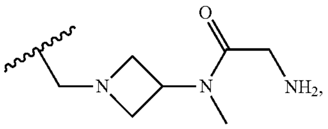

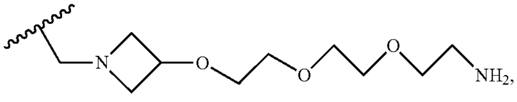 and/or

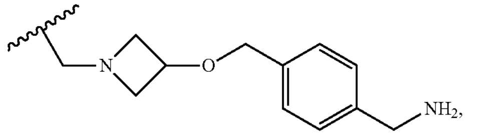

wherein each

indicates a point of attachment to the rest of the formula. In some of such embodiments, in one instance, $R^5$ is pentyl and

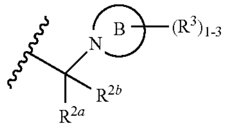

is one or more of the groups indicated above.

In some or any of the preceding embodiments of compounds of Formula (I-P), Formula (I), Formula (II) and/or Formula (III), $R^{1a}$, $R^{1b}$, $R^{2a}$ and $R^{2b}$ are hydrogen, $R^5$ is pentyl, and ring B is an N-linked azetidinyl ring substituted with two $R^3$ which, together with the atom to which they are attached, form a spiro-heterocycloalkyl. In some of such embodiments, the spiro-heterocycloalkyl is selected from spiro-azetidinyl, spiro-morpholinyl, spiro-(gem dimethyl) morpholinyl, or spiro-piperidinyl and is optionally substituted as described herein. In some or any of the preceding embodiments of compounds of Formula (I-P), Formula (I), Formula (II) and/or Formula (III), $R^{1a}$, $R^{1b}$, $R^{2a}$ and $R^{2b}$ are hydrogen, $R^5$ is pentyl, and ring B is an azetidine ring substituted with 1-2 $R^3$ where each is independently selected from —OH, —$NH_2$, —$CH_3$,

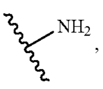, 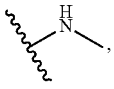, 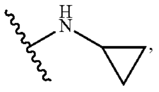,

-continued

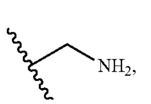 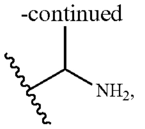 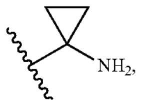

and combinations thereof. In some or any of the preceding embodiments of compounds of Formula (I-P), Formula (I), Formula (II) and/or Formula (III), $R^{1a}$, $R^{1b}$, $R^{2a}$ and $R^{2b}$ are hydrogen, $R^5$ is pentyl, and ring B is an N-linked azetidine substituted with

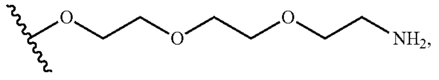

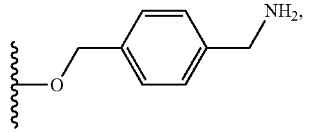 or

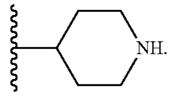

In some or any of the preceding embodiments of compounds of Formula (I-P), Formula (I), Formula (II) and/or Formula (III), $R^{1a}$, $R^{1b}$, $R^{2a}$ and $R^{2b}$ are hydrogen, $R^5$ is pentyl, and ring B is an N-linked azetidine substituted with any combination of $R^3$(s) described herein and/or in this paragraph.

In some or any of the preceding embodiments of compounds of Formula (I-P), Formula (I), Formula (II) and/or Formula (III), $R^{1a}$, $R^{1b}$, $R^{2a}$ and $R^{2b}$ are hydrogen, $R^5$ is pentyl, and ring B is an N-linked morpholinyl or piperidinyl substituted with two $R^3$ which, together with the atom to which they are attached, form a spiro-heterocycloalkyl. In some of such embodiments, the spiro-heterocycloalkyl is an azetidinyl ring, or a piperidinyl ring. In some or any of the preceding embodiments of compounds of Formula (I-P), Formula (I), Formula (II) and/or Formula (III), $R^{1a}$, $R^{1b}$, $R^{2a}$ and $R^{2b}$ are hydrogen, $R^5$ is pentyl, and ring B is an N-linked piperidinyl ring substituted with a partially saturated heteroaryl. In some or any of the preceding embodiments of compounds of Formula (I-P), Formula (I), Formula (II) and/or Formula (III), $R^{1a}$, $R^{1b}$, $R^{2a}$ and $R^{2b}$ are hydrogen, $R^5$ is pentyl, and ring B is a piperazinyl ring substituted with a heteroaryl ring optionally substituted with $C_{1-3}$alkyl. In some or any of the preceding embodiments of compounds of Formula (I-P), Formula (I), Formula (II) and/or Formula (III), $R^{1a}$, $R^{1b}$, $R^{2a}$ and $R^{2b}$ are hydrogen, $R^5$ is pentyl, and ring B is a N-linked heteroaryl substituted with 1-2 $R^3$. In some of such embodiments, ring B is a N-linked triazolyl substituted with 1-2 $R^3$. In some or any of the preceding embodiments of compounds of Formula (I-P), Formula (I), Formula (II) and/or Formula (III), $R^3$ is methyl. In some or any of the preceding embodiments of compounds of Formula (I-P), Formula (I), Formula (II) and/or Formula (III), $R^{1a}$, $R^{1b}$, $R^{2a}$ and $R^{2b}$ are hydrogen, $R^5$ is pentyl, and ring B is an N-linked ring substituted with any combination of $R^3$(s) described herein and/or in this paragraph.

In some or any of the preceding embodiments of compounds of Formula (I-P), Formula (I), Formula (II) and/or Formula (III), $R^{1a}$, $R^{1b}$, $R^{2a}$ and $R^{2b}$ are hydrogen, $R^5$ is pentyl, and ring A is a phenyl ring substituted with one methoxy group at the position ortho to the group

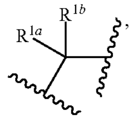

wherein each

indicates a point of attachment to the rest of the formula. In some or any of the preceding embodiments of compounds of Formula (I-P), Formula (I), Formula (II) and/or Formula (III), $R^{1a}$, $R^{1b}$, $R^{2a}$ and $R^{2b}$ are hydrogen, $R^5$ is pentyl, and ring A is a phenyl ring substituted with two methoxy groups at the positions ortho to the group

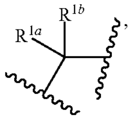

wherein each

indicates a point of attachment to the rest of the formula.

In one aspect, a compound of Formula (I-P), Formula (I), Formula (II) and/or Formula (III), or a pharmaceutically acceptable salt, solvate or N-oxide thereof, is selected from the group consisting of

2

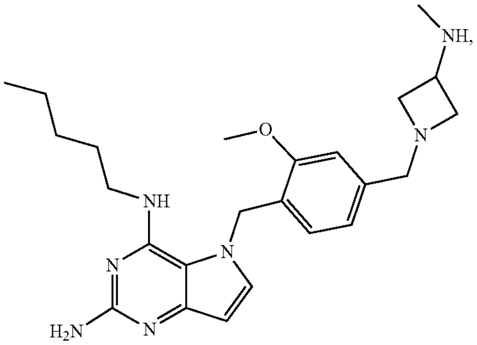

3

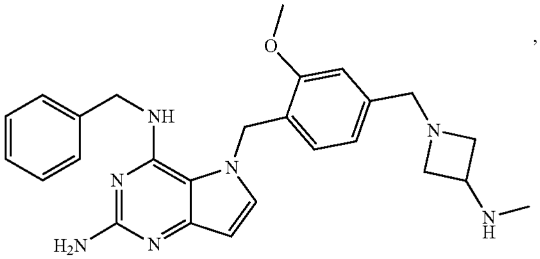

4

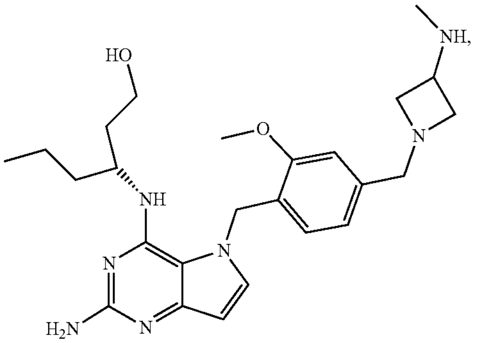

5

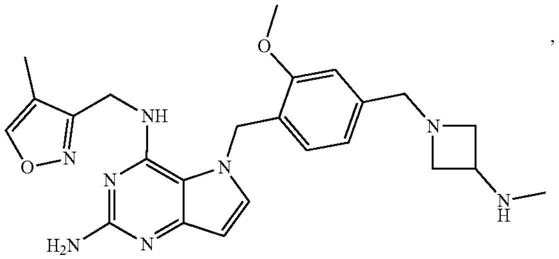

6

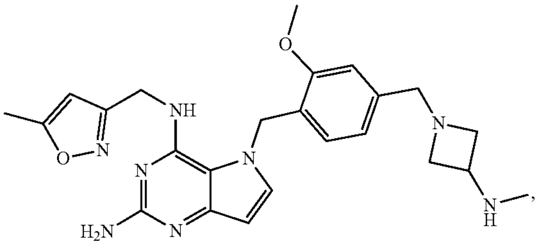

7

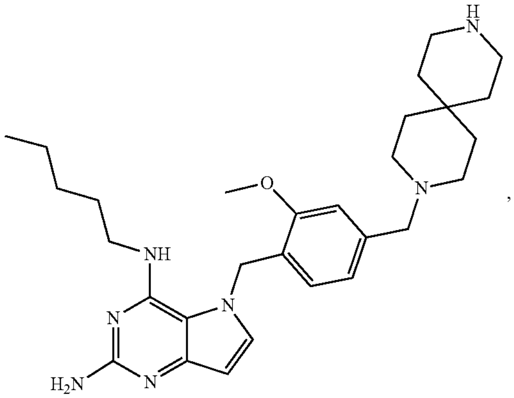

-continued
8
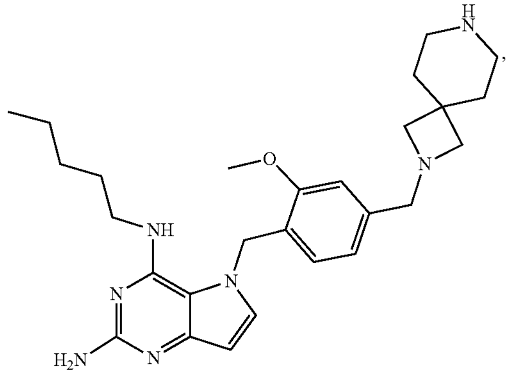
,
9
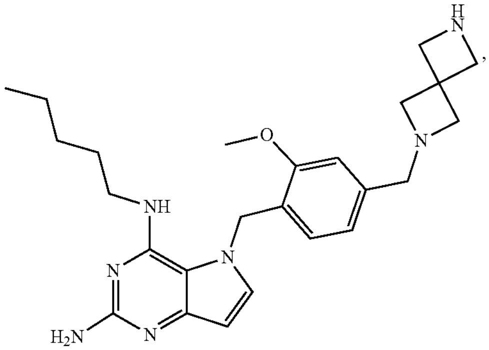
,
10
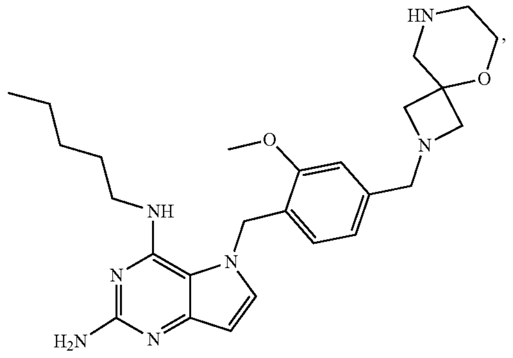
,
11
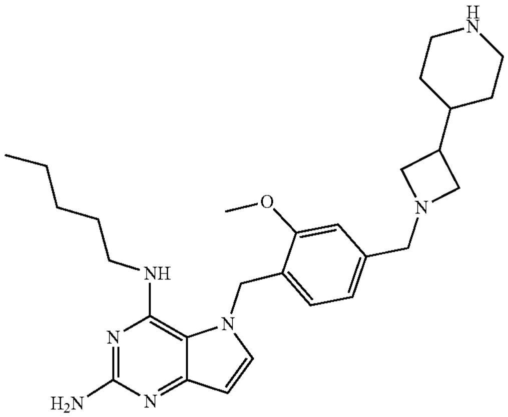
,
12
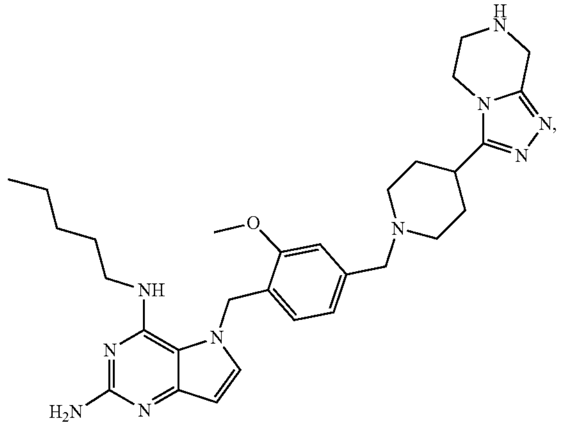
,
13
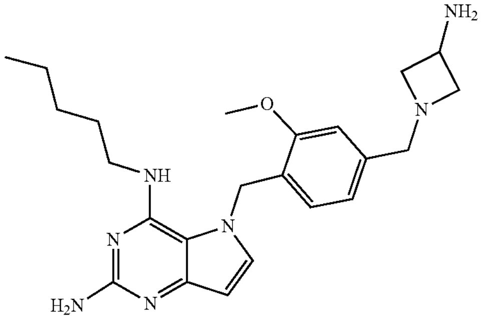
14
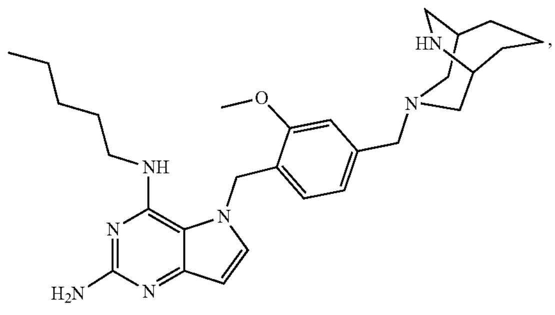
,
15
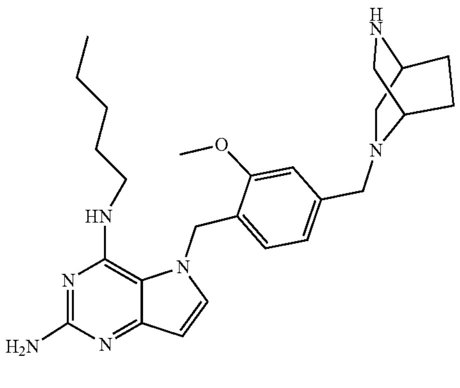
, -continued
16
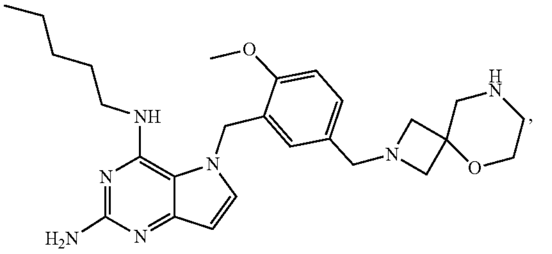
17
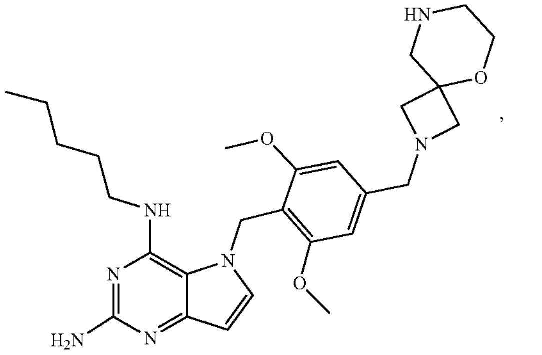
18
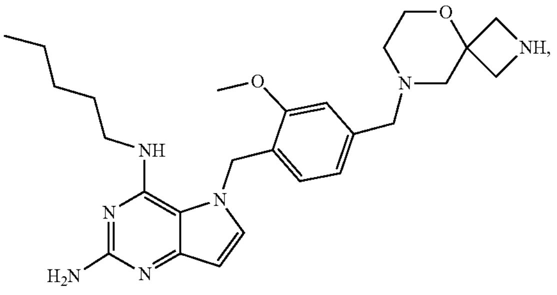
19
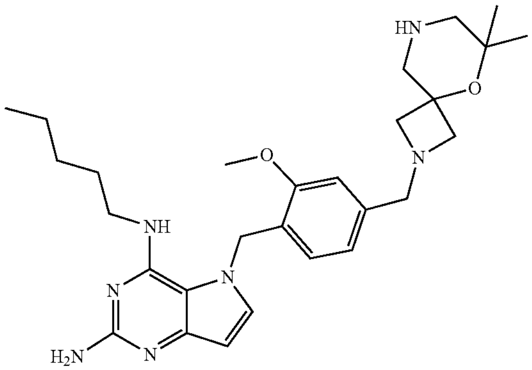
20
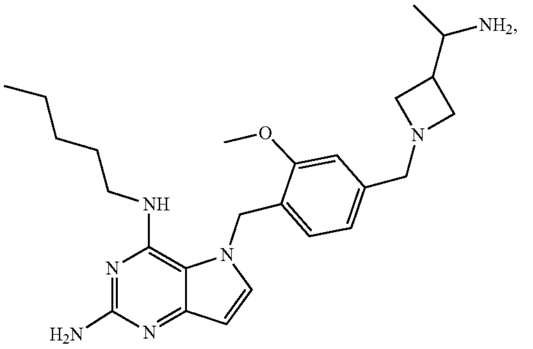
21
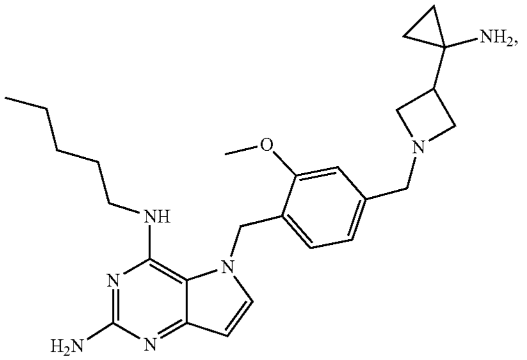
22
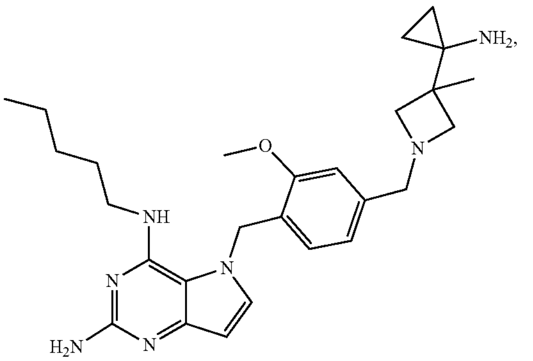
23
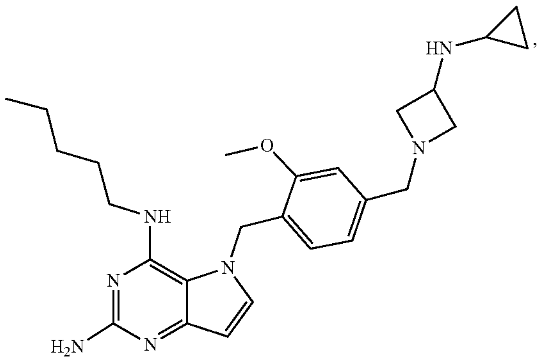

-continued

24

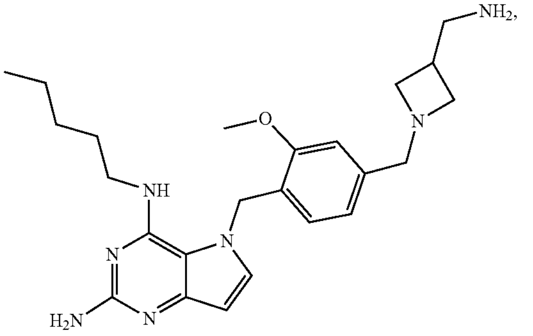

25

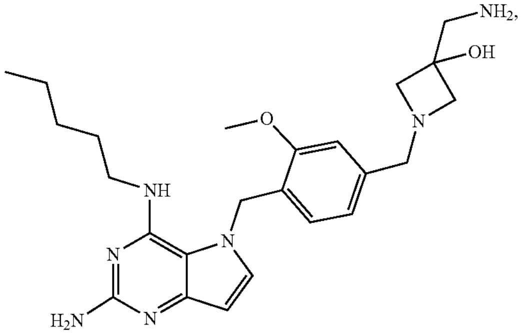

26

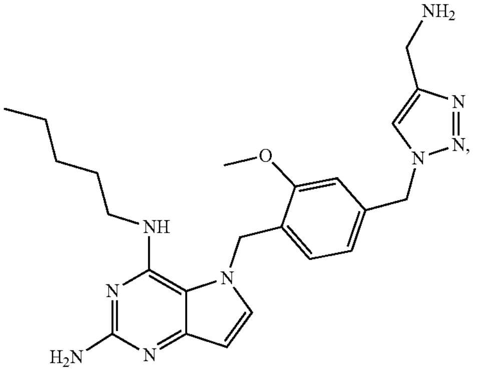

27

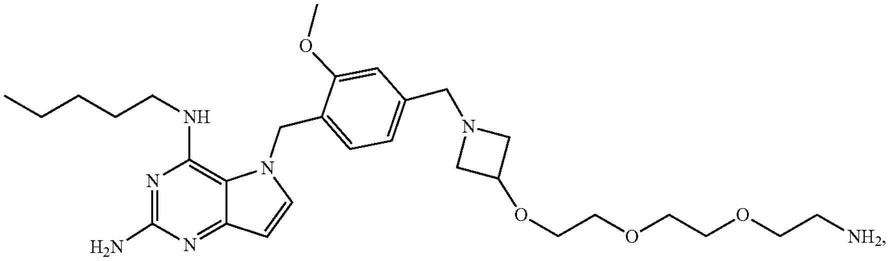

28

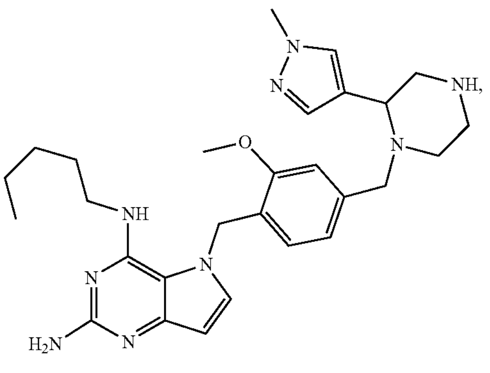

and

30

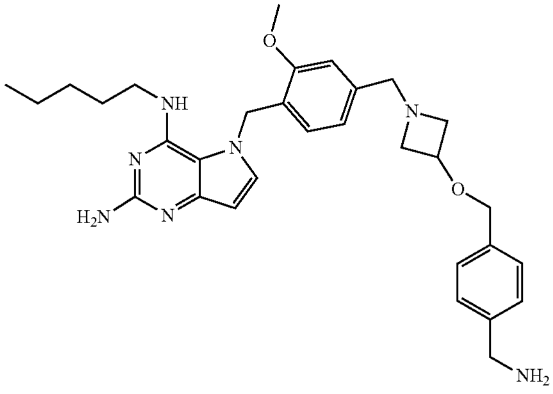

.

The compounds described above are used as payloads in the antibody drug conjugates described herein. In addition to the payloads described above, the molecular payload can be any molecular entity that one of skill in the art might desire to conjugate to the polypeptide. In certain embodiments, the payload is a therapeutic moiety (e.g., a compound of Formula (I-P), Formula (I), or subformula thereof, as described herein). In such embodiments, the antibody conjugate can be used to target the therapeutic moiety (e.g., a TLR7 agonist of Formula (I-P), Formula (I), or subformula thereof, described herein) to its molecular target. Other TLR7 agonists are known to one of skill in the art, including, and not limited to, 4-amino-2-butoxy-7,8-dihydro-8-[[3-(1-pyrrolidinylmethyl)phenyl]methyl]-6(5H)-pteridinone (vesatolimod, GS9620, CAS No. 1228585-88-3), 1-(2-Methylpropyl)-1H-imidazole[4,5-c]quinolone-4-amine (imiquimod, CAS No. 99011-02-6), 1-(4-amino-2-(ethoxymethyl)-1H-imidazo[4,5-c]quinolin-1-yl)-2-methylpropan-2-ol (resquimod, CAS No. 144875-48-9), N-[4-(4-amino-2-ethyl-1H-imidazo[4,5-c]quinolin-1-yl)butyl]methanesulfonamide (3M-001), 2-propylthiazolo[4,5-c]quinolin-4-amine (3M-002), 4-amino-2-(ethoxymethyl)-α,α-dimethyl-6,7,8,9-tetrahydro-1H-imidazo[4,5-c]quinolone-1-ethanol hydrate (3M-003), N-(1-(4-Amino-2-(ethoxymethyl)-1H-imidazo[4,5-c]quinolin-1-yl)-2-methylpropan-2-yl)methanesulfonamide (CAS No. 642473-62-9, 3M-011, or 854A), and N-(4-(4-amino-2-ethyl-1H-imidazo[4,5-c]quinolin-1-yl)butyl) methanesulfonamide (CAS No. 532959-63-0, 3M-852A, PF-4878691), 2-methyl-1-(2,2,4-trimethylpent-4-en-1-yl)-1H-imidazo[4,5-c]quinolin-4-amine (S-34240), loxoribine, CL264, ssRNA40, R848, and SM-276 001.

3. Conjugates

Provided herein are conjugates of antibodies with TLR7 agonists (e.g., any TLR7 agonist described herein). The conjugates comprise an antibody to a suitable antigen (e.g., a tumor antigen), or an antigen binding fragment thereof, covalently linked directly or indirectly, via a linker, to a payload. In certain embodiments, the antibody is linked to one payload. In further embodiments, the antibody is linked to more than one payload. In certain embodiments, the antibody is linked to one, two, three, four, five, six, seven, eight, or more payloads. Accordingly, the drug to antibody ratio (DAR) may vary from 1 to 30.

The payload can be any payload deemed useful by the practitioner of skill. In certain embodiments, the payload is a therapeutic moiety. In certain embodiments, the payload is a diagnostic moiety, e.g. a label. Useful payloads are described in the sections and examples below.

The linker can be any linker capable of forming at least one bond to the antibody and at least one bond to a payload. Useful linkers are described in the sections and examples below.

The antibody is typically a protein comprising multiple polypeptide chains. In certain embodiments, the antibody is a heterotetramer comprising two identical light (L) chains and two identical heavy (H) chains. Each light chain can be linked to a heavy chain by one covalent disulfide bond. Each heavy chain can be linked to the other heavy chain by one or more covalent disulfide bonds. Each heavy chain and each light chain can also have one or more intrachain disulfide bonds. As is known to those of skill in the art, each heavy chain typically comprises a variable domain ($V_H$) followed by a number of constant domains. Each light chain typically comprises a variable domain at one end ($V_L$) and a constant domain. As is known to those of skill in the art, antibodies typically have selective affinity for their target molecules, i.e. antigens.

The antibodies provided herein can have any antibody form known to those of skill in the art. They can be full-length, or fragments. Exemplary full length antibodies include IgA, IgA1, IgA2, IgD, IgE, IgG, IgG1, IgG2, IgG3, IgG4, IgM, etc. Exemplary fragments include Fv, Fab, Fc, scFv, scFv-Fc, etc.

In certain embodiments, the antibody of the conjugate comprises one, two, three, four, five, or six of the CDR sequences described herein. In certain embodiments, the antibody of the conjugate comprises a heavy chain variable domain ($V_H$) described herein. In certain embodiments, the antibody of the conjugate comprises a light chain variable domain ($V_L$) described herein. In certain embodiments, the antibody of the conjugate comprises a heavy chain variable domain ($V_H$) described herein and a light chain variable domain ($V_L$) described herein. In certain embodiments, the antibody of the conjugate comprises a paired heavy chain variable domain and a light chain variable domain described herein ($V_H$-$V_L$ pair).

In certain embodiments, the antibody conjugate can be formed from an antibody that comprises one or more reactive groups. In certain embodiments, the antibody conjugate can be formed from an antibody comprising all naturally encoded amino acids. Those of skill in the art will recognize that several naturally encoded amino acids include reactive groups capable of conjugation to a payload or to a linker. These reactive groups include cysteine side chains, lysine side chains, and amino-terminal groups. In these embodiments, the antibody conjugate can comprise a payload or linker linked to the residue of an antibody reactive group. In these embodiments, the payload precursor or linker precursor comprises a reactive group capable of forming a bond with an antibody reactive group. Typical reactive groups include maleimide groups, activated carbonates (including but not limited to, p-nitrophenyl ester), activated esters (including but not limited to, N-hydroxysuccinimide, p-nitrophenyl ester, and aldehydes). Particularly useful reactive groups include maleimide and succinimide, for instance N-hydroxysuccinimide, for forming bonds to cysteine and lysine side chains. Further reactive groups are described in the sections and examples below.

In further embodiments, the antibody comprises one or more modified amino acids having a reactive group, as described herein. Typically, the modified amino acid is not a naturally encoded amino acid. These modified amino acids can comprise a reactive group useful for forming a covalent bond to a linker precursor or to a payload precursor. One of skill in the art can use the reactive group to link the polypeptide to any molecular entity capable of forming a covalent bond to the modified amino acid. Thus, provided herein are conjugates comprising an antibody comprising a modified amino acid residue linked to a payload directly or indirectly via a linker. Exemplary modified amino acids are described in the sections below. Generally, the modified amino acids have reactive groups capable of forming bonds to linkers or payloads with complementary reactive groups.

In certain embodiments, the non-natural amino acids are positioned at select locations in a polypeptide chain of the antibody. These locations were identified as providing optimum sites for substitution with the non-natural amino acids. Each site is capable of bearing a non-natural amino acid with optimum structure, function and/or methods for producing the antibody.

In certain embodiments, a site-specific position for substitution provides an antibody that is stable. Stability can be measured by any technique apparent to those of skill in the art.

In certain embodiments, a site-specific position for substitution provides an antibody that has optimal functional properties. For instance, the antibody can show little or no loss of binding affinity for its target antigen compared to an antibody without the site-specific non-natural amino acid. In certain embodiments, the antibody can show enhanced binding compared to an antibody without the site-specific non-natural amino acid.

In certain embodiments, a site-specific position for substitution provides an antibody that can be made advantageously. For instance, in certain embodiments, the antibody shows advantageous properties in its methods of synthesis. In certain embodiments, the antibody can show little or no loss in yield in production compared to an antibody without the site-specific non-natural amino acid. In certain embodiments, the antibody can show enhanced yield in production compared to an antibody without the site-specific non-natural amino acid. In certain embodiments, the antibody can show little or no loss of tRNA suppression compared to an antibody without the site-specific non-natural amino acid. In certain embodiments, the antibody can show enhanced tRNA suppression in production compared to an antibody without the site-specific non-natural amino acid.

In certain embodiments, a site-specific position for substitution provides an antibody that has advantageous solubility. In certain embodiments, the antibody can show little or no loss in solubility compared to an antibody without the site-specific non-natural amino acid. In certain embodiments, the antibody can show enhanced solubility compared to an antibody without the site-specific non-natural amino acid.

In certain embodiments, a site-specific position for substitution provides an antibody that has advantageous expression. In certain embodiments, the antibody can show little or no loss in expression compared to an antibody without the site-specific non-natural amino acid. In certain embodiments, the antibody can show enhanced expression compared to an antibody without the site-specific non-natural amino acid.

In certain embodiments, a site-specific position for substitution provides an antibody that has advantageous folding. In certain embodiments, the antibody can show little or no loss in proper folding compared to an antibody without the site-specific non-natural amino acid. In certain embodiments, the antibody can show enhanced folding compared to an antibody without the site-specific non-natural amino acid.

In certain embodiments, a site-specific position for substitution provides an antibody that is capable of advantageous conjugation. As described below, several non-natural amino acids have side chains or functional groups that facilitate conjugation of the antibody to a second agent, either directly or via a linker. In certain embodiments, the antibody can show enhanced conjugation efficiency compared to an antibody without the same or other non-natural amino acids at other positions. In certain embodiments, the antibody can show enhanced conjugation yield compared to an antibody without the same or other non-natural amino acids at other positions. In certain embodiments, the antibody can show enhanced conjugation specificity compared to an antibody without the same or other non-natural amino acids at other positions.

In some embodiments, one or more non-natural amino acids are located at selected site-specific positions in at least one polypeptide chain of the antibody. The polypeptide chain can be any polypeptide chain of the antibody without limitation, including either light chain or either heavy chain. The site-specific position can be in any domain of the antibody, including any variable domain and any constant domain.

In certain embodiments, the antibodies provided herein comprise one, or more than one, non-natural amino acids at site-specific positions. In certain embodiments, the antibodies provided herein comprise two non-natural amino acids at site-specific positions. In certain embodiments, the antibodies provided herein comprise three non-natural amino acids at site-specific positions. In certain embodiments, the antibodies provided herein comprise more than three non-natural amino acids at site-specific positions.

In certain embodiments, the antibodies provided herein comprise one or more non-natural amino acids each at a position independently selected from the group consisting of heavy chain or light chain residues HC-F404, HC-K121, HC-Y180, HC-F241, HC-221, LC-T22, LC-S7, LC-N152, LC-K42, LC-E161, LC-D170, HC-S136, HC-S25, HC-A40, HC-S119, HC-S190, HC-K222, HC-R19, HC-Y52, or HC-S70, according to the Kabat or Chothia or EU numbering scheme, or a post-translationally modified variant thereof. In certain embodiments, the antibodies provided herein comprise one or more non-natural amino acids each at a position independently selected from the group consisting of HC-180, HC-222, LC-7, or LC-42, according to the Kabat or Chothia or EU numbering scheme, or a post-translationally modified variant thereof. In these designations, HC indicates a heavy chain residue, and LC indicates a light chain residue. In certain embodiments, the non-natural amino acids are at HC-F404. In certain embodiments, the non-natural amino acids are at HC-Y180. In certain embodiments, the non-natural amino acids are at HC-F404 and HC-Y180. In certain embodiments, the non-natural amino acids are at HC-K222. In certain embodiments, the non-natural amino acids are at LC-S7. In certain embodiments, the non-natural amino acids are at LC-K42. In certain embodiments, the non-natural amino acids are at HC-Y180, HC-K222, LC-S7, and/or LC-K42. In certain embodiments, the non-natural amino acids are HC-F241, HC-K121, and/or HC-S190. In certain embodiments, the non-natural amino acids are the same. In certain embodiments, the non-natural amino acids are different. In certain embodiments, the non-natural amino acids are residues of Formula (30), herein.

In some embodiments, the antibody sequence may encompass a Q-tag sequence that is compatible with transglutaminase conjugation. In some embodiments, the one or more glutamine residues are in Q tags independently selected from the group consisting of LLQGA (SEQ ID NO: 1), YAHQAHY (SEQ ID NO: 2), YRYRQ (SEQ ID NO: 3), PNPQLPF (SEQ ID NO: 4), PKPQQFM (SEQ ID NO: 5), GQQQLG (SEQ ID NO: 6), WALQRPH (SEQ ID NO: 7), WELQRPY (SEQ ID NO: 8), YPMQGWF (SEQ ID NO: 9), LSLSQG (SEQ ID NO: 10), GGGLLQGG (SEQ ID NO: 11), GLLQG (SEQ ID NO: 12), GSPLAQSHGG (SEQ ID NO: 13), GLLQGGG (SEQ ID NO: 14), GLLOGG (SEQ ID NO: 15), GLLQ (SEQ ID NO: 16), LLQLLQGA (SEQ ID NO: 17), LLQGA (SEQ ID NO: 18), LLQYQGA (SEQ ID NO: 19), LLQGSG (SEQ ID NO: 20), LLQYQG (SEQ ID NO: 21), LLQLLQG (SEQ ID NO: 22), SLLQG (SEQ ID NO: 23), LLQLQ (SEQ ID NO: 24), LLQLLQ (SEQ ID NO: 25), LLQGR (SEQ ID NO: 26), LLQGPA (SEQ ID NO: 27), LLQGPP (SEQ ID NO: 28) or GGLLQGPP (SEQ ID NO: 29).

In some embodiments, the acyl donor glutamine-containing tag comprises at least one Gln. In some embodiments, the acyl donor glutamine-containing tag comprises an amino acid sequence XXQX, wherein X is any amino acid (e.g., conventional amino acid Leu, Ala, Gly, Ser, Val, Phe, Tyr, His, Arg, Asn, Glu, Asp, Cys, Gin, Ile, Met, Pro, Thr, Lys, or Trp or nonconventional amino acid). In some embodiments, the acyl donor glutamine-containing tag (Q tag) comprises an amino acid sequence selected from the group consisting of LLQGG (SEQ ID NO: 30), LLQG (SEQ ID NO: 31), LSLSQG (SEQ ID NO: 32), GGGLLOGG (SEQ ID NO: 33), GLLQG (SEQ ID NO: 34), GSPLAQSHGG (SEQ ID NO: 35), GLLQGGG (SEQ ID NO: 36), GLLQGG (SEQ ID NO: 37), GLLQ (SEQ ID NO: 38), LLQLLQGA (SEQ ID NO: 39), LLQGA (SEQ ID NO: 40), LLQYQGA (SEQ ID NO: 41), LLQGSG (SEQ ID NO: 42), LLQYQG (SEQ ID NO: 43), LLQLLQG (SEQ ID NO: 44), SLLQG (SEQ ID NO: 45), LLQLQ (SEQ ID NO: 46), LLQLLQ (SEQ ID NO: 47), LLQGR (SEQ ID NO: 48). In some embodiments, the acyl donor glutamine-containing tag (Q tag) comprises an amino acid sequence selected from the group consisting of LLQGPA (SEQ ID NO: 49), LLQGPP (SEQ ID NO: 50) or GGLLQGPP (SEQ ID NO: 51). In some embodiments, the acyl donor glutamine-containing tag (Q tag) comprises an amino acid sequence selected from the group consisting of LLQGG (SEQ ID NO: 52), and LLQGA (SEQ ID NO: 53). In such embodiments, a linker-payload bearing an amino group can be conjugated to the side chain of one or more glutamine (Q) residues in the antibody in the presence of transglutaminase.

In certain embodiments, provided herein are conjugates according to Formula (C1) or (C2):

(C1)

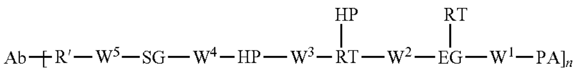

(C2)

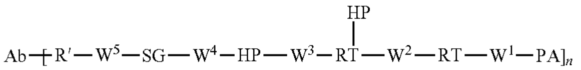

or a pharmaceutically acceptable salt, solvate, stereoisomer, regioisomer, or tautomer thereof, wherein:

- Ab is a residue of an antibody or an antigen binding fragment thereof;
- PA is a payload;
- $W^1$, $W^2$, $W^3$, $W^4$, and $W^5$ are each independently a single bond, absent, or a divalent attaching group;
- EG is absent, or an eliminator group;
- each RT in the backbone of Formula (C1) or (C2) is absent or is a release trigger group, or RT, when bonded to EG and EG is an eliminator group, is hydrogen or a release trigger group;
- each HP is a single bond, absent, or a monovalent or divalent hydrophilic group;
- SG is a single bond, absent, or a divalent spacer group;
- R' is a divalent residue of a terminal conjugating group; and
- subscript n is an integer selected from 1 to 30.

In some embodiments, n is an integer selected from 1 to 8. In some embodiments, n is 2. In some embodiments, n is 3. In some embodiments, n is 4. In some embodiments, n is 5. In some embodiments, n is 6. In some embodiments, n is 7. In some embodiments, n is 8.

3.1 Attaching Groups

Attaching groups facilitate incorporation of eliminator groups, release trigger groups, hydrophobic groups, spacer groups, and/or conjugating groups into a compound. Useful attaching groups are known to, and are apparent to, those of skill in the art. Examples of useful attaching groups are provided herein. In certain embodiments, attaching groups are designated $W^1$, $W^2$, $W^3$, $W^4$, or $W^5$. In certain embodiments, an attaching group can comprise a divalent ketone, divalent ester, divalent ether, divalent amide, divalent amine, alkylene, arylene, sulfide, disulfide, carbonylene, or a combination thereof. In certain embodiments an attaching group can comprise $—C(O)—$, $—O—$, $—C(O)NH—$, $—C(O)NH$-alkyl-, $—OC(O)NH—$, $—SC(O)NH—$, $—NH—$, $—NH$-alkyl-, $—C(O)N(CH_3)—$, $—C(O)N(CH_3)$-alkyl-, $—N(CH_3)—$, $—N(CH_3)$-alkyl-, $—N(CH_3)CH_2CH_2N(CH_3)—$, $—C(O)CH_2CH_2CH_2C(O)—$, $—S—$, $—S—S—$, $—OCH_2CH_2O—$, or the reverse (e.g. $—NHC(O)—$) thereof, or a combination thereof.

3.2 Eliminator Groups

Eliminator groups facilitate separation of a biologically active portion of a compound or conjugate described herein from the remainder of the compound or conjugate in vivo and/or in vitro. Eliminator groups can also facilitate separation of a biologically active portion of a compound or conjugate described herein in conjunction with a release trigger group. For example, the eliminator group and the release trigger group can react in a Releasing Reaction to release a biologically active portion of a compound or conjugate described herein from the compound or conjugate in vivo and/or in vitro. Upon initiation of the Releasing Reaction by the release trigger, the eliminator group cleaves the biologically active moiety, or a prodrug form of the biologically active moiety, and forms a stable, non-toxic entity that has no further effect on the activity of the biologically active moiety.

In certain embodiments, the eliminator group is designated EG herein. Useful eliminator groups include those described herein. In certain embodiments, the eliminator group is:

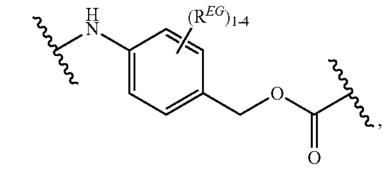

,

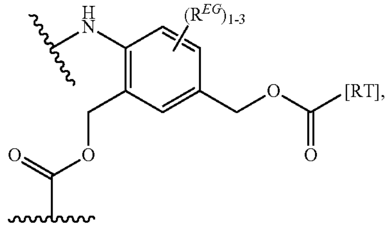

or

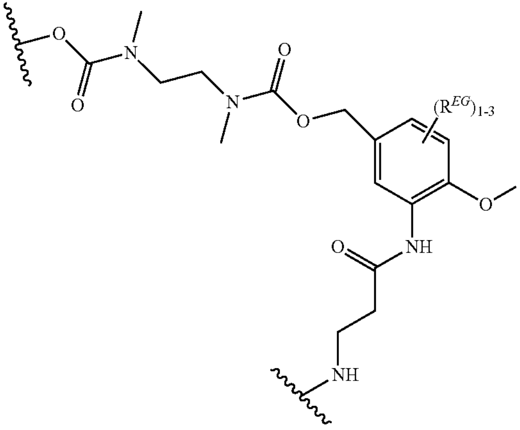

Wherein each $R^{EG}$ is independently selected from the group consisting of hydrogen, alkyl, biphenyl, $—CF_3$, $—NO_2$, $—CN$, fluoro, bromo, chloro, alkoxyl, alkylamino, dialkylamino, alkyl-$C(O)O—$, alkylamino-$C(O)—$ and dialkylamino$C(O)—$. In each structure, the phenyl ring can be bound to one, two, three, or in some cases, four $R^{EG}$ groups. In the second and third structures, those of skill will recognize that EG is bonded to an RT that is not within the backbone of formula (C1) as indicated in the above description of formula (C1). In some embodiments, each $R^{EG}$ is independently selected from the group consisting of hydrogen, alkyl, biphenyl, $—CF_3$, alkoxyl, alkylamino, dialkylamino, alkyl-C(O)O—, alkylamino-C(O)— and dialkylaminoC(O)—. In further embodiments, each $R^{EG}$ is independently selected from the group consisting of hydrogen, $—NO_2$, —CN, fluoro, bromo, and chloro. In certain embodiments, the eliminator group is

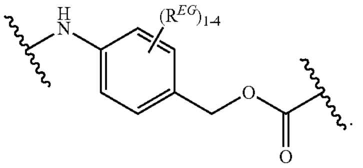

In certain embodiments, the eliminator group is

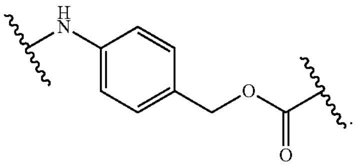 [SMILES: *Nc1ccc(COC(*)=O)cc1]

In certain embodiments, the eliminator group is

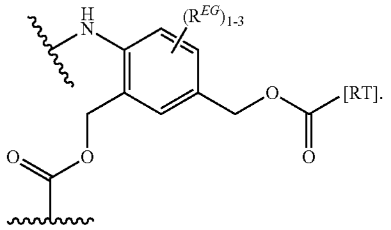

certain embodiments, the eliminator group is

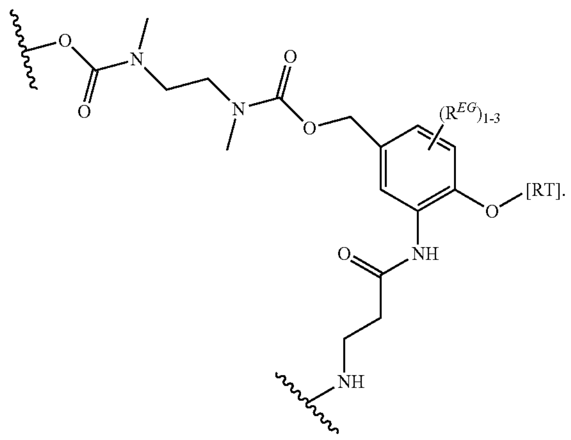

In some embodiments, the eliminator group is:

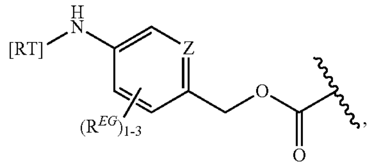

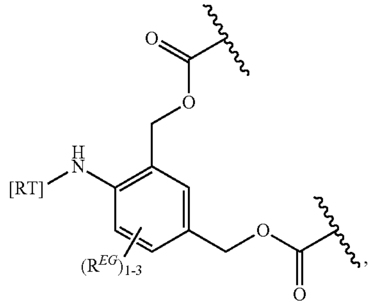

or

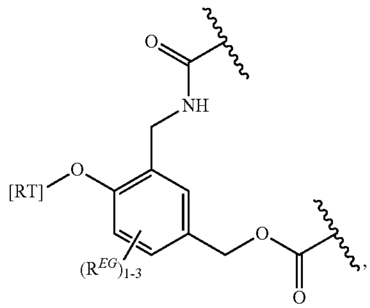

wherein Z may be CH or N, each $R^{EG}$ is independently selected from the group consisting of hydrogen, alkyl, biphenyl, $—CF_3$, $—NO_2$, —CN, fluoro, bromo, chloro, alkoxyl, alkylamino, dialkylamino, alkyl-C(O)O—, alkylamino-C(O)— and dialkylaminoC(O)—. In each structure, the phenyl ring can be bound to one, two, three, or in some cases, four $R^{EG}$ groups. In the first and second structures, those of skill will recognize that EG is bonded to an RT that is not within the backbone of formula (C1) as indicated in the above description of formula (C1). In some embodiments, each $R^{EG}$ is independently selected from the group consisting of hydrogen, alkyl, biphenyl, $—CF_3$, alkoxyl, alkylamino, dialkylamino, alkyl-C(O)O—, alkylamino-C(O)—, and dialkylaminoC(O)—. In further embodiments, each $R^{EG}$ is independently selected from the group consisting of hydrogen, $—NO_2$, —CN, fluoro, bromo, and chloro. In some embodiments, each $R^{EG}$ in the EG is hydrogen. In certain embodiments, the eliminator group is

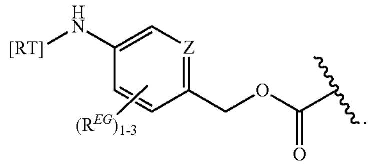

In certain embodiments, the eliminator group is

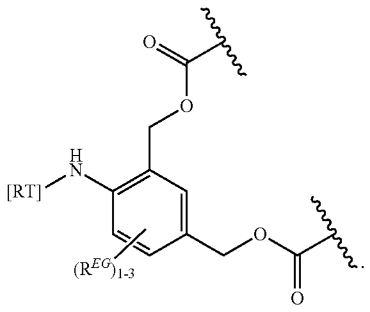

In certain embodiments, the eliminator group is

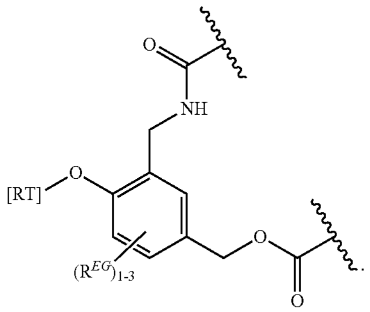

3.3 Release Trigger Groups

Release trigger groups facilitate separation of a biologically active portion of a compound or conjugate described herein from the remainder of the compound or conjugate in vivo and/or in vitro. Release trigger groups can also facilitate separation of a biologically active portion of a compound or conjugate described herein in conjunction with an eliminator group. For example, the eliminator group and the release trigger group can react in a Releasing Reaction to release a biologically active portion of a compound or conjugate described herein from the compound or conjugate in vivo and/or in vitro. In certain embodiment, the release trigger can act through a biologically-driven reaction with high tumor:nontumor specificity, such as the proteolytic action of an enzyme overexpressed in a tumor environment.

In certain embodiments, the release trigger group is designated RT herein. In certain embodiments, RT is divalent and bonded within the backbone of formula (C1). In other embodiments, RT is monovalent and bonded to EG as depicted above. Useful release trigger groups include those described herein. In certain embodiments, the release trigger group comprises a residue of a natural or non-natural amino acid or residue of a sugar ring. In certain embodiments, the release trigger group is:

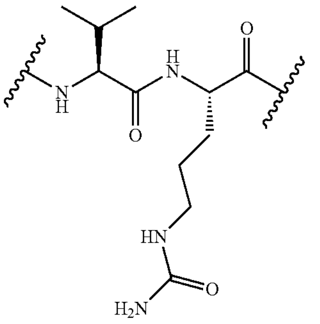

or

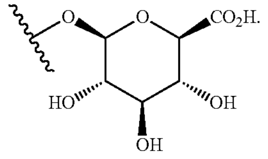

Those of skill will recognize that the first structure is divalent and can be bonded within the backbone of Formula (C1) or as depicted in Formula (C2), and that the second structure is monovalent and can be bonded to EG as depicted in formula (C1) above.

In certain embodiments, the release trigger group is

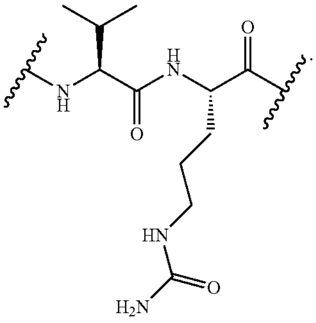 [SMILES: *N[C@H](C(=O)N[C@@H](CCCNC(N)=O)C(*)=O)C(C)C]

In certain embodiments, the release trigger group is

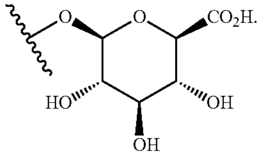 [SMILES: *O[C@H]1O[C@@H](C(=O)O)[C@H](O)[C@@H](O)[C@@H]1O]

In some embodiments, the release trigger group is a protease-cleavable $R_1$-Val-$X_1$ peptide according to the structure of:

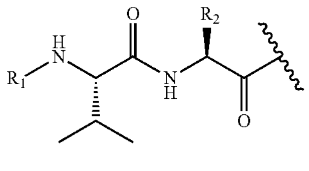

wherein $R_1$ is a bond to the rest of the compound or

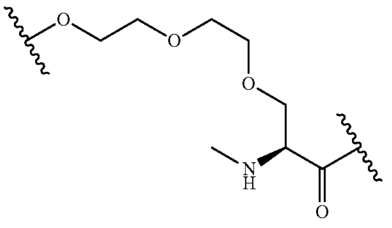 [SMILES: *OCCOCCOC[C@H](NC)C(*)=O]

and $R_2$ is $—CH_3$, $—CH_2CH_2CO_2H$, or $—(CH_2)_3NHCONH_2$; a legumain-cleavable Ala-Ala-Asn (AAN) or Ala-Ala-Asp (AAD) peptide according to the structure of:

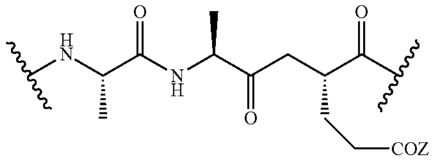

where Z is OH or $NH_2$; or a β-glucuronidase-cleavable β-glucuronide according to the structure of:

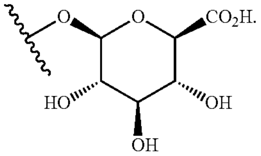 [SMILES: *O[C@H]1O[C@@H](C(=O)O)[C@H](O)[C@@H](O)[C@@H]1O]

Those of skill will recognize that

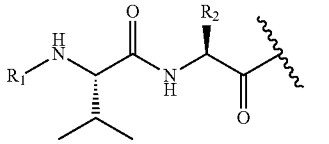

and

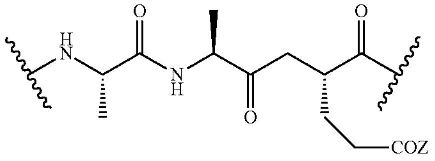

are divalent structures and can be bonded within the backbone of Formula (C1) or as depicted in Formula (C2). The structure

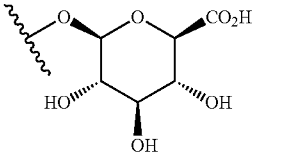 [SMILES: *O[C@H]1O[C@@H](C(=O)O)[C@H](O)[C@@H](O)[C@@H]1O]

is monovalent and can be bonded to EG as depicted in formula (C1) above.

3.4 Hydrophilic Groups

Hydrophilic groups facilitate increasing the hydrophilicity of the compounds described herein. It is believed that increased hydrophilicity allows for greater solubility in aqueous solutions, such as aqueous solutions found in biological systems. Hydrophilic groups can also function as spacer groups, which are described in further detail herein.

In certain embodiments, the hydrophilic group is designated HP herein. Useful hydrophilic groups include those described herein. In certain embodiments, the hydrophilic group is a divalent poly(ethylene glycol). In certain embodiments, the hydrophilic group is a divalent poly(ethylene glycol) according to the formula:

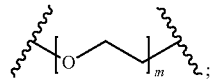

wherein m is an integer selected from 1 to 13, optionally 1 to 4, optionally 2 to 4, or optionally 4 to 8.

In some embodiments, the hydrophilic group is a divalent poly(ethylene glycol) according to the following formula:

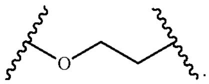 [SMILES: *CCO*]

In some other embodiments, the hydrophilic group is a divalent poly(ethylene glycol) according to the following formula:

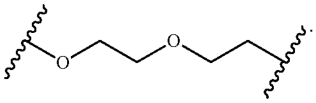 [SMILES: *CCOCCO*]

In other embodiments, the hydrophilic group is a divalent poly(ethylene glycol) according to the following formula:

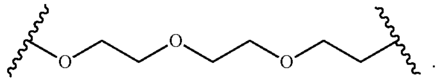 [SMILES: *CCOCCOCCO*]

In other embodiments, the hydrophilic group is a divalent poly(ethylene glycol) according to the following formula:

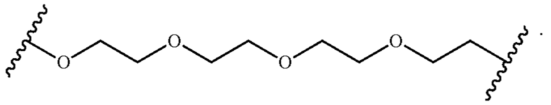 [SMILES: *CCOCCOCCOCCO*]

In some embodiments, the hydrophilic group can bear a chain-presented sulfonic acid according to the formula:

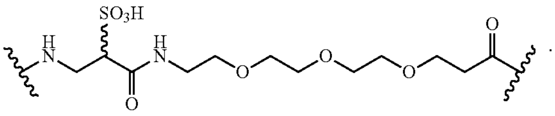 [SMILES: *NCC(C(=O)NCCOCCOCCOCCC(*)=O)S(=O)(=O)O]

3.5 Spacer Groups

Spacer groups facilitate spacing of the conjugating group from the other groups of the compounds described herein. This spacing can lead to more efficient conjugation of the compounds described herein to a second compound as well as more efficient cleavage of the active catabolite. The spacer group can also stabilize the conjugating group and lead to improved overall antibody-drug conjugate properties.

In certain embodiments, the spacer group is designated SG herein. Useful spacer groups include those described herein. In certain embodiments, the spacer group is:

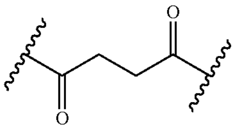
,

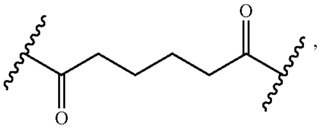
, or

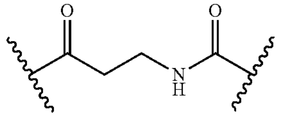
.

In certain embodiments, the spacer group, $W^4$, and the hydrophilic group combine to form a divalent poly(ethylene glycol) according to the formula:

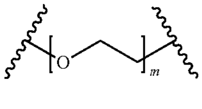
;

wherein m is an integer selected from 1 to 13, optionally 1 to 4, optionally 2 to 4, or optionally 4 to 8.

In some embodiments, the SG is H

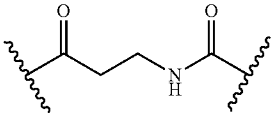
.

In some embodiments, the divalent poly(ethylene glycol) has the following formula:

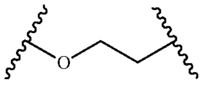
.

In some other embodiments, the divalent poly(ethylene glycol) has the following formula:

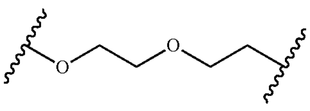
.

In other embodiments, the divalent poly(ethylene glycol) has the following formula:

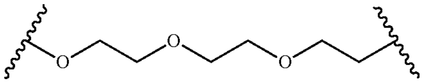
.

In other embodiments, the divalent poly(ethylene glycol) has the following formula:

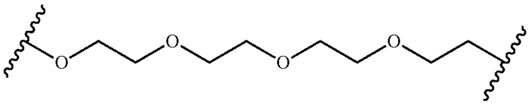
.

In some embodiments, the hydrophilic group can bear a chain-presented sulfonic acid according to the formula:

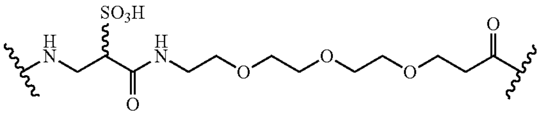
.

3.6 Conjugating Groups and Residues Thereof

Conjugating groups facilitate conjugation of the payloads described herein to a second compound, such as an antibody described herein. In certain embodiments, the conjugating group is designated R herein. Conjugating groups can react via any suitable reaction mechanism known to those of skill in the art. In certain embodiments, a conjugating group reacts through a [3+2] alkyne-azide cycloaddition reaction, inverse-electron demand Diels-Alder ligation reaction, thiol-electrophile reaction, or carbonyl-oxyamine reaction, as described in detail herein. In certain embodiments, the conjugating group comprises an alkyne, strained alkyne, tetrazine, thiol, para-acetyl-phenylalanine residue, oxyamine, maleimide, or azide. In certain embodiments, the conjugating group is:

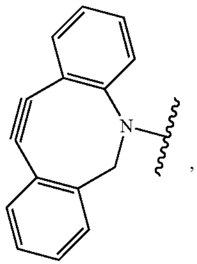
,
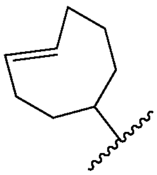
,
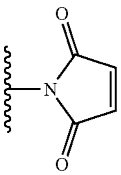
,

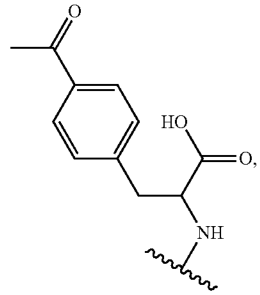

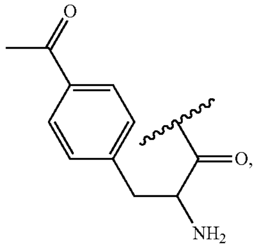

-continued

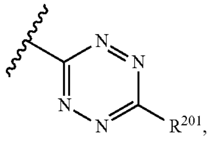

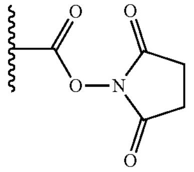

,

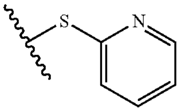

,

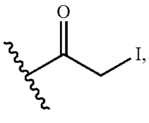

,

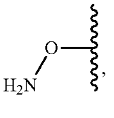

,

—$N_3$, or —SH; wherein $R^{201}$ is lower alkyl. In an embodiment, $R^{201}$ is methyl, ethyl, or propyl. In an embodiment, $R^{201}$ is methyl. Additional conjugating groups are described in, for example, U.S. Patent Publication No. 2014/0356385, U.S. Patent Publication No. 2013/0189287, U.S. Patent Publication No. 2013/0251783, U.S. Pat. Nos. 8,703,936, 9,145,361, 9,222,940, and 8,431,558.

After conjugation, a divalent residue of the conjugating group is formed and is bonded to the residue of a second compound. The structure of the divalent residue is determined by the type of conjugation reaction employed to form the conjugate.

In certain embodiments when a conjugate is formed through a [3+2] alkyne-azide cycloaddition reaction, the divalent residue of the conjugating group comprises a triazole ring or fused cyclic group comprising a triazole ring. In certain embodiment when a conjugate is formed through a strain-promoted [3+2] alkyne-azide cycloaddition (SPAAC) reaction, the divalent residue of the conjugating group is:

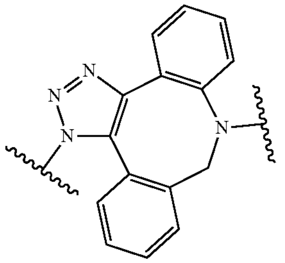

and/or

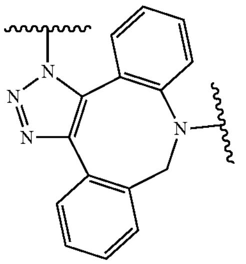

In certain embodiments when a conjugate is formed through a tetrazine inverse electron demand Diels-Alder ligation reaction, the divalent residue of the conjugating group comprises a fused bicyclic ring having at least two adjacent nitrogen atoms in the ring. In certain embodiments when a conjugate is formed through a tetrazine inverse electron demand Diels-Alder ligation reaction, the divalent residue of the conjugating group is:

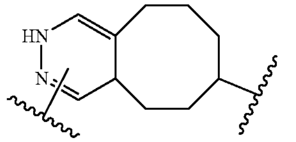

or

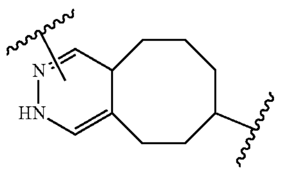

In certain embodiments when a conjugate is formed through a thiol-maleimide reaction, the divalent residue of the conjugating group comprises succinimidylene and a sulfur linkage. In certain embodiments when a conjugate is formed through a thiol-maleimide reaction, the divalent residue of the conjugating group is:

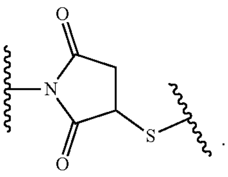 [SMILES: *SC1CC(=O)N(*)C1=O]

In certain embodiments, a conjugate is formed through a thiol-N-hydroxysuccinimide reaction using the following group:

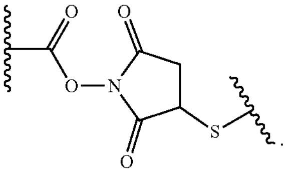 [SMILES: *SC1CC(=O)N(OC(*)=O)C1=O]

The reaction involved for formation of the conjugate comprises the following step:

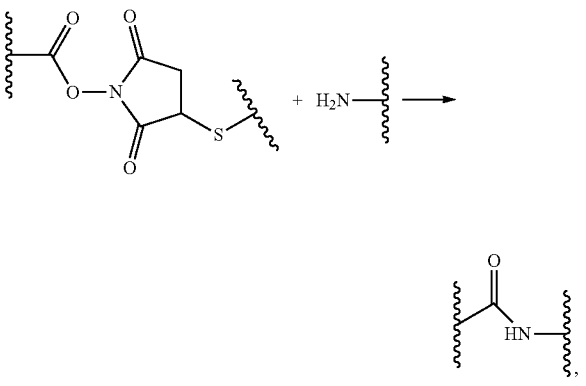

and the resulting divalent residue of the conjugating group is:

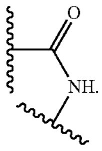 [SMILES: *NC(*)=O]

In certain embodiments when a conjugate is formed through a carbonyl-oxyamine reaction, the divalent residue of the conjugating group comprises a divalent residue of a non-natural amino acid. In certain embodiments when a conjugate is formed through a carbonyl-oxyamine reaction, the divalent residue of the conjugating group is:

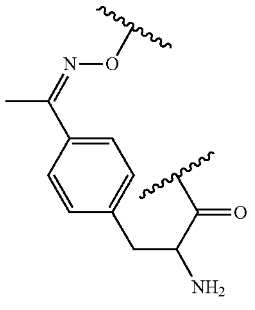

or

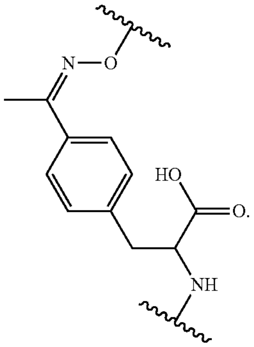

In certain embodiments when a conjugate is formed through a carbonyl-oxyamine reaction, the divalent residue of the conjugating group comprises an oxime linkage. In certain embodiments when a conjugate is formed through a carbonyl-oxyamine reaction, the divalent residue of the conjugating group is:

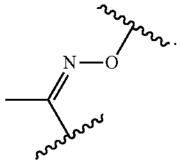 [SMILES: *O/N=C(\*)C]

In some embodiment, provided herein is a conjugate according to Formula (C1) or (C2) or a pharmaceutically acceptable salt, solvate, stereoisomer, or tautomer thereof, wherein EG comprises phenylene, carboxylene, amine, or a combination thereof. In an embodiment, provided herein is a conjugate according to Formula (C1) or (C2), or a pharmaceutically acceptable salt, solvate, stereoisomer, or tautomer thereof: wherein EG is:

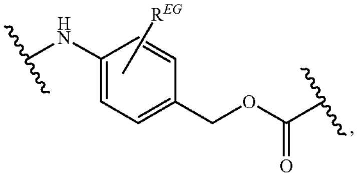

-continued

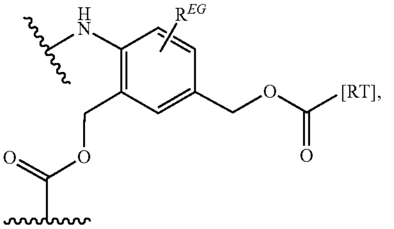

or

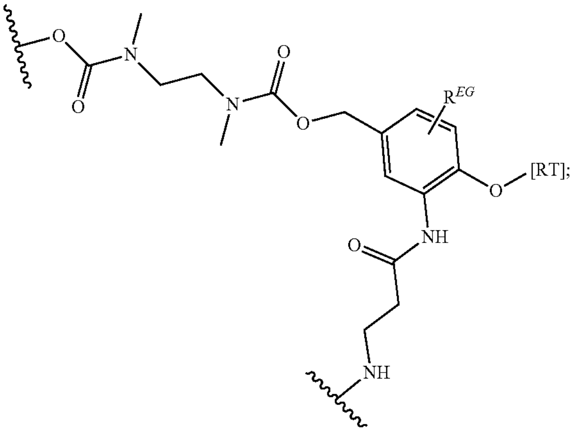

wherein each $R^{EG}$ is independently selected from the group consisting of hydrogen, alkyl, biphenyl, —$CF_3$, —$NO_2$, —CN, fluoro, bromo, chloro, alkoxyl, alkylamino, dialkylamino, alkyl-C(O)O—, alkylamino-C(O)— and dialkylaminoC(O)—. In each structure, the phenyl ring can be bound to one, two, three, or in some cases, four $R^{EG}$ groups. In the second and third structures, those of skill will recognize that EG is bonded to an RT that is not within the backbone of Formula C1 as indicated in the above description of Formula C1. In some embodiments, each $R^{EG}$ is independently selected from the group consisting of hydrogen, alkyl, biphenyl, —$CF_3$, alkoxyl, alkylamino, dialkylamino, alkyl-C(O)O—, alkylamino-C(O)— and dialkylaminoC(O)—. In further embodiments, each $R^{EG}$ is independently selected from the group consisting of hydrogen, —$NO_2$, —CN, fluoro, bromo, and chloro.

In some embodiments, provided herein is a conjugate according to Formula (C1) or (C2) or a pharmaceutically acceptable salt, solvate, stereoisomer, or tautomer thereof; wherein EG comprises phenylene, carboxylene, amine, or a combination thereof. In an embodiment, provided herein is a conjugate according to Formula (C1) or (C2), or a pharmaceutically acceptable salt, solvate, stereoisomer, or tautomer thereof; wherein EG is:

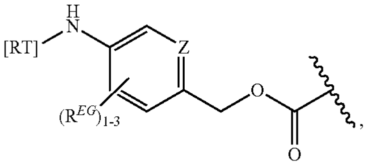

-continued

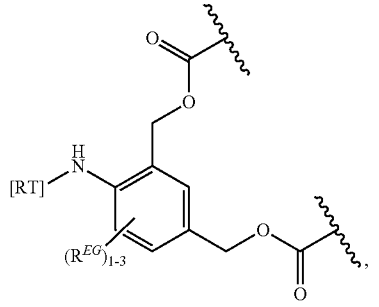

, or

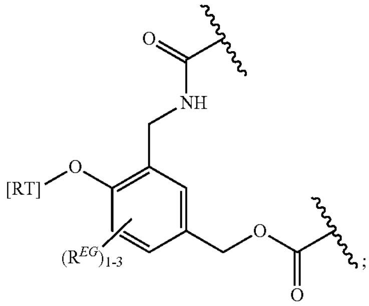

;

wherein Z may be CH or N, each $R^{EG}$ is independently selected from the group consisting of hydrogen, alkyl, biphenyl, —$CF_3$, —$NO_2$, —CN, fluoro, bromo, chloro, alkoxyl, alkylamino, dialkylamino, alkyl-C(O)O—, alkylamino-C(O)— and dialkylaminoC(O)—. In each structure, the phenyl ring can be bound to one, two, three, or in some cases, four $R^{EG}$ groups. In the second and third structures, those of skill will recognize that EG is bonded to an RT that is not within the backbone of Formula C1 as indicated in the above description of Formula C1. In some embodiments, each $R^{EG}$ is independently selected from the group consisting of hydrogen, alkyl, biphenyl, —$CF_3$, alkoxyl, alkylamino, dialkylamino, alkyl-C(O)O—, alkylamino-C(O)— and dialkylaminoC(O)—. In further embodiments, each $R^{EG}$ is independently selected from the group consisting of hydrogen, —$NO_2$, —CN, fluoro, bromo, and chloro. In some embodiments, each $R^{EG}$ in the EG is hydrogen.

In some embodiments, provided herein is a conjugate according to Formula (C1) or (C2), or a pharmaceutically acceptable salt, solvate, stereoisomer, or tautomer thereof; wherein RT comprises a residue of a natural or non-natural amino acid or a residue of a sugar. In an embodiment, provided herein is a conjugate according to Formula (C1) or (C2), or a pharmaceutically acceptable salt, solvate, stereoisomer, or tautomer thereof; wherein RT is:

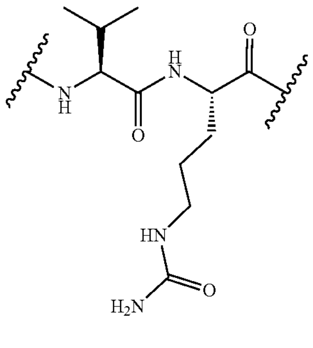

or

-continued

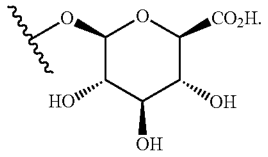

Those of skill will recognize that the first structure is divalent and can be bonded within the backbone as depicted in Formula (C2), and that the second structure is monovalent and can be bonded to EG as depicted in Formula (C1) above.

In some embodiments, provided herein is a conjugate according to Formula (C1) or (C2), or a pharmaceutically acceptable salt, solvate, stereoisomer, or tautomer thereof; wherein RT comprises a residue of a natural or non-natural amino acid or a residue of a sugar. In an embodiment, provided herein is a conjugate according to Formula (C1) or (C2), or a pharmaceutically acceptable salt, solvate, stereoisomer, or tautomer thereof; wherein RT is:

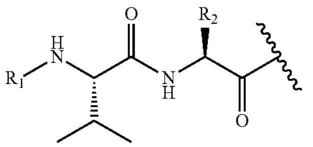

wherein $R_1$ is a bond to the rest of the compound or

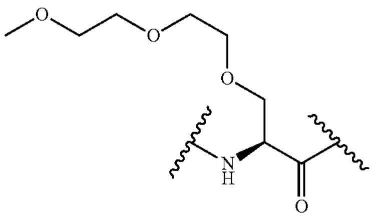 [SMILES: *N[C@@H](COCCOCCOC)C(*)=O]

and $R_2$ is —$CH_3$, —$CH_2CH_2CO_2H$, or —$(CH_2)_3NHCONH_2$; a legumain-cleavable Ala-Ala-Asn (AAN) or Ala-Ala-Asp (AAD) peptide according to the structure of:

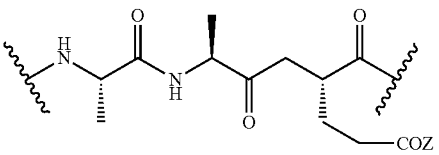

where Z is OH or $NH_2$; or a β-glucuronidase-cleavable β-glucuronide according to the structure of:

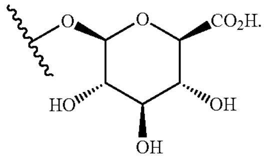 [SMILES: *O[C@H]1O[C@@H](C(=O)O)[C@H](O)[C@@H](O)[C@@H]1O]

Those of skill will recognize that

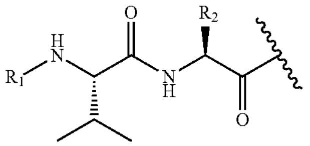

and

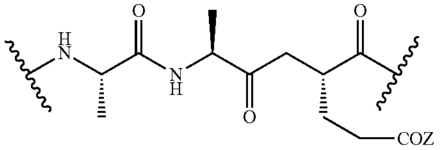

are divalent structures and can be bonded within the backbone of Formula (C1) or as depicted in Formula (C2). The structure

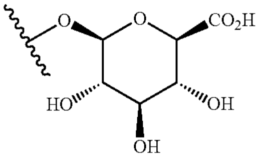 [SMILES: *O[C@H]1O[C@@H](C(=O)O)[C@H](O)[C@@H](O)[C@@H]1O]

is monovalent and can be bonded to EG as depicted in formula (C1) above.

In an embodiment, provided herein is a conjugate according to Formula (C1) or (C2), or a pharmaceutically acceptable salt, solvate, stereoisomer, or tautomer thereof; wherein HP comprises poly(ethylene glycol). In an embodiment, provided herein is a conjugate according to Formula (C1) or (C2), or a pharmaceutically acceptable salt, solvate, stereoisomer, or tautomer thereof, wherein HP is:

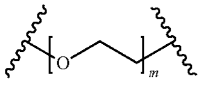

wherein m is an integer selected from 1 to 13.

In an embodiment, provided herein is a conjugate according to Formula (C1) or (C2), or a pharmaceutically acceptable salt, solvate, stereoisomer, or tautomer thereof; wherein SG comprises $C_1$-$C_{10}$ alkylene, $C_4$-$C_6$ alkylene, carbonylene, or combination thereof. In an embodiment, provided herein is a conjugate according to Formula (C1) or (C2), or a pharmaceutically acceptable salt, solvate, stereoisomer, or tautomer thereof; wherein SG is:

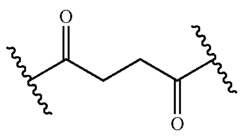

or

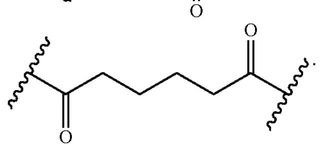

In an embodiment, provided herein is a conjugate according to Formula (C1) or (C2), or a pharmaceutically acceptable salt, solvate, stereoisomer, or tautomer thereof; wherein $W^1$, $W^2$, $W^3$, $W^4$, and $W^5$ are each independently a single bond, absent, or comprise a divalent ketone, divalent ester, divalent ether, divalent amide, divalent amine, alkylene, arylene, sulfide, disulfide, carbonylene, or a combination thereof. In an embodiment, provided herein is a conjugate according to Formula (C1) or (C2), or a pharmaceutically acceptable salt, solvate, stereoisomer, or tautomer thereof, wherein $W^1$, $W^2$, $W^3$, $W^4$, and $W^5$ are each independently a single bond, absent, or comprise —C(O)—, —O—, —C(O)NH—, —C(O)NH-alkyl-, —OC(O)NH—, —SC(O)NH—, —NH—, —NH-alkyl-, —$C(O)N(CH_3)$—, —$C(O)N(CH_3)$-alkyl-, —$N(CH_3)$—, —$N(CH_3)$-alkyl-, —$N(CH_3)CH_2CH_2N(CH_3)$—, —$C(O)CH_2CH_2CH_2C(O)$—, —S—, —S—S—, —$OCH_2CH_2O$—, or the reverse (e.g. —NHC(O)—) thereof, or a combination thereof.

In an embodiment, provided herein is a conjugate according to Formula (C1) or (C2), or a pharmaceutically acceptable salt, solvate, stereoisomer, or tautomer thereof; wherein R' comprises a triazolyl ring. In an embodiment, provided herein is a conjugate according to Formula (C1) or (C2), or a pharmaceutically acceptable salt, solvate, stereoisomer, or tautomer thereof; wherein R' is a triazolyl ring or fused cyclic group comprising a triazolyl ring. In an embodiment, provided herein is a conjugate according to Formula (C1) or (C2), or a pharmaceutically acceptable salt, solvate, stereoisomer, or tautomer thereof; wherein R' is:

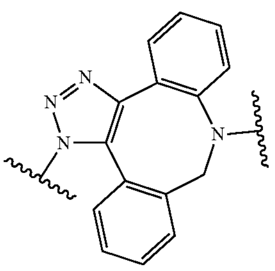

or

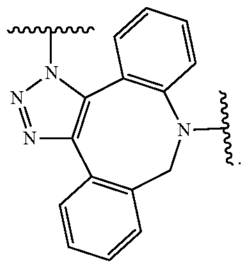

In an embodiment, provided herein is a conjugate according to Formula (C1) or (C2), or a pharmaceutically acceptable salt, solvate, stereoisomer, or tautomer thereof; wherein R' comprises a fused bicyclic ring having at least two adjacent nitrogen atoms in the ring. In an embodiment, provided herein is a conjugate according to Formula (C1) or (C2), or a pharmaceutically acceptable salt, solvate, stereoisomer, or tautomer thereof; wherein R' is:

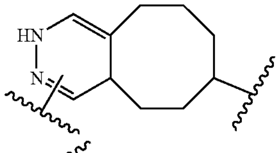

or

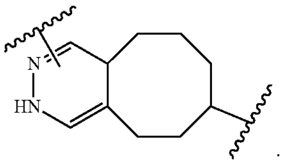

In an embodiment, provided herein is a conjugate according to Formula (C1) or (C2), or a pharmaceutically acceptable salt, solvate, stereoisomer, or tautomer thereof; wherein R' comprises a sulfur linkage. In an embodiment, provided herein is a conjugate according to Formula (C1) or (C2), or a pharmaceutically acceptable salt, solvate, stereoisomer, or tautomer thereof; wherein R' is:

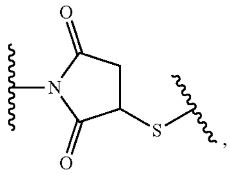
,
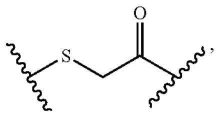
, or
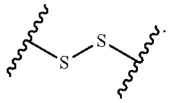
.

In an embodiment, provided herein is a conjugate according to Formula (C1) or (C2), or a pharmaceutically acceptable salt, solvate, stereoisomer, or tautomer thereof; wherein R' comprises a divalent residue of a non-natural amino acid. In an embodiment, provided herein is a conjugate according to Formula (C1) or (C2), or a pharmaceutically acceptable salt, solvate, stereoisomer, or tautomer thereof; wherein R' is:

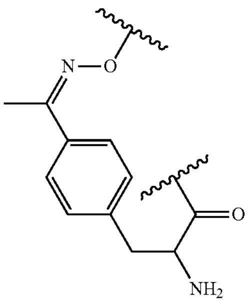
or
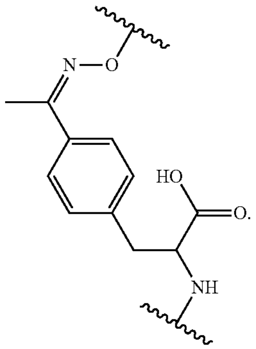

In an embodiment, provided herein is a conjugate according to Formula (C1) or (C2), or a pharmaceutically acceptable salt, solvate, stereoisomer, or tautomer thereof; wherein comprises an oxime linkage. In an embodiment, provided herein is a conjugate according to Formula (C1) or (C2), or a pharmaceutically acceptable salt, solvate, stereoisomer, or tautomer thereof; wherein R' is:

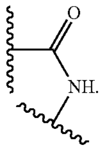

In an embodiment, provided herein is a conjugate according to Formula (C1) or (C2), or a pharmaceutically acceptable salt, solvate, stereoisomer, or tautomer thereof; wherein comprises an oxime linkage. In an embodiment, provided herein is a conjugate according to Formula (C1) or (C2), or a pharmaceutically acceptable salt, solvate, stereoisomer, or tautomer thereof; wherein R' is:

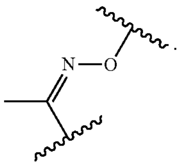 [SMILES: *O/N=C(\*)C]
.

In an embodiment, provided herein is a conjugate according to Formula (C1) or (C2), or a pharmaceutically acceptable salt, solvate, stereoisomer, or tautomer thereof; wherein R' is:

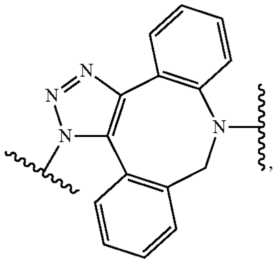
,
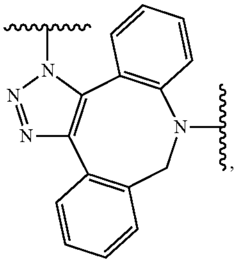
,
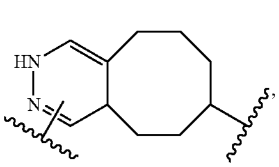
,
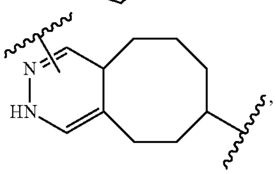
,
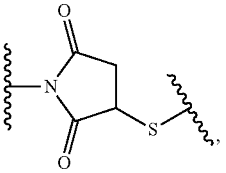
,
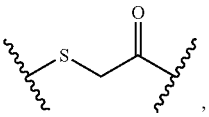
,
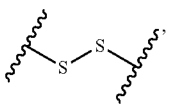
,
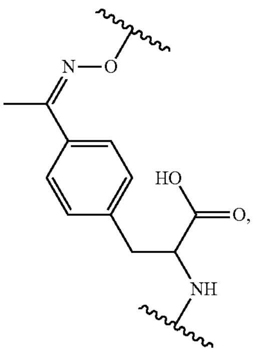
,
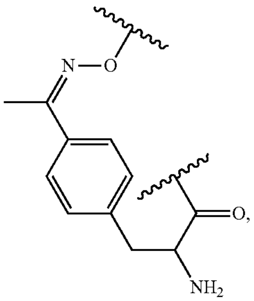
,
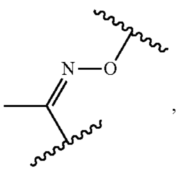 [SMILES: *O/N=C(\*)C]
, or
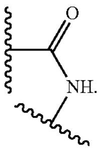

In an embodiment, provided herein is a compound according to Formula (C1) or (C2), or a pharmaceutically acceptable salt, solvate, stereoisomer, or tautomer thereof; wherein Ab is a residue of any compound known to be useful for conjugation to a payload, described herein, and an optional linker, described herein. In an embodiment, provided herein is a compound according to Formula (C1) or (C2), or a pharmaceutically acceptable salt, solvate, stereoisomer, or tautomer thereof, wherein Ab is a residue of an antibody chain, or an antigen binding fragment thereof.

In an aspect, provided herein is an antibody conjugate comprising payload, described herein, and an optional linker, described herein, linked to an antibody, wherein Ab is a residue of the antibody. In an embodiment, provided herein is an antibody conjugate according to Formula (C1) or (C2), or a pharmaceutically acceptable salt, solvate, stereoisomer, or tautomer thereof, wherein: Ab is a residue of the antibody; and R' comprises a triazole ring or fused cyclic group comprising a triazole ring. In an embodiment, provided herein is an antibody conjugate according to Formula (C1) or (C2), or a pharmaceutically acceptable salt, solvate, stereoisomer, or tautomer thereof, wherein: Ab is a residue of the antibody; and R' is:

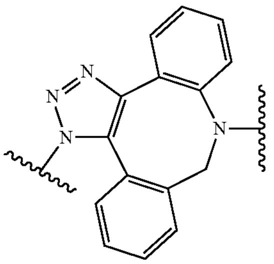

or

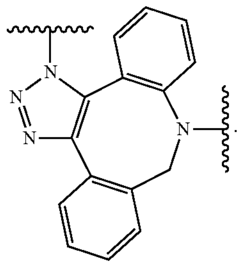

In an embodiment, provided herein is an antibody conjugate according to Formula (C1) or (C2), or a pharmaceutically acceptable salt, solvate, stereoisomer, or tautomer thereof, wherein: Ab is a residue of the antibody or an antigen binding fragment thereof, and R' comprises a fused bicyclic ring, wherein the fused bicyclic ring has at least two adjacent nitrogen atoms in the ring. In an embodiment, provided herein is an antibody conjugate according to Formula (C1) or (C2), or a pharmaceutically acceptable salt, solvate, stereoisomer, or tautomer thereof, wherein: Ab is a residue of the antibody or an antigen binding fragment thereof; and R' is:

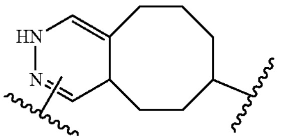

or

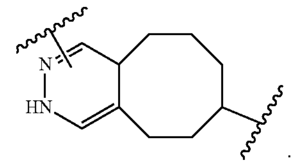

In an embodiment, provided herein is an antibody conjugate according to Formula ($C_1$) or (C2), or a pharmaceutically acceptable salt, solvate, stereoisomer, or tautomer thereof, wherein: Ab is a residue of the polypeptide; and R' comprises a sulfur linkage. In an embodiment, provided herein is an antibody conjugate according to Formula (C1) or (C2), or a pharmaceutically acceptable salt, solvate, stereoisomer, or tautomer thereof, wherein: Ab is a residue of the polypeptide; and R' is:

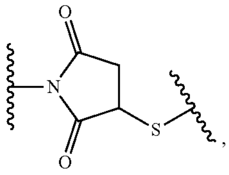

,

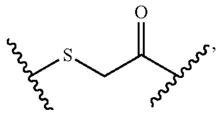

, or

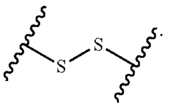

In an embodiment, provided herein is an antibody conjugate according to Formula ($C_1$) or (C2), or a pharmaceutically acceptable salt, solvate, stereoisomer, or tautomer thereof, wherein: Ab is a residue of the polypeptide; and R' comprises a divalent residue of a non-natural amino acid. In an embodiment, provided herein is an antibody conjugate according to Formula (C1) or (C2), or a pharmaceutically acceptable salt, solvate, stereoisomer, or tautomer thereof, wherein: Ab is a residue of the polypeptide; and R' is:

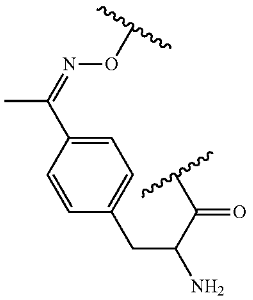

or

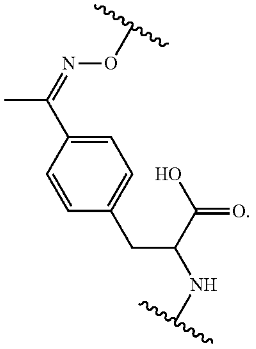

In an embodiment, provided herein is an antibody conjugate according to Formula ($C_1$) or (C2), or a pharmaceutically acceptable salt, solvate, stereoisomer, or tautomer thereof, wherein: Ab is a residue of the polypeptide; and R' comprises an oxime linkage. In an embodiment, provided herein is an antibody conjugate according to Formula (C1) or (C2), or a pharmaceutically acceptable salt, solvate, stereoisomer, or tautomer thereof, wherein: Ab is a residue of the polypeptide; and R' is:

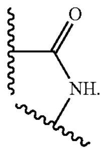

In an embodiment, provided herein is an antibody conjugate according to Formula ($C_1$) or (C2), or a pharmaceutically acceptable salt, solvate, stereoisomer, or tautomer thereof, wherein: Ab is a residue of the polypeptide; and R' comprises an oxime linkage. In an embodiment, provided herein is an antibody conjugate according to Formula (C1) or (C2), or a pharmaceutically acceptable salt, solvate, stereoisomer, or tautomer thereof, wherein: Ab is a residue of the polypeptide; and R' is:

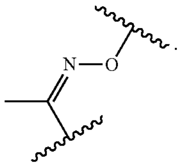

In an embodiment, provided herein is a conjugate according to any of the following formulas, where Ab indicates a residue of the antibody or an antigen binding fragment thereof and PA indicates a payload moiety, and regioisomers thereof. Those of skill will recognize that Ab can bind at more than one position. Each regioisomer and mixtures thereof are provided herein.

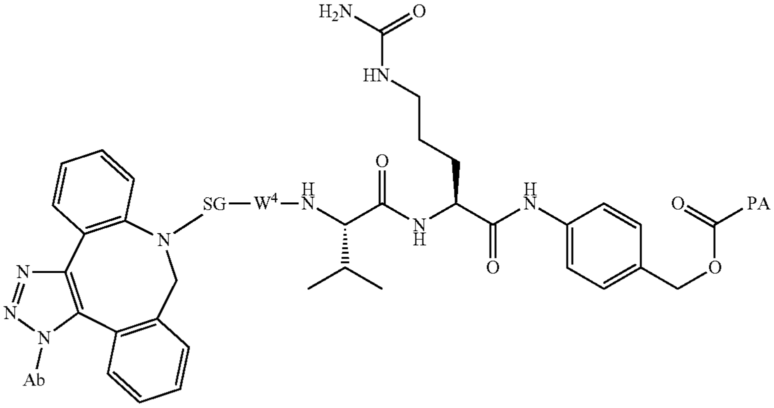

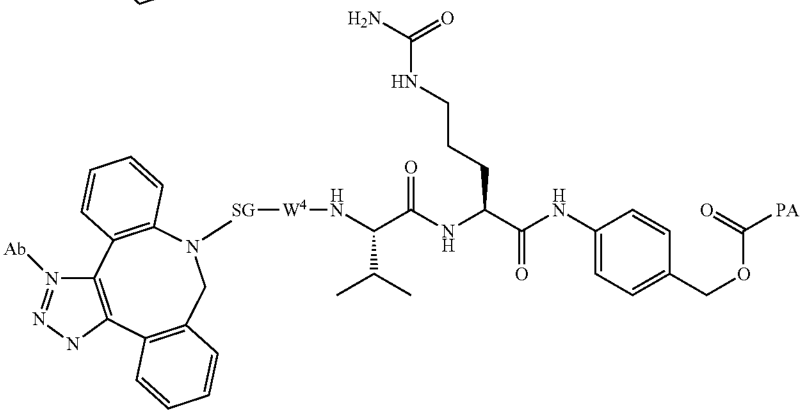

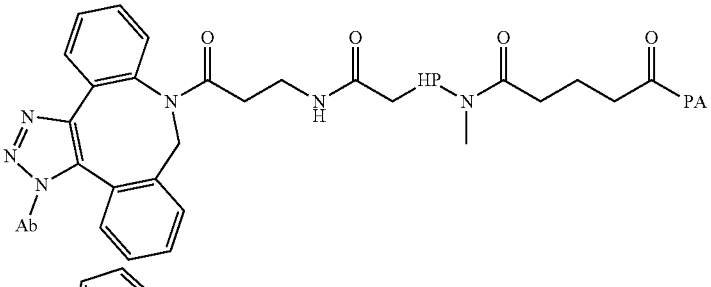

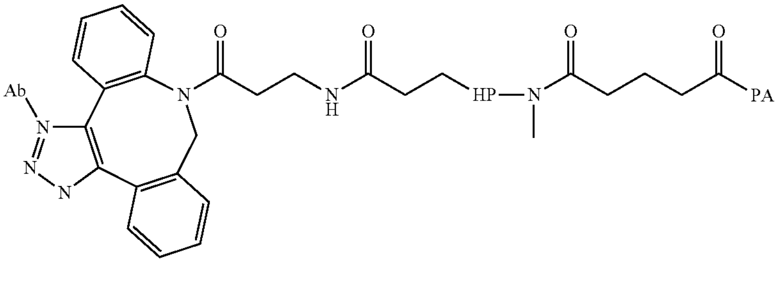

-continued

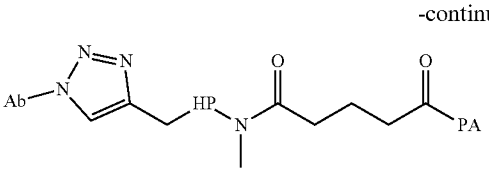

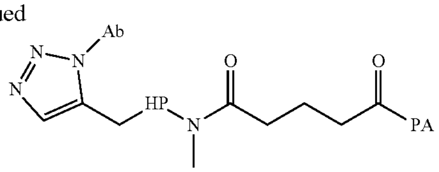

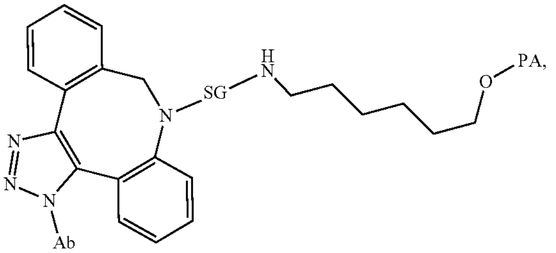

or

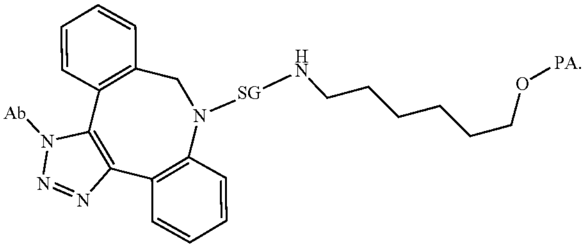

In an embodiment, provided herein is a conjugate according to any of the following formulas, where Ab indicates a residue of the antibody and PA indicates a payload moiety:

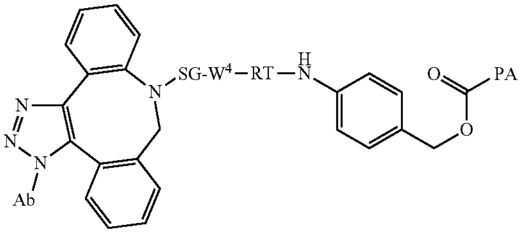

or

-continued

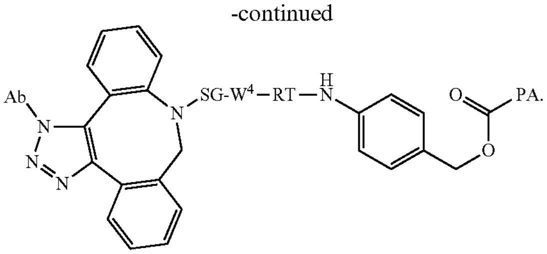

In an embodiment, provided herein is a conjugate according to any of the following formulas, where Ab indicates a residue of the antibody or antigen binding fragment thereof and PA indicates a payload moiety:

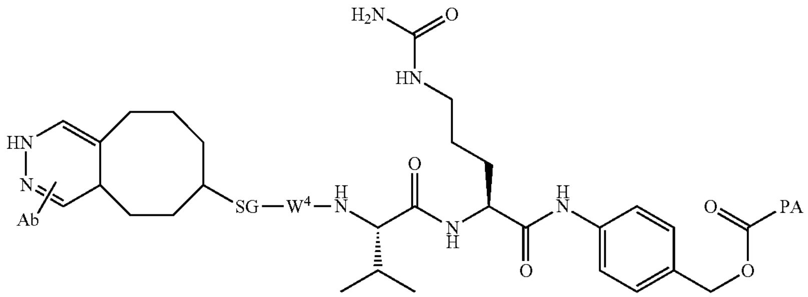

-continued
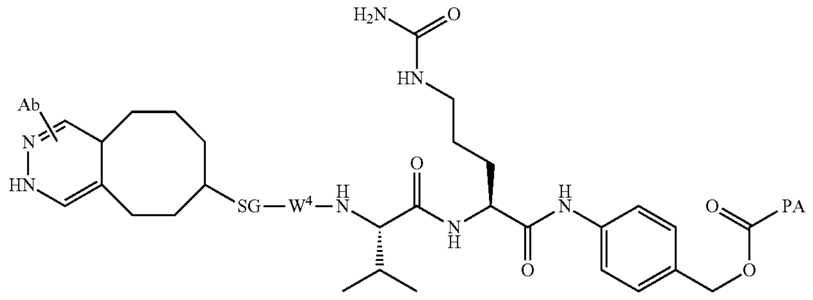
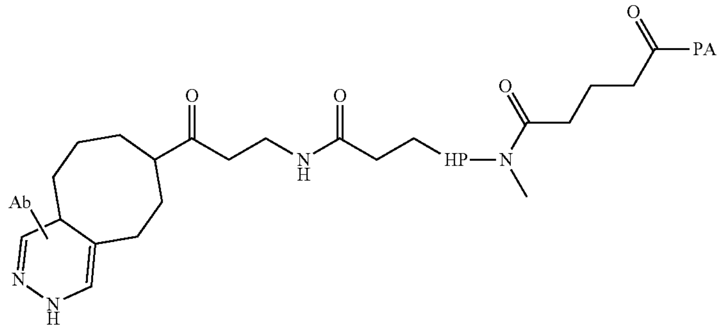
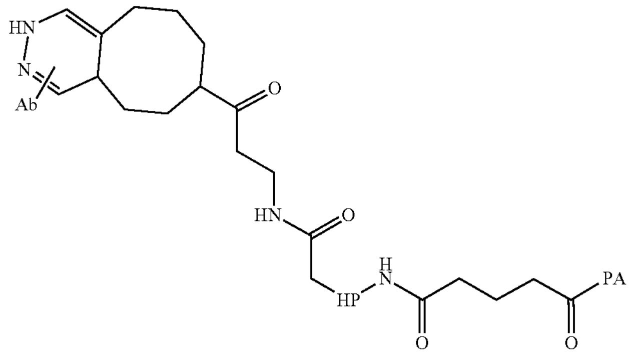
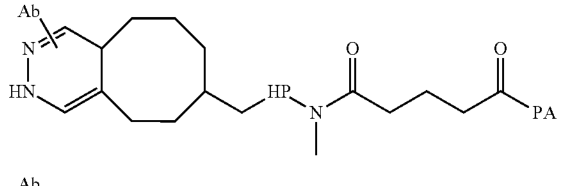
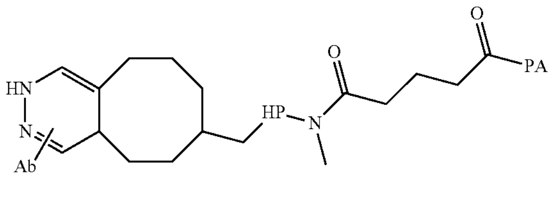
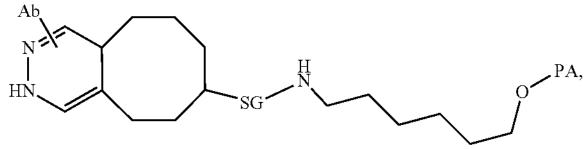
or
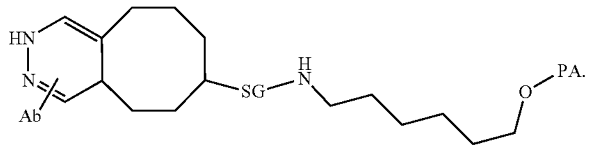

In an embodiment, provided herein is a conjugate according to any of Formulas 101a-105b, where Ab indicates a residue of the antibody or an antigen binding fragment thereof and PA indicates a payload moiety:
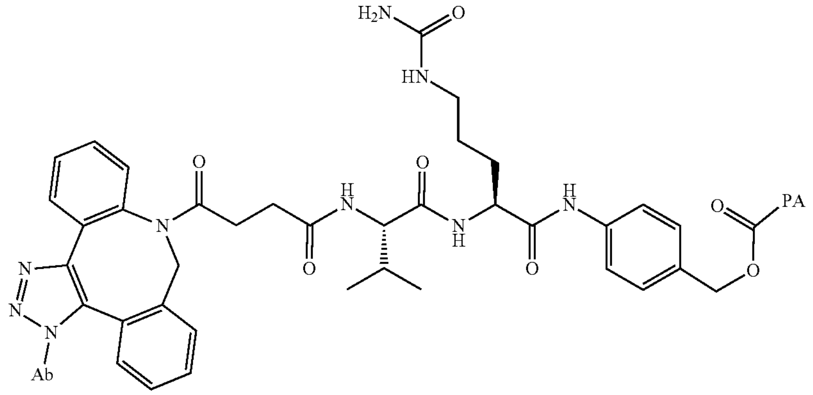
(101a)
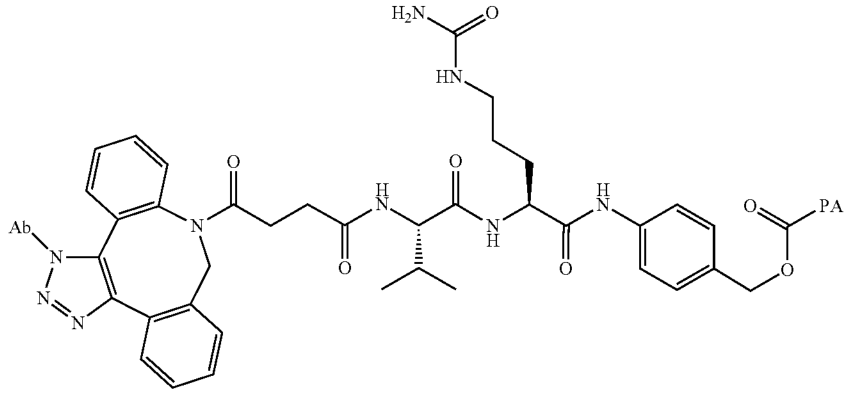
(101b)
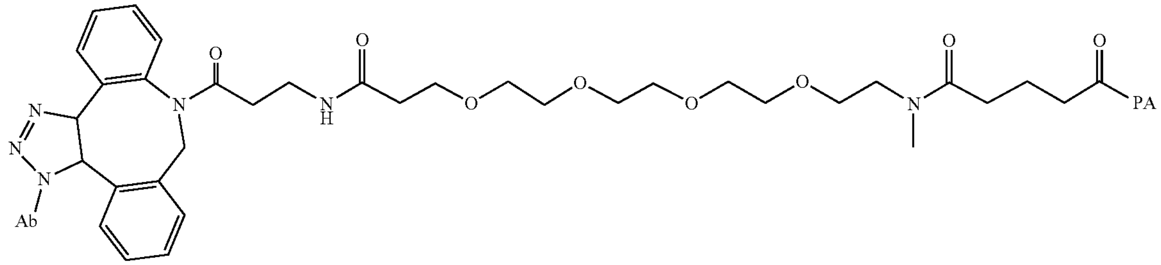
(102a)
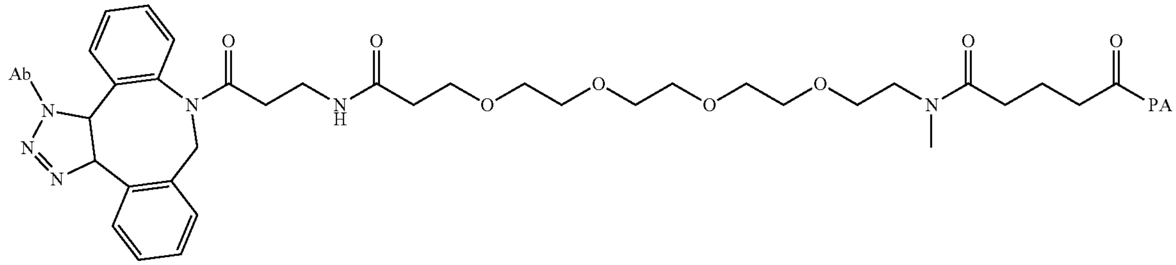
(102b)
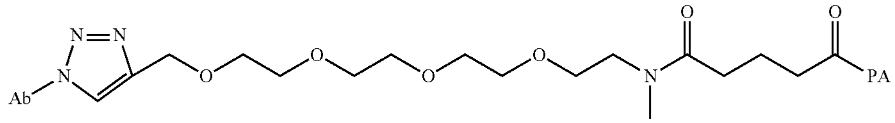
(103a)

-continued (103b)

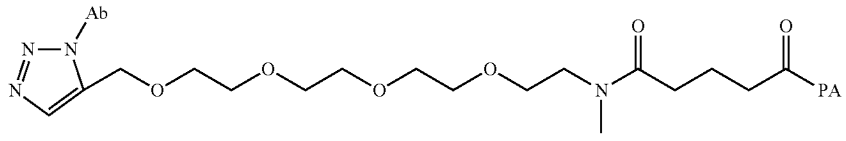

(104a)

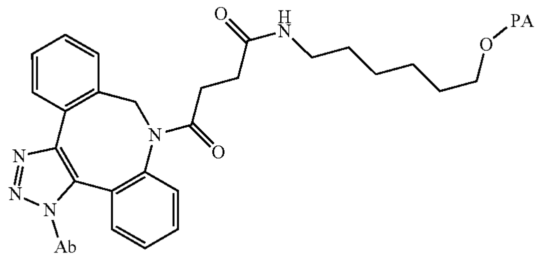

(104b)

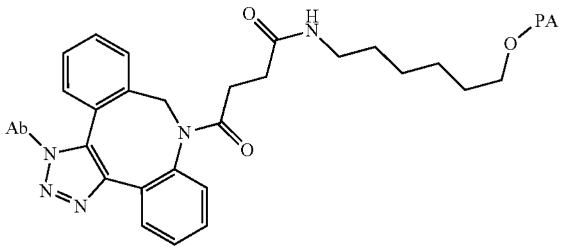

(105a)

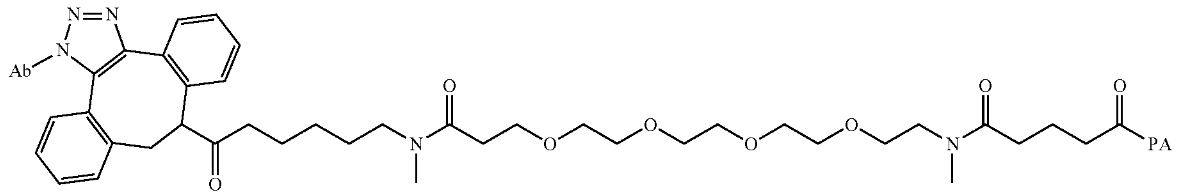

(105b)

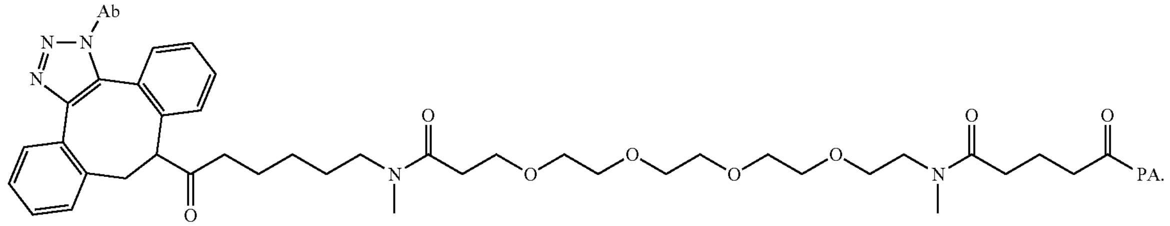

In any of the foregoing embodiments, the conjugate comprises n number of PA moieties, wherein n is an integer selected from 1 to 8. In some embodiments, n is 2. In some embodiments, n is 3. In some embodiments, n is 4. In some embodiments, n is 5. In some embodiments, n is 6. In some embodiments, n is 7. In some embodiments, n is 8. Those of skill in the art will recognize that Formulas (101a) and (101b) are regioisomers based on the nitrogen atom in the triazole to which the antibody is attached. Similarly, Formulas (102a) and (102b), (103a) and (103b), (104a) and (104b), (105a) and (105b) are pairs of regioisomers.

In particular embodiments, provided herein are antibody conjugates according to any of Formulas 101a-105b wherein Ab comprises a residue of a non-natural amino acid according to Formula (30), below. In particular embodiments, provided herein are antibody conjugates according to any of Formulas 101a-105b wherein Ab comprises a residue of anon-natural amino acid according to Formula (30), below, at heavy chain position 404 according to the EU numbering system. In particular embodiments, provided herein are antibody conjugates according to any of Formulas 101a-105b wherein Ab comprises a residue of a non-natural amino acid according to Formula (30), below, at heavy chain position 180 according to the EU numbering system. In particular embodiments, provided herein are antibody conjugates according to any of Formulas 101a-105b wherein Ab comprises a residue of a non-natural amino acid according to Formula (30), below, at heavy chain position 241 according to the EU numbering system. In particular embodiments, provided herein are antibody conjugates according to any of Formulas 101a-105b wherein Ab comprises a residue of a non-natural amino acid according to Formula (30), below, at heavy chain position 222 according to the EU numbering system. In particular embodiments, provided herein are antibody conjugates according to any of Formulas 101a-105b wherein Ab comprises a residue of a non-natural amino acid according to Formula (30), below, at light chain position 7 according to the Kabat or Chothia numbering system. In particular embodiments, provided herein are antibody conjugates according to any of Formulas 101a-105b wherein Ab comprises a residue of the non-natural amino acid according to Formula (30), below, at light chain position 42 according to the Kabat or Chothia numbering system. In certain embodiments, PA is a residue of a compound of Formula (I) described herein.

(30)

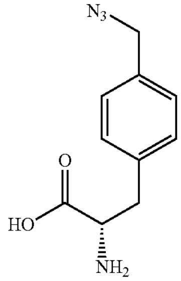

Those of skill will recognize that amino acids such as Formula (30) are incorporated into polypeptides and antibodies as residues. For instance, a residue of Formula (30) can be according to the following Formula (30'):

(30')

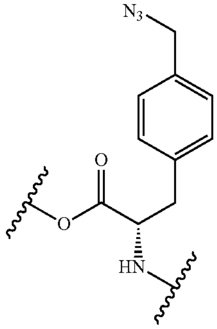

Further modification, for instance at —$N_3$ is also encompassed within the term residue herein.

In particular embodiments, provided herein are antibody conjugates according to any of Formulas 101a-105b wherein Ab comprises a residue of the non-natural amino acid according to Formula (56), below. In particular embodiments, provided herein are antibody conjugates according to any of Formulas 101a-105b wherein Ab comprises a residue of the non-natural amino acid according to Formula (56), below, at heavy chain position 404 according to the EU numbering system. In particular embodiments, provided herein are antibody conjugates according to any of Formulas 101a-105b wherein Ab comprises a residue of the non-natural amino acid according to Formula (56), below, at heavy chain position 180 according to the EU numbering system. In particular embodiments, provided herein are antibody conjugates according to any of Formulas 101a-105b wherein Ab comprises a residue of the non-natural amino acid according to Formula (56), below, at heavy chain position 241 according to the EU numbering system. In particular embodiments, provided herein are antibody conjugates according to any of Formulas 101a-105b wherein Ab comprises a residue of the non-natural amino acid according to Formula (56), below, at heavy chain position 222 according to the EU numbering system. In particular embodiments, provided herein are antibody conjugates according to any of Formulas 101a-105b wherein Ab comprises a residue of the non-natural amino acid according to Formula (56), below, at light chain position 7 according to the Kabat or Chothia numbering system. In particular embodiments, provided herein are antibody conjugates according to any of Formulas 101a-105b wherein Ab comprises a residue of the non-natural amino acid according to Formula (56), below, at light chain position 42 according to the Kabat or Chothia numbering system. In certain embodiments, PA is a residue of a compound of Formula (I-P), (I), (II), and/or (III) described herein. The non-natural amino acid according to Formula (56) is as follows:

(56)

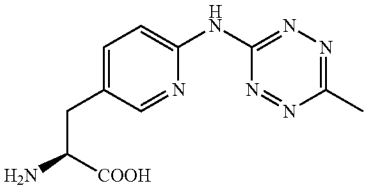

In particular embodiments, provided herein are antibody conjugates according to any of Formulas 101a-105b wherein Ab comprises a non-natural amino acid residue of para-azidomethyl-L-phenylalanine. In particular embodiments, provided herein are antibody conjugates according to any of Formulas 101a-105b wherein Ab comprises the non-natural amino acid residue para-azidomethyl-L-phenylalanine at heavy chain position 404 according to the EU numbering system. In particular embodiments, provided herein are antibody conjugates according to any of Formulas 101a-105b wherein Ab comprises a non-natural amino acid residue of para-azidomethyl-L-phenylalanine at heavy chain position 180 according to the EU numbering system. In particular embodiments, provided herein are antibody conjugates according to any of Formulas 101a-105b wherein Ab comprises a non-natural amino acid residue of para-azidomethyl-L-phenylalanine at heavy chain position 241 according to the EU numbering system. In particular embodiments, provided herein are antibody conjugates according to any of Formulas 101a-105b wherein Ab comprises a non-natural amino acid residue of para-azidomethyl-L-phenylalanine at heavy chain position 222 according to the EU numbering system. In particular embodiments, provided herein are antibody conjugates according to any of Formulas 101a-105b wherein Ab comprises a non-natural amino acid residue para-azidomethyl-L-phenylalanine at light chain position 7 according to the Kabat or Chothia numbering system. In particular embodiments, provided herein are antibody conjugates according to any of Formulas 101a-105b wherein Ab comprises a non-natural amino acid residue para-azidomethyl-L-phenylalanine at light chain position 42 according to the Kabat or Chothia numbering system. In certain embodiments, PA is a residue of a compound of Formula (I) described herein.

In particular embodiments, provided herein are antibody drug conjugates of compounds of Formula (I-P), Formula (I), Formula (II) and/or Formula (III) described herein. In one aspect, provided herein is an antibody drug conjugate according to Formula (V):

Formula (V)

$$Ab \text{---}[L\text{---}PA]_n$$

or a pharmaceutically acceptable salt, solvate, stereoisomer, tautomer, or mixture of regioisomers thereof, wherein Ab is an antibody or an antigen binding fragment thereof;

L is a linker;

PA is a payload (e.g., a residue of a compound of Formula (I-P), (I), (II), and/or (III)); and subscript n is an integer selected from 1 to 30.

In some instances of Formula (V), is

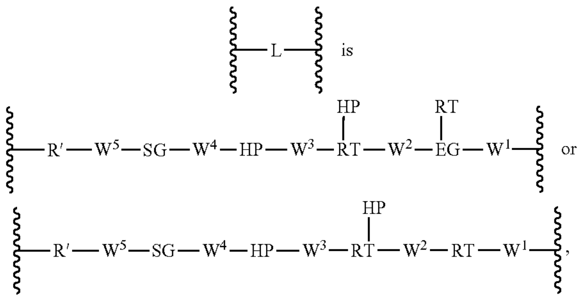

wherein $W^1$, $W^2$, $W^3$, $W^4$, SG, RT, HP, EG and R' are as defined herein for Formulas ($C_1$) and ($C_2$), in some or any embodiments. In some other instances of Formula (V),

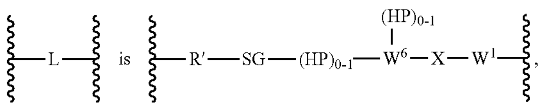

wherein $W^1$, $W^6$, SG, X, HP, and R' are as defined herein for Formula (VI), in some or any embodiments In another aspect, provided herein is an antibody conjugate according to the structure of Formula (VI):

Formula (VI)

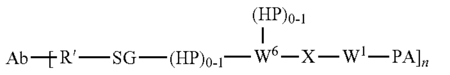

or a pharmaceutically acceptable salt, solvate, stereoisomer, tautomer, or mixture of regioisomers thereof, wherein:

$W^1$ is independently, at each occurrence, a single bond, absent or a divalent attaching group;

X is independently, at each occurrence, absent,

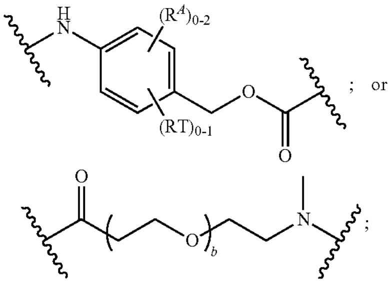

subscript b is an integer selected from 1 to 10;

$R^A$, when present, is independently, at each occurrence, selected from $C_{1-3}$alkyl;

RT, when present, is independently, at each occurrence, a release trigger group;

HP, when present, is independently, at each occurrence, a hydrophilic group;

$W^6$ is independently, at each occurrence, a residue of a peptide, or absent;

SG is independently, at each occurrence, absent, or a divalent spacer group;

R' is independently, at each occurrence, a divalent residue of a conjugated group; subscript n is an integer selected from 1 to 30;

Ab is an antibody or an antigen binding fragment thereof; and

PA is independently, at each occurrence, a residue of a compound of Formula (I-P), (I), (II), or (III) wherein PA is bonded to the rest of the molecule via —$NR^{3a}$—, the —NH— of —$C(R^{3c})_2NH$—, the nitrogen of an $R^3$ heterocycloalkyl, the nitrogen of an $R^3$ partially saturated heteroaryl, the —NH— of —O—$CH_2$-(phenyl)-$CH_2$—NH—, or a nitrogen of ring B. In another embodiment, provided herein is an antibody conjugate according to the structure of Formula (VI-P):

Formula (VI-P)

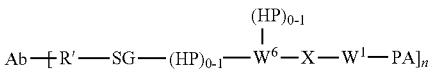

or a pharmaceutically acceptable salt, solvate, stereoisomer, tautomer, or mixture of regioisomers thereof, wherein:

$W^1$ is a single bond, absent or a divalent attaching group;

X is independently, at each occurrence, absent,

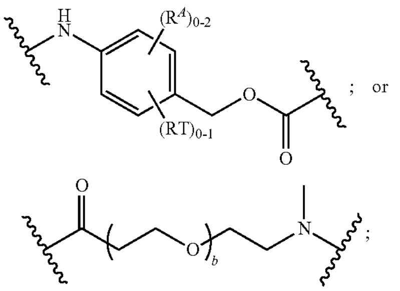

subscript b is an integer from 1 to 10;

$R^A$, when present, is independently, at each occurrence, selected from $C_{1-3}$alkyl;

RT, when present, is independently, at each occurrence, a release trigger group;

HP, when present, is a hydrophilic group;

$W^6$ is independently, at each occurrence, a peptide, or absent;

SG is independently, at each occurrence, absent, or a divalent spacer group;

R' is independently, at each occurrence, a divalent residue of a conjugated group;

subscript n is an integer from 1 to 30;

Ab is an antibody or an antigen binding fragment thereof; and

PA is a payload of a compound

Formula (I)

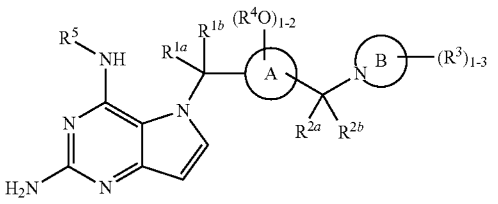

or a pharmaceutically acceptable salt, solvate or N-oxide thereof;

wherein $R^{1a}$, $R^{1b}$, $R^{2a}$, and $R^{2b}$ are independently, at each occurrence, selected from hydrogen, and $C_{1-6}$alkyl;

ring A is cycloalkyl, heterocycloalkyl, monocyclic aryl, monocyclic heteroaryl, fused bicyclic aryl, or fused bicyclic heteroaryl, where heterocycloalkyl and each heteroaryl comprise 1, 2, 3 or 4 heteroatoms selected from N, S, and O;

ring B is a 4-membered N-linked heterocycloalkyl, which is further substituted with 1-2 $R^3$; wherein $R^3$ is, independently, at each occurrence, —$N(R^{3a})_2$, —$OR^{3b}$, —$C(R^{3c})_2NH_2$, $C_{1-6}$alkyl, heterocycloalkyl, heteroaryl, or partially saturated heteroaryl, or two $R^3$ attached to the same carbon, together with the carbon atom to which they are attached, form a spiro-heterocycloalkyl; wherein heterocycloalkyl, spiro-heterocycloalkyl, heteroaryl and partially saturated heteroaryl include 1, 2, 3 or 4 heteroatoms selected from N, S, and O, and are optionally further substituted with 1-2 $C_{1-3}$alkyl;

or ring B is a 5-6 membered N-linked heterocycloalkyl, which is further substituted with 1-3 $R^3$; wherein $R^3$ is, independently, at each occurrence, —$N(R^{3a})_2$, —$OR^{3b}$, —$C(R^{3c})_2NH_2$, heterocycloalkyl, heteroaryl, or partially saturated heteroaryl, or two $R^3$ attached to the same carbon, together with the carbon atom to which they are attached, form a spiro-heterocycloalkyl; wherein heterocycloalkyl, spiro-heterocycloalkyl, heteroaryl and partially saturated heteroaryl include 1, 2, 3 or 4 heteroatoms selected from N, S, and O, and are optionally further substituted with 1-2 $C_{1-3}$alkyl;

or ring B is a 7-10 membered N-linked heterocycloalkyl, which is further substituted with 1-3 $R^3$, or a 5-10 membered N-linked heteroaryl which is further substituted with 1-3 $R^3$; wherein $R^3$ is, independently, at each occurrence, —$N(R^{3a})_2$, —$OR^{3b}$, —$C(R^{3c})_2NH_2$, $C_{1-6}$alkyl, heterocycloalkyl, heteroaryl, or partially saturated heteroaryl, or two $R^3$ attached to the same carbon, together with the carbon atom to which they are attached, form a spiro-heterocycloalkyl; wherein heterocycloalkyl, spiro-heterocycloalkyl, heteroaryl and partially saturated heteroaryl include 1, 2, 3 or 4 heteroatoms selected from N, S, and O, and are optionally further substituted with 1-2 $C_{1-3}$alkyl;

$R^{3a}$ is independently, at each occurrence, selected from hydrogen, $C_{1-6}$alkyl, —C(═O)—$CH_2NH_2$, and cycloalkyl;

$R^{3b}$ is independently, at each occurrence, selected from hydrogen,

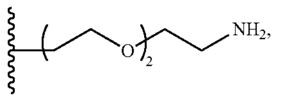

and —$CH_2$-aryl-$CH_2NH_2$;

$R^{3c}$ is independently, at each occurrence, selected from hydrogen, and $C_{1-6}$alkyl, or two $R^{3c}$, together with the carbon atom to which they are attached, form a cycloalkyl;

$R^4$ is $C_{1-6}$alkyl; and $R^5$ is $C_{1-6}$cycloalkyl, or $C_{1-6}$alkyl optionally substituted with halo, hydroxy, alkoxy, amino, $C_{1-6}$alkylamino, $C_{1-6}$dialkylamino, $C_{1-6}$cycloalkyl, aryl or heteroaryl, wherein heteroaryl includes 1, 2, 3 or 4 heteroatoms selected from N, S, and O, and wherein cycloalkyl, aryl and heteroaryl are optionally further substituted with halo, hydroxy, alkyl, or haloalkyl; and wherein PA is bonded to the rest of the molecule via an amino group of $R^3$ or via an amino group of ring B.

In some embodiments, the compound according to Formula (VI) is according to Formula (VIa), (VIb), (VIc), (VId), or (VIe):

Formula (VIa)

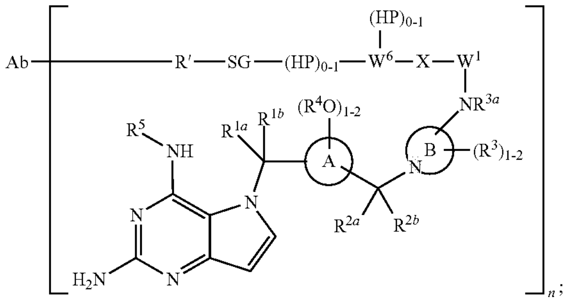

;

Formula (VIb)

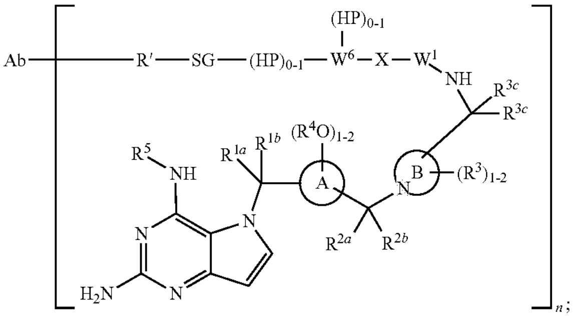

;

-continued

Formula (VIc)

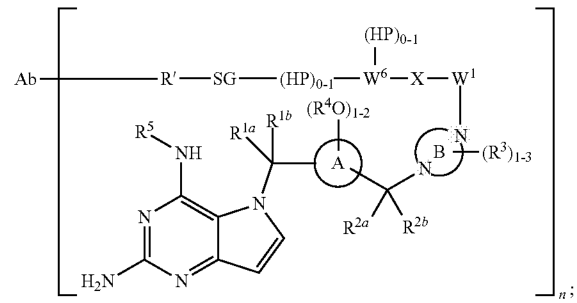

Formula (VId)

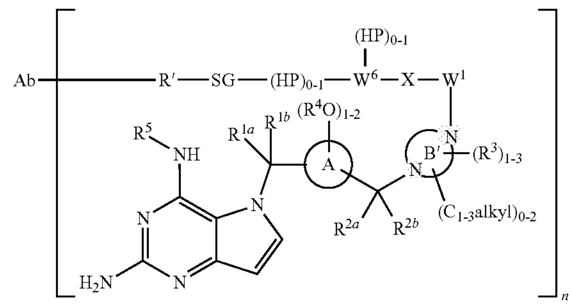

where B' is spiro-heterocycloalkyl which includes 1, 2, 3 or 4 heteroatoms independently selected from N, S, and O; or Formula (VIe)

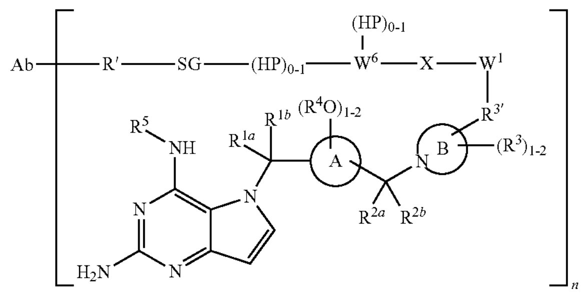

where $R^{3'}$ is heterocycloalkyl or partially saturated heteroaryl, each of which includes 1, 2, 3 or 4 heteroatoms independently selected from N, S, and O, provided that at least one nitrogen is present in the $R^{3'}$ ring and is attached to $W^1$; or $R^{3'}$ is —O—$CH_2$-(phenyl)-$CH_2$—NH— where the NH is attached to $W^1$.

In some instances of Formula (VI), (VIa), (VIb), (VIc), (VId), and (VIe), SG is absent,

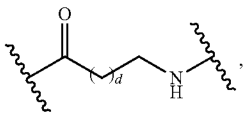, 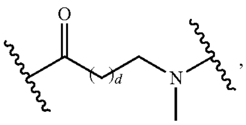, or

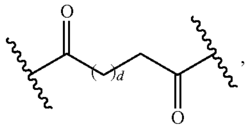, wherein subscript d is an integer selected from 1 to 10, wherein each

indicates a point of attachment to the rest of the formula. In some instances, SG is

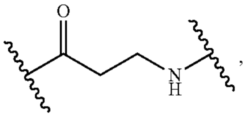, 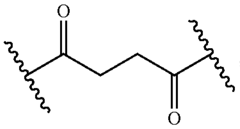,

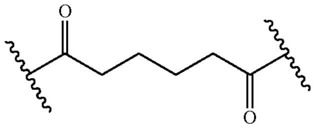, or

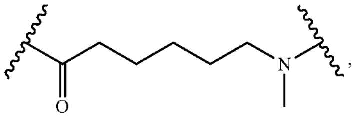, wherein each

indicates a point of attachment to the rest of the formula.

In some instances of Formula (VI), (VIa), (VIb), (VIc), (VId), and (VIe), $W^1$, when present, is

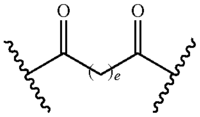, 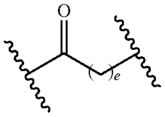 or

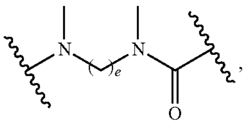, wherein subscript e is an integer selected from 1 to 10, wherein each

indicates a point of attachment to the rest of the formula. In some instances, $W^1$, when present, is

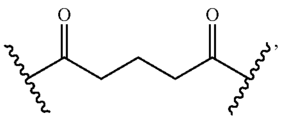
,

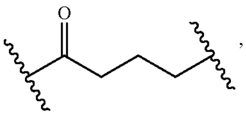
, or

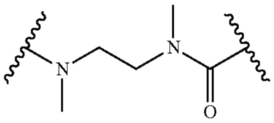

wherein each

indicates a point of attachment to the rest of the formula.

In some instances of Formula (VI), (VIa), (VIb), (VIc), (VId), and (VIe), when $W^6$ is a residue of a peptide, the residue of the peptide may comprise natural and/or non-natural amino acid residues. In some instances of Formula (VI), $W^6$, when present, is a tripeptide residue. In some of such instances, $W^6$ is

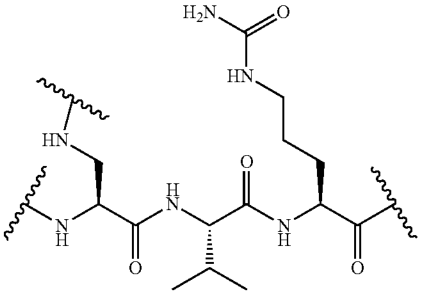
,

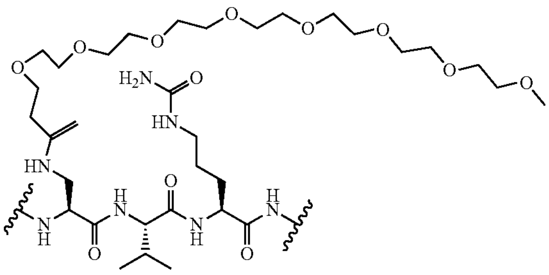
,

-continued or

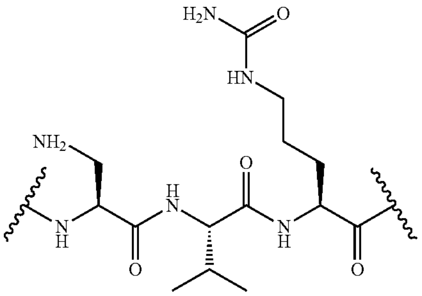
, wherein each

indicates a point of attachment to the rest of the formula. In some instances of Formula (VI), $W^6$, when present, is a dipeptide residue. In some of such instances, $W^6$, when present, is

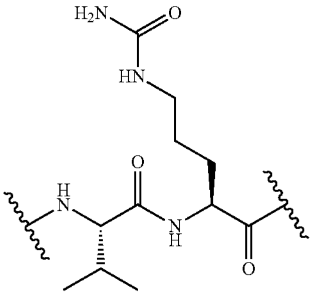
or

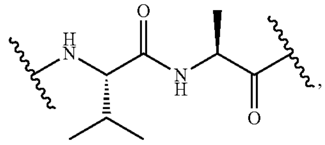
, wherein each

indicates a point of attachment to the rest of the formula.

In some instance of Formula (VI), (VIa), (VIb), (VIc), (VId), and (VIe), RT is

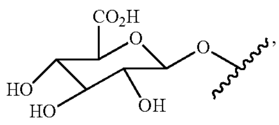 [SMILES: *OC1OC(C(=O)O)C(O)C(O)C1O]
, wherein

indicates a point of attachment to the rest of the formula.

In some instances of Formula (VI), (VIa), (VIb), (VIc), (VId), and (VIe), HP, when present is a PEG group. In some instances of Formula (VI), HP, when present, is

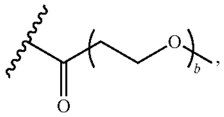
or
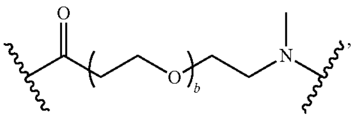

wherein subscript b is an integer selected from 1 to 10, and

indicates a point of attachment to the rest of the formula.

In some instances of Formula (VI), (VIa), (VIb), (VIc), (VId), and (VIe), R' is:

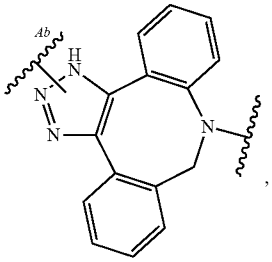
,
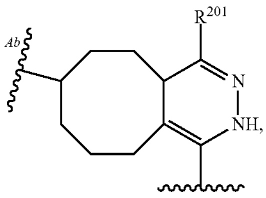

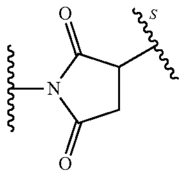
,
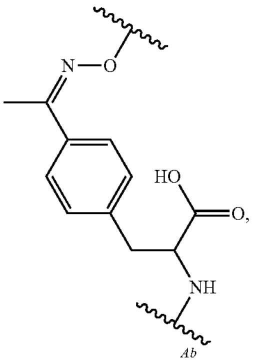

-continued

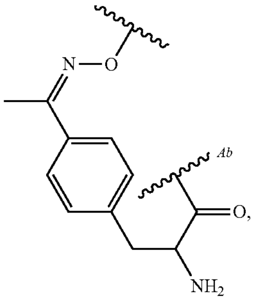
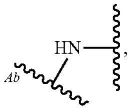

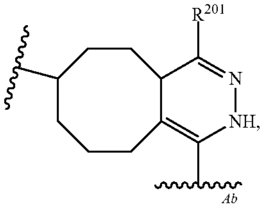
or
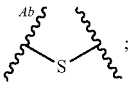
;

wherein $R^{201}$ is $C_{1-6}$alkyl, wherein each

indicates a point of attachment to the rest of the formula,

indicates a point of attachment to the antibody, or an antigen binding fragment thereof, and

indicates a point of attachment to the antibody, or an antigen binding fragment thereof, via a sulfur atom of a cysteine residue.

In specific embodiments, antibody conjugates described herein are selected from the group consisting of:
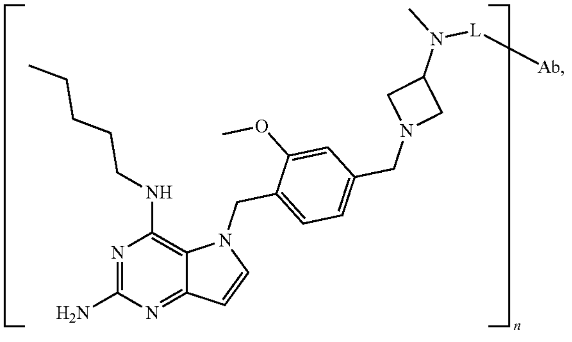
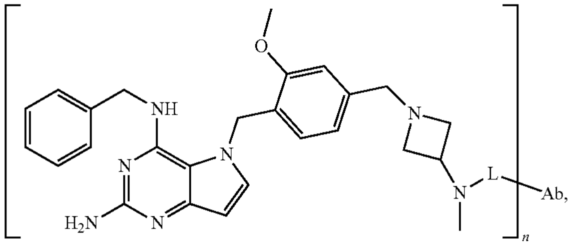
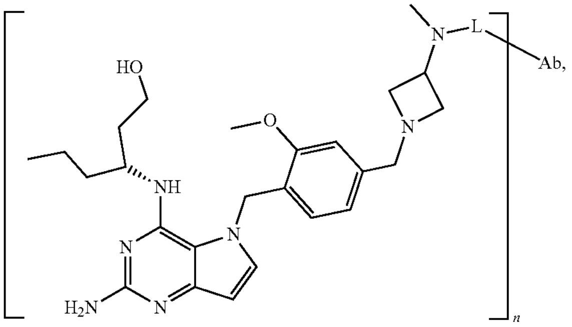
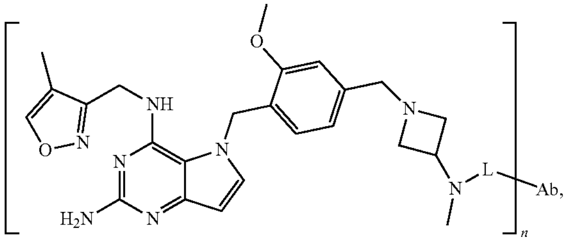
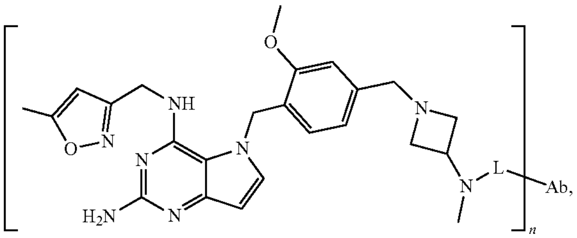
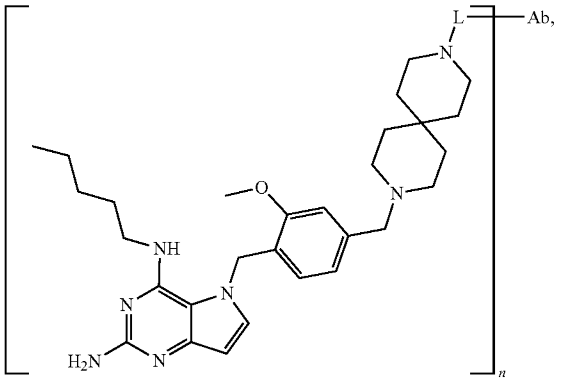
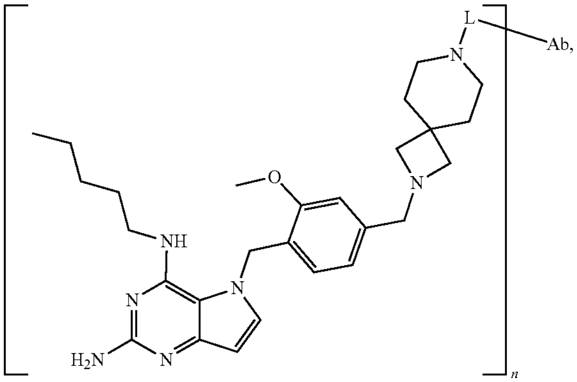
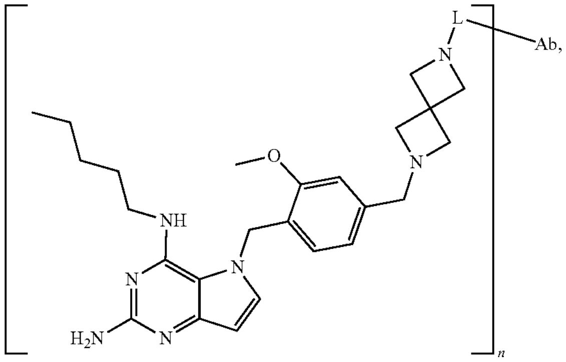

-continued
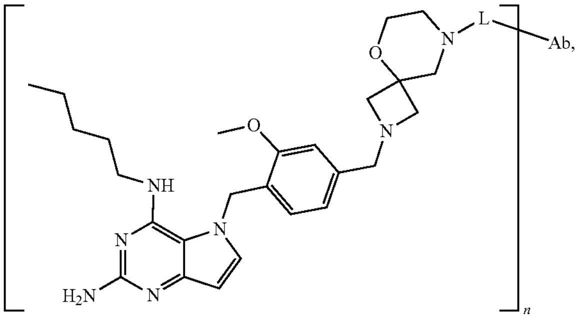
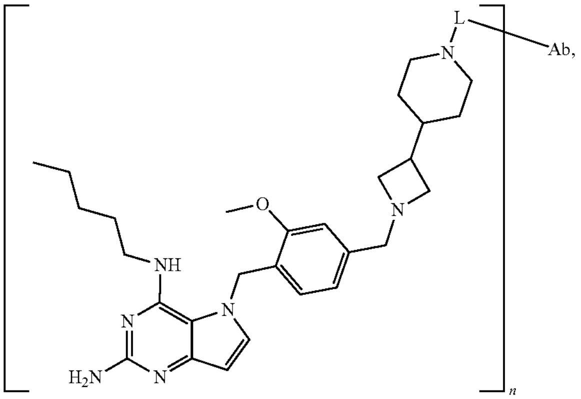
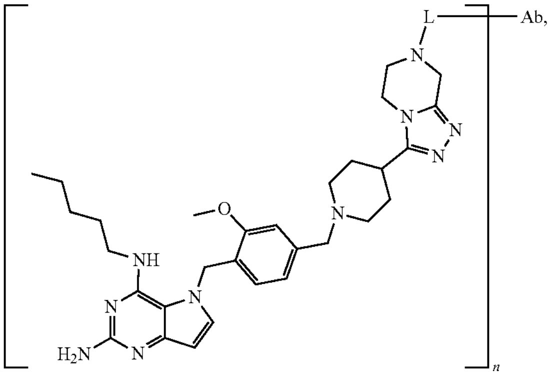
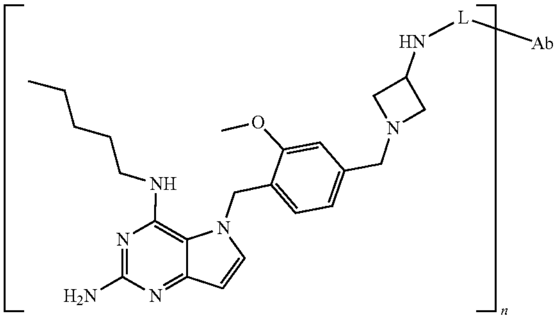
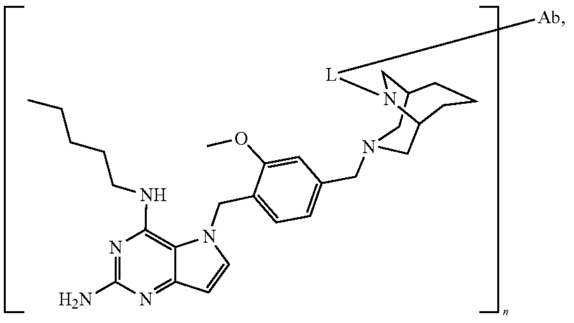
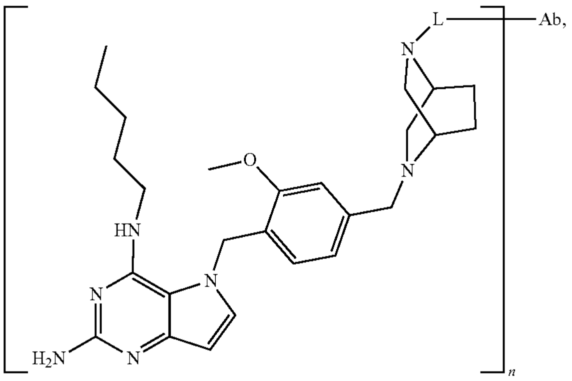
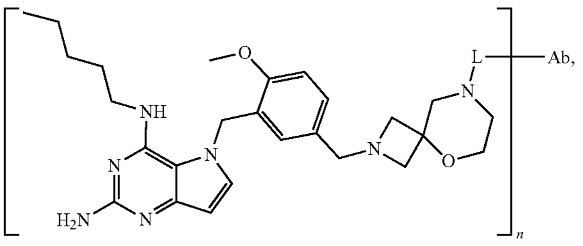
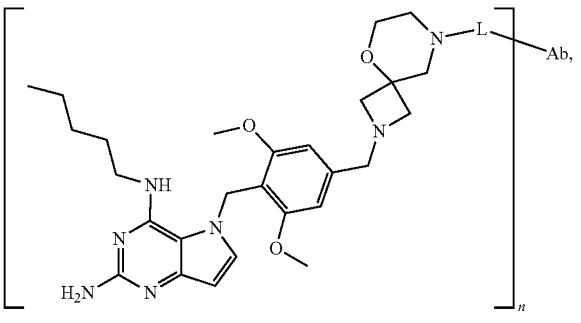

-continued
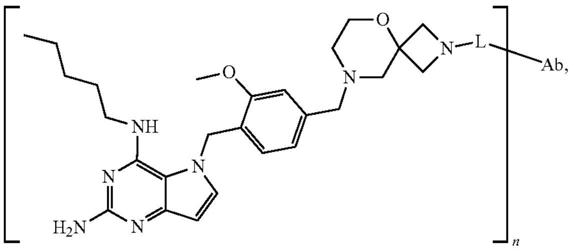
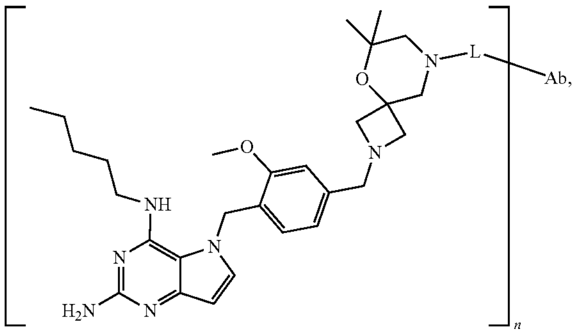
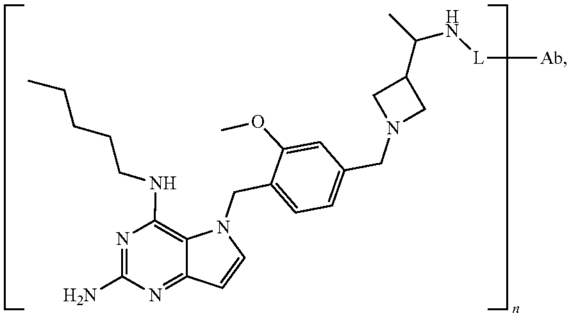
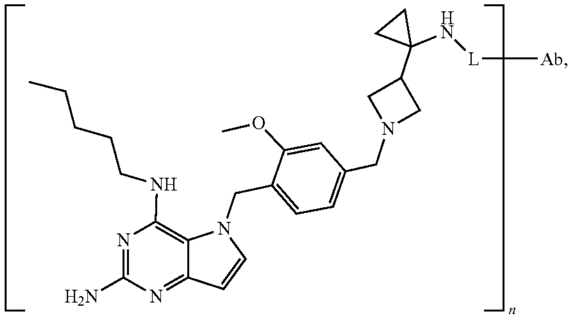
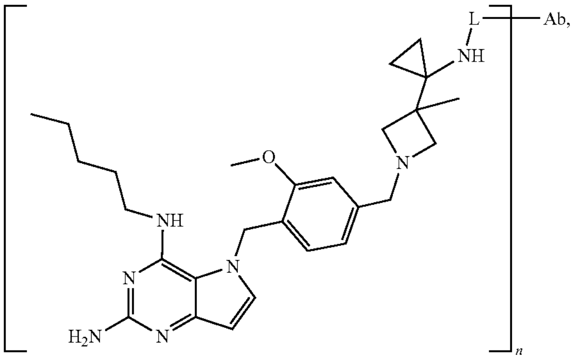
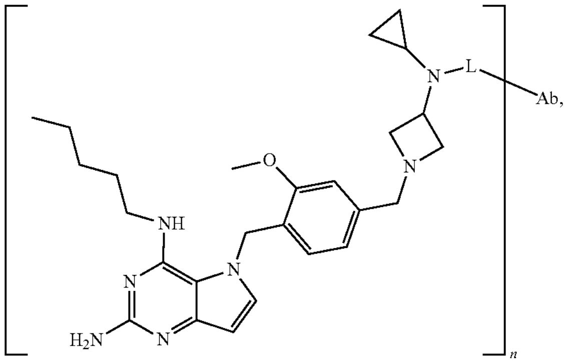
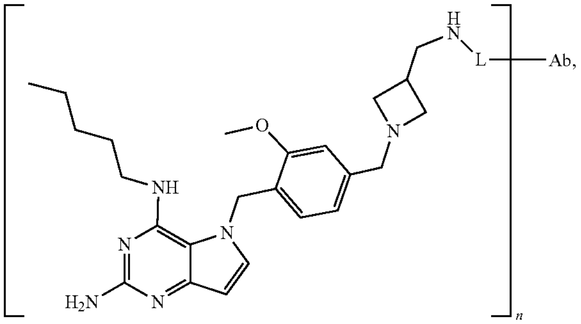
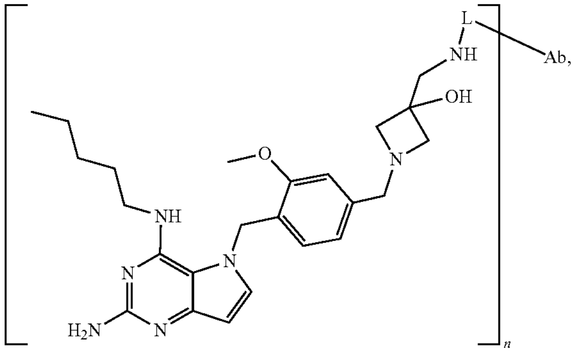

-continued
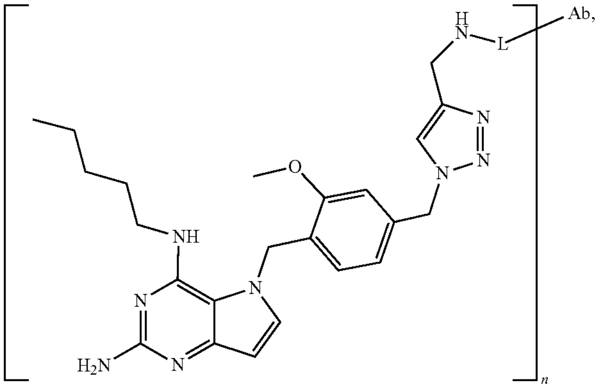
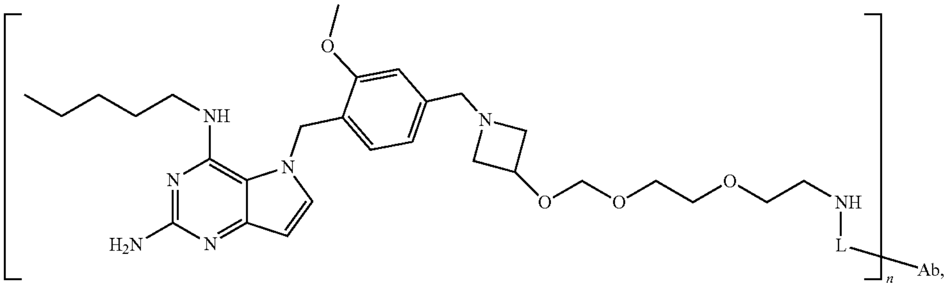
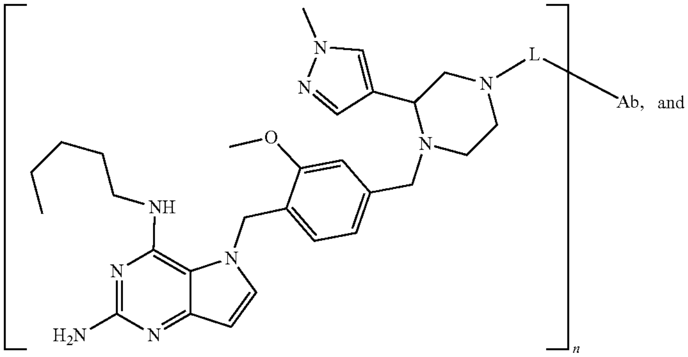
and
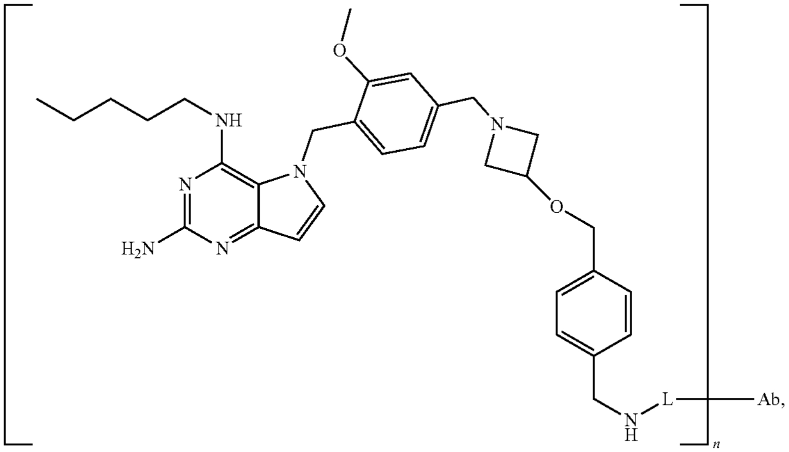

or a pharmaceutically acceptable salt, solvate, stereoisomer, tautomer or mixture of regioisomers thereof;

wherein each

indicates a point of attachment to the rest of the formula;

L is a linker; and

Ab is an antibody or an antigen binding fragment thereof.

In some embodiments, antibody drug conjugates of Formula (VI) described herein are selected from the group consisting of:

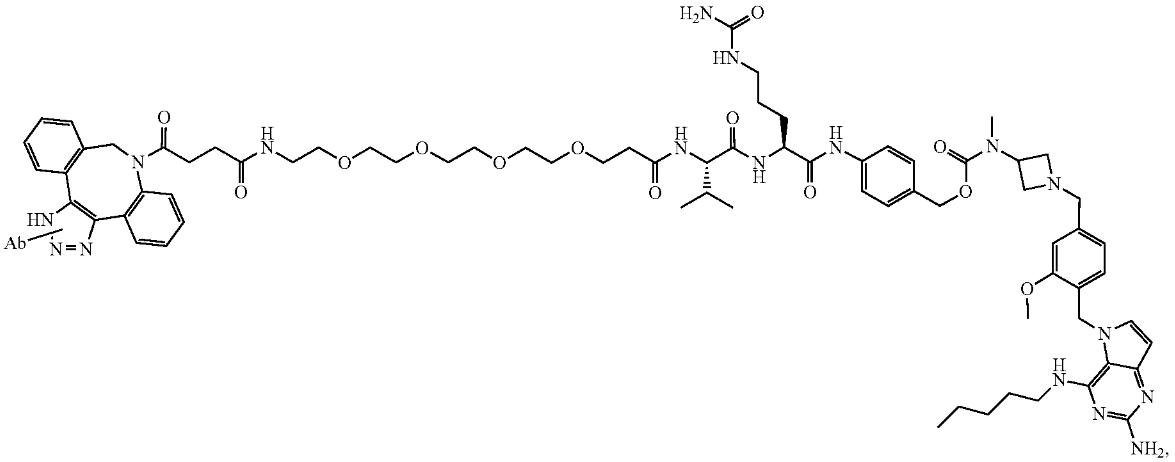

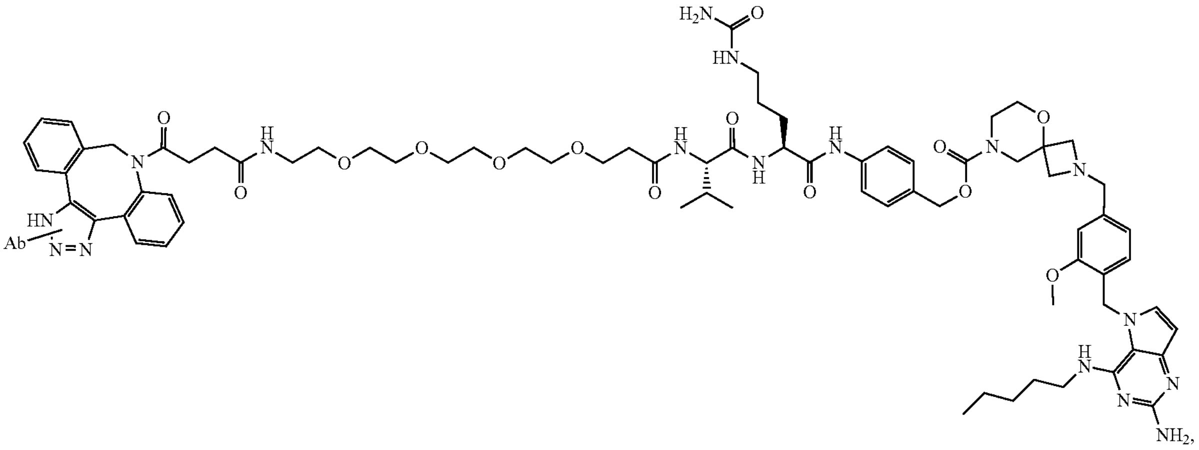

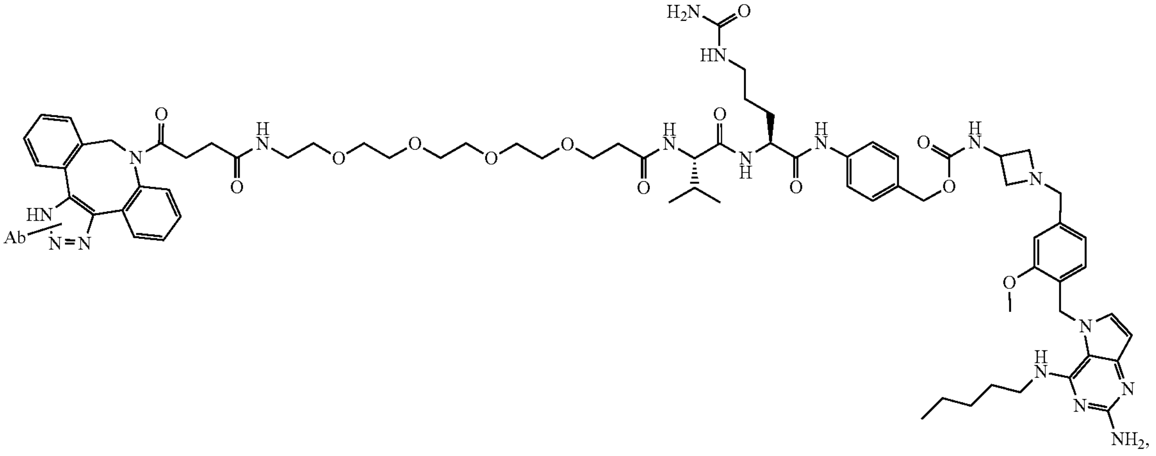

and

-continued

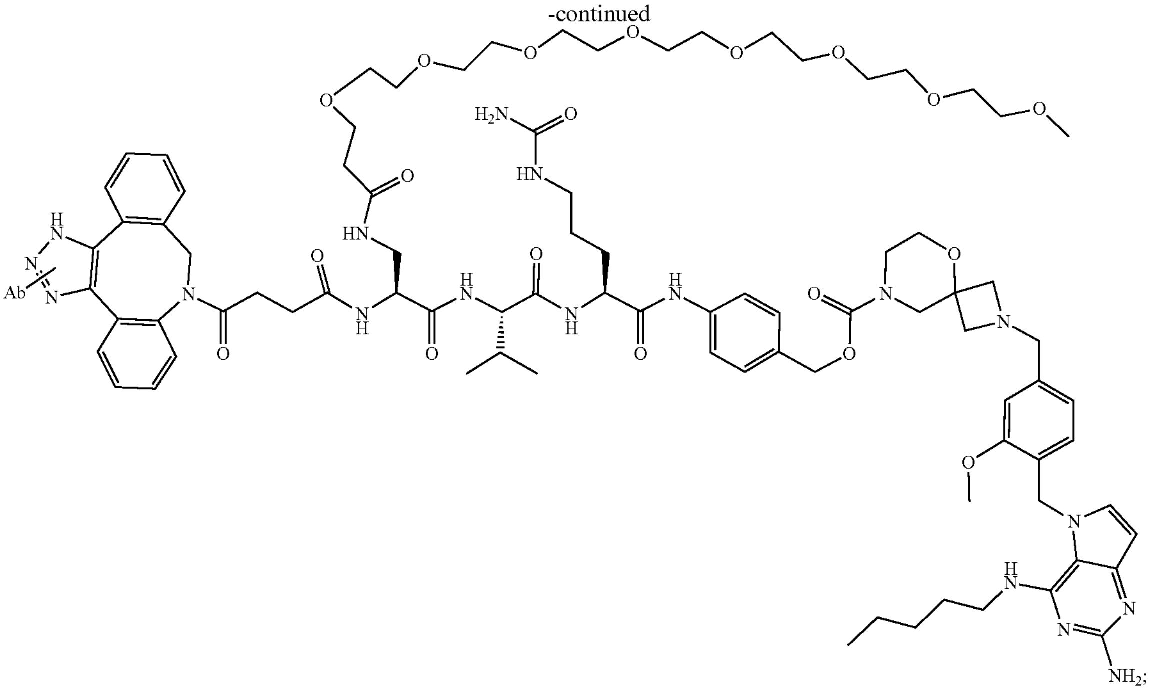

or a pharmaceutically acceptable salt, solvate, stereoisomer, tautomer or mixture of regioisomers thereof.

As used herein, when an antibody is conjugated to a linker precursor, for convenience the conjugate is depicted herein, in some or any embodiments, as follows:

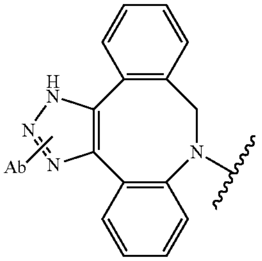

, wherein

indicates the point of attachment to the rest of the molecule. It will be understood by those of skill in the art that the antibody may be bonded to one of two nitrogens on the triazole, thereby forming two possible regioisomers as shown below:

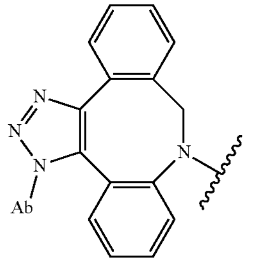

and/or

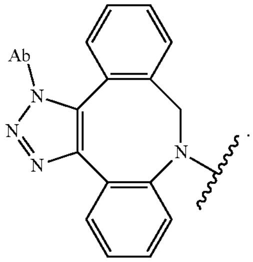

.

As such, either regioisomer or a mixture of possible regioisomers are provided herein. When more than two regioisomers are possible, all individual regioisomers, and all mixtures thereof, are provided herein.

In some instances, the antibody, or an antigen binding fragment thereof, is selected from the group consisting of anti-BCMA, anti-Muc16, trastuzumab, sofitizumab, anti-GFP, and anti-FolRa, or an antigen binding fragment thereof.

In some instances, the antibody, or an antigen binding fragment thereof, comprises Y180 (pAMF) mutations, F404 pAMF mutations, or both.

In any of the preceding embodiments of Formula (V) or (VI), subscript n is 1-30, 1-10, 1-8, 1-6, 1-4, or 1-2. In some instances, subscript n is 1. In some instances, subscript n is 2. In some instances, subscript n is 3. In some instances, subscript n is 4. In some instances, subscript n is 5. In some instances, subscript n is 6. In some instances, subscript n is 7. In some instances, subscript n is 8. In some instances, subscript n is a number greater than 8.

Also contemplated with the scope of embodiments presented herein are antibody drug conjugates where the antibody is selected from various therapeutic antibodies approved for use, in clinical trials, or in development for clinical use. Such therapeutic antibodies include, but are not limited to, rituximab (Rituxan®, IDEC/Genentech/Roche)

(see, for example, U.S. Pat. No. 5,736,137), a chimeric anti-CD20 antibody approved to treat Non-Hodgkin's lymphoma; HuMax-CD20, an anti-CD20 currently being developed by Genmab, an anti-CD20 antibody described in U.S. Pat. No. 5,500,362, AME-133 (Applied Molecular Evolution), hA20 (Immunomedics, Inc.), HumaLYM (Intracel), and PR070769 (PCT Application No. PCT/US2003/040426), trastuzumab (Herceptin®, Genentech) (see, for example, U.S. Pat. No. 5,677,171), a humanized anti-Her2/neu antibody approved to treat breast cancer; pertuzumab (rhuMab-2C4, Omnitarg®), currently being developed by Genentech; an anti-Her2 antibody (U.S. Pat. No. 4,753,894; cetuximab (Erbitux®, Imclone) (U.S. Pat. No. 4,943,533; PCT Publication No. WO 96/40210), a chimeric anti-EGFR antibody in clinical trials for a variety of cancers; ABX-EGF (U.S. Pat. No. 6,235,883), currently being developed by Abgenix-Immunex-Amgen; HuMax-EGFr (U.S. Pat. No. 7,247,301), currently being developed by Genmab; 425, EMD55900, EMD62000, and EMD72000 (Merck KGaA) (U.S. Pat. No. 5,558,864; Murthy, et al. (1987) Arch. Biochem. Biophys. 252(2): 549-60; Rodeck, et al. (1987) J. Cell. Biochem. 35(4): 315-20; Kettleborough, et al. (1991) Protein Eng. 4(7): 773-83); ICR62 (Institute of Cancer Research) (PCT Publication No. WO 95/20045; Modjtahedi, et al. (1993) J. Cell. Biophys. 22 (I-3): 129-46; Modjtahedi, et al. (1993) Br. J. Cancer 67(2): 247-53; Modjtahedi, et al. (1996) Br. J. Cancer 73(2): 228-35; Modjtahedi, et al. (2003) Int. J. Cancer 105(2): 273-80); TheraCIM hR3 (YM Biosciences, Canada and Centro de Immunologia Molecular, Cuba (U.S. Pat. Nos. 5,891,996; 6,506,883; Mateo, et al. (1997) Immunotechnol. 3(1): 71-81); mAb-806 (Ludwig Institute for Cancer Research, Memorial Sloan-Kettering) (Jungbluth, et al. (2003) Proc. Natl. Acad. Sci. USA. 100(2): 639-44); KSB-102 (KS Biomedix); MR1-1 (IVAX, National Cancer Institute) (PCT Publication No. WO 01/62931A2); and SC100 (Scancell) (PCT Publication No. WO 01/88138); alemtuzumab (Campath®, Millenium), a humanized mAb currently approved for treatment of B-cell chronic lymphocytic leukemia; muromonab-CD3 (Orthoclone OKT3®), an anti-CD3 antibody developed by Ortho Biotech/Johnson & Johnson, ibritumomab tiuxetan (Zevalin®), an anti-CD20 antibody developed by IDEC/Schering AG, gemtuzumab ozogamicin (Mylotarg®), an anti-CD33 (p67 protein) antibody developed by Celltech/Wyeth, alefacept (Amevive®), an anti-LFA-3 Fc fusion developed by Biogen), abciximab (ReoPro®), developed by Centocor/Lilly, basiliximab (Simulect®), developed by Novartis, palivizumab (Synagis®), developed by Medimmune, infliximab (Remicade®), an anti-TNFalpha antibody developed by Centocor, adalimumab (Humira®), an anti-TNFalpha antibody developed by Abbott, Humicade®, an anti-TNFalpha antibody developed by Celltech, golimumab (CNTO-148), a fully human TNF antibody developed by Centocor, etanercept (Enbrel®), an p75 TNF receptor Fc fusion developed by Immunex/Amgen, Ienercept, an p55TNF receptor Fc fusion previously developed by Roche, ABX-CBL, an anti-CD147 antibody being developed by Abgenix, ABX-IL8, an anti-IL8 antibody being developed by Abgenix, ABX-MA1, an anti-MUC18 antibody being developed by Abgenix, Pemtumomab (R1549, 90Y-muHMFG1), an anti-MUC1 in development by Antisoma, Therex (R1550), an anti-MUC1 antibody being developed by Antisoma, AngioMab (AS1405), being developed by Antisoma, HuBC-1, being developed by Antisoma, Thioplatin (AS1407) being developed by Antisoma, Antegren® (natalizumab), an anti-alpha-4-beta-1 (VLA-4) and alpha-4-beta-7 antibody being developed by Biogen, VLA-1 mAb, an anti-VLA-1 integrin antibody being developed by Biogen, LTBR mAb, an anti-lymphotoxin beta receptor (LTBR) antibody being developed by Biogen, CAT-152, an anti-TGF-β antibody being developed by Cambridge Antibody Technology, ABT 874 (J695), an anti-IL-12 p40 antibody being developed by Abbott, CAT-192, an anti-TGFβ1 antibody being developed by Cambridge Antibody Technology and Genzyme, CAT-213, an anti-Eotaxin1 antibody being developed by Cambridge Antibody Technology, LymphoStat-B® an anti-Blys antibody being developed by Cambridge Antibody Technology and Human Genome Sciences Inc., TRAIL-R1 mAb, an anti-TRAIL-R1 antibody being developed by Cambridge Antibody Technology and Human Genome Sciences, Inc., Avastin® bevacizumab, rhuMAb-VEGF), an anti-VEGF antibody being developed by Genentech, an anti-HER receptor family antibody being developed by Genentech, Anti-Tissue Factor (ATF), an anti-Tissue Factor antibody being developed by Genentech, Xolair® (Omalizumab), an anti-IgE antibody being developed by Genentech, Raptiva® (Efalizumab), an anti-CD11a antibody being developed by Genentech and Xoma, MLN-02 Antibody (formerly LDP-02), being developed by Genentech and Millenium Pharmaceuticals, HuMax CD4, an anti-CD4 antibody being developed by Genmab, HuMax-IL15, an anti-IL15 antibody being developed by Genmab and Amgen, HuMax-Inflam, being developed by Genmab and Medarex, HuMax-Cancer, an anti-Heparanase I antibody being developed by Genmab and Medarex and Oxford GcoSciences, HuMax-Lymphoma, being developed by Genmab and Amgen, HuMax-TAC, being developed by Genmab, IDEC-131, and anti-CD40L antibody being developed by IDEC Pharmaceuticals, IDEC-151 (Clenoliximab), an anti-CD4 antibody being developed by IDEC Pharmaceuticals, IDEC-114, an anti-CD80 antibody being developed by IDEC Pharmaceuticals, IDEC-152, an anti-CD 23 being developed by IDEC Pharmaceuticals, anti-macrophage migration factor (MIF) antibodies being developed by IDEC Pharmaceuticals, BEC2, an anti-idiotypic antibody being developed by Imclone, IMC-1C11, an anti-KDR antibody being developed by Imclone, DC101, an anti-flk-1 antibody being developed by Imclone, anti-VE cadherin antibodies being developed by Imclone, CEA-Cide® (Iabetuzumab), an anti-carcinoembryonic antigen (CEA) antibody being developed by Immunomedics, LymphoCide® (Epratuzumab), an anti-CD22 antibody being developed by Immunomedics, AFP-Cide, being developed by Immunomedics, MyelomaCide, being developed by Immunomedics, LkoCide, being developed by Immunomedics, ProstaCide, being developed by Immunomedics, MDX-010, an anti-CTLA4 antibody being developed by Medarex, MDX-060, an anti-CD30 antibody being developed by Medarex, MDX-070 being developed by Medarex, MDX-018 being developed by Medarex, Osidem® (IDM-1), and anti-Her2 antibody being developed by Medarex and Immuno-Designed Molecules, HuMax®-CD4, an anti-CD4 antibody being developed by Medarex and Genmab, HuMax-IL15, an anti-IL15 antibody being developed by Medarex and Genmab, CNTO 148, an anti-TNFα antibody being developed by Medarex and Centocor/J&J, CNTO 1275, an anti-cytokine antibody being developed by Centocor/J&J, MOR101 and MOR102, anti-intercellular adhesion molecule-1 (ICAM-1) (CD54) antibodies being developed by MorphoSys, MOR201, an anti-fibroblast growth factor receptor 3 (FGFR-3) antibody being developed by MorphoSys, Nuvion® (visilizumab), an anti-CD3 antibody being developed by Protein Design Labs, HuZAF®, an anti-gamma interferon antibody being developed by Protein Design Labs, Anti-α5β1 Integrin, being developed by Protein Design Labs, anti-IL-12, being developed by Protein Design Labs, ING-1, an anti-Ep-CAM antibody being developed by Xoma, Xolair® (Omalizumab) a humanized anti-IgE antibody developed by Genentech and Novartis, and MLN01, an anti-Beta2 integrin antibody being developed by Xoma. In another embodiment, the therapeutics include KRN330 (Kirin); huA33 antibody (A33, Ludwig Institute for Cancer Research); CNTO 95 (alpha V integrins, Centocor); MEDI-522 (alpha Vβ3integrin, Medimmune); volociximab (alpha Vβ1 integrin, Biogen/PDL); Human mAb 216 (B cell glycosolated epitope, NCl); BiTE MT103 (bispecific CD19×CD3, Medimmune); 4G7×H22 (Bispecific Bcell×FcgammaR1, Medarex/Merck KGa); rM28 (Bispecific CD28×MAPG, EP Patent No. EP1444268); MDX447 (EMD 82633) (Bispecific CD64×EGFR, Medarex); Catumaxomab (removab) (Bispecific EpCAM×anti-CD3, Trion/Fres); Ertumaxomab (bispecific HER2/CD3, Fresenius Biotech); oregovomab (OvaRex) (CA-125, ViRexx); Rencarex® (WX G250) (carbonic anhydrase IX, Wilex); CNTO 888 (CCL2, Centocor); TRC105 (CD105 (endoglin), Tracon); BMS-663513 (CD137 agonist, Bristol Myers Squibb); MDX-1342 (CD19, Medarex); Siplizumab (MEDI-507) (CD2, Medimmune); Ofatumumab (Humax-CD20) (CD20, Genmab); Rituximab (Rituxan) (CD20, Genentech); veltuzumab (hA20) (CD20, Immunomedics); Epratuzumab (CD22, Amgen); lumiliximab (IDEC 152) (CD23, Biogen); muromonab-CD3 (CD3, Ortho); HuM291 (CD3 fc receptor, PDL Biopharma); HeFi-1, CD30, NCl); MDX-060 (CD30, Medarex); MDX-1401 (CD30, Medarex); SGN-30 (CD30, Seattle Genentics); SGN-33 (Lintuzumab) (CD33, Seattle Genentics); Zanolimumab (HuMax-CD4) (CD4, Genmab); HCD122 (CD40, Novartis); SGN-40 (CD40, Seattle Genentics); Campath1h (Alemtuzumab) (CD52, Genzyme); MDX-1411 (CD70, Medarex); hLL1 (EPB-1) (CD74.38, Immunomedics); Galiximab (IDEC-144) (CD80, Biogen); MT293 (TRC093/D93) (cleaved collagen, Tracon); HuLuc63 (CS1, PDL Pharma); ipilimumab (MDX-010) (CTLA4, Bristol Myers Squibb); Tremelimumab (Ticilimumab, CP-675,2) (CTLA4, Pfizer); HGS-ETR1 (Mapatumumab) (DR4TRAIL-R1 agonist, Human Genome Science/Glaxo Smith Kline); AMG-655 (DR5, Amgen); Apomab (DR5, Genentech); CS-1008 (DR5, Daiichi Sankyo); HGS-ETR2 (lexatumumab) (DR5TRAIL-R2 agonist, HGS); Cetuximab (Erbitux) (EGFR, Imclone); IMC-11F8, (EGFR, Imclone); Nimotuzumab (EGFR, YM Bio); Panitumumab (Vectabix) (EGFR, Amgen); Zalutumumab (HuMaxEGFr) (EGFR, Genmab); CDX-110 (EGFRvIII, AVANT Immunotherapeutics); adecatumumab (MT201) (Epcam, Merck); edrecolomab (Panorex, 17-1A) (Epcam, Glaxo/Centocor); MORAb-003 (folate receptor a, Morphotech); KW-2871 (ganglioside GD3, Kyowa); MORAb-009 (GP-9, Morphotech); CDX-1307 (MDX-1307) (hCGb, Celldex); Trastuzumab (Herceptin) (HER2, Celldex); Pertuzumab (rhuMAb 2C4) (HER2 (DI), Genentech); apolizumab (HLA-DR beta chain, PDL Pharma); AMG-479 (IGF-1R, Amgen); anti-IGF-1R R1507 (IGF1-R, Roche); CP 751871 (IGF1-R, Pfizer); IMC-A12 (IGF1-R, Imclone); BIIB022 (IGF-1R, Biogen); Mik-beta-1 (IL-2Rb (CD122), Hoffman LaRoche); CNTO 328 (IL6, Centocor); Anti-KIR (1-7F9) (Killer cell Ig-like Receptor (KIR), Novo); Hu3S193 (Lewis (y), Wyeth, Ludwig Institute of Cancer Research); hCBE-11 (LTOR, Biogen); HuHMFG1 (MUC1, Antisoma/NCl); RAV12 (N-linked carbohydrate epitope, Raven); CAL (parathyroid hormone-related protein (PTH-rP), University of California); CT-011 (PD1, CureTech); MDX-1106 (ono-4538) (PD1, Medarex/Ono); MAb CT-011 (PD1, Curetech); IMC-3G3 (PDGFRa, Imclone); bavituximab (phosphatidylserine, Peregrine); huJ591 (PSMA, Cornell Research Foundation); muJ591 (PSMA, Cornell Research Foundation); GC1008 (TGFb (pan) inhibitor (IgG4), Genzyme); Infliximab (Remicade) (TNFa, Centocor); A27.15 (transferrin receptor, Salk Institute, INSERN WO 2005/111082); E2.3 (transferrin receptor, Salk Institute); Bevacizumab (Avastin) (VEGF, Genentech); HuMV833 (VEGF, Tsukuba Research Lab, PCT Publication No. WO/2000/034337, University of Texas); IMC-18F1 (VEGFR1, Imclone); IMC-1121 (VEGFR2, Imclone).

Examples of useful bispecific parent antibodies include, but are not limited to, those with one antibody directed against a tumor cell antigen and the other antibody directed against a cytotoxic trigger molecule such as anti-FcγRI/anti-CD 15, anti-p185$^{HER2}$/FcγRIII (CD16), anti-CD3/anti-malignant B-cell (1D10), anti-CD3/anti-p185$^{HER2}$, anti-CD3/anti-p97, anti-CD3/anti-renal cell carcinoma, anti-CD3/anti-OVCAR-3, anti-CD3/L-D1 (anti-colon carcinoma), anti-CD3/anti-melanocyte stimulating hormone analog, anti-EGF receptor/anti-CD3, anti-CD3/anti-CAMA1, anti-CD3/anti-CD19, anti-CD3/MoV18, anti-neural cell adhesion molecule (NCAM)/anti-CD3, anti-folate binding protein (FBP)/anti-CD3, anti-pan carcinoma associated antigen (AMOC-31)/anti-CD3; bispecific antibodies with one antibody which binds specifically to a tumor antigen and another antibody which binds to a toxin such as anti-saporin/anti-Id-1, anti-CD22/anti-saporin, anti-CD7/anti-saporin, anti-CD38/anti-saporin, anti-CEA/anti-ricin A chain, anti-interferon-α (IFN-α)/anti-hybridoma idiotype, anti-CEA/anti-vinca alkaloid; bispecific antibodies for converting enzyme activated prodrugs such as anti-CD30/anti-alkaline phosphatase (which catalyzes conversion of mitomycin phosphate prodrug to mitomycin alcohol); bispecific antibodies which can be used as fibrinolytic agents such as anti-fibrin/anti-tissue plasminogen activator (tPA), anti-fibrin/anti-urokinase-type plasminogen activator (uPA); bispecific antibodies for targeting immune complexes to cell surface receptors such as anti-low density lipoprotein (LDL)/anti-Fc receptor (e.g. FcγRI, FcγRII or FcγRIII); bispecific antibodies for use in therapy of infectious diseases such as anti-CD3/anti-herpes simplex virus (HSV), anti-T-cell receptor: CD3 complex/anti-influenza, anti-FcγR/anti-HIV; bispecific antibodies for tumor detection in vitro or in vivo such as anti-CEA/anti-EOTUBE, anti-CEA/anti-DPTA, anti-anti-p185$^{HER2}$/anti-hapten; bispecific antibodies as vaccine adjuvants (see Fanger, M W et al., Crit Rev Immunol. 1992; 12(34):101-24, which is incorporated by reference herein); and bispecific antibodies as diagnostic tools such as anti-rabbit IgG/anti-ferritin, anti-horse radish peroxidase (HRP)/anti-hormone, anti-somatostatin/anti-substance P, anti-HRP/anti-FITC, anti-CEA/anti-β-galactosidase (see Nolan, O et R. O'Kennedy, Biochim Biophys Acta. 1990 Aug. 1; 1040 (1):1-11, which is incorporated by reference herein). Examples of trispecific antibodies include anti-CD3/anti-CD4/anti-CD37, anti-CD3/anti-CD5/anti-CD37 and anti-CD3/anti-CD8/anti-CD37.

In any of the foregoing embodiments wherein the antibody conjugate has a structure according to Formulas (V) and (VI), the bracketed structure can be covalently bonded to one or more non-natural amino acids of the antibody, wherein the one or more non-natural amino acids are located at sites independently selected from the group consisting of: HC-F241, HC-F404, HC-Y180, and LC-K42, and combinations thereof, according to the Kabat or EU numbering scheme of Kabat. In some embodiments, the bracketed structure is covalently bonded to one or more non-natural amino acids at site HC-F404 of the antibody. In some embodiments, the bracketed structure is covalently bonded to one or more non-natural amino acids at site HC-Y180 of the antibody. In some embodiments, the bracketed structure is covalently bonded to one or more non-natural amino acids at site HC-F241 of the antibody. In some embodiments, the bracketed structure is covalently bonded to one or more non-natural amino acids at site LC-K42 of the antibody. In some embodiments, the bracketed structure is covalently bonded to one or more non-natural amino acids at sites HC-F404 and HC-Y180 of the antibody. In some embodiments, the bracketed structure is covalently bonded to one or more non-natural amino acids at sites HC-F241, HC-F404 and HC-Y180 of the antibody. In some embodiments, at least one bracketed structure is covalently bonded to a non-natural amino acid at site HC-F404 of the antibody, and at least one bracketed structure is covalently bonded a non-natural amino acid at site HC-Y180 of the antibody. In some embodiments, the bracketed structure is covalently bonded to one or more non-natural amino acids at sites HC-Y180 and LC-K42 of the antibody. In some embodiments, the bracketed structure is covalently bonded to one or more non-natural amino acids at sites HC-F404 and LC-K42 of the antibody. In particular embodiments, each non-natural amino acid is a residue according to Formula (30).

In additional embodiments, an antibody conjugate can have a further payload selected from the group consisting of a label, a dye, a polymer, a water-soluble polymer, polyethylene glycol, a derivative of polyethylene glycol, a photocrosslinker, a cytotoxic compound, a radionuclide, a drug, an affinity label, a photoaffinity label, a reactive compound, a resin, a second protein or polypeptide or polypeptide analog, an antibody or antibody fragment, a metal chelator, a cofactor, a fatty acid, a carbohydrate, a polynucleotide, a DNA, a RNA, an antisense polynucleotide, a peptide, a water-soluble dendrimer, a cyclodextrin, an inhibitory ribonucleic acid, a biomaterial, a nanoparticle, a spin label, a fluorophore, a metal-containing moiety, a radioactive moiety, a novel functional group, a group that covalently or noncovalently interacts with other molecules, a photocaged moiety, a photoisomerizable moiety, biotin, a derivative of biotin, a biotin analogue, a moiety incorporating a heavy atom, a chemically cleavable group, a photocleavable group, an elongated side chain, a carbon-linked sugar, a redox-active agent, an amino thioacid, a toxic moiety, an isotopically labeled moiety, a biophysical probe, a phosphorescent group, a chemiluminescent group, an electron dense group, a magnetic group, an intercalating group, a chromophore, an energy transfer agent, a biologically active agent, a detectable label, a small molecule, or any combination thereof. In an embodiment, the payload is a label, a dye, a polymer, a cytotoxic compound, a radionuclide, a drug, an affinity label, a resin, a protein, a polypeptide, a polypeptide analog, an antibody, antibody fragment, a metal chelator, a cofactor, a fatty acid, a carbohydrate, a polynucleotide, a DNA, a RNA, a peptide, a fluorophore, or a carbon-linked sugar. In another embodiment, the payload is a label, a dye, a polymer, a drug, an antibody, antibody fragment, a DNA, an RNA, or a peptide.

In certain embodiments, the conjugate comprises one or more water soluble polymers. A wide variety of macromolecular polymers and other molecules can be linked to the polypeptides described herein to modulate biological properties of the polypeptide, and/or provide new biological properties to the polypeptide. These macromolecular polymers can be linked to the polypeptide via a naturally encoded amino acid, via a non-naturally encoded amino acid, or any functional substituent of a natural or modified amino acid, or any substituent or functional group added to a natural or modified amino acid. The molecular weight of the polymer may be of a wide range, including but not limited to, between about 100 Da and about 100,000 Da or more.

The polymer selected may be water soluble so that a protein to which it is attached does not precipitate in an aqueous environment, such as a physiological environment. The polymer may be branched or unbranched. Preferably, for therapeutic use of the end-product preparation, the polymer will be pharmaceutically acceptable.

In certain embodiments, the proportion of polyethylene glycol molecules to polypeptide molecules will vary, as will their concentrations in the reaction mixture. In general, the optimum ratio (in terms of efficiency of reaction in that there is minimal excess unreacted protein or polymer) may be determined by the molecular weight of the polyethylene glycol selected and on the number of available reactive groups available. As relates to molecular weight, typically the higher the molecular weight of the polymer, the fewer number of polymer molecules which may be attached to the protein. Similarly, branching of the polymer should be taken into account when optimizing these parameters. Generally, the higher the molecular weight (or the more branches) the higher the polymer:protein ratio.

The water soluble polymer may be any structural form including but not limited to linear, forked or branched. Typically, the water soluble polymer is a poly(alkylene glycol), such as poly(ethylene glycol) (PEG), but other water soluble polymers can also be employed. By way of example, PEG is used to describe certain embodiments.

PEG is a well-known, water soluble polymer that is commercially available or can be prepared by ring-opening polymerization of ethylene glycol according to methods well known in the art (Sandler and Karo, Polymer Synthesis, Academic Press, New York, Vol. 3, pages 138-161). The term "PEG" is used broadly to encompass any polyethylene glycol molecule, without regard to size or to modification at an end of the PEG, and can be represented as linked to a polypeptide by the formula: $X'O—(CH_2CH_2O)_n—CH_2CH_2—Y$ where n is 2 to 10,000, X is H or a terminal modification, including but not limited to, a $C_{1-4}$ alkyl, and Y is the attachment point to the polypeptide.

In some cases, a PEG terminates on one end with hydroxy or methoxy, i.e., X' is H or $CH_3$ ("methoxy PEG"). Alternatively, the PEG can terminate with a reactive group, thereby forming a bifunctional polymer. Typical reactive groups can include those reactive groups that are commonly used to react with the functional groups found in the 20 common amino acids (including but not limited to, maleimide groups, activated carbonates (including but not limited to, p-nitrophenyl ester), activated esters (including but not limited to, N-hydroxysuccinimide, p-nitrophenyl ester, and aldehydes) as well as functional groups that are inert to the 20 common amino acids but that react specifically with complementary functional groups present in non-naturally encoded amino acids (including but not limited to, azide groups, alkyne groups). It is noted that the other end of the PEG, which is shown in the above formula by Y, will attach either directly or indirectly to a polypeptide via a naturally-occurring or non-naturally encoded amino acid. For instance, Y may be an amide, carbamate or urea linkage to an amine group (including but not limited to, the epsilon amine of lysine or the N-terminus) of the polypeptide. Alternatively, Y may be a maleimide linkage to a thiol group (including but not limited to, the thiol group of cysteine). Alternatively, Y may be a linkage to a residue not commonly accessible via the 20 common amino acids. For example, an azide group on the PEG can be reacted with an alkyne group on the polypeptide to form a Huisgen [3+2] cycloaddition product. Alternatively, an alkyne group on the PEG can be reacted with an azide group present in a non-naturally encoded amino acid, such as the modified amino acids described herein, to form a similar product. In some embodiments, a strong nucleophile (including but not limited to, hydrazine, hydrazide, hydroxylamine, semicarbazide) can be reacted with an aldehyde or ketone group present in a non-naturally encoded amino acid to form a hydrazone, oxime or semicarbazone, as applicable, which in some cases can be further reduced by treatment with an appropriate reducing agent. Alternatively, the strong nucleophile can be incorporated into the polypeptide via a non-naturally encoded amino acid and used to react preferentially with a ketone or aldehyde group present in the water soluble polymer.

Any molecular mass for a PEG can be used as practically desired, including but not limited to, from about 100 Daltons (Da) to 100,000 Da or more as desired (including but not limited to, sometimes 0.1-50 kDa or 10-40 kDa). Branched chain PEGs, including but not limited to, PEG molecules with each chain having a MW ranging from 1-100 kDa (including but not limited to, 1-50 kDa or 5-20 kDa) can also be used. A wide range of PEG molecules are described in, including but not limited to, the Shearwater Polymers, Inc. catalog, and the Nektar Therapeutics catalog, incorporated herein by reference.

Generally, at least one terminus of the PEG molecule is available for reaction with the antibody. For example, PEG derivatives bearing alkyne and azide moieties for reaction with amino acid side chains can be used to attach PEG to non-naturally encoded amino acids as described herein. If the non-naturally encoded amino acid comprises an azide, then the PEG will typically contain either an alkyne moiety to effect formation of the [3+2] cycloaddition product or an activated PEG species (i.e., ester, carbonate) containing a phosphine group to effect formation of the amide linkage. Alternatively, if the non-naturally encoded amino acid comprises an alkyne, then the PEG will typically contain an azide moiety to effect formation of the [3+2] Huisgen cycloaddition product. If the non-naturally encoded amino acid comprises a carbonyl group, the PEG will typically comprise a potent nucleophile (including but not limited to, a hydrazide, hydrazine, hydroxylamine, or semicarbazide functionality) in order to effect formation of corresponding hydrazone, oxime, and semicarbazone linkages, respectively. In other alternatives, a reverse of the orientation of the reactive groups described herein can be used, i.e., an azide moiety in the non-naturally encoded amino acid can be reacted with a PEG derivative containing an alkyne.

In some embodiments, the polypeptide variant with a PEG derivative contains a chemical functionality that is reactive with the chemical functionality present on the side chain of the non-naturally encoded amino acid.

In certain embodiments, the payload is an azide- or acetylene-containing polymer comprising a water soluble polymer backbone having an average molecular weight from about 800 Da to about 100,000 Da. The polymer backbone of the water-soluble polymer can be poly(ethylene glycol). However, it should be understood that a wide variety of water soluble polymers including but not limited to poly (ethylene)glycol and other related polymers, including poly (dextran) and poly(propylene glycol), are also suitable for use and that the use of the term PEG or poly(ethylene glycol) is intended to encompass and include all such molecules. The term PEG includes, but is not limited to, poly(ethylene glycol) in any of its forms, including bifunctional PEG, multiarmed PEG, derivatized PEG, forked PEG, branched PEG, pendent PEG (i.e. PEG or related polymers having one or more functional groups pendent to the polymer backbone), or PEG with degradable linkages therein.

The polymer backbone can be linear or branched. Branched polymer backbones are generally known in the art. Typically, a branched polymer has a central branch core moiety and a plurality of linear polymer chains linked to the central branch core. PEG is commonly used in branched forms that can be prepared by addition of ethylene oxide to various polyols, such as glycerol, glycerol oligomers, pentaerythritol and sorbitol. The central branch moiety can also be derived from several amino acids, such as lysine. The branched poly(ethylene glycol) can be represented in general form as $R(\text{-PEG-OH})_m$ in which R is derived from a core moiety, such as glycerol, glycerol oligomers, or pentaerythritol, and m represents the number of arms. Multi-armed PEG molecules, such as those described in U.S. Pat. Nos. 5,932,462 5,643,575; 5,229,490; 4,289,872; U.S. Pat. Appl. 2003/0143596; WO 96/21469; and WO 93/21259, each of which is incorporated by reference herein in its entirety, can also be used as the polymer backbone.

Branched PEG can also be in the form of a forked PEG represented by $PEG(\text{-YCHZ}_2)_n$, where Y is a linking group and Z is an activated terminal group linked to CH by a chain of atoms of defined length.

Yet another branched form, the pendant PEG, has reactive groups, such as carboxyl, along the PEG backbone rather than at the end of PEG chains.

In addition to these forms of PEG, the polymer can also be prepared with weak or degradable linkages in the backbone. For example, PEG can be prepared with ester linkages in the polymer backbone that are subject to hydrolysis. As shown herein, this hydrolysis results in cleavage of the polymer into fragments of lower molecular weight: $\text{-PEG-CO}_2\text{-PEG-}+H_2O \rightarrow \text{PEG-CO}_2H+\text{HO-PEG-}$ It is understood by those skilled in the art that the term poly(ethylene glycol) or PEG represents or includes all the forms known in the art including but not limited to those disclosed herein.

Many other polymers are also suitable for use. In some embodiments, polymer backbones that are water-soluble, with from 2 to about 300 termini, are particularly suitable. Examples of suitable polymers include, but are not limited to, other poly(alkylene glycols), such as poly(propylene glycol) ("PPG"), copolymers thereof (including but not limited to copolymers of ethylene glycol and propylene glycol), terpolymers thereof, mixtures thereof, and the like. Although the molecular weight of each chain of the polymer backbone can vary, it is typically in the range of from about 800 Da to about 100,000 Da, often from about 6,000 Da to about 80,000 Da.

Those of ordinary skill in the art will recognize that the foregoing list for substantially water soluble backbones is by no means exhaustive and is merely illustrative, and that all polymeric materials having the qualities described herein are contemplated as being suitable for use.

In some embodiments the polymer derivatives are "multi-functional", meaning that the polymer backbone has at least two termini, and possibly as many as about 300 termini, functionalized or activated with a functional group. Multi-functional polymer derivatives include, but are not limited to, linear polymers having two termini, each terminus being bonded to a functional group which may be the same or different.

4. Linkers

In certain embodiments, the antibodies can be linked to the payloads with one or more linkers capable of reacting with an antibody amino acid and with a payload group. The one or more linkers can be any linkers apparent to those of skill in the art.

The term "linker" is used herein to refer to groups or bonds that normally are formed as the result of a chemical reaction and typically are covalent linkages.

Useful linkers include those described herein. In certain embodiments, the linker is any divalent or multivalent linker known to those of skill in the art. Useful divalent linkers include alkylene, substituted alkylene, heteroalkylene, substituted heteroalkylene, arylene, substituted arylene, heteroarlyene, and substituted heteroarylene. In certain embodiments, the linker is $C_{1-10}$ alkylene or $C_{1-10}$ heteroalkylene. In some embodiments, the $C_{1-10}$heteoalkylene is PEG.

In certain embodiments, the linker is hydrolytically stable. Hydrolytically stable linkages means that the linkages are substantially stable in water and do not react with water at useful pH values, including but not limited to, under physiological conditions for an extended period of time, perhaps even indefinitely. In certain embodiments, the linker is hydrolytically unstable. Hydrolytically unstable or degradable linkages mean that the linkages are degradable in water or in aqueous solutions, including for example, blood. Enzymatically unstable or degradable linkages mean that the linkage can be degraded by one or more enzymes.

As understood in the art, PEG and related polymers may include degradable linkages in the polymer backbone or in the linker group between the polymer backbone and one or more of the terminal functional groups of the polymer molecule. For example, ester linkages formed by the reaction of PEG carboxylic acids or activated PEG carboxylic acids with alcohol groups on a biologically active agent generally hydrolyze under physiological conditions to release the agent.

Other hydrolytically degradable linkages include, but are not limited to, carbonate linkages; imine linkages resulted from reaction of an amine and an aldehyde; phosphate ester linkages formed by reacting an alcohol with a phosphate group; hydrazone linkages which are reaction product of a hydrazide and an aldehyde; acetal linkages that are the reaction product of an aldehyde and an alcohol; orthoester linkages that are the reaction product of a formate and an alcohol; peptide linkages formed by an amine group, including but not limited to, at an end of a polymer such as PEG, and a carboxyl group of a peptide; and oligonucleotide linkages formed by a phosphoramidite group, including but not limited to, at the end of a polymer, and a 5' hydroxyl group of an oligonucleotide.

A number of different cleavable linkers are known to those of skill in the art. See U.S. Pat. Nos. 4,618,492; 4,542,225, and 4,625,014. The mechanisms for release of an agent from these linker groups include, for example, irradiation of a photolabile bond and acid-catalyzed hydrolysis. U.S. Pat. No. 4,671,958, for example, includes a description of immunoconjugates comprising linkers which are cleaved at the target site in vivo by the proteolytic enzymes of the patient's complement system. The length of the linker may be predetermined or selected depending upon a desired spatial relationship between the polypeptide and the molecule linked to it. In view of the large number of methods that have been reported for attaching a variety of radiodiagnostic compounds, radiotherapeutic compounds, drugs, toxins, and other agents to polypeptides one skilled in the art will be able to determine a suitable method for attaching a given agent to a polypeptide.

The linker may have a wide range of molecular weight or molecular length. Larger or smaller molecular weight linkers may be used to provide a desired spatial relationship or conformation between the polypeptide and the linked entity. Linkers having longer or shorter molecular length may also be used to provide a desired space or flexibility between the polypeptide and the linked entity. Similarly, a linker having a particular shape or conformation may be utilized to impart a particular shape or conformation to the polypeptide or the linked entity, either before or after the polypeptide reaches its target. The functional groups present on each end of the linker may be selected to modulate the release of a polypeptide or a payload under desired conditions. This optimization of the spatial relationship between the polypeptide and the linked entity may provide new, modulated, or desired properties to the molecule.

In some embodiments, provided herein water-soluble bifunctional linkers that have a dumbbell structure that includes: a) an azide, an alkyne, a hydrazine, a hydrazide, a hydroxylamine, or a carbonyl-containing moiety on at least a first end of a polymer backbone; and b) at least a second functional group on a second end of the polymer backbone. The second functional group can be the same or different as the first functional group. The second functional group, in some embodiments, is not reactive with the first functional group. In some embodiments, water-soluble compounds that comprise at least one arm of a branched molecular structure are provided. For example, the branched molecular structure can be a dendritic structure.

In some embodiments, the linker is derived from a linker precursor selected from the group consisting of N-succinimidyl-3-(2-pyridyldithio)propionate (SPDP), N-succinimidyl 4-(2-pyridyldithio)pentanoate (SPP), N-succinimidyl 4-(2-pyridyldithio)butanoate (SPDB), N-succinimidyl-4-(2-pyridyldithio)-2-sulfo-butanoate (sulfo-SPDB), N-succinimidyl iodoacetate (SIA), N-succinimidyl(4-iodoacetyl) aminobenzoate (SIAB), maleimide PEG NHS, N-succinimidyl 4-(maleimidomethyl)cyclohexanecarboxylate (SMCC), N-sulfosuccinimidyl 4-(maleimidomethyl)cyclohexanecarboxylate (sulfo-SMCC) or 2,5-dioxopyrrolidin-1-yl 17-(2,5-dioxo-2,5-dihydro-TH-pyrrol-1-yl)-5,8,11,14-tetraoxo-4,7,10,13-tetraazaheptadecan-1-oate (CX1-1). In a specific embodiment, the linker is derived from the linker precursor N-succinimidyl 4-(maleimidomethyl)cyclohexanecarboxylate (SMCC).

In some embodiments, the linker is derived from a linker precursor selected from the group consisting of dipeptides, tripeptides, tetrapeptides, and pentapeptides. In such embodiments, the linker can be cleaved by a protease. Exemplary dipeptides include, but are not limited to, valine-citrulline (vc or val-cit), alanine-phenylalanine (AF or ala-phe); phenylalanine-lysine (FK or phe-lys); phenylalanine-homolysine (phe-homolys); and N-methyl-valine-citrulline (Me-val-cit). Exemplary tripeptides include, but are not limited to, glycine-valine-citrulline (gly-val-cit), glycine-glycine-glycine (gly-gly-gly), and glycine-methoxyethoxyethyl)serine-valine (gly-val-citalanine OMESerValAla).

In some embodiments, a linker comprises a self-immolative spacer. In certain embodiments, the self-immolative spacer comprises p-aminobenzyl. In some embodiments, a p-aminobenzyl alcohol is attached to an amino acid unit via an amide bond, and a carbamate, methylcarbamate, or carbonate is made between the benzyl alcohol and the payload (Hamann et al. (2005) Expert Opin. Ther. Patents (2005) 15:1087-1103). In some embodiments, the linker comprises p-aminobenzyloxycarbonyl (PAB). Other examples of self-immolative spacers include, but are not limited to, aromatic compounds that are electronically similar to the PAB group, such as 2-aminoimidazol-5-methanol derivatives (U.S. Pat. No. 7,375,078; Hay et al. (1999) Bioorg. Med. Chem. Lett. 9:2237) and ortho- or para-aminobenzylacetals. In some embodiments, spacers can be used that undergo cyclization upon amide bond hydrolysis, such as substituted and unsubstituted 4-aminobutyric acid amides (Rodrigues et al. (1995) Chemistry Biology 2:223), appropriately substituted bicyclo[2.2.1] and bicyclo[2.2.2] ring systems (Storm et al. (1972) J. Amer. Chem. Soc. 94:5815) and 2-aminophenylpropionic acid amides (Amsberry, et al. (1990) J. Org. Chem. 55:5867). Linkage of a drug to the α-carbon of a glycine residue is another example of a self-immolative spacer that may be useful in conjugates (Kingsbury et al. (1984) J. Med. Chem. 27:1447).

In certain embodiments, linker precursors can be combined to form larger linkers. For instance, in certain embodiments, linkers comprise the dipeptide valine-citrulline and p-aminobenzyloxycarbonyl. These are also referenced as citValCit-PAB linkers.

In certain embodiments, the payloads can be linked to the linkers, referred to herein as a linker-payload, with one or more linker groups capable of reacting with an antibody amino acid group. The one or more linkers can be any linkers apparent to those of skill in the art or those set forth herein.

Linker precursors can be prepared as described herein in the Examples section, and/or by standard techniques, or obtained from commercial sources, e.g. WO 2019/055931, WO 2019/055909, WO 2017/132617, WO 2017/132615, each incorporated by reference in its entirety.

Additional linkers are disclosed herein, such as, for example, the linker precursors (A)-(H) and (J)-(M) discussed below.

4.1 Linker-Payloads

In one aspect, provided herein are linker payload compounds of Formula (IV):

Formula (IV)

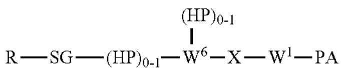

or a pharmaceutically acceptable salt, solvate, stereoisomer, tautomer, or mixture of regioisomers thereof, wherein:

$W^1$ is a single bond, absent or a divalent attaching group;

X is absent

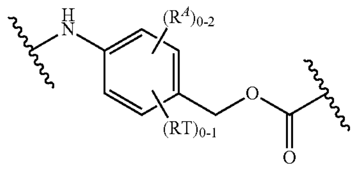

; or

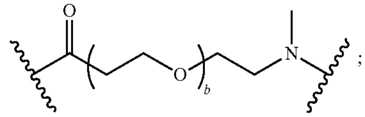

;

subscript b is an integer selected from 1 to 10;

each $R^A$, when present, is independently, at each occurrence, selected from $C_{1-3}$alkyl;

RT, when present, is a release trigger group;

each HP, when present, is a hydrophilic group;

$W^6$ is a residue of a peptide, or absent;

SG is absent, or a divalent spacer group;

R is hydrogen, or a terminal conjugating group; and

PA is a residue of a compound of Formula (I-P), (I), (II), or (III) wherein PA is bonded to the rest of the molecule via —$NR^{3a}$—, the —NH— of —$C(R^{3c})_2$NH—, the nitrogen of an $R^3$ heterocycloalkyl, the nitrogen of an $R^3$ partially saturated heteroaryl, the —NH— of —O—$CH_2$-(phenyl)-$CH_2$—NH—, or a nitrogen of ring B. In one embodiment, provided herein are linker payload compounds of Formula (IV-P):

Formula (IV-P)

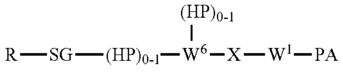

or a pharmaceutically acceptable salt, solvate, stereoisomer, tautomer, or mixture of regioisomers thereof, wherein:

$W^1$ is a single bond, absent or a divalent attaching group;

X is absent,

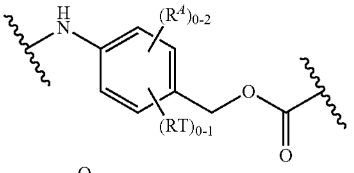

; or

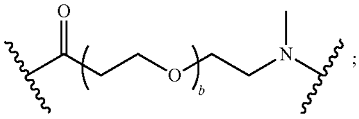

;

subscript b is an integer from 1 to 10;

$R^A$, when present, is independently, at each occurrence, selected from $C_{1-3}$alkyl;

RT, when present, is a release trigger group;

HP, when present, is a hydrophilic group;

$W^6$ is a peptide, or absent;

SG is absent, or a divalent spacer group;

R is hydrogen, a terminal conjugating group, or a divalent residue of a terminal conjugating group; and PA is a payload of Formula (I)

Formula (I)

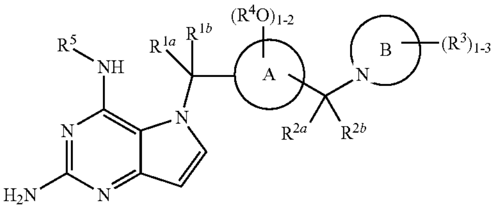

or a pharmaceutically acceptable salt, solvate or N-oxide thereof;

wherein $R^{1a}$, $R^{1b}$, $R^{2a}$, and $R^{2b}$ are independently, at each occurrence, selected from hydrogen, and $C_{1-6}$alkyl;

ring A is cycloalkyl, heterocycloalkyl, monocyclic aryl, monocyclic heteroaryl, fused bicyclic aryl, or fused bicyclic heteroaryl, where heterocycloalkyl and each heteroaryl comprise 1, 2, 3 or 4 heteroatoms selected from N, S, and O;

ring B is a 4-membered N-linked heterocycloalkyl, which is further substituted with 1-2 $R^3$; wherein $R^3$ is, independently, at each occurrence, —$N(R^{3a})_2$, —$OR^{3b}$, —$C(R^{3c})_2NH_2$, $C_{1-6}$alkyl, heterocycloalkyl, heteroaryl, or partially saturated heteroaryl, or two $R^3$ attached to the same carbon, together with the carbon atom to which they are attached, form a spiro-heterocycloalkyl; wherein heterocycloalkyl, spiro-heterocycloalkyl, heteroaryl and partially saturated heteroaryl include 1, 2, 3 or 4 heteroatoms selected from N, S, and O, and are optionally further substituted with 1-2 $C_{1-3}$alkyl;

or ring B is a 5-6 membered N-linked heterocycloalkyl, which is further substituted with 1-3 $R^3$; wherein $R^3$ is, independently, at each occurrence, —$N(R^{3a})_2$, —$OR^{3b}$, —$C(R^{3c})_2NH_2$, heterocycloalkyl, heteroaryl, or partially saturated heteroaryl, or two $R^3$ attached to the same carbon, together with the carbon atom to which they are attached, form a spiro-heterocycloalkyl; wherein heterocycloalkyl, spiro-heterocycloalkyl, heteroaryl and partially saturated heteroaryl include 1, 2, 3 or 4 heteroatoms selected from N, S, and O, and are optionally further substituted with 1-2 $C_{1-3}$alkyl;

or ring B is a 7-10 membered N-linked heterocycloalkyl, which is further substituted with 1-3 $R^3$, or a 5-10 membered N-linked heteroaryl which is further substituted with 1-3 $R^3$; wherein $R^3$ is, independently, at each occurrence, —$N(R^{3a})_2$, —$OR^{3b}$, —$C(R^{3c})_2NH_2$, $C_{1-6}$alkyl, heterocycloalkyl, heteroaryl, or partially saturated heteroaryl, or two $R^3$ attached to the same carbon, together with the carbon atom to which they are attached, form a spiro-heterocycloalkyl; wherein heterocycloalkyl, spiro-heterocycloalkyl, heteroaryl and partially saturated heteroaryl include 1, 2, 3 or 4 heteroatoms selected from N, S, and O, and are optionally further substituted with 1-2 $C_{1-3}$alkyl;

$R^{3a}$ is independently, at each occurrence, selected from hydrogen, $C_{1-6}$alkyl, —C(=O)—$CH_2NH_2$, and cycloalkyl;

$R^{3b}$ is independently, at each occurrence, selected from hydrogen,

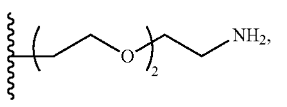

and —$CH_2$-aryl-$CH_2NH_2$;

$R^{3c}$ is independently, at each occurrence, selected from hydrogen, and $C_{1-6}$alkyl, or two $R^{3c}$, together with the carbon atom to which they are attached, form a cycloalkyl;

$R^4$ is $C_{1-6}$alkyl; and $R^5$ is $C_{1-6}$cycloalkyl, or $C_{1-6}$alkyl optionally substituted with halo, hydroxy, alkoxy, amino, $C_{1-6}$alkylamino, $C_{1-6}$dialkylamino, $C_{1-6}$cycloalkyl, aryl or heteroaryl, wherein heteroaryl includes 1, 2, 3 or 4 heteroatoms selected from N, S, and O, and wherein cycloalkyl, aryl and heteroaryl are optionally further substituted with halo, hydroxy, alkyl, or haloalkyl; and wherein PA is bonded to the rest of the molecule via an amino group of $R^3$ or via an amino group of ring B.

In some embodiments of Formula (IV), PA is any residue of a compound, or any group of compounds, of Formula (I), (II) or (III) described herein.

In some embodiments, the compound according to Formula (IV) is according to Formula (IVa), (IVb), (IVc), (IVd), or (IVe):

Formula (IVa)

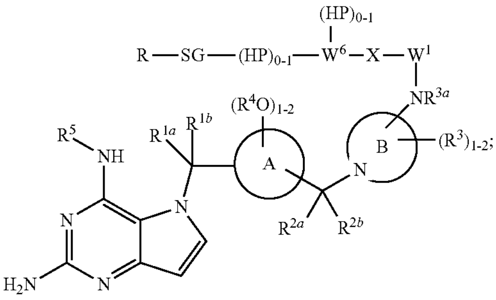

Formula (IVb)

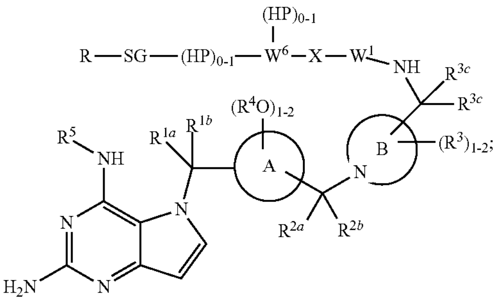

Formula (IVc)

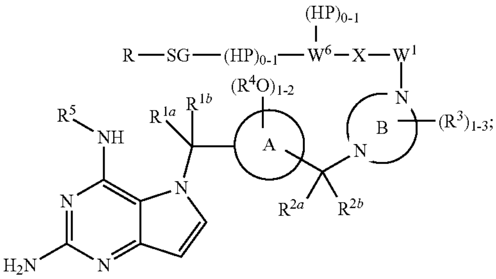

Formula (IVd)

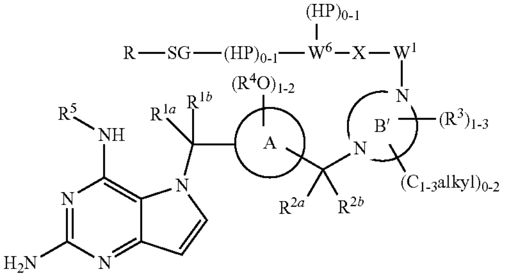

where B' is spiro-heterocycloalkyl which includes 1, 2, 3 or 4 heteroatoms independently selected from N, S, and O; or Formula (IVe)

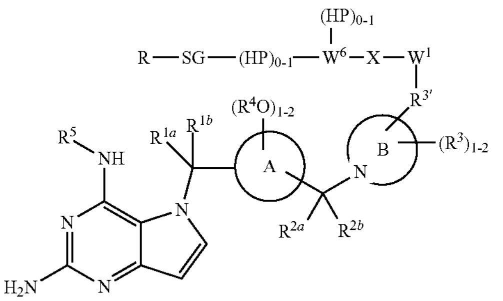

where $R^{3'}$ is heterocycloalkyl or partially saturated heteroaryl, each of which includes 1, 2, 3 or 4 heteroatoms independently selected from N, S, and O, provided that at least one nitrogen is present in the $R^{3'}$ ring and is attached to $W^1$; or $R^{3'}$ is —O—$CH_2$-(phenyl)-$CH_2$—NH— where the NH is attached to $W^1$.

In some instances of Formula (IV), SG is absent,

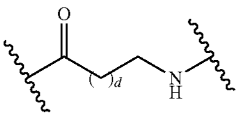, 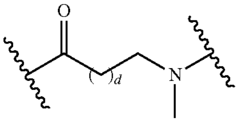, or

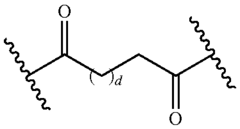, wherein subscript d is an integer selected from 1 to 10, wherein each

indicates a point of attachment to the rest of the formula.

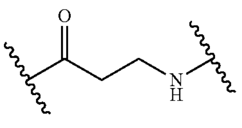, 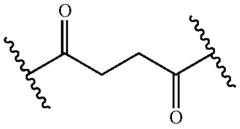,

In some instances of Formula (IV), SG is

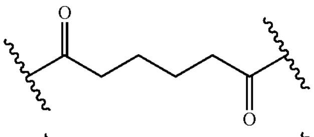, or

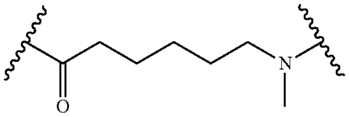, wherein each

indicates a point of attachment to the rest of the formula.

In some instances of Formula (IV), $W^1$, when present, is

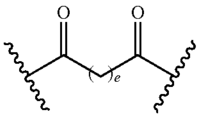, 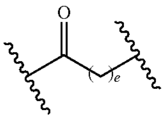 or

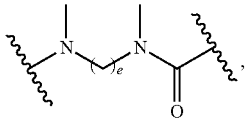, wherein subscript e is an integer selected from 1 to 10, wherein each

indicates a point of attachment to the rest of the formula.

In some instances of Formula (IV), $W^1$, when present, is

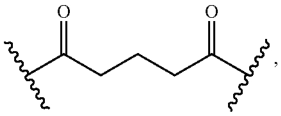, 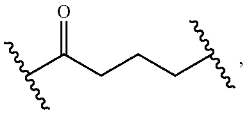, or

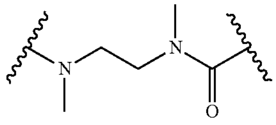

wherein each

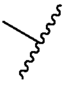

indicates a point of attachment to the rest of the formula.

In some instances of Formula (IV), $W^6$, is a residue of a peptide and comprises natural and/or non-natural amino acids. In some instances of Formula (IV), $W^6$, when present, is a tripeptide residue. In some instances of Formula (IV), $W^6$, when present, is

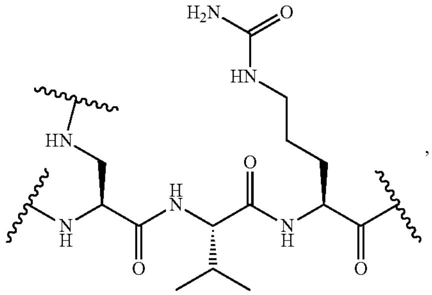

,

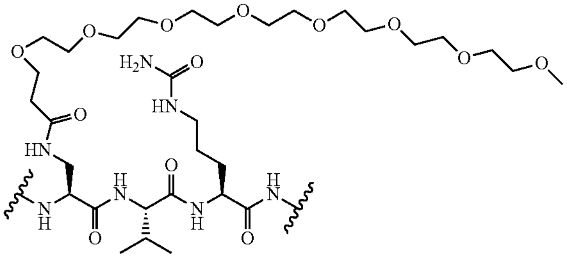

, or

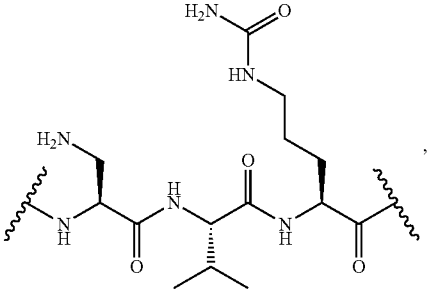

, wherein each

indicates a point of attachment to the rest of the formula.

In some instances of Formula (IV), $W^6$, when present, is a dipeptide residue. In some instances of Formula (IV), $W^6$, when present, is

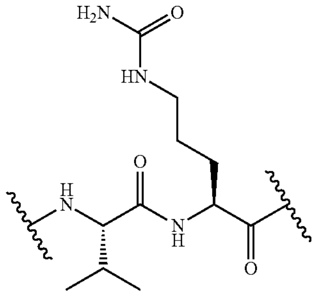

or

-continued

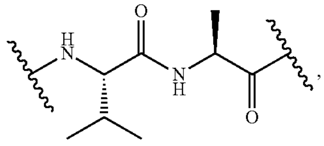

, wherein each

indicates a point of attachment to the rest of the formula.

In some instances of Formula (IV), RT is

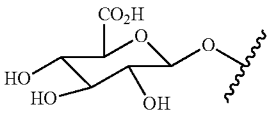

, wherein

indicates a point of attachment to the rest of the formula.

In some instances of Formula (IV), HP, when present is a PEG group. In some instances of Formula (IV), HP when present is

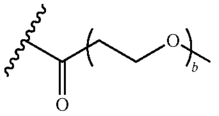

or

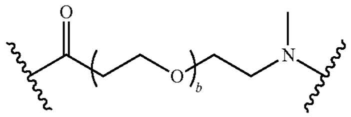

wherein subscript b is an integer selected from 1 to 10, and

indicates a point of attachment to the rest of the formula.

In some instances of Formula (IV), R is:
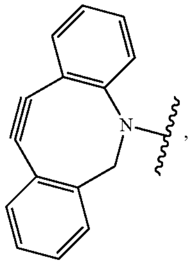,
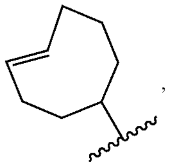,
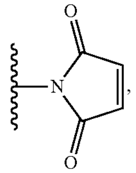,
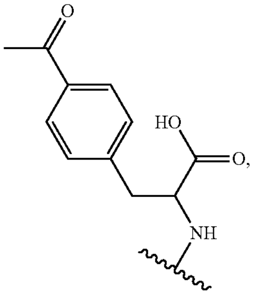
-continued
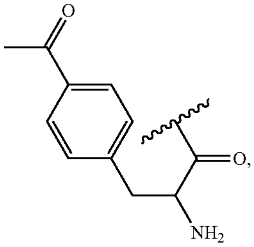
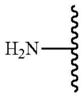,
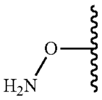
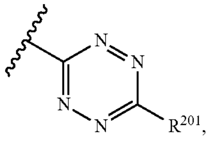
—$N_3$, or —SH; wherein $R^{201}$ is $C_{1-6}$alkyl, and each
indicates a point of attachment to the rest of the formula.
In some embodiments, linker payload compounds of Formula (VI) are selected from the group consisting of:
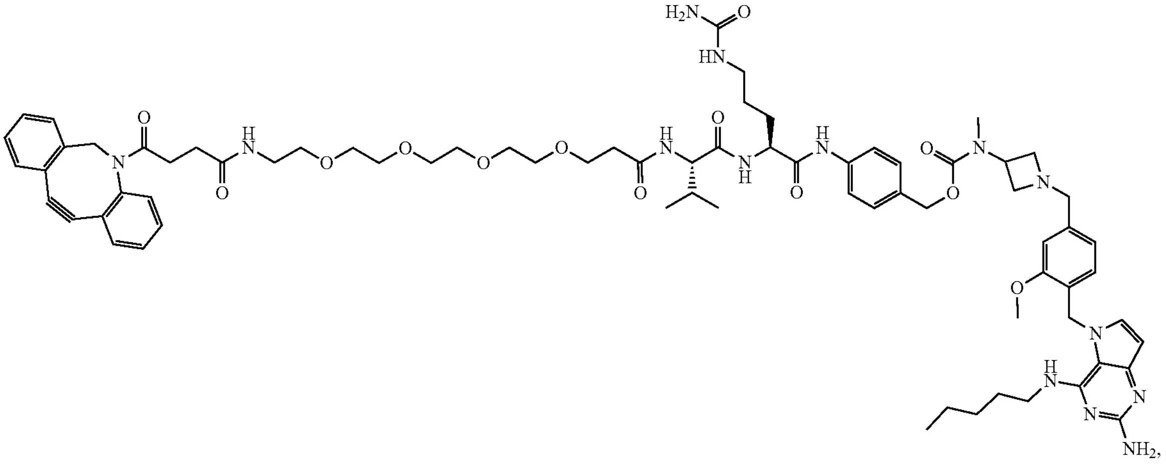

-continued
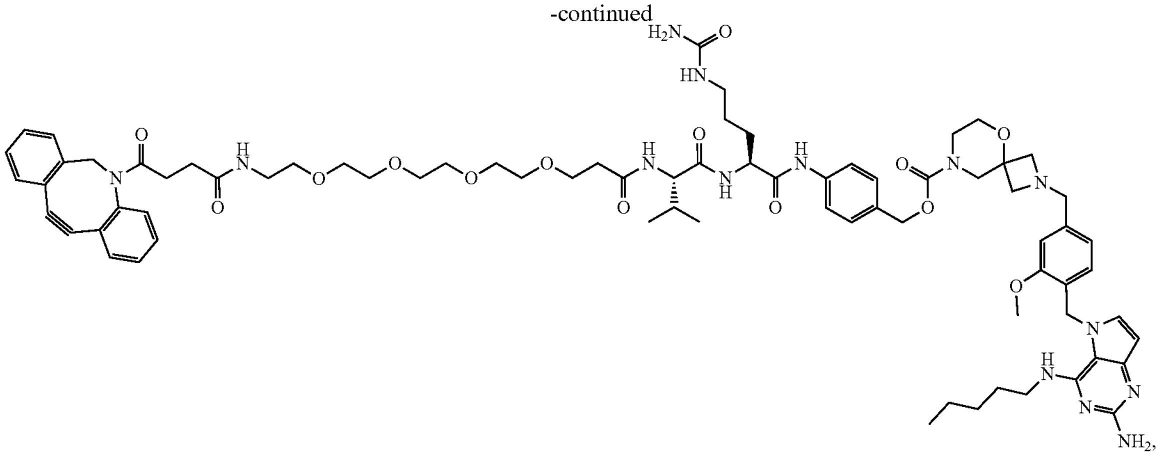
,
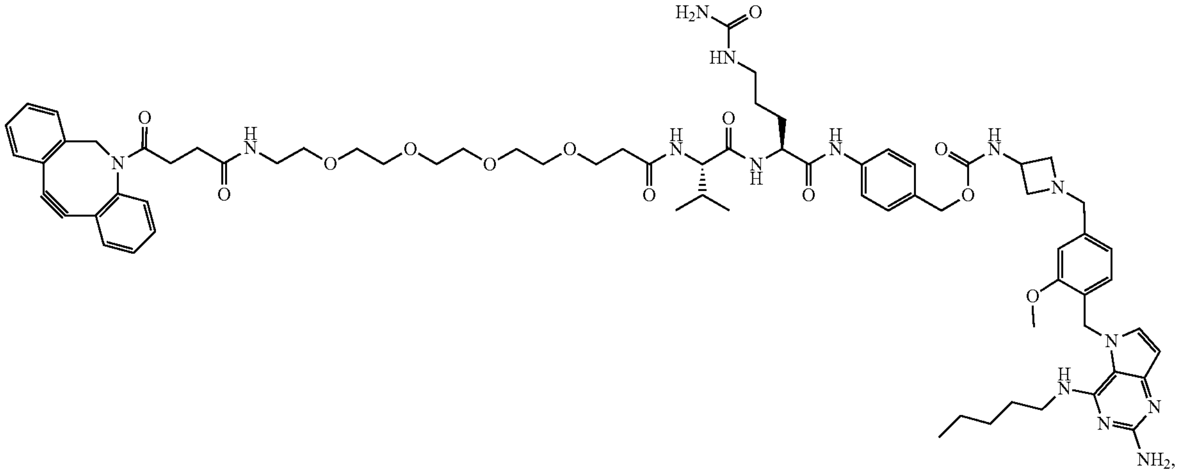
,
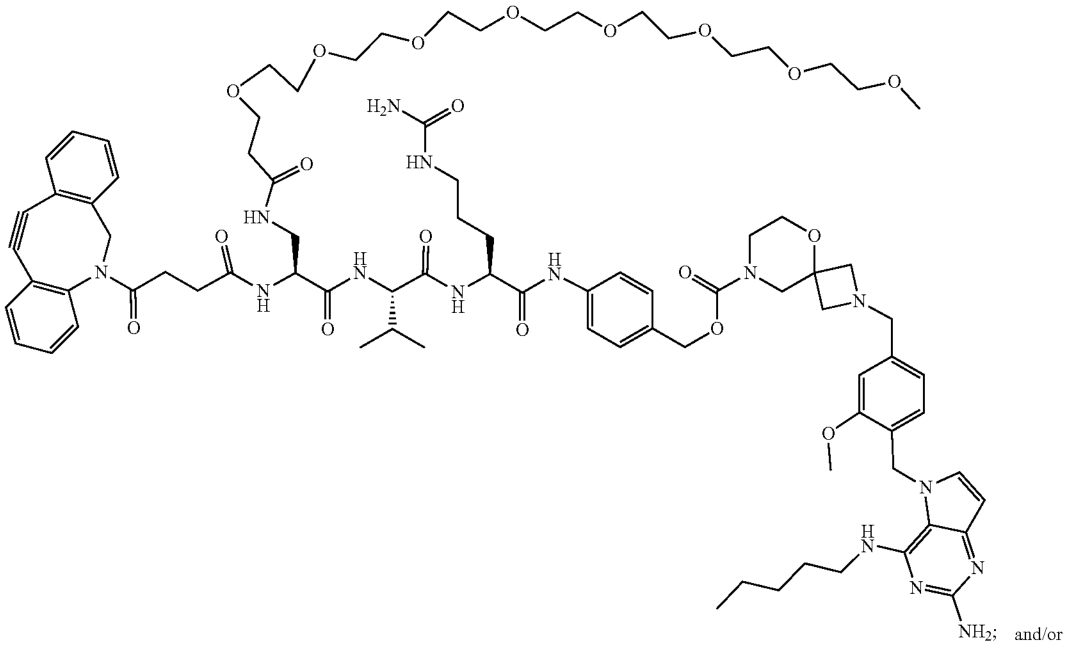
; and/or

-continued

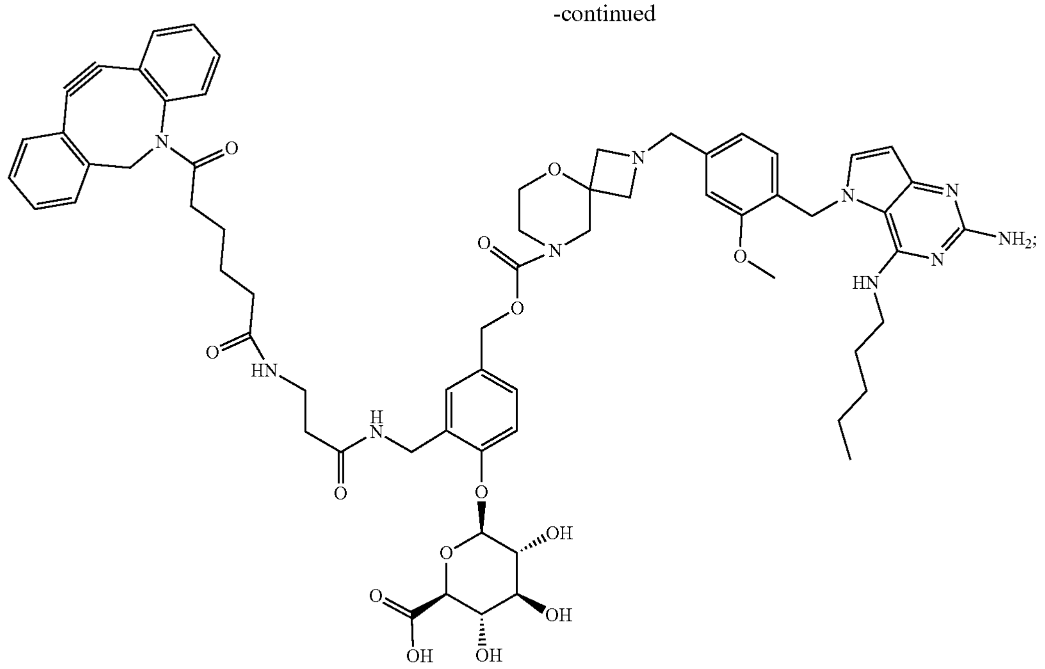

or a pharmaceutically acceptable salt, solvate, stereoisomer, tautomer or mixture of regioisomers thereof.

5. Antibody Specificity

The conjugates comprise antibodies that selectively bind human antigens. In some embodiments, the antibody binds to a homolog of a human antigen. In some aspects, the antibody binds to a homolog of the human antigen from a species selected from monkeys, mice, dogs, cats, rats, cows, horses, goats and sheep. In some aspects, the homolog is a cynomolgus monkey homolog. In some aspects, the homolog is a mouse or murine homolog.

In some embodiments, the antibody comprises a light chain. In some aspects, the light chain is a kappa light chain. In some aspects, the light chain is a lambda light chain.

In some embodiments, the antibody comprises a heavy chain. In some aspects, the heavy chain is an IgA. In some aspects, the heavy chain is an IgD. In some aspects, the heavy chain is an IgE. In some aspects, the heavy chain is an IgG. In some aspects, the heavy chain is an IgM. In some aspects, the heavy chain is an IgG1. In some aspects, the heavy chain is an IgG2. In some aspects, the heavy chain is an IgG3. In some aspects, the heavy chain is an IgG4. In some aspects, the heavy chain is an IgA1. In some aspects, the heavy chain is an IgA2.

In some embodiments, the antibody is an antibody fragment. In some aspects, the antibody fragment is an Fv fragment. In some aspects, the antibody fragment is a Fab fragment. In some aspects, the antibody fragment is a $F(ab')_2$ fragment. In some aspects, the antibody fragment is a Fab' fragment. In some aspects, the antibody fragment is an scFv (sFv) fragment. In some aspects, the antibody fragment is an scFv-Fc fragment.

In some embodiments, the antibody is a monoclonal antibody. In some embodiments, the antibody is a polyclonal antibody.

In some embodiments, the antibody is a chimeric antibody. In some embodiments, the antibody is a humanized antibody. In some embodiments, the antibody is a human antibody. In some embodiments, the antibody is an affinity matured antibody.

The antibody conjugates provided herein may be useful for the treatment of a variety of diseases and conditions including cancers (e.g., any cancer described herein). In some embodiments, the antibody conjugates provided herein may be useful for the treatment of cancers of solid tumors.

6. Glycosylation Variants

In certain embodiments, an antibody may be altered to increase, decrease or eliminate the extent to which it is glycosylated. Glycosylation of polypeptides is typically either “N-linked” or “O-linked.”

“N-linked” glycosylation refers to the attachment of a carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site.

“O-linked” glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition or deletion of N-linked glycosylation sites to the antibody may be accomplished by altering the amino acid sequence such that one or more of the above-described tripeptide sequences is created or removed. Addition or deletion of O-linked glycosylation sites may be accomplished by addition, deletion, or substitution of one or more serine or threonine residues in or to (as the case may be) the sequence of an antibody.

7. Modified Amino Acids

When the antibody conjugate comprises a modified amino acid, the modified amino acid can be any modified amino acid deemed suitable by the practitioner. In particular embodiments, the modified amino acid comprises a reactive group useful for forming a covalent bond to a linker precursor or to a payload precursor. In certain embodiments, the modified amino acid is a non-natural amino acid. In certain embodiments, the reactive group is selected from the group consisting of amino, carboxy, acetyl, hydrazino, hydrazido, semicarbazido, sulfanyl, azido and alkynyl. Modified amino acids are also described in, for example, WO 2013/185115 and WO 2015/006555, each of which is incorporated herein by reference in its entirety.

The term "residue of an amino acid" and "amino acid residue" refer to the product of an amide coupling or peptide coupling of an amino acid to a suitable coupling partner; wherein, for example, a water molecule is expelled after the amide or peptide coupling of the amino acid, resulting in the product having the amino acid residue incorporated therein. In some embodiments, the amino acid residue is according to

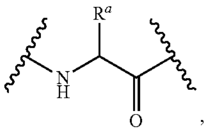
,
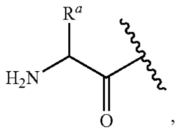
, or
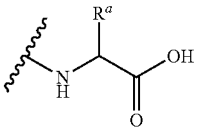

where $R^a$ is the side chain of an amino acid. In some embodiments, the amino acid residue is according to

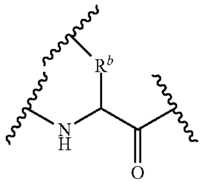
,
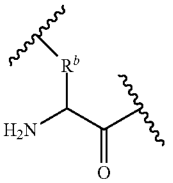
,
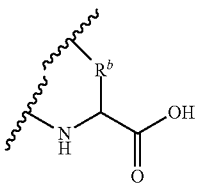
, or
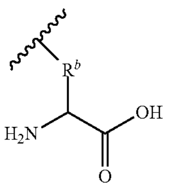
, where $R^b$ is a residue of a side chain of an amino acid, e.g. a C(O) residue of C(O)OH in the side chain of an aspartic acid or an NH residue of $NH_2$ in the side chain of a lysine.

The term "residue of a peptide" and "peptide residue" refer to the product of an amide coupling or peptide coupling of an amino acid to a suitable coupling partner; wherein, for example, a water molecule is expelled after the amide or peptide coupling of the amino acid, resulting in the product having the peptide residue incorporated therein. In some embodiments, the peptide residue is according to

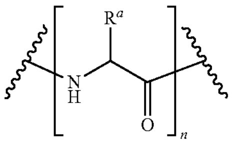
,
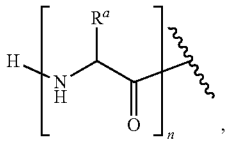
, or
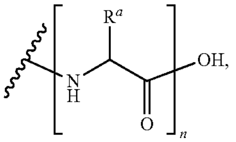

where n is 2 or more and where $R^a$ is the side chain of an amino acid. In some embodiments, the peptide residue is according to

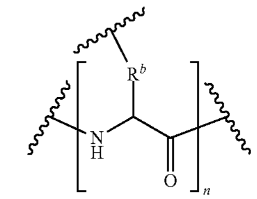
,
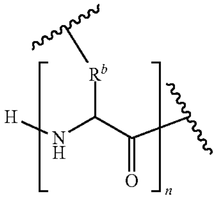
,
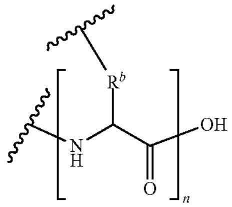
, or
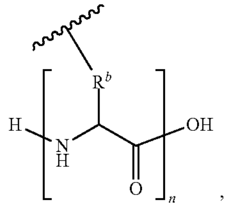
, where n is 2 or more and where $R^b$ is a residue of a side chain of an amino acid, e.g. a C(O) residue of C(O)OH in the side chain of an aspartic acid or an NH residue of $NH_2$ in the side chain of a lysine. In some embodiments, n is 2-50, 2-25, 2-10, 1-5, or 2-3. In some embodiments, n is 2. In some embodiments, n is 3.

In certain embodiments, the amino acid residue is according to any of the following formulas:

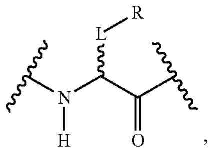
,
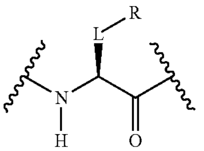
or
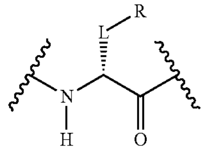
.

Those of skill in the art will recognize that antibodies are generally comprised of L-amino acids However, with non-natural amino acids, the present methods and compositions provide the practitioner with the ability to use L-, D- or racemic non-natural amino acids at the site-specific positions. In certain embodiments, the non-natural amino acids described herein include D-versions of the natural amino acids and racemic versions of the natural amino acids.

In the above formulas, the wavy lines indicate bonds that connect to the remainder of the polypeptide chains of the antibodies. These non-natural amino acids can be incorporated into polypeptide chains just as natural amino acids are incorporated into the same polypeptide chains. In certain embodiments, the non-natural amino acids are incorporated into the polypeptide chain via amide bonds as indicated in the formulas.

In the above formulas R designates any functional group without limitation, so long as the amino acid residue is not identical to a natural amino acid residue. In certain embodiments, R can be a hydrophobic group, a hydrophilic group, a polar group, an acidic group, a basic group, a chelating group, a reactive group, a therapeutic moiety or a labeling moiety. In certain embodiments, R is selected from the group consisting of $R^1NR^{2z}R^{3z}$, $R^{1z}C({=}O)R^{2z}$, $R^{1z}C({=}O)OR^{2z}$, $R^{1z}N_3$, $R^{1z}C(\equiv CH)$. In these embodiments, $R^{1z}$ is selected from the group consisting of a bond, alkylene, heteroalkylene, arylene, heteroarylene. $R^{2z}$ and $R^{3z}$ are each independently selected from the group consisting of hydrogen, alkyl and heteroalkyl.

In some embodiments, the non-naturally encoded amino acids include side chain functional groups that react efficiently and selectively with functional groups not found in the 20 common amino acids (including but not limited to, azido, ketone, aldehyde and aminooxy groups) to form stable conjugates. For example, antigen-binding polypeptide that includes a non-naturally encoded amino acid containing an azido functional group can be reacted with a polymer (including but not limited to, poly(ethylene glycol) or, alternatively, a second polypeptide containing an alkyne moiety to form a stable conjugate resulting for the selective reaction of the azide and the alkyne functional groups to form a Huisgen [3+2] cycloaddition product.

Exemplary non-naturally encoded amino acids that may be suitable for use in the present invention and that are useful for reactions with water soluble polymers include, but are not limited to, those with carbonyl, aminooxy, hydrazine, hydrazide, semicarbazide, azide and alkyne reactive groups. In some embodiments, non-naturally encoded amino acids comprise a saccharide moiety. Examples of such amino acids include N-acetyl-L-glucosaminyl-L-serine, N-acetyl-L-galactosaminyl-L-serine, N-acetyl-L-glucosaminyl-L-threonine, N-acetyl-L-glucosaminyl-L-asparagine and O-mannosaminyl-L-serine. Examples of such amino acids also include examples where the naturally-occurring N- or O-linkage between the amino acid and the saccharide is replaced by a covalent linkage not commonly found in nature-including but not limited to, an alkene, an oxime, a thioether, an amide and the like. Examples of such amino acids also include saccharides that are not commonly found in naturally-occurring proteins such as 2-deoxy-glucose, 2-deoxygalactose and the like.

Many of the non-naturally encoded amino acids provided herein are commercially available, e.g., from Sigma-Aldrich (St. Louis, Mo., USA), Novabiochem (a division of EMD Biosciences, Darmstadt, Germany), or Peptech (Burlington, Mass., USA). Those that are not commercially available are optionally synthesized as provided herein or using standard methods known to those of skill in the art. For organic synthesis techniques, see, e.g., Organic Chemistry by Fessendon and Fessendon, (1982, Second Edition, Willard Grant Press, Boston Mass.); Advanced Organic Chemistry by March (Third Edition, 1985, Wiley and Sons, New York); and Advanced Organic Chemistry by Carey and Sundberg (Third Edition, Parts A and B, 1990, Plenum Press, New York). See, also, U.S. Patent Application Publications 2003/0082575 and 2003/0108885, which is incorporated by reference herein. In addition to unnatural amino acids that contain unnatural side chains, unnatural amino acids that may be suitable for use in the present invention also optionally comprise modified backbone structures, including but not limited to, as illustrated by the structures of Formula II and III:

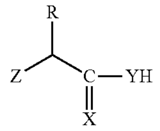

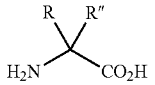

wherein Z typically comprises OH, $NH_2$, SH, NH—R", or S—R"; X and Y, which can be the same or different, typically comprise S or O, and R and R", which are optionally the same or different, are typically independently selected from the same list of constituents for the R group described above for the unnatural amino acids having Formula I as well as hydrogen. For example, unnatural amino acids of the invention optionally comprise substitutions in the amino or carboxyl group as illustrated by Formulas II and III. Unnatural amino acids of this type include, but are not limited to, α-hydroxy acids, α-thioacids, α-aminothiocarboxylates, including but not limited to, with side chains corresponding to the common twenty natural amino acids or unnatural side chains. In addition, substitutions at the α-carbon optionally include, but are not limited to, L, D, or α-α-disubstituted amino acids such as D-glutamate, D-alanine, D-methyl-O-tyrosine, aminobutyric acid, and the like. Other structural alternatives include cyclic amino acids, such as proline analogues as well as 3, 4, 6, 7, 8, and 9 membered ring proline analogues, P and y amino acids such as substituted β-alanine and γ-amino butyric acid.

Many unnatural amino acids are based on natural amino acids, such as tyrosine, glutamine, phenylalanine, and the like, and are suitable for use in the present invention. Tyrosine analogs include, but are not limited to, para-substituted tyrosines, ortho-substituted tyrosines, and meta substituted tyrosines, where the substituted tyrosine comprises, including but not limited to, a keto group (including but not limited to, an acetyl group), a benzoyl group, an amino group, a hydrazine, an hydroxyamine, a thiol group, a carboxy group, an isopropyl group, a methyl group, a $C_6$-$C_{20}$ straight chain or branched hydrocarbon, a saturated or unsaturated hydrocarbon, an O-methyl group, a polyether group, a nitro group, an alkynyl group or the like. In addition, multiply substituted aryl rings are also contemplated. Glutamine analogs that may be suitable for use in the present invention include, but are not limited to, α-hydroxy derivatives, γ-substituted derivatives, cyclic derivatives, and amide substituted glutamine derivatives. Example phenylalanine analogs that may be suitable for use in the present invention include, but are not limited to, para-substituted phenylalanines, ortho-substituted phenyalanines, and meta-substituted phenylalanines, where the substituent comprises, including but not limited to, a hydroxy group, a methoxy group, a methyl group, an allyl group, an aldehyde, an azido, an iodo, a bromo, a keto group (including but not limited to, an acetyl group), a benzoyl, an alkynyl group, or the like. Specific examples of unnatural amino acids that may be suitable for use in the present invention include, but are not limited to, a p-acetyl-L-phenylalanine, an O-methyl-L-tyrosine, an L-3-(2-naphthyl)alanine, a 3-methyl-phenylalanine, an O-4-allyl-L-tyrosine, a 4-propyl-L-tyrosine, a tri-O-acetyl-GlcNAcβ-serine, an L-Dopa, a fluorinated phenylalanine, an isopropyl-L-phenylalanine, a p-azido-L-phenylalanine, a p-azido-methyl-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, an isopropyl-L-phenylalanine, and a p-propargyloxy-phenylalanine, and the like. Examples of structures of a variety of unnatural amino acids that may be suitable for use in the present invention are provided in, for example, WO 2002/085923 entitled "In vivo incorporation of unnatural amino acids." See also Kiick et al., (2002) Incorporation of azides into recombinant proteins for chemoselective modification by the Staudinger ligation, PNAS 99:19-24, for additional methionine analogs.

Many of the unnatural amino acids suitable for use in the present invention are commercially available, e.g., from Sigma (USA) or Aldrich (Milwaukee, Wis., USA). Those that are not commercially available are optionally synthesized as provided herein or as provided in various publications or using standard methods known to those of skill in the art. For organic synthesis techniques, see, e.g., Organic Chemistry by Fessendon and Fessendon, (1982, Second Edition, Willard Grant Press, Boston Mass.); Advanced Organic Chemistry by March (Third Edition, 1985, Wiley and Sons, New York); and Advanced Organic Chemistry by Carey and Sundberg (Third Edition, Parts A and B, 1990, Plenum Press, New York). Additional publications describing the synthesis of unnatural amino acids include, e.g., WO 2002/085923 entitled "In vivo incorporation of Unnatural Amino Acids;" Matsoukas et al., (1995) J. Med. Chem., 38, 4660-4669; King, F. E. & Kidd, D. A. A. (1949) A New Synthesis of Glutamine and of γ-Dipeptides of Glutamic Acid from Phthylated Intermediates. J. Chem. Soc., 3315-3319; Friedman, O. M. & Chatterrji, R. (1959) Synthesis of Derivatives of Glutamine as Model Substrates for Anti-Tumor Agents. J. Am. Chem. Soc. 81, 3750-3752; Craig, J. C. et al. (1988) Absolute Configuration of the Enantiomers of 7-Chloro-4 [[4-(diethylamino)-1-methylbutyl]amino]quinoline (Chloroquine). J. Org. Chem. 53, 1167-1170; Azoulay, M., Vilmont, M. & Frappier, F. (1991) Glutamine analogues as Potential Antimalarials, Eur. J. Med. Chem. 26, 201-5; Koskinen, A. M. P. & Rapoport, H. (1989) Synthesis of 4-Substituted Prolines as Conformationally Constrained Amino Acid Analogues. J. Org. Chem. 54, 1859-1866; Christie, B. D. & Rapoport, H. (1985) Synthesis of Optically Pure Pipecolates from L-Asparagine. Application to the Total Synthesis of (+)-Apovincamine through Amino Acid Decarbonylation and Iminium Ion Cyclization. J. Org. Chem. 1989:1859-1866; Barton et al., (1987) Synthesis of Novel a-Amino-Acids and Derivatives Using Radical Chemistry: Synthesis of L- and D-a-Amino-Adipic Acids, L-a-aminopimelic Acid and Appropriate Unsaturated Derivatives. Tetrahedron Lett. 43:4297-4308; and, Subasinghe et al., (1992) Quisqualic acid analogues: synthesis of beta-heterocyclic 2-aminopropanoic acid derivatives and their activity at a novel quisqualate-sensitized site. J. Med. Chem. 35:4602-7. See also, patent applications entitled "Protein Arrays," filed Dec. 22, 2003, Ser. No. 10/744,899 and Ser. No. 60/435,821 filed on Dec. 22, 2002.

Amino acids with a carbonyl reactive group allow for a variety of reactions to link molecules (including but not limited to, PEG or other water soluble molecules) via nucleophilic addition or aldol condensation reactions among others.

Exemplary carbonyl-containing amino acids can be represented as follows:

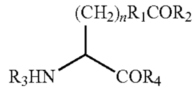

wherein n is 0-10; $R_1$ is an alkyl, aryl, substituted alkyl, or substituted aryl; $R_2$ is H, alkyl, aryl, substituted alkyl, and substituted aryl; and $R_3$ is H, an amino acid, a polypeptide, or an amino terminus modification group, and $R_4$ is H, an amino acid, a polypeptide, or a carboxy terminus modification group. In some embodiments, n is 1, $R_1$ is phenyl and $R_2$ is a simple alkyl (i.e., methyl, ethyl, or propyl) and the ketone moiety is positioned in the para position relative to the alkyl side chain. In some embodiments, n is 1, $R_1$ is phenyl and $R_2$ is a simple alkyl (i.e., methyl, ethyl, or propyl) and the ketone moiety is positioned in the meta position relative to the alkyl side chain.

In some examples, a non-naturally encoded amino acid bearing adjacent hydroxyl and amino groups can be incorporated into the polypeptide as a "masked" aldehyde functionality. For example, 5-hydroxylysine bears a hydroxyl group adjacent to the epsilon amine. Reaction conditions for generating the aldehyde typically involve addition of molar excess of sodium metaperiodate under mild conditions to avoid oxidation at other sites within the polypeptide. The pH of the oxidation reaction is typically about 7.0. A typical reaction involves the addition of about 1.5 molar excess of sodium meta periodate to a buffered solution of the polypeptide, followed by incubation for about 10 minutes in the dark. See, e.g. U.S. Pat. No. 6,423,685, which is incorporated by reference herein.

The carbonyl functionality can be reacted selectively with a hydrazine-, hydrazide-, hydroxylamine-, or semicarbazide-containing reagent under mild conditions in aqueous solution to form the corresponding hydrazone, oxime, or semicarbazone linkages, respectively, that are stable under physiological conditions. See, e.g., Jencks, W. P., J. Am. Chem. Soc. 81, 475-481 (1959); Shao, J. and Tam, J. P., J. Am. Chem. Soc. 117:3893-3899 (1995). Moreover, the unique reactivity of the carbonyl group allows for selective modification in the presence of the other amino acid side chains. See, e.g., Comish, V. W., et al., J. Am. Chem. Soc. 118:8150-8151 (1996); Geoghegan, K. F. & Stroh, J. G., Bioconjug. Chem. 3:138-146 (1992); Mahal, L. K., et al., Science 276:1125-1128 (1997).

Non-naturally encoded amino acids containing a nucleophilic group, such as a hydrazine, hydrazide or semicarbazide, allow for reaction with a variety of electrophilic groups to form conjugates (including but not limited to, with PEG or other water soluble polymers).

Exemplary hydrazine, hydrazide or semicarbazide-containing amino acids can be represented as follows:

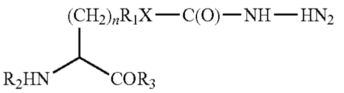

wherein n is 0-10; $R_1$ is an alkyl, aryl, substituted alkyl, or substituted aryl or not present; X, is O, N, or S or not present; $R_2$ is H, an amino acid, a polypeptide, or an amino terminus modification group, and $R_3$ is H, an amino acid, a polypeptide, or a carboxy terminus modification group.

In some embodiments, n is 4, $R_1$ is not present, and X is N. In some embodiments, n is 2, $R_1$ is not present, and X is not present. In some embodiments, n is 1, $R_1$ is phenyl, X is O, and the oxygen atom is positioned para to the aliphatic group on the aryl ring.

Hydrazide-, hydrazine-, and semicarbazide-containing amino acids are available from commercial sources. For instance, L-glutamate-γ-hydrazide is available from Sigma Chemical (St. Louis, Mo.). Other amino acids not available commercially can be prepared by one skilled in the art. See, e.g., U.S. Pat. No. 6,281,211, which is incorporated by reference herein.

Polypeptides containing non-naturally encoded amino acids that bear hydrazide, hydrazine or semicarbazide functionalities can be reacted efficiently and selectively with a variety of molecules that contain aldehydes or other functional groups with similar chemical reactivity. See, e.g., Shao, J. and Tam, J., J. Am. Chem. Soc. 117:3893-3899 (1995). The unique reactivity of hydrazide, hydrazine and semicarbazide functional groups makes them significantly more reactive toward aldehydes, ketones and other electrophilic groups as compared to the nucleophilic groups present on the 20 common amino acids (including but not limited to, the hydroxyl group of serine or threonine or the amino groups of lysine and the N-terminus).

Non-naturally encoded amino acids containing an aminooxy (also called a hydroxylamine) group allow for reaction with a variety of electrophilic groups to form conjugates (including but not limited to, with PEG or other water soluble polymers). Like hydrazines, hydrazides and semicarbazides, the enhanced nucleophilicity of the aminooxy group permits it to react efficiently and selectively with a variety of molecules that contain aldehydes or other functional groups with similar chemical reactivity. See, e.g., Shao, J. and Tam, J., J. Am. Chem. Soc. 117:3893-3899 (1995); H. Hang and C. Bertozzi, Acc. Chem. Res. 34: 727-736 (2001). Whereas the result of reaction with a hydrazine group is the corresponding hydrazone, however, an oxime results generally from the reaction of an aminooxy group with a carbonyl-containing group such as a ketone.

Exemplary amino acids containing aminooxy groups can be represented as follows:

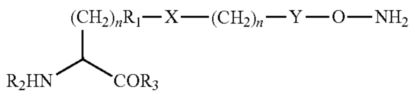

wherein n is 0-10; $R_1$ is an alkyl, aryl, substituted alkyl, or substituted aryl or not present; X is O, N, S or not present; m is 0-10; Y═C(O) or not present; $R_2$ is H, an amino acid, a polypeptide, or an amino terminus modification group, and $R_3$ is H, an amino acid, a polypeptide, or a carboxy terminus modification group. In some embodiments, n is 1, $R_1$ is phenyl, X is O, m is 1, and Y is present. In some embodiments, n is 2, $R_1$ and X are not present, m is O, and Y is not present.

Aminooxy-containing amino acids can be prepared from readily available amino acid precursors (homoserine, serine and threonine). See, e.g., M. Carrasco and R. Brown, J. Org. Chem. 68: 8853-8858 (2003). Certain aminooxy-containing amino acids, such as L-2-amino-4-(aminooxy)butyric acid), have been isolated from natural sources (Rosenthal, G. et al., Life Sci. 60: 1635-1641 (1997). Other aminooxy-containing amino acids can be prepared by one skilled in the art.

The unique reactivity of azide and alkyne functional groups makes them extremely useful for the selective modification of polypeptides and other biological molecules. Organic azides, particularly aliphatic azides, and alkynes are generally stable toward common reactive chemical conditions. In particular, both the azide and the alkyne functional groups are inert toward the side chains (i.e., R groups) of the 20 common amino acids found in naturally-occurring polypeptides. When brought into close proximity, however, the "spring-loaded" nature of the azide and alkyne groups is revealed and they react selectively and efficiently via Huisgen [3+2] cycloaddition reaction to generate the corresponding triazole. See, e.g., Chin J., et al., Science 301:964-7 (2003); Wang, Q., et al., J. Am. Chem. Soc. 125, 3192-3193 (2003); Chin, J. W., et al., J. Am. Chem. Soc. 124:9026-9027 (2002).

Because the Huisgen cycloaddition reaction involves a selective cycloaddition reaction (see, e.g., Padwa, A., in COMPREHENSIVE ORGANIC SYNTHESIS, Vol. 4, (ed. Trost, B. M., 1991), p. 1069-1109; Huisgen, R. in 1,3-DIPOLAR CYCLOADDITION CHEMISTRY, (ed. Padwa, A., 1984), p. 1-176) rather than a nucleophilic substitution, the incorporation of non-naturally encoded amino acids bearing azide and alkyne-containing side chains permits the resultant polypeptides to be modified selectively at the position of the non-naturally encoded amino acid. Cycloaddition reaction involving azide or alkyne-containing antibody can be carried out at room temperature under aqueous conditions by the addition of Cu(II) (including but not limited to, in the form of a catalytic amount of $CuSO_4$) in the presence of a reducing agent for reducing Cu(II) to Cu(I), in situ, in catalytic amount. See, e.g., Wang, Q., et al., J. Am. Chem. Soc. 125, 3192-3193 (2003); Tomoe, C. W., et al., J. Org. Chem. 67:3057-3064 (2002); Rostovtsev, et al., Angew. Chem. Int. Ed. 41:2596-2599 (2002). Exemplary reducing agents include, including but not limited to, ascorbate, metallic copper, quinine, hydroquinone, vitamin K, glutathione, cysteine, $Fe^{2+}$, $Co^{2+}$, and an applied electric potential.

In some cases, where a Huisgen [3+2] cycloaddition reaction between an azide and an alkyne is desired, the antigen-binding polypeptide comprises a non-naturally encoded amino acid comprising an alkyne moiety and the water soluble polymer to be attached to the amino acid comprises an azide moiety. Alternatively, the converse reaction (i.e., with the azide moiety on the amino acid and the alkyne moiety present on the water soluble polymer) can also be performed.

The azide functional group can also be reacted selectively with a water soluble polymer containing an aryl ester and appropriately functionalized with an aryl phosphine moiety to generate an amide linkage. The aryl phosphine group reduces the azide in situ and the resulting amine then reacts efficiently with a proximal ester linkage to generate the corresponding amide. See, e.g., E. Saxon and C. Bertozzi, Science 287, 2007-2010 (2000). The azide-containing amino acid can be either an alkyl azide (including but not limited to, 2-amino-6-azido-1-hexanoic acid) or an aryl azide (p-azido-phenylalanine).

Exemplary water soluble polymers containing an aryl ester and a phosphine moiety can be represented as follows:

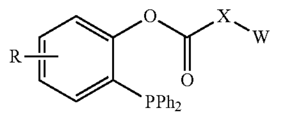

wherein X can be O, N, S or not present, Ph is phenyl, W is a water soluble polymer and R can be H, alkyl, aryl, substituted alkyl and substituted aryl groups. Exemplary R groups include but are not limited to —$CH_2$, —$C(CH_3)_3$, —OR", —NR"R"', —SR", -halogen, —C(O)R", —CONR"R"', —$S(O)_2R$", —$S(O)_2NR$"R"', —CN and —$NO_2$. R" and R"' each independently refer to hydrogen, substituted or unsubstituted heteroalkyl, substituted or unsubstituted aryl, including but not limited to, aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R" and R" groups when more than one of these groups is present. When R" and R"' are attached to the same nitrogen atom, they can be combined with the nitrogen atom to form a 5-, 6-, or 7-membered ring. For example, —NR"R"' is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (including but not limited to, —$CF_3$ and —$CH_2CF_3$) and acyl (including but not limited to, —C(O)$CH_3$, —C(O)$CF_3$, —C(O)$CH_2OCH_3$, and the like).

The azide functional group can also be reacted selectively with a water soluble polymer containing a thioester and appropriately functionalized with an aryl phosphine moiety to generate an amide linkage. The aryl phosphine group reduces the azide in situ and the resulting amine then reacts efficiently with the thioester linkage to generate the corresponding amide. Exemplary water soluble polymers containing a thioester and a phosphine moiety can be represented as follows:

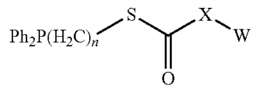

wherein n is 1-10; X can be O, N, S or not present, Ph is phenyl, and W is a water soluble polymer.

Exemplary alkyne-containing amino acids can be represented as follows:

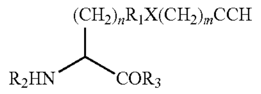

wherein n is 0-10; $R_1$ is an alkyl, aryl, substituted alkyl, or substituted aryl or not present; X is O, N, S or not present; m is 0-10, $R_2$ is H, an amino acid, a polypeptide, or an amino terminus modification group, and $R_3$ is H, an amino acid, a polypeptide, or a carboxy terminus modification group. In some embodiments, n is 1, $R_1$ is phenyl, X is not present, m is 0 and the acetylene moiety is positioned in the para position relative to the alkyl side chain. In some embodiments, n is 1, $R_1$ is phenyl, X is O, m is 1 and the propargyloxy group is positioned in the para position relative to the alkyl side chain (i.e., O-propargyl-tyrosine). In some embodiments, n is 1, $R_1$ and X are not present and m is O (i.e., propargylglycine).

Alkyne-containing amino acids are commercially available. For example, propargylglycine is commercially available from Peptech (Burlington, Mass.). Alternatively, alkyne-containing amino acids can be prepared according to standard methods. For instance, p-propargyloxyphenylalanine can be synthesized, for example, as described in Deiters, A., et al., J. Am. Chem. Soc. 125: 11782-11783 (2003), and 4-alkynyl-L-phenylalanine can be synthesized as described in Kayser, B., et al., Tetrahedron 53(7): 2475-2484 (1997). Other alkyne-containing amino acids can be prepared by one skilled in the art.

Exemplary azide-containing amino acids can be represented as follows:

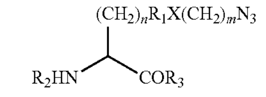

wherein n is 0-10; $R_1$ is an alkyl, aryl, substituted alkyl, substituted aryl or not present; X is O, N, S or not present; m is 0-10; $R_2$ is H, an amino acid, a polypeptide, or an amino terminus modification group, and $R_3$ is H, an amino acid, a polypeptide, or a carboxy terminus modification group. In some embodiments, n is 1, $R_1$ is phenyl, X is not present, m is O and the azide moiety is positioned para to the alkyl side chain. In some embodiments, n is 0-4 and $R_1$ and X are not present, and m=0. In some embodiments, n is 1, $R_1$ is phenyl, X is O, m is 2 and the P-azidoethoxy moiety is positioned in the para position relative to the alkyl side chain.

Azide-containing amino acids are available from commercial sources. For instance, 4-azidophenylalanine can be obtained from Chem-Impex International, Inc. (Wood Dale, Ill.). For those azide-containing amino acids that are not commercially available, the azide group can be prepared relatively readily using standard methods known to those of skill in the art, including but not limited to, via displacement of a suitable leaving group (including but not limited to, halide, mesylate, tosylate) or via opening of a suitably protected lactone. See, e.g., Advanced Organic Chemistry by March (Third Edition, 1985, Wiley and Sons, New York).

The unique reactivity of beta-substituted aminothiol functional groups makes them extremely useful for the selective modification of polypeptides and other biological molecules that contain aldehyde groups via formation of the thiazolidine. See, e.g., J. Shao and J. Tam, J. Am. Chem. Soc. 1995, 117 (14) 3893-3899. In some embodiments, beta-substituted aminothiol amino acids can be incorporated into antibodies and then reacted with water soluble polymers comprising an aldehyde functionality. In some embodiments, a water soluble polymer, drug conjugate or other payload can be coupled to an antibody polypeptide comprising a beta-substituted aminothiol amino acid via formation of the thiazolidine.

Particular examples of useful non-natural amino acids include, but are not limited to, p-acetyl-L-phenylalanine, O-methyl-L-tyrosine, L-3-(2-naphthyl)alanine, 3-methyl-phenylalanine, O-4-allyl-L-tyrosine, 4-propyl-L-tyrosine, tri-O-acetyl-GlcNAc b-serine, L-Dopa, fluorinated phenylalanine, isopropyl-L-phenylalanine, p-azido-methyl-L-phenylalanine, p-azido-L-phenylalanine, p-acyl-L-phenylalanine, p-benzoyl-L-phenylalanine, L-phosphoserine, phosphonoserine, phosphonotyrosine, p-iodo-phenylalanine, p-bromophenylalanine, p-amino-L-phenylalanine, isopropyl-L-phenylalanine, and p-propargyloxy-phenylalanine. Further useful examples include N-acetyl-L-glucosaminyl-L-serine, N-acetyl-L-galactosaminyl-L-serine, N-acetyl-L-glucosaminyl-L-threonine, N-acetyl-L-glucosaminyl-L-asparagine and O-mannosaminyl-L-serine.

In particular embodiments, the non-natural amino acids are selected from p-acetyl-phenylalanine, p-ethynyl-phenylalanine, p-propargyloxyphenylalanine, p-azido-methyl-phenylalanine, and p-azido-phenylalanine. One particularly useful non-natural amino acid is p-azido phenylalanine. This amino acid residue is known to those of skill in the art to facilitate Huisgen [3+2] cycloaddition reactions (so-called “click” chemistry reactions) with, for example, compounds bearing alkynyl groups. This reaction enables one of skill in the art to readily and rapidly conjugate to the antibody at the site-specific location of the non-natural amino acid.

In certain embodiments, the first reactive group is an alkynyl moiety (including but not limited to, in the unnatural amino acid p-propargyloxyphenylalanine, where the propargyl group is also sometimes referred to as an acetylene moiety) and the second reactive group is an azido moiety, and [3+2] cycloaddition chemistry can be used. In certain embodiments, the first reactive group is the azido moiety (including but not limited to, in the unnatural amino acid p-azido-L-phenylalanine) and the second reactive group is the alkynyl moiety.

In the above formulas, each L represents a divalent linker. The divalent linker can be any divalent linker known to those of skill in the art. Generally, the divalent linker is capable of forming covalent bonds to the functional moiety R and the cognate reactive group (e.g., alpha carbon) of the non-natural amino acid. Useful divalent linkers a bond, alkylene, substituted alkylene, heteroalkylene, substituted heteroalkylene, arylene, substituted arylene, heteroarlyene and substituted heteroarylene. In certain embodiments, L is $C_{1-10}$ alkylene or $C_{1-10}$ heteroalkylene.

The non-natural amino acids used in the methods and compositions described herein have at least one of the following four properties: (1) at least one functional group on the sidechain of the non-natural amino acid has at least one characteristics and/or activity and/or reactivity orthogonal to the chemical reactivity of the 20 common, genetically-encoded amino acids (i.e., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine), or at least orthogonal to the chemical reactivity of the naturally occurring amino acids present in the polypeptide that includes the non-natural amino acid; (2) the introduced non-natural amino acids are substantially chemically inert toward the 20 common, genetically-encoded amino acids; (3) the non-natural amino acid can be stably incorporated into a polypeptide, preferably with the stability commensurate with the naturally-occurring amino acids or under typical physiological conditions, and further preferably such incorporation can occur via an in vivo system; and (4) the non-natural amino acid includes an oxime functional group or a functional group that can be transformed into an oxime group by reacting with a reagent, preferably under conditions that do not destroy the biological properties of the polypeptide that includes the non-natural amino acid (unless of course such a destruction of biological properties is the purpose of the modification/transformation), or where the transformation can occur under aqueous conditions at a pH between about 4 and about 8, or where the reactive site on the non-natural amino acid is an electrophilic site. Any number of non-natural amino acids can be introduced into the polypeptide. Non-natural amino acids may also include protected or masked oximes or protected or masked groups that can be transformed into an oxime group after deprotection of the protected group or unmasking of the masked group. Non-natural amino acids may also include protected or masked carbonyl or dicarbonyl groups, which can be transformed into a carbonyl or dicarbonyl group after deprotection of the protected group or unmasking of the masked group and thereby are available to react with hydroxylamines or oximes to form oxime groups.

In further embodiments, non-natural amino acids that may be used in the methods and compositions described herein include, but are not limited to, amino acids comprising a photoactivatable cross-linker, spin-labeled amino acids, fluorescent amino acids, metal binding amino acids, metal-containing amino acids, radioactive amino acids, amino acids with novel functional groups, amino acids that covalently or non-covalently interact with other molecules, photocaged and/or photoisomerizable amino acids, amino acids comprising biotin or a biotin analogue, glycosylated amino acids such as a sugar substituted serine, other carbohydrate modified amino acids, keto-containing amino acids, aldehyde-containing amino acids, amino acids comprising polyethylene glycol or other polyethers, heavy atom substituted amino acids, chemically cleavable and/or photocleavable amino acids, amino acids with an elongated side chains as compared to natural amino acids, including but not limited to, polyethers or long chain hydrocarbons, including but not limited to, greater than about 5 or greater than about 10 carbons, carbon-linked sugar-containing amino acids, redox-active amino acids, amino thioacid containing amino acids, and amino acids comprising one or more toxic moiety.

In some embodiments, non-natural amino acids comprise a saccharide moiety. Examples of such amino acids include N-acetyl-L-glucosaminyl-L-serine, N-acetyl-L-galactosaminyl-L-serine, N-acetyl-L-glucosaminyl-L-threonine, N-acetyl-L-glucosaminyl-L-asparagine and O-mannosaminyl-L-serine. Examples of such amino acids also include examples where the naturally-occurring N- or O-linkage between the amino acid and the saccharide is replaced by a covalent linkage not commonly found in nature-including but not limited to, an alkene, an oxime, a thioether, an amide and the like. Examples of such amino acids also include saccharides that are not commonly found in naturally-occurring proteins such as 2-deoxy-glucose, 2-deoxygalactose and the like.

The chemical moieties incorporated into antibodies via incorporation of non-natural amino acids offer a variety of advantages and manipulations of polypeptides. For example, the unique reactivity of a carbonyl or dicarbonyl functional group (including a keto- or aldehyde-functional group) allows selective modification of antibodies with any of a number of hydrazine- or hydroxylamine-containing reagents in vivo and in vitro. A heavy atom non-natural amino acid, for example, can be useful for phasing x-ray structure data. The site-specific introduction of heavy atoms using non-natural amino acids also provides selectivity and flexibility in choosing positions for heavy atoms. Photoreactive non-natural amino acids (including but not limited to, amino acids with benzophenone and arylazides (including but not limited to, phenylazide) side chains), for example, allow for efficient in vivo and in vitro photocrosslinking of polypeptides. Examples of photoreactive non-natural amino acids include, but are not limited to, p-azido-phenylalanine and p-benzoyl-phenylalanine. The antibodies with the photoreactive non-natural amino acids may then be crosslinked at will by excitation of the photoreactive group-providing temporal control. In a non-limiting example, the methyl group of a non-natural amino can be substituted with an isotopically labeled, including but not limited to, with a methyl group, as a probe of local structure and dynamics, including but not limited to, with the use of nuclear magnetic resonance and vibrational spectroscopy.

Amino acids with an electrophilic reactive group allow for a variety of reactions to link molecules via various chemical reactions, including, but not limited to, nucleophilic addition reactions. Such electrophilic reactive groups include a carbonyl- or dicarbonyl-group (including a keto- or aldehyde group), a carbonyl-like- or dicarbonyl-like-group (which has reactivity similar to a carbonyl- or dicarbonyl-group and is structurally similar to a carbonyl- or dicarbonyl-group), a masked carbonyl- or masked dicarbonyl-group (which can be readily converted into a carbonyl- or dicarbonyl-group), or a protected carbonyl- or protected dicarbonyl-group (which has reactivity similar to a carbonyl- or dicarbonyl-group upon deprotection). Such amino acids include amino acids according to the structure of Formula (AA):

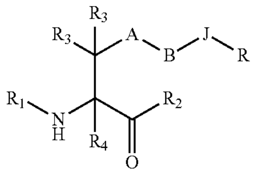

wherein: A is optional, and when present is lower alkylene, substituted lower alkylene, lower cycloalkylene, substituted lower cycloalkylene, lower alkenylene, substituted lower alkenylene, lower alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene; B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, $—S(O)_k—$ where k is 1, 2, or 3, $—S(O)_k$(alkylene or substituted alkylene)-, —C(O)—, $—NS(O)_2—$, $—OS(O)_2—$, —C(O)-(alkylene or substituted alkylene)-, —C(S)—, —C(S)-(alkylene or substituted alkylene)-, —N(R")—, —NR"-(alkylene or substituted alkylene)-, —C(O)N(R")—, —CON(R")-(alkylene or substituted alkylene)-, —CSN(R")—, —CSN(R")-(alkylene or substituted alkylene)-, —N(R")CO-(alkylene or substituted alkylene)-, —N(R")C(O)O—, $—S(O)_kN(R")—$, —N(R")C(O)N(R")—, —N(R")C(S)N(R")—, $—N(R")S(O)_kN(R")—$, —N(R")—N=, —C(R")=N—, —C(R")=N—N(R")—, —C(R")=N—N=, $—C(R")_2—N=N—$, and $—C(R")_2—N(R")—N(R")—$, where each R" in B is independently H, alkyl, or substituted alkyl; J is

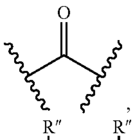,
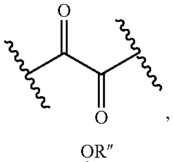,
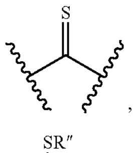,
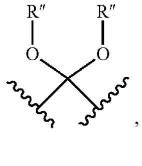,
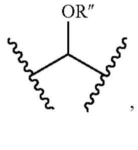,
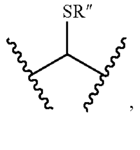,

-continued

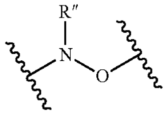, or
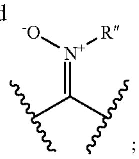;

R is H, alkyl, substituted alkyl, cycloalkyl, or substituted cycloalkyl; each R" in J is independently H, alkyl, substituted alkyl, or a protecting group, or when more than one R" group is present, two R" optionally form a heterocycloalkyl; $R_1$ is H, an amino protecting group, resin, amino acid, polypeptide, or polynucleotide; and $R_2$ is OH, an ester protecting group, resin, amino acid, polypeptide, or polynucleotide; each of $R_3$ and $R_4$ is independently H, halogen, lower alkyl, or substituted lower alkyl, or $R_3$ and $R_4$ or two $R_3$ groups optionally form a cycloalkyl or a heterocycloalkyl; or the -A-B-J-R groups together form a bicyclic or tricyclic cycloalkyl or heterocycloalkyl comprising at least one carbonyl group, including a dicarbonyl group, protected carbonyl group, including a protected dicarbonyl group, or masked carbonyl group, including a masked dicarbonyl group; or the -J-R group together forms a monocyclic or bicyclic cycloalkyl or heterocycloalkyl comprising at least one carbonyl group, including a dicarbonyl group, protected carbonyl group, including a protected dicarbonyl group, or masked carbonyl group, including a masked dicarbonyl group; with a proviso that when A is phenylene and each $R_3$ is H, B is present; and that when A is $—(CH_2)_4—$ and each $R_3$ is H, B is not $—NHC(O)(CH_2CH_2)—$; and that when A and B are absent and each $R_3$ is H, R is not methyl. Such non-natural amino acids may be in the form of a salt, or may be incorporated into a non-natural amino acid polypeptide, polymer, polysaccharide, or a polynucleotide and optionally post translationally modified.

In certain embodiments, compounds of Formula (AA) are stable in aqueous solution for at least 1 month under mildly acidic conditions. In certain embodiments, compounds of Formula (AA) are stable for at least 2 weeks under mildly acidic conditions. In certain embodiments, compound of Formula (AA) are stable for at least 5 days under mildly acidic conditions. In certain embodiments, such acidic conditions are pH 2 to 8.

In certain embodiments of compounds of Formula (AA), B is lower alkylene, substituted lower alkylene, —O-(alkylene or substituted alkylene)-, —C(R")=N—N(R")—, —N(R")CO—, —C(O)—, —C(R")=N—, —C(O)-(alkylene or substituted alkylene)-, —CON(R")-(alkylene or substituted alkylene)-, —S(alkylene or substituted alkylene)-, —S(O)(alkylene or substituted alkylene)-, or $—S(O)_2$(alkylene or substituted alkylene)-. In certain embodiments of compounds of Formula (AA), B is $—O(CH_2)—$, —CH=N—, —CH=N—NH—, $—NHCH_2—$, —NHCO—, —C(O)—, $—C(O)—(CH_2)—$, $—CONH—(CH_2)—$, $—SCH_2—$, $—S(=O)CH_2—$, or $—S(O)_2CH_2—$. In certain embodiments of compounds of Formula (AA), R is $C_{1-6}$ alkyl or cycloalkyl. In certain embodiments of compounds of Formula (AA) R is $—CH_3$, $—CH(CH_3)_2$, or cyclopropyl. In certain embodiments of compounds of Formula (AA), $R_1$ is H, tert-butyloxycarbonyl (Boc), 9-Fluorenylmethoxycarbonyl (Fmoc), N-acetyl, tetrafluoroacetyl (TFA), or benzyloxycarbonyl (Cbz). In certain embodiments of compounds of Formula (AA), $R_1$ is a resin, amino acid, polypeptide, or polynucleotide. In certain embodiments of compounds of Formula (AA), $R_2$ is OH, O-methyl, O-ethyl, or O-t-butyl. In certain embodiments of compounds of Formula (AA), $R_2$ is a resin, amino acid, polypeptide, or polynucleotide. In certain embodiments of compounds of Formula (AA), $R_2$ is a polynucleotide. In certain embodiments of compounds of Formula (AA), $R_2$ is ribonucleic acid (RNA). In certain embodiments of compounds of Formula (AA), $R_2$ is tRNA. In certain embodiments of compounds of Formula (AA), the tRNA specifically recognizes a selector codon. In certain embodiments of compounds of Formula (AA) the selector codon is selected from the group consisting of an amber codon, ochre codon, opal codon, a unique codon, a rare codon, an unnatural codon, a five-base codon, and a four-base codon. In certain embodiments of compounds of Formula (AA), $R_2$ is a suppressor tRNA.

In certain embodiments of compounds of Formula (AA),

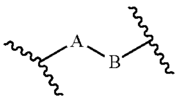

is selected from the group consisting of: (i) A is substituted lower alkylene, $C_4$-arylene, substituted arylene, heteroarylene, substituted heteroarylene, alkarylene, substituted alkarylene, aralkylene, or substituted aralkylene; B is optional, and when present is a divalent linker selected from the group consisting of lower alkylene, substituted lower alkylene, lower alkenylene, substituted lower alkenylene, —O—, —O-(alkylene or substituted alkylene)-, —S—, —S(O)—, —$S(O)_2$—, —$NS(O)_2$—, —$OS(O)_2$—, —C(O)—, —C(O)-(alkylene or substituted alkylene)-, —C(S)—, —N(R")—, —C(O)N(R")—, —CON(R")-(alkylene or substituted alkylene)-, —CSN(R")—, —N(R")CO-(alkylene or substituted alkylene)-, —N(R")C(O)O—, —N(R")C(S)—, —S(O)N(R"), —$S(O)_2$N(R"), —N(R")C(O)N(R")—, —N(R")C(S)N(R")—, —N(R")S(O)N(R")—, —N(R")$S(O)_2$N(R")—, —N(R")—N═, —C(R")═N—N(R")—, —C(R")═N—N═, —$C(R")_2$—N═N—, and —$C(R")_2$—N(R")—N(R")—; (ii) A is optional, and when present is substituted lower alkylene, $C_4$-arylene, substituted arylene, heteroarylene, substituted heteroarylene, alkarylene, substituted alkarylene, aralkylene, or substituted aralkylene; B is a divalent linker selected from the group consisting of lower alkylene, substituted lower alkylene, lower alkenylene, substituted lower alkenylene, —O—, —O-(alkylene or substituted alkylene)-, —S—, —S(O)—, —$S(O)_2$—, —$NS(O)_2$—, —$OS(O)_2$—, —C(O)—, —C(O)-(alkylene or substituted alkylene)-, —C(S)—, —N(R")—, —C(O)N(R")—, —CON(R")-(alkylene or substituted alkylene)-, —CSN(R")—, —N(R")CO-(alkylene or substituted alkylene)-, —N(R")C(O)O—, —N(R")C(S)—, —S(O)N(R"), —$S(O)_2$N(R"), —N(R")C(O)N(R")—, —N(R")C(S)N(R")—, —N(R")S(O)N(R")—, —N(R")$S(O)_2$ N(R")—, —N(R")—N═, —C(R")═N—N('R")—, —C(R")═N—N═, —$C(R")_2$—N═N—, and —$C(R")_2$—N(R")—N(R")—; (iii) A is lower alkylene; B is optional, and when present is a divalent linker selected from the group consisting of lower alkylene, substituted lower alkylene, lower alkenylene, substituted lower alkenylene, —O—, —O-(alkylene or substituted alkylene)-, —S—, —S(O)—, —$S(O)_2$—, —$NS(O)_2$—, —$OS(O)_2$—, —C(O)—, —C(O)-(alkylene or substituted alkylene)-, —C(S)—, —N(R")—, —C(O)N(R")—, —CSN(R")—, —CON(R")-(alkylene or substituted alkylene)-, —N(R")C(O)O—, —N(R")C(S)—, —S(O)N(R"), —$S(O)_2$N(R"), —N(R")C(O)N(R")—, —N(R")C(S)N(R")—, —N(R")S(O)N(R")—, —N(R")S$(O)_2$ N(R")—, —N(R")—N═, —C(R")═N—N(R")—, —C(R")═N—N═, —$C(R")_2$—N═N—, and —$C(R")_2$—N(R")—N(R")—; and (iv) A is phenylene; B is a divalent linker selected from the group consisting of lower alkylene, substituted lower alkylene, lower alkenylene, substituted lower alkenylene, —O—, —O-(alkylene or substituted alkylene)-, —S—, —S(O)—, —$S(O)_2$—, —$NS(O)_2$—, —$OS(O)_2$—, —C(O)—, —C(O)-(alkylene or substituted alkylene)-, —C(S)—, —N(R")—, —C(O)N(R")—, —CON(R")-(alkylene or substituted alkylene)-, —CSN(R")—, —N(R")CO-(alkylene or substituted alkylene)-, —N(R")C(O)O—, —N(R")C(S)—, —S(O)N(R"), —$S(O)_2$N(R"), —N(R")C(O)N(R")—, —N(R")C(S)N(R')—, —N(R")S(O)N(R")—, —N(R")$S(O)_2$N(R")—, —N(R")—N═, —C(R")'N—N(R")—, —C(R")═N—N═, —$C(R")_2$—N═N—, and —$C(R")_2$—N(R")—N(R")—; J is

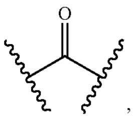, 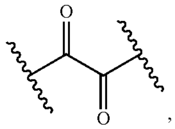, 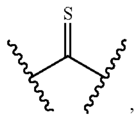,
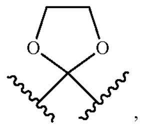, 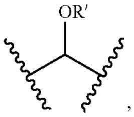, 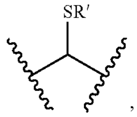,
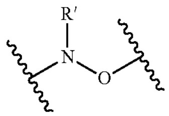, or 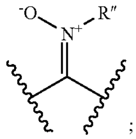;

each R' in J is independently H, alkyl, or substituted alkyl; $R_1$ is optional, and when present, is H, an amino protecting group, resin, amino acid, polypeptide, or polynucleotide; and $R_2$ is optional, and when present, is OH, an ester protecting group, resin, amino acid, polypeptide, or polynucleotide; and each $R_3$ and $R_4$ is independently H, halogen, lower alkyl, or substituted lower alkyl; and R is H, alkyl, substituted alkyl, cycloalkyl, or substituted cycloalkyl.

In certain embodiments, the non-natural amino acid can be according to formula BB:

Formula BB

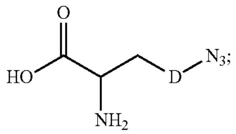

or a salt thereof, wherein: D is —Ar—$W_3$— or —$W_1$—$Y_1$—C(O)—$Y_2$—$W_2$—; Ar is

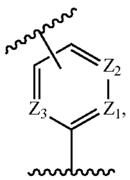, 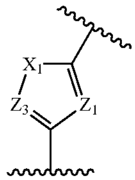, 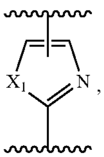, 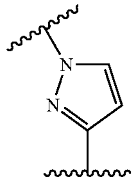,

-continued

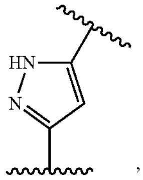 , 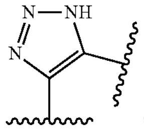 , or 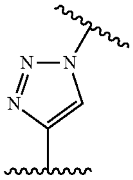 ;

each of $W_1$, $W_2$, and $W_3$ is independently a single bond or lower alkylene; each $X_1$ is independently —NH—, —O—, or —S—; each $Y_1$ is independently a single bond, —NH—, or —O—; each $Y_2$ is independently a single bond, —NH—, —O—, or an N-linked or C-linked pyrrolidinylene; and one of $Z_1$, $Z_2$, and $Z_3$ is —N— and the others of $Z_1$, $Z_2$, and $Z_3$ are independently —CH—. In certain embodiments, the non-natural amino acid is according to formula BBa:

Formula BBa

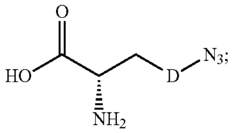

where D is a defined in the context of formula BB. In certain embodiments, the non-natural amino acid is according formula BBb:

Formula BBb

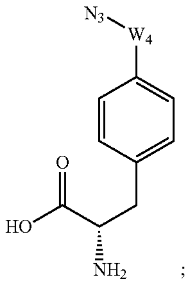

or a salt thereof, wherein $W_4$ is $C_1$-$C_{10}$ alkylene. In a further embodiment, $W_4$ is $C_1$-$C_5$ alkylene. In an embodiment, $W_4$ is $C_1$-$C_3$ alkylene. In an embodiment, $W_4$ is $C_1$ alkylene. In particular embodiments, the non-natural amino acid is selected from the group consisting of:

(1)

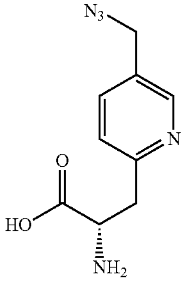

-continued (2)

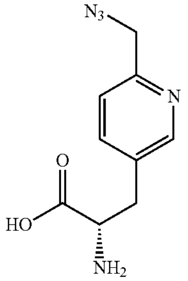

(3)

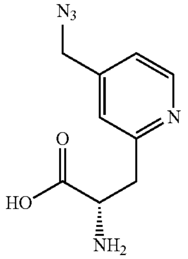

(4)

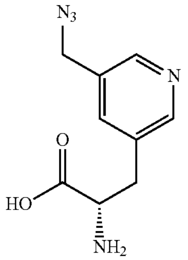

(5)

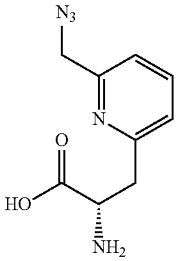

(6)

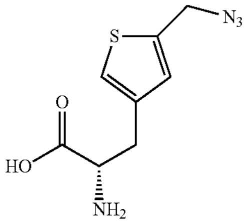

(7)

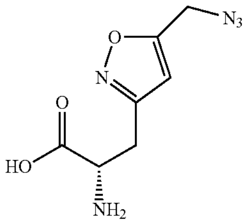

-continued
(8)
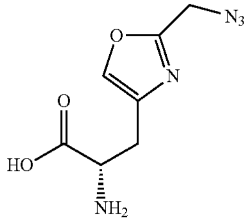
(9)
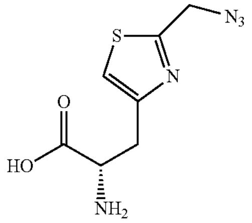
(10)
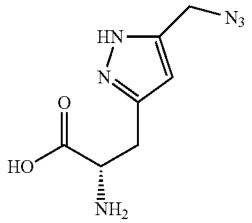
(11)
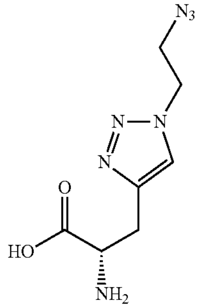
(12)
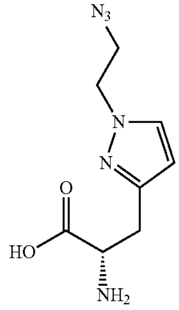
(13)
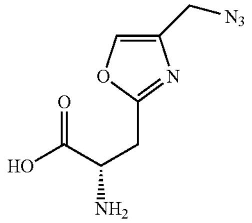
-continued
(14)
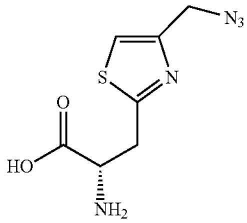
(15)
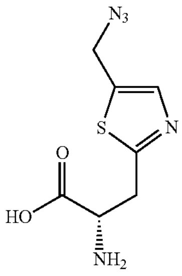
(16)
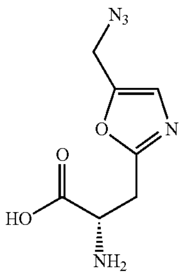
(17)
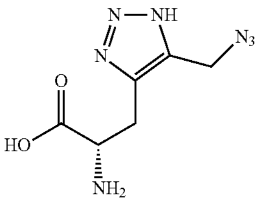
(18)
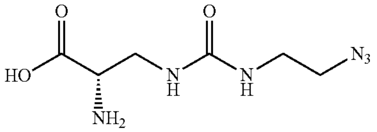
(19)
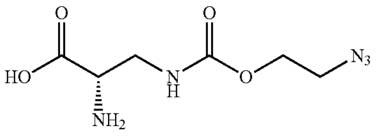
(20)
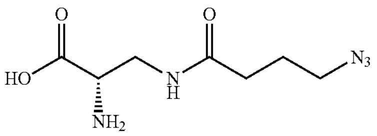
(21)
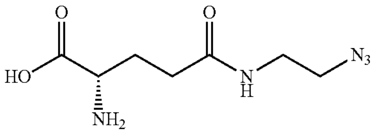

-continued (22)

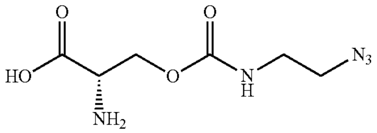

(23)

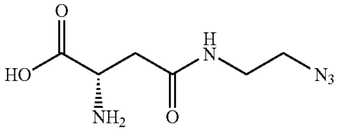

(24)

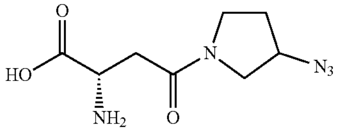

(25)

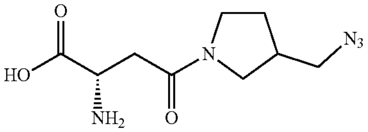

(26)

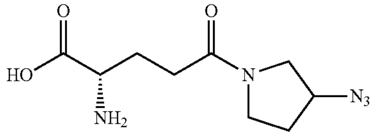

(27)

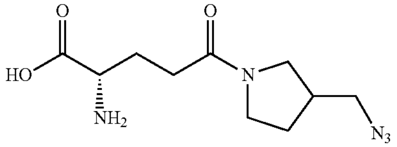

(28)

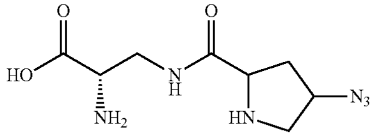

(29)

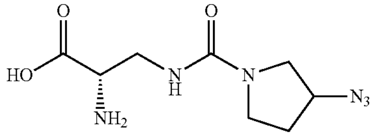

(30)

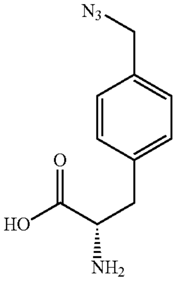

; and (40)

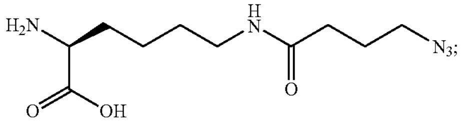

or a salt thereof. Such non-natural amino acids may be in the form of a salt, or may be incorporated into a non-natural amino acid polypeptide, polymer, polysaccharide, or a polynucleotide and optionally post translationally modified.

In certain embodiments, the modified amino acid is according to formula CC:

Formula CC

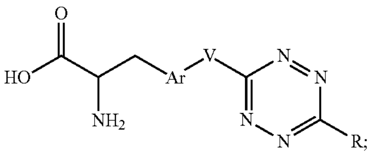

or a salt thereof, wherein Ar is:

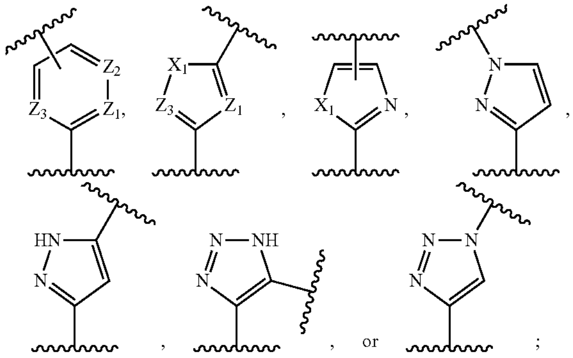

V is a single bond, lower alkylene, or —$W_1$—$W_2$—; one of $W_1$ and $W_2$ is absent or lower alkylene, and the other is —NH—, —O—, or —S—; each $X_1$ is independently —NH—, —O—, or —S—; one of $Z_1$, $Z_2$, and $Z_3$ is —CH— or —N— and the others of $Z_1$, $Z_2$, and $Z_3$ are each independently —CH—; and R is lower alkyl. In certain embodiments, when Ar is

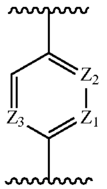

and V is —NH—, then one of $Z_1$, $Z_2$, and $Z_3$ is —N—. In certain embodiments, V is a single bond, —NH—, or —$CH_2NH$—.

In certain embodiments, Ar is

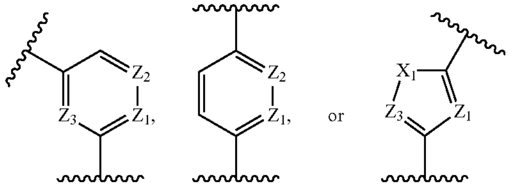

and $Z_1$, $Z_2$, $Z_3$ and $X_1$ are as defined in the context of formula CC. In certain embodiments according to this paragraph, V is $-W_1-W_2-$; one of $W_1$ and $W_2$ is absent or $-CH_2-$, and the other is —NH—, —O—, or —S—. In certain embodiments according to this paragraph, V is a single bond, —NH—, or $-CH_2NH-$. In certain embodiments according to this paragraph, $Z_1$ is N. In certain embodiments according to this paragraph, $Z_2$ is N. In certain embodiments according to this paragraph, $Z_3$ is N. In certain embodiments according to this paragraph, $Z_1$ is CH, $Z_3$ is CH and $X_1$ is S.

In certain embodiments, Ar is

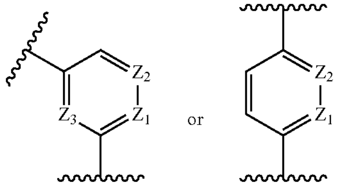

and $Z_1$, $Z_2$, and $Z_3$ are as defined in the context of formula CC. In certain embodiments according to this paragraph, V is $-W_1-W_2-$; one of $W_1$ and $W_2$ is absent or $-CH_2-$, and the other is —NH—, —O—, or —S—. In certain embodiments according to this paragraph, V is a single bond, —NH—, or $-CH_2NH-$. In certain embodiments according to this paragraph, $Z_1$ is N. In certain embodiments according to this paragraph, $Z_2$ is N. In certain embodiments according to this paragraph, $Z_3$ is N.

In certain embodiments, Ar is

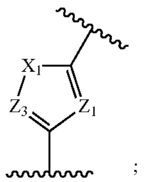

and $Z_1$, $Z_3$ and $X_1$ are as defined in the context of formula CC. In certain embodiments according to this paragraph, V is $-W_1-W_2-$; one of $W_1$ and $W_2$ is absent or $-CH_2-$, and the other is —NH—, —O—, or —S—. In certain embodiments according to this paragraph, V is a single bond, —NH—, or $-CH_2NH-$. In certain embodiments according to this paragraph, $Z_1$ is N. In certain embodiments according to this paragraph, $Z_3$ is N. In certain embodiments according to this paragraph, $Z_1$ is CH, $Z_3$ is CH and $X_1$ is S.

In certain embodiments, the modified amino acid is according to Formula CCa:

Formula CCa

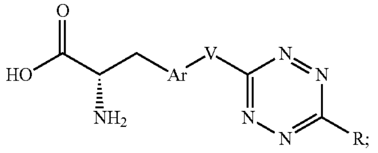

where Ar, V, and R are defined in the context of formula CC.

In an embodiment, compounds of either of formulas CC and CCa are provided wherein V is a single bond. In another embodiment, compounds of either of formulas CC and CCa are provided wherein V is —NH—. In another embodiment, compounds of either of formulas CC and CCa are provided wherein V is $-CH_2NH-$.

In certain embodiments, the modified amino acid is according to Formula DD:

Formula DD

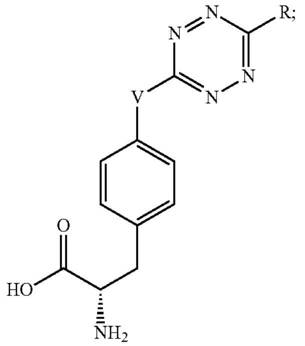

or a salt thereof, wherein V and R are as defined in Formula CC. In certain embodiments according to this paragraph, V is $-W_1-W_2-$; one of $W_1$ and $W_2$ is absent or $-CH_2-$, and the other is —NH—, —O—, or —S—. In certain embodiments, V is a single bond, —NH—, or $-CH_2NH-$. In certain embodiments, V is a single bond or $-CH_2NH-$; and R is methyl.

In certain embodiments, the modified amino acid is according to Formula EE:

Formula EE

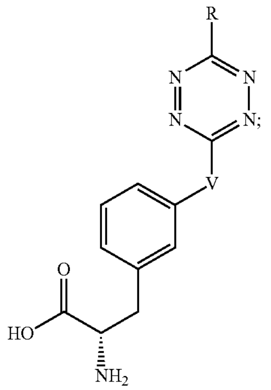

or a salt thereof, wherein V and R are as defined in Formula CC. In certain embodiments according to this paragraph, V is $-W_1-W_2-$; one of $W_1$ and $W_2$ is absent or $-CH_2-$, and the other is —NH—, —O—, or —S—. In certain embodiments, V is a single bond, —NH—, or $-CH_2NH-$. In certain embodiments, V is a single bond, —NH—, or $-CH_2NH-$; and R is methyl.

In certain embodiments, the modified amino acid is according to Formula FF:

Formula FF

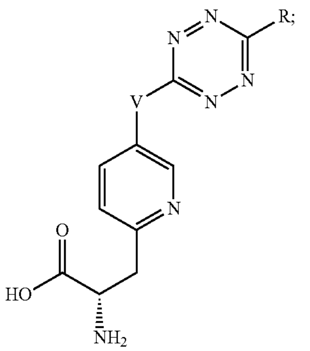

or a salt thereof, wherein V and R are as defined in Formula CC. In certain embodiments according to this paragraph, V is —$W_1$—$W_2$—; one of $W_1$ and $W_2$ is absent or —$CH_2$—, and the other is —NH—, —O—, or —S—. In certain embodiments, V is a single bond, —NH—, or —$CH_2NH$—. In certain embodiments, V is a single bond, —NH—, or —$CH_2NH$—; and R is methyl.

In certain embodiments, the modified amino acid is according to Formula GG:

Formula GG

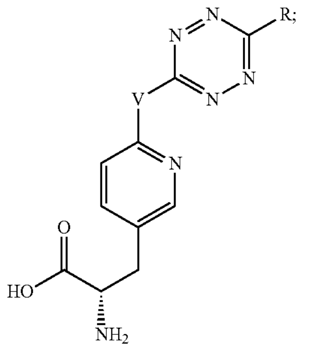

or a salt thereof, wherein V and R are as defined in Formula CC. In certain embodiments according to this paragraph, V is —$W_1$—$W_2$—; one of $W_1$ and $W_2$ is absent or —$CH_2$—, and the other is —NH—, —O—, or —S—. In certain embodiments, V is a single bond, —NH—, or —$CH_2NH$—. In certain embodiments, V is a single bond, —NH—, or —$CH_2NH$—; and R is methyl.

In certain embodiments, the modified amino acid is according to Formula HH:

Formula HH

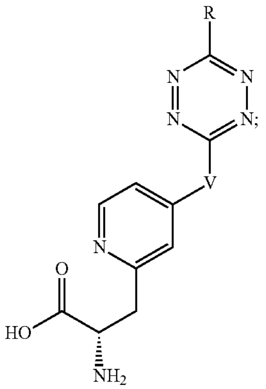

or a salt thereof, wherein V and R are as defined in Formula CC. In certain embodiments according to this paragraph, V is —$W_1$—$W_2$—; one of $W_1$ and $W_2$ is absent or —$CH_2$—, and the other is —NH—, —O—, or —S—. In certain embodiments, V is a single bond, —NH—, or —$CH_2NH$—. In certain embodiments, V is a single bond, —NH—, or —$CH_2NH$—; and R is methyl.

In certain embodiments, the modified amino acid is according to Formula JJ:

Formula JJ

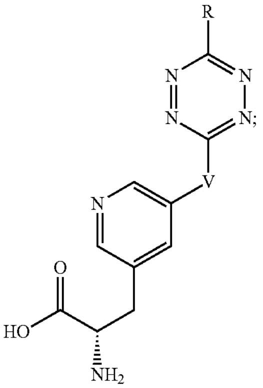

or a salt thereof, wherein V and R are as defined in Formula CC. In certain embodiments according to this paragraph, V is —$W_1$—$W_2$—; one of $W_1$ and $W_2$ is absent or —$CH_2$—, and the other is —NH—, —O—, or —S—. In certain embodiments, V is a single bond, —NH—, or —$CH_2NH$—. In certain embodiments, V is a single bond, —NH—, or —$CH_2NH$—; and R is methyl.

In certain embodiments, the modified amino acid is according to Formula KK:

Formula KK

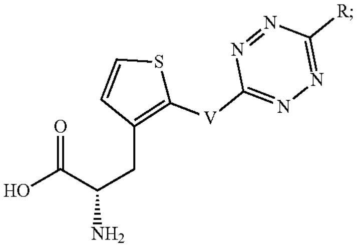

or a salt thereof, wherein V and R are as defined in Formula CC. In certain embodiments according to this paragraph, V is —$W_1$—$W_2$—; one of $W_1$ and $W_2$ is absent or —$CH_2$—, and the other is —NH—, —O—, or —S—. In certain embodiments, V is a single bond, —NH—, or —$CH_2$NH—. In certain embodiments, V is a single bond, —NH—, or —$CH_2$NH—; and R is methyl.

In certain embodiments, the modified amino acid is according to Formula LL:

Formula LL

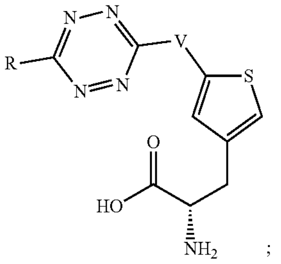

or a salt thereof, wherein V and R are as defined in Formula CC. In certain embodiments according to this paragraph, V is —$W_1$—$W_2$—; one of $W_1$ and $W_2$ is absent or —$CH_2$—, and the other is —NH—, —O—, or —S—. In certain embodiments, V is a single bond, —NH—, or —$CH_2$NH—. In certain embodiments, V is a single bond, —NH—, or —$CH_2$NH—; and R is methyl.

In certain embodiments, the modified amino acid is according to any of formulas 51-62:

(51)

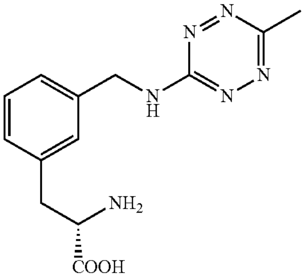

-continued (52)

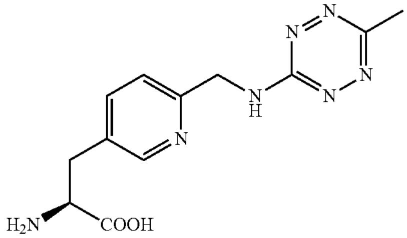

(53)

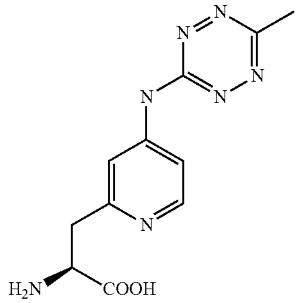

(54)

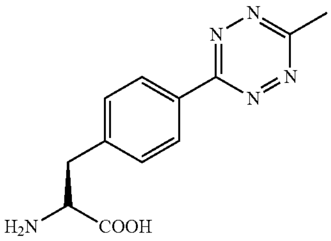

(55)

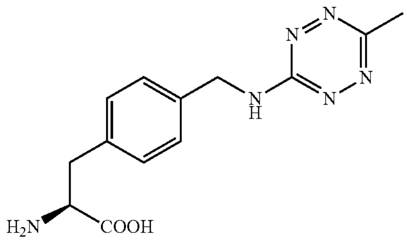

(56)

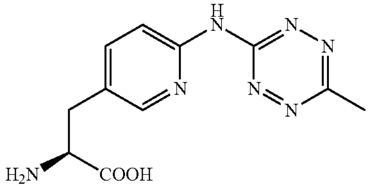

(57)

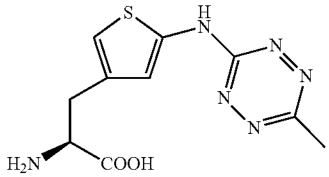

(58)

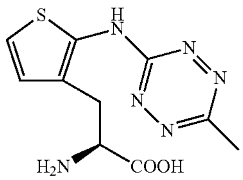

-continued (59)

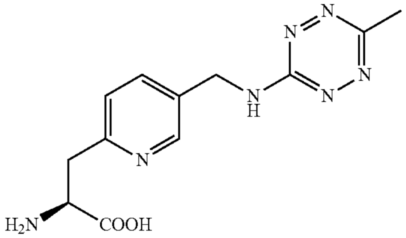

(60)

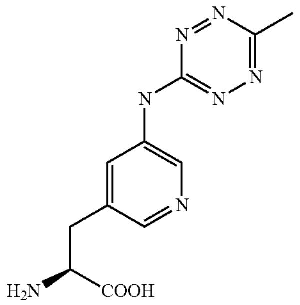

(61)

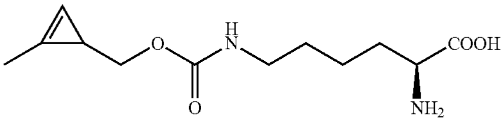

(62)

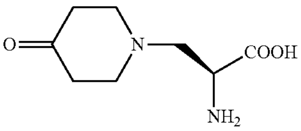

or a salt thereof.

In certain embodiments, the non-natural amino acid is selected from the group consisting of compounds 30, 53, 56, 59, 60, 61, and 62 above. In certain embodiments, the non-natural amino acid is compound 30. In certain embodiments, the non-natural amino acid is compound 56. In some embodiments, the non-natural amino acid is compound 61. In some embodiments, the non-natural amino acid is compound 62.

8. Forms and Formulations of Compounds

In some embodiments, provided herein are:

(a) compounds as described herein, e.g., of Formula I and/or II and/or III and/or V and/or VI, and pharmaceutically acceptable salts and compositions thereof;

(b) compounds as described herein, e.g., of Formula I and/or II and/or III and/or V and/or VI, and pharmaceutically acceptable salts and compositions thereof for use in the treatment and/or prophylaxis of cancer (e.g, pancreatic cancer, multiple myeloma);

(c) processes for the preparation of compounds as described herein, e.g., of Formula I and/or II and/or III and/or V and/or VI, as described in more detail elsewhere herein and/or in the examples section;

(d) pharmaceutical formulations comprising a compound as described herein, e.g., of Formula I and/or II and/or III and/or V and/or VI, or a pharmaceutically acceptable salt thereof together with a pharmaceutically acceptable carrier or diluent;

(e) pharmaceutical formulations comprising a compound as described herein, e.g., of Formula I and/or II and/or III and/or V and/or VI, or a pharmaceutically acceptable salt thereof together with one or more other effective anti-cancer agents, optionally in a pharmaceutically acceptable carrier or diluent;

(f) use of a compound of Formula I and/or II and/or III and/or V and/or VI, or a pharmaceutical composition comprising Formula I and/or II and/or III and/or V and/or VI, for the treatment of cancer and/or an inflammatory condition. The use includes the administration of an effective amount of a compound as described herein, e.g., of Formula I and/or II and/or III and/or V and/or VI, its pharmaceutically acceptable salt or composition; or (g) a method for the treatment of cancer and/or an inflammatory condition that includes the administration of an effective amount of a compounds as described herein, e.g., of Formula I and/or II and/or III and/or V and/or VI, its pharmaceutically acceptable salt or composition in combination and/or alternation with one or more effective anti-cancer agent.

Optically Active Compounds

It is appreciated that compounds provided herein have several chiral centers and may exist in and be isolated in optically active and racemic forms. Some compounds may exhibit polymorphism. It is to be understood that any racemic, optically-active, diastereomeric, polymorphic, or stereoisomeric form, or mixtures thereof, of a compound provided herein, which possess the useful properties described herein is within the scope of the invention. It being well known in the art how to prepare optically active forms (for example, by resolution of the racemic form by recrystallization techniques, by synthesis from optically-active starting materials, by chiral synthesis, or by chromatographic separation using a chiral stationary phase).

Likewise, most amino acids are chiral (designated as L or D, wherein the L enantiomer is the naturally occurring configuration) and can exist as separate enantiomers.

Examples of methods to obtain optically active materials are known in the art, and include at least the following.

i) physical separation of crystals—a technique whereby macroscopic crystals of the individual enantiomers are manually separated. This technique can be used if crystals of the separate enantiomers exist, i.e., the material is a conglomerate, and the crystals are visually distinct;

ii) simultaneous crystallization—a technique whereby the individual enantiomers are separately crystallized from a solution of the racemate, possible only if the latter is a conglomerate in the solid state;

iii) enzymatic resolutions—a technique whereby partial or complete separation of a racemate by virtue of differing rates of reaction for the enantiomers with an enzyme;

iv) enzymatic asymmetric synthesis—a synthetic technique whereby at least one step of the synthesis uses an enzymatic reaction to obtain an enantiomerically pure or enriched synthetic precursor of the desired enantiomer;

v) chemical asymmetric synthesis—a synthetic technique whereby the desired enantiomer is synthesized from an achiral precursor under conditions that produce asymmetry (i.e., chirality) in the product, which may be achieved using chiral catalysts or chiral auxiliaries;

vi) diastereomer separations—a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations—a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) kinetic resolutions—this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors—a synthetic technique whereby the desired enantiomer is obtained from non-chiral starting materials and where the stereochemical integrity is not or is only minimally compromised over the course of the synthesis;

x) chiral liquid chromatography—a technique whereby the enantiomers of a racemate are separated in a liquid mobile phase by virtue of their differing interactions with a stationary phase. The stationary phase can be made of chiral material or the mobile phase can contain an additional chiral material to provoke the differing interactions;

xi) chiral gas chromatography—a technique whereby the racemate is volatilized and enantiomers are separated by virtue of their differing interactions in the gaseous mobile phase with a column containing a fixed non-racemic chiral adsorbent phase;

xii) extraction with chiral solvents—a technique whereby the enantiomers are separated by virtue of preferential dissolution of one enantiomer into a particular chiral solvent;

xiii) transport across chiral membranes—a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane which allows only one enantiomer of the racemate to pass through.

In some embodiments, provided herein are compositions of compounds of Formula (I-p) and/or Formula I and/or II and/or III and/or V and/or VI, that are substantially free of a designated enantiomer of that compound. In certain embodiments, in the methods and compounds of this invention, the compounds are substantially free of enantiomers. In some embodiments, the composition includes that includes a compound that is at least 85, 90%, 95%, 98%, 99% to 100% by weight, of the compound, the remainder comprising other chemical species or enantiomers.

Isotopically Enriched Compounds

Also provided herein are isotopically enriched compounds, including but not limited to isotopically enriched compounds of Formula (I-p) and/or Formula I and/or II and/or III and/or V and/or VI.

Isotopic enrichment (for example, deuteration) of pharmaceuticals to improve pharmacokinetics ("PK"), pharmacodynamics ("PD"), and toxicity profiles, has been demonstrated previously with some classes of drugs. See, for example, Lijinsky et. al., Food Cosmet. Toxicol., 20: 393 (1982); Lijinsky et. al., J. Nat. Cancer Inst., 69: 1127 (1982); Mangold et. al., Mutation Res. 308: 33 (1994); Gordon et. al., Drug Metab. Dispos., 15: 589 (1987); Zello et. al., Metabolism, 43: 487 (1994); Gately et. al., J. Nucl. Med., 27: 388 (1986); Wade D, Chem. Biol. Interact. 117: 191 (1999).

Isotopic enrichment of a drug can be used, for example, to (1) reduce or eliminate unwanted metabolites, (2) increase the half-life of the parent drug, (3) decrease the number of doses needed to achieve a desired effect, (4) decrease the amount of a dose necessary to achieve a desired effect, (5) increase the formation of active metabolites, if any are formed, and/or (6) decrees the production of deleterious metabolites in specific tissues and/or create a more effective drug and/or a safer drug for combination therapy, whether the combination therapy is intentional or not.

Replacement of an atom for one of its isotopes often will result in a change in the reaction rate of a chemical reaction. This phenomenon is known as the Kinetic Isotope Effect ("KIE"). For example, if a C—H bond is broken during a rate-determining step in a chemical reaction (i.e. the step with the highest transition state energy), substitution of a deuterium for that hydrogen will cause a decrease in the reaction rate and the process will slow down. This phenomenon is known as the Deuterium Kinetic Isotope Effect ("DKIE"). (See, e.g., Foster et al., Adv. Drug Res., vol. 14, pp. 1-36 (1985); Kushner et al., Can. J. Physiol. Pharmacol., vol. 77, pp. 79-88 (1999)).

The magnitude of the DKIE can be expressed as the ratio between the rates of a given reaction in which a C—H bond is broken, and the same reaction where deuterium is substituted for hydrogen. The DKIE can range from about 1 (no isotope effect) to very large numbers, such as 50 or more, meaning that the reaction can be fifty, or more, times slower when deuterium is substituted for hydrogen. High DKIE values may be due in part to a phenomenon known as tunneling, which is a consequence of the uncertainty principle. Tunneling is ascribed to the small mass of a hydrogen atom, and occurs because transition states involving a proton can sometimes form in the absence of the required activation energy. Because deuterium has more mass than hydrogen, it statistically has a much lower probability of undergoing this phenomenon.

Tritium ("T") is a radioactive isotope of hydrogen, used in research, fusion reactors, neutron generators and radiopharmaceuticals. Tritium is a hydrogen atom that has 2 neutrons in the nucleus and has an atomic weight close to 3. It occurs naturally in the environment in very low concentrations, most commonly found as $T_2O$. Tritium decays slowly (half-life=12.3 years) and emits a low energy beta particle that cannot penetrate the outer layer of human skin. Internal exposure is the main hazard associated with this isotope, yet it must be ingested in large amounts to pose a significant health risk. As compared with deuterium, a lesser amount of tritium must be consumed before it reaches a hazardous level. Substitution of tritium ("T") for hydrogen results in yet a stronger bond than deuterium and gives numerically larger isotope effects. Similarly, substitution of isotopes for other elements, including, but not limited to, $^{13}C$ or $^{14}C$ for carbon, $^{33}S$, $^{34}S$, or $^{36}S$ for sulfur, $^{15}N$ for nitrogen, and $^{17}O$ or $^{18}O$ for oxygen, may lead to a similar kinetic isotope effect.

For example, the DKIE was used to decrease the hepatotoxicity of halothane by presumably limiting the production of reactive species such as trifluoroacetyl chloride. However, this method may not be applicable to all drug classes. For example, deuterium incorporation can lead to metabolic switching. The concept of metabolic switching asserts that xenogens, when sequestered by Phase I enzymes, may bind transiently and re-bind in a variety of conformations prior to the chemical reaction (e.g., oxidation). This hypothesis is supported by the relatively vast size of binding pockets in many Phase I enzymes and the promiscuous nature of many metabolic reactions. Metabolic switching can potentially lead to different proportions of known metabolites as well as altogether new metabolites. This new metabolic profile may impart more or less toxicity.

The animal body expresses a variety of enzymes for the purpose of eliminating foreign substances, such as therapeutic agents, from its circulation system. Examples of such enzymes include the cytochrome P450 enzymes ("CYPs"), esterases, proteases, reductases, dehydrogenases, and monoamine oxidases, to react with and convert these foreign substances to more polar intermediates or metabolites for renal excretion. Some of the most common metabolic reactions of pharmaceutical compounds involve the oxidation of a carbon-hydrogen (C—H) bond to either a carbon-oxygen (C—O) or carbon-carbon (C—C) pi-bond. The resultant metabolites may be stable or unstable under physiological conditions, and can have substantially different pharmacokinetic, pharmacodynamic, and acute and long-term toxicity profiles relative to the parent compounds. For many drugs, such oxidations are rapid. These drugs therefore often require the administration of multiple or high daily doses.

Therefore, isotopic enrichment at certain positions of a compound provided herein will produce a detectable KIE that will affect the pharmacokinetic, pharmacologic, and/or toxicological profiles of a compound provided herein in comparison with a similar compound having a natural isotopic composition.

9. Preparation of Compounds of Formula (I) and Subformulas

SCHEME 1

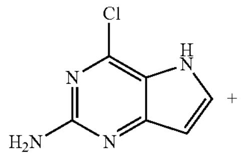

1.1

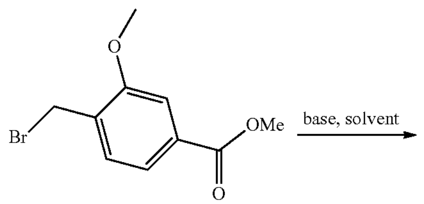

1.2

-continued

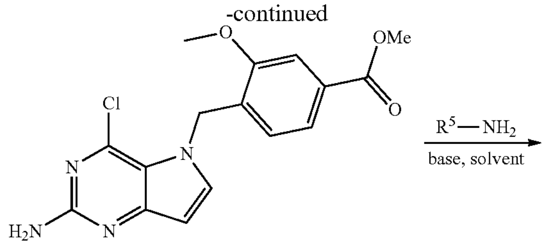

1.3

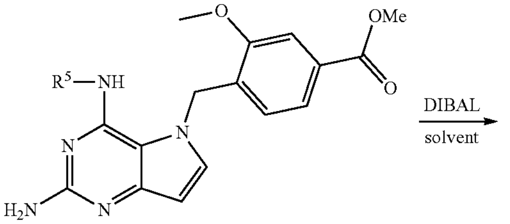

1.4

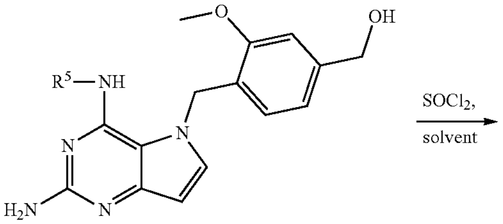

1.5

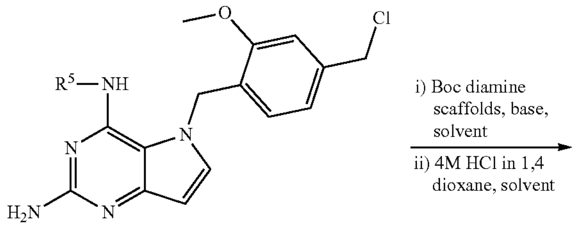

1.6

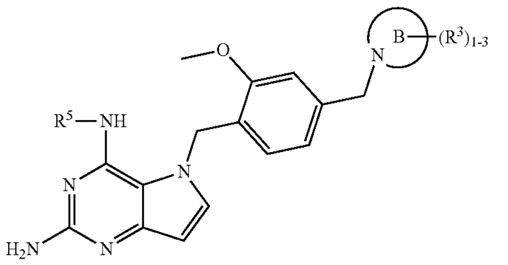

Formula (I)

In a group of embodiments, compounds of Formula (I) are prepared as shown in Scheme 1 above. The reaction of compound 1.1 with compound 1.2 provides intermediate 1.3. The reaction can be carried out in the presence of any suitable base (e.g., cesium carbonate, sodium carbonate, potassium carbonate) and any suitable aprotic solvent (e.g., DMF, THF, dioxane). The chloride in compound 1.3 reacts with an amine $R^5$—$NH_2$ to provide the intermediate 1.4 and the reaction is carried out in the presence of any suitable base (e.g., DIPEA, TEA) and an aprotic solvent (e.g., NMP, DMF). The ester group in compound 1.3 is reduced to an alcohol (compound 1.4) in the presence of any suitable reducing agent (e.g., LAH, DIBAL). The hydroxy group in compound 1.5 is converted to a leaving group (e.g. chloride, bromide, triflate) in the presence of suitable reagents (e.g., thionyl chloride, thionyl bromide, trifluoromethane-sulfonate) and solvents (e.g., dichloromethane, dichloroethane) to provide compound 1.6. Reaction of compound 1.6 with a suitably protected diamine in the presence of a base (e.g., DIPEA, TEA) and a solvent (e.g, dichloromethane, dichloroethane) followed by removal of the protecting group provides compound of Formula (I). Additional methods for synthesis of compounds of Formula (I) and subformulas thereof are described in the Examples section. As used herein, "compounds of Formula (I) and subformulas thereof" refers to compounds of Formula (I), and/or Formula (II) and/or Formula (III).

9. Preparation of Antibody Conjugates

9.1. Antigen Preparation

The protein to be used for isolation of the antibodies may be intact antigen or a fragment of an antigen. The intact protein, or fragment of the antigen, may be in the form of an isolated protein or protein expressed by a cell. Other forms of antigens useful for generating antibodies will be apparent to those skilled in the art.

9.2. Monoclonal Antibodies

Monoclonal antibodies may be obtained, for example, using the hybridoma method first described by Kohler et al., *Nature,* 1975, 256:495-497 (incorporated by reference in its entirety), and/or by recombinant DNA methods (see e.g., U.S. Pat. No. 4,816,567, incorporated by reference in its entirety). Monoclonal antibodies may also be obtained, for example, using phage or yeast-based libraries. See e.g., U.S. Pat. Nos. 8,258,082 and 8,691,730, each of which is incorporated by reference in its entirety.

In the hybridoma method, a mouse or other appropriate host animal is immunized to elicit lymphocytes that produce or are capable of producing antibodies that will specifically bind to the protein used for immunization. Alternatively, lymphocytes may be immunized in vitro. Lymphocytes are then fused with myeloma cells using a suitable fusing agent, such as polyethylene glycol, to form a hybridoma cell. See Goding J. W., *Monoclonal Antibodies: Principles and Practice* $3^{rd}$ ed. (1986) Academic Press, San Diego, CA, incorporated by reference in its entirety.

The hybridoma cells are seeded and grown in a suitable culture medium that contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Useful myeloma cells are those that fuse efficiently, support stable high-level production of antibody by the selected antibody-producing cells, and are sensitive media conditions, such as the presence or absence of HAT medium. Among these, preferred myeloma cell lines are murine myeloma lines, such as those derived from MOP-21 and MC-11 mouse tumors (available from the Salk Institute Cell Distribution Center, San Diego, CA), and SP-2 or X63-Ag8-653 cells (available from the American Type Culture Collection, Rockville, MD). Human myeloma and mouse-human heteromyeloma cell lines also have been described for the production of human monoclonal antibodies. See e.g., Kozbor, *J. Immunol.,* 1984, 133:3001, incorporated by reference in its entirety.

After the identification of hybridoma cells that produce antibodies of the desired specificity, affinity, and/or biological activity, selected clones may be subcloned by limiting dilution procedures and grown by standard methods. See Goding, supra. Suitable culture media for this purpose include, for example, D-MEM or RPMI-1640 medium. In addition, the hybridoma cells may be grown in vivo as ascites tumors in an animal.

DNA encoding the monoclonal antibodies may be readily isolated and sequenced using conventional procedures (e.g., by using oligonucleotide probes that are capable of binding specifically to genes encoding the heavy and light chains of the monoclonal antibodies). Thus, the hybridoma cells can serve as a useful source of DNA encoding antibodies with the desired properties. Once isolated, the DNA may be placed into expression vectors, which are then transfected into host cells such as bacteria (e.g., *E. coli*), yeast (e.g., *Saccharomyces* or *Pichia* sp.), COS cells, Chinese hamster ovary (CHO) cells, or myeloma cells that do not otherwise produce antibody, to produce the monoclonal antibodies.

9.3. Humanized Antibodies

Humanized antibodies may be generated by replacing most, or all, of the structural portions of a non-human monoclonal antibody with corresponding human antibody sequences. Consequently, a hybrid molecule is generated in which only the antigen-specific variable, or CDR, is composed of non-human sequence. Methods to obtain humanized antibodies include those described in, for example, Winter and Milstein, *Nature,* 1991, 349:293-299; Rader et al., *Proc. Nat. Acad. Sci. U.S.A.,* 1998, 95:8910-8915; Steinberger et al., *J. Biol. Chem.,* 2000, 275:36073-36078; Queen et al., *Proc. Nat. Acad. Sci. U.S.A.,* 1989, 86:10029-10033; and U.S. Pat. Nos. 5,585,089, 5,693,761, 5,693,762, and 6,180,370; each of which is incorporated by reference in its entirety.

9.4. Human Antibodies

Human antibodies can be generated by a variety of techniques known in the art, for example by using transgenic animals (e.g., humanized mice). See, e.g., Jakobovits et al., *Proc. Natl. Acad. Sci. U.S.A.,* 1993, 90:2551; Jakobovits et al., *Nature,* 1993, 362:255-258; Bruggermann et al., *Year in Immuno.,* 1993, 7:33; and U.S. Pat. Nos. 5,591,669, 5,589,369 and 5,545,807; each of which is incorporated by reference in its entirety. Human antibodies can also be derived from phage-display libraries (see e.g., Hoogenboom et al., *J. Mol. Biol.,* 1991, 227:381-388; Marks et al., *J Mol. Biol.,* 1991, 222:581-597; and U.S. Pat. Nos. 5,565,332 and 5,573,905; each of which is incorporated by reference in its entirety). Human antibodies may also be generated by in vitro activated B cells (see e.g., U.S. Pat. Nos. 5,567,610 and 5,229,275, each of which is incorporated by reference in its entirety). Human antibodies may also be derived from yeast-based libraries (see e.g., U.S. Pat. No. 8,691,730, incorporated by reference in its entirety).

9.5. Conjugation

The antibody conjugates can be prepared by standard techniques. In certain embodiments, an antibody is contacted with a payload precursor under conditions suitable for forming a bond from the antibody to the payload to form an antibody-payload conjugate. In certain embodiments, an antibody is contacted with a linker precursor under conditions suitable for forming a bond from the antibody to the linker. The resulting antibody-linker is contacted with a payload precursor under conditions suitable for forming a bond from the antibody-linker to the payload to form an antibody-linker-payload conjugate. In certain embodiments, a payload precursor is contacted with a linker precursor under conditions suitable for forming a bond from the payload to the linker. The resulting payload-linker is contacted with an antibody under conditions suitable for forming a bond from the payload-linker to the antibody to form an antibody-linker-payload conjugate. Suitable linkers for preparing the antibody conjugates are disclosed herein, and exemplary conditions for conjugation are described in the Examples below.

In some embodiments, a conjugate is prepared by contacting an antibody as disclosed herein with a linker precursor according to a structure of any of (A)-(H) and (J)-(M):

(A)

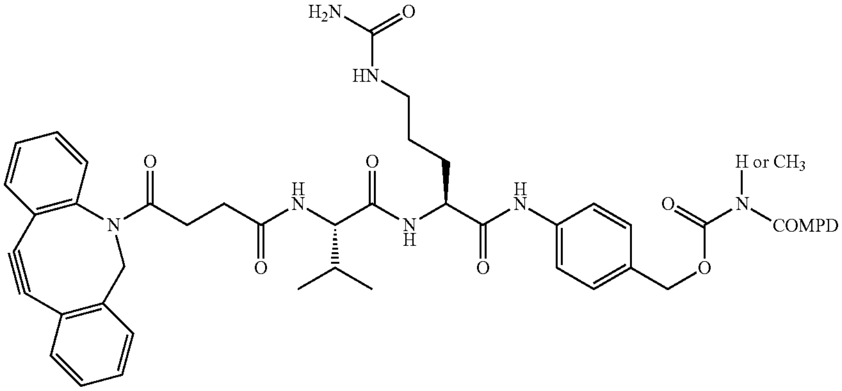

wherein COMPD is the remaining portion of a compound of Formula (I-P), and/or Formula (I), and/or (II), and/or (III) that is attached to a primary or secondary amino group of $R^3$.

(B)

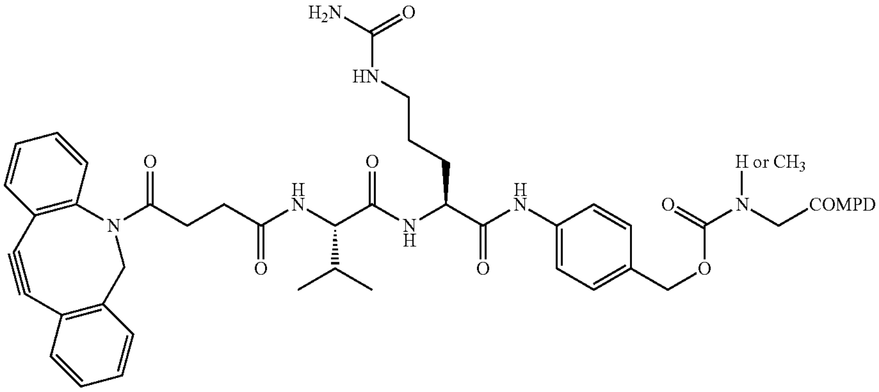

wherein COMPD is the remaining portion of a compound of Formula I-P, and/or Formula (I), and/or (II), and/or (III) that is attached to the —$CH_2$-(primary or secondary amino) group of $R^3$.

(C)

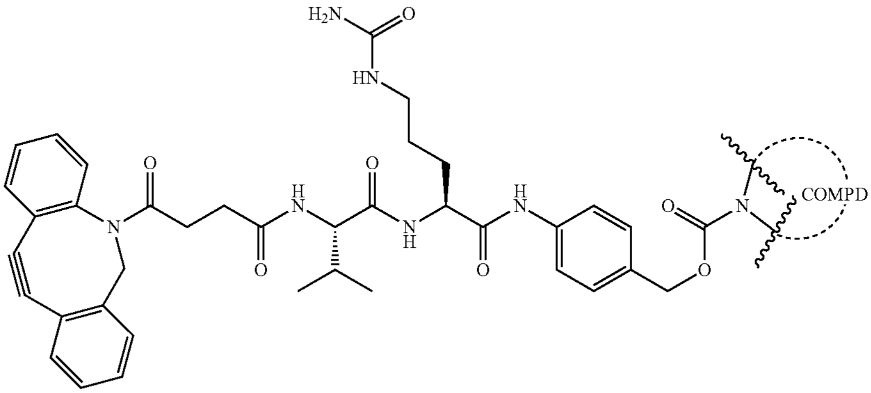

wherein COMPD is the remaining portion of a compound of Formula (I-P), and/or Formula (I), and/or (II), and/or (III) that is attached to a —NH moiety that is part of ring B or a spiro-heterocycle of $R^3$.

(D)

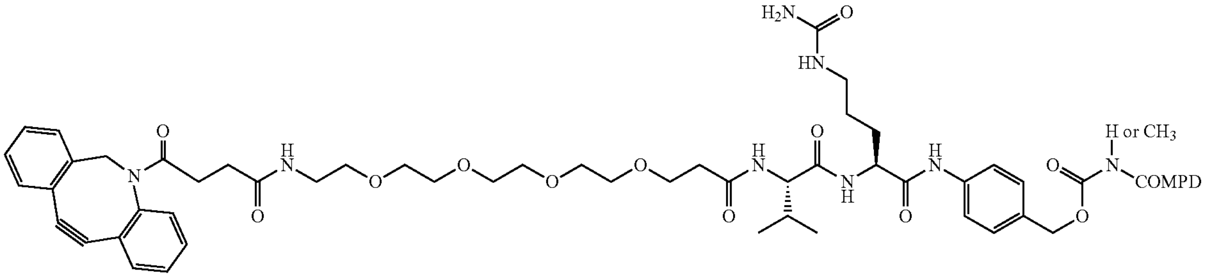

wherein COMPD is the remaining portion of a compound of Formula (I-P), and/or Formula (I), and/or (II), and/or (III) that is attached to a primary or secondary amino group of $R^3$.

(E)

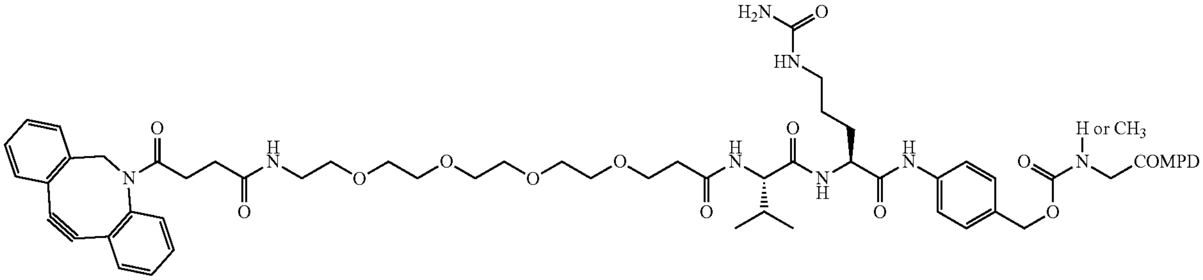

wherein COMPD is the remaining portion of a compound of Formula (I-P), and/or Formula (I), and/or (II), and/or (III) that is attached to a primary or secondary amino group of $R^3$.

(F)

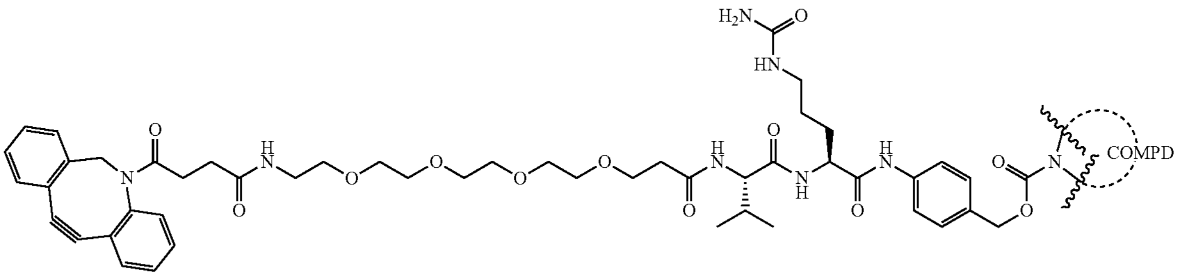

wherein COMPD is the remaining portion of a compound of Formula (I-P), and/or Formula (I), and/or (II), and/or (III) that is attached to a —NH moiety that is part of ring B or a spiro-heterocycle of $R^3$
(G)
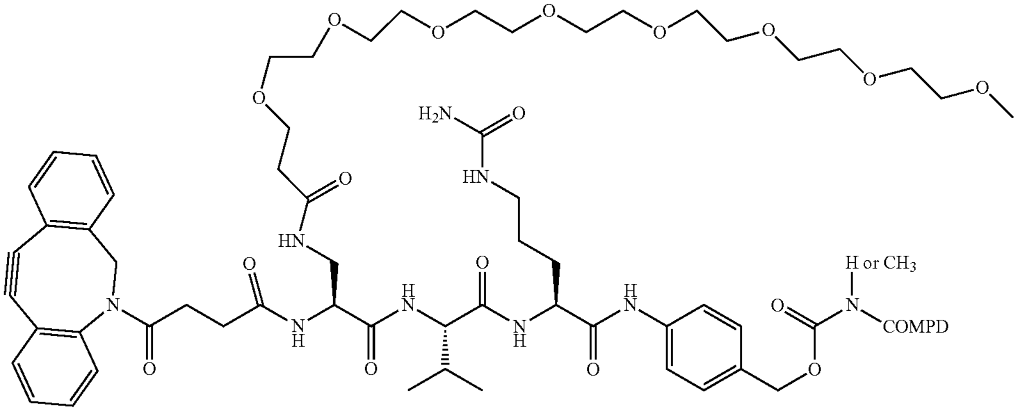
wherein COMPD is the remaining portion of a compound of Formula (I-P), and/or Formula (I), and/or (II), and/or (III) that is attached to a primary or secondary amino group of $R^3$.
(H)
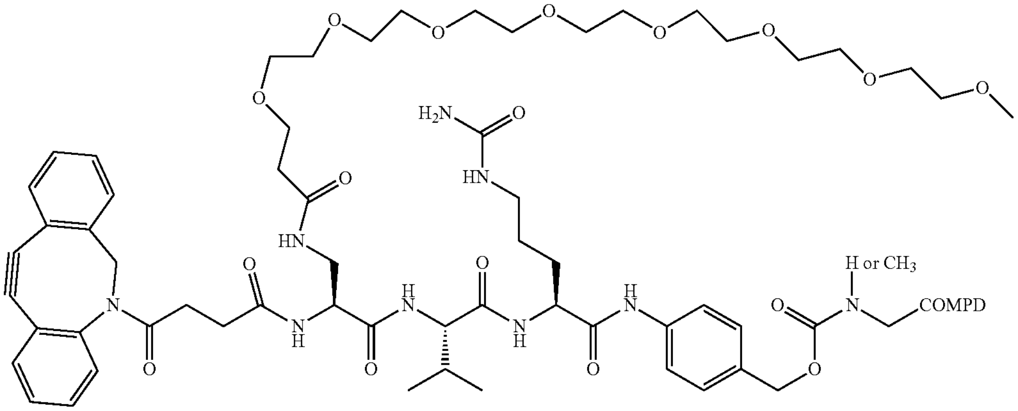

wherein COMPD is the remaining portion of a compound of Formula (I-P), and/or Formula (I), and/or (II), and/or (III) that is attached to a primary or secondary amino group of $R^3$.
(J)
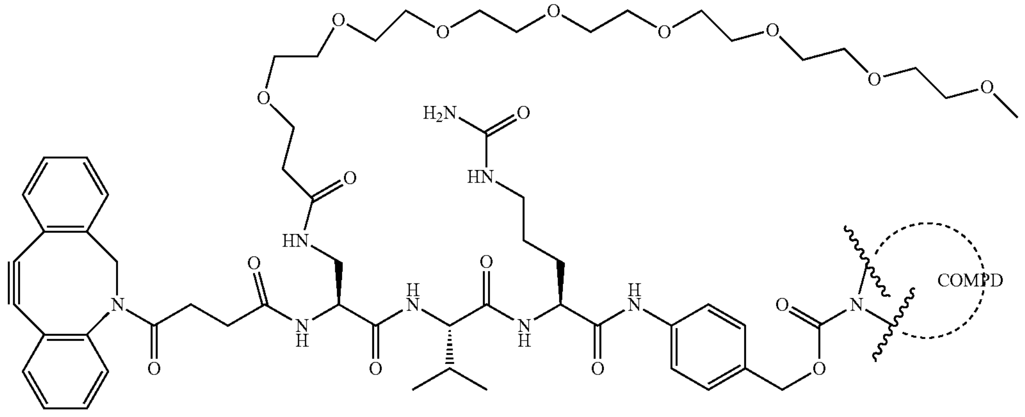
wherein COMPD is the remaining portion of a compound of Formula (I-P), and/or Formula (I), and/or (II), and/or (III) that is attached to a —NH moiety that is part of ring B or a spiro-heterocycle of $R^3$
(K)
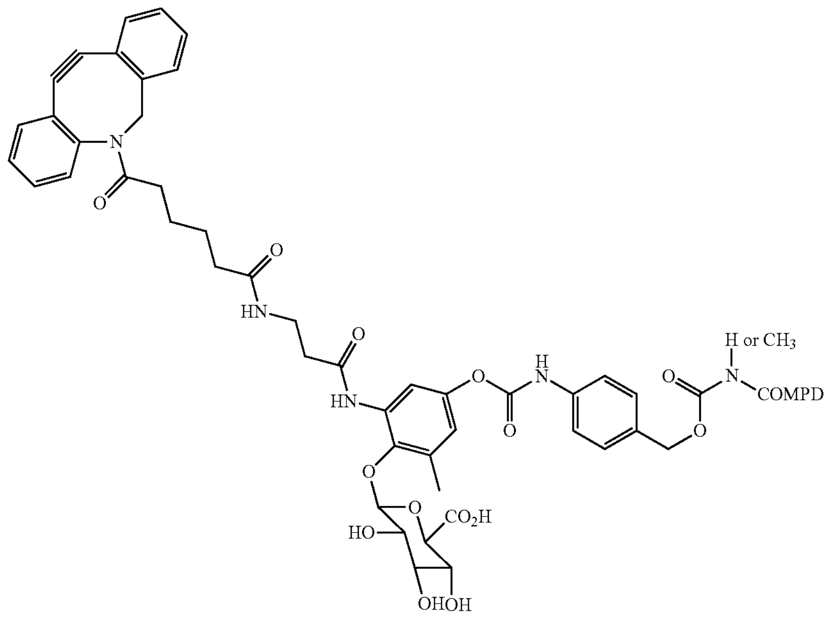

wherein COMPD is the remaining portion of a compound of Formula (I-P), and/or Formula (I), and/or (II), and/or (III) that is attached to a primary or secondary amino group of $R^3$.
(L)
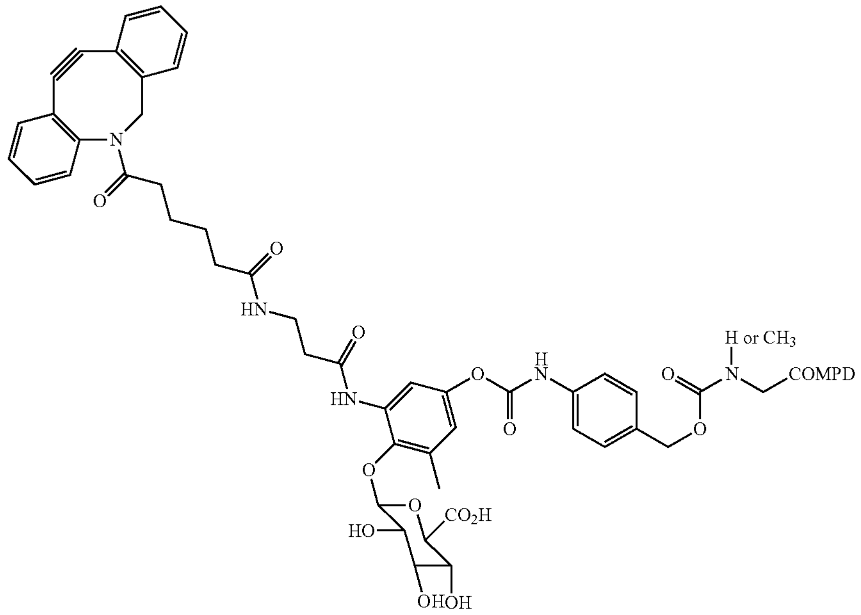
wherein COMPD is the remaining portion of a compound of Formula (I-P), and/or Formula (I), and/or (II), and/or (III) that is attached to a primary or secondary amino group of $R^3$.
(M)
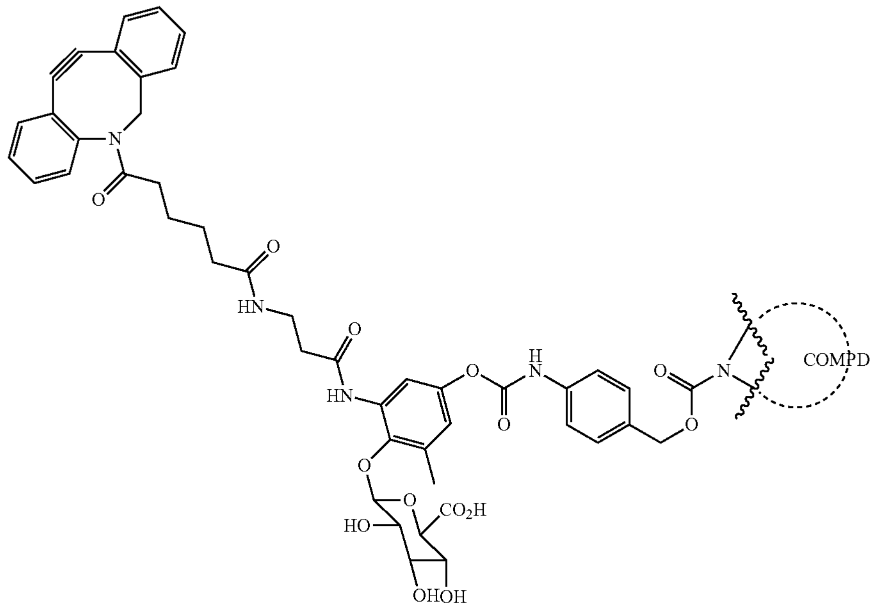

wherein COMPD is the remaining portion of a compound of Formula (I-P), and/or Formula (I), and/or (II), and/or (III) that is attached to a —NH moiety that is part of ring B or a spiro-heterocycle of $R^3$.

10. Vectors, Host Cells, and Recombinant Methods

Embodiments are also directed to the provision of isolated nucleic acids encoding antibodies, vectors and host cells comprising the nucleic acids, and recombinant techniques for the production of the antibodies.

For recombinant production of the antibody, the nucleic acid(s) encoding it may be isolated and inserted into a replicable vector for further cloning (i.e., amplification of the DNA) or expression. In some aspects, the nucleic acid may be produced by homologous recombination, for example as described in U.S. Pat. No. 5,204,244, incorporated by reference in its entirety.

Many different vectors are known in the art. The vector components generally include, but are not limited to, one or more of the following: a signal sequence, an origin of replication, one or more marker genes, an enhancer element, a promoter, and a transcription termination sequence, for example as described in U.S. Pat. No. 5,534,615, incorporated by reference in its entirety.

Illustrative examples of suitable host cells are provided below. These host cells are not meant to be limiting.

Suitable host cells include any prokaryotic (e.g., bacterial), lower eukaryotic (e.g., yeast), or higher eukaryotic (e.g., mammalian) cells. Suitable prokaryotes include eubacteria, such as Gram-negative or Gram-positive organisms, for example, Enterobacteriaceae such as *Escherichia* (*E. coli*), *Enterobacter, Erwinia, Klebsiella, Proteus, Salmonella* (*S. typhimurium*), *Serratia* (*S. marcescans*), *Shigella*, Bacilli (*B. subtilis* and *B. licheniformis*), *Pseudomonas* (*P. aeruginosa*), and *Streptomyces*. One useful *E. coli* cloning host is *E. coli* 294, although other strains such as *E. coli* B, *E. coli* X1776, and *E. coli* W3110 are suitable.

In addition to prokaryotes, eukaryotic microbes such as filamentous fungi or yeast are also suitable cloning or expression hosts for antibody-encoding vectors. *Saccharomyces cerevisiae*, or common baker's yeast, is a commonly used lower eukaryotic host microorganism. However, a number of other genera, species, and strains are available and useful, such as *Spodoptera frugiperda* (e.g., SF9), *Schizosaccharomyces pombe, Kluyveromyces* (*K lactis, K. fragilis, K. bulgaricus K. wickeramii, K. waltii, K. drosophilarum, K. thermotolerans*, and *K. marxianus*), *Yarrowia, Pichia pastoris, Candida* (*C. albicans*), *Trichoderma reesia, Neurospora crassa, Schwanniomyces* (*S. occidentalis*), and filamentous fungi such as, for example *Penicillium, Tolypocladium*, and *Aspergillus* (*A. nidulans* and *A. niger*).

Useful mammalian host cells include COS-7 cells, HEK293 cells; baby hamster kidney (BHK) cells; Chinese hamster ovary (CHO); mouse sertoli cells; African green monkey kidney cells (VERO-76), and the like.

The host cells used to produce the antibody of this invention may be cultured in a variety of media. Commercially available media such as, for example, Ham's F10, Minimal Essential Medium (MEM), RPMI-1640, and Dulbecco's Modified Eagle's Medium (DMEM) are suitable for culturing the host cells. In addition, any of the media described in Ham et al., *Meth. Enz.,* 1979, 58:44; Barnes et al., *Anal. Biochem.,* 1980, 102:255; and U.S. Pat. Nos. 4,767,704, 4,657,866, 4,927,762, 4,560,655, and 5,122,469, or WO 90/03430 and WO 87/00195 may be used. Each of the foregoing references is incorporated by reference in its entirety.

Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics, trace elements (defined as inorganic compounds usually present at final concentrations in the micromolar range), and glucose or an equivalent energy source. Any other necessary supplements may also be included at appropriate concentrations that would be known to those skilled in the art.

The culture conditions, such as temperature, pH, and the like, are those previously used with the host cell selected for expression, and will be apparent to the ordinarily skilled artisan.

When using recombinant techniques, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. For example, Carter et al. (*Bio/Technology,* 1992, 10:163-167) describes a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation.

In some embodiments, the antibody is produced in a cell-free system. In some aspects, the cell-free system is an in vitro transcription and translation system as described in Yin et al., *mAbs*, 2012, 4:217-225, incorporated by reference in its entirety. In some aspects, the cell-free system utilizes a cell-free extract from a eukaryotic cell or from a prokaryotic cell. In some aspects, the prokaryotic cell is *E. coli*. Cell-free expression of the antibody may be useful, for example, where the antibody accumulates in a cell as an insoluble aggregate, or where yields from periplasmic expression are low. The antibodies produced in a cell-free system may be aglycosylated depending on the source of the cells.

Where the antibody is secreted into the medium, supernatants from such expression systems are generally first concentrated using a commercially available protein concentration filter, for example, an Amicon® or Millipore® Pellcon® ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being a particularly useful purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., *J. Immunol. Meth.,* 1983, 62:1-13, incorporated by reference in its entirety). Protein G is useful for all mouse isotypes and for human γ3 (Guss et al., *EMBO J.,* 1986, 5:1567-1575, incorporated by reference in its entirety).

The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_{H3}$ domain, the BakerBond ABX© resin is useful for purification.

Other techniques for protein purification, such as fractionation on an ion-exchange column, ethanol precipitation, Reverse Phase HPLC, chromatography on silica, chromatography on heparin Sepharose®, chromatofocusing, SDS-PAGE, and ammonium sulfate precipitation are also available, and can be applied by one of skill in the art.

Following any preliminary purification step(s), the mixture comprising the antibody of interest and contaminants may be subjected to low pH hydrophobic interaction chromatography using an elution buffer at a pH between about 2.5 to about 4.5, generally performed at low salt concentrations (e.g., from about 0 to about 0.25 M salt).

11. Pharmaceutical Compositions and Methods of Administration

The antibody conjugates provided herein can be formulated into pharmaceutical compositions using methods available in the art and those disclosed herein. Any of the antibody conjugates provided herein can be provided in the appropriate pharmaceutical composition and be administered by a suitable route of administration.

The methods provided herein encompass administering pharmaceutical compositions comprising at least one antibody conjugate provided herein and one or more compatible and pharmaceutically acceptable carriers. In this context, the term "pharmaceutically acceptable" means approved by a regulatory agency of the Federal or a state government or listed in the U.S. Pharmacopeia or other generally recognized pharmacopeia for use in animals, and more particularly in humans. The term "carrier" includes a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water can be used as a carrier when the pharmaceutical composition is administered intravenously. Saline solutions and aqueous dextrose and glycerol solutions can also be employed as liquid carriers, particularly for injectable solutions. Examples of suitable pharmaceutical carriers are described in Martin, E. W., Remington's Pharmaceutical Sciences.

In clinical practice the pharmaceutical compositions or antibody conjugates provided herein may be administered by any route known in the art. Exemplary routes of administration include, but are not limited to, the inhalation, intraarterial, intradermal, intramuscular, intraperitoneal, intravenous, nasal, parenteral, pulmonary, and subcutaneous routes. In some embodiments, a pharmaceutical composition or antibody conjugate provided herein is administered parenterally.

The compositions for parenteral administration can be emulsions or sterile solutions. Parenteral compositions may include, for example, propylene glycol, polyethylene glycol, vegetable oils, and injectable organic esters (e.g., ethyl oleate). These compositions can also contain wetting, isotonizing, emulsifying, dispersing and stabilizing agents. Sterilization can be carried out in several ways, for example using a bacteriological filter, by radiation or by heating. Parenteral compositions can also be prepared in the form of sterile solid compositions which can be dissolved at the time of use in sterile water or any other injectable sterile medium.

In some embodiments, a composition provided herein is a pharmaceutical composition or a single unit dosage form. Pharmaceutical compositions and single unit dosage forms provided herein comprise a prophylactically or therapeutically effective amount of one or more prophylactic or therapeutic antibody conjugates.

The pharmaceutical composition may comprise one or more pharmaceutical excipients. Any suitable pharmaceutical excipient may be used, and one of ordinary skill in the art is capable of selecting suitable pharmaceutical excipients. Non-limiting examples of suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical composition or dosage form depends on a variety of factors well known in the art including, but not limited to, the way in which the dosage form will be administered to a subject and the specific antibody in the dosage form. The composition or single unit dosage form, if desired, can also contain minor amounts of wetting or emulsifying agents, or pH buffering agents. Accordingly, the pharmaceutical excipients provided below are intended to be illustrative, and not limiting. Additional pharmaceutical excipients include, for example, those described in the *Handbook of Pharmaceutical Excipients*, Rowe et al. (Eds.) 6th Ed. (2009), incorporated by reference in its entirety.

In some embodiments, the pharmaceutical composition comprises an anti-foaming agent. Any suitable anti-foaming agent may be used. In some aspects, the anti-foaming agent is selected from an alcohol, an ether, an oil, a wax, a silicone, a surfactant, and combinations thereof. In some aspects, the anti-foaming agent is selected from a mineral oil, a vegetable oil, ethylene bis stearamide, a paraffin wax, an ester wax, a fatty alcohol wax, a long chain fatty alcohol, a fatty acid soap, a fatty acid ester, a silicon glycol, a fluorosilicone, a polyethylene glycol-polypropylene glycol copolymer, polydimethylsiloxane-silicon dioxide, ether, octyl alcohol, capryl alcohol, sorbitan trioleate, ethyl alcohol, 2-ethylhexanol, dimethicone, oleyl alcohol, simethicone, and combinations thereof.

In some embodiments, the pharmaceutical composition comprises a co-solvent. Illustrative examples of co-solvents include ethanol, poly(ethylene) glycol, butylene glycol, dimethylacetamide, glycerin, and propylene glycol.

In some embodiments, the pharmaceutical composition comprises a buffer. Illustrative examples of buffers include acetate, borate, carbonate, lactate, malate, phosphate, citrate, hydroxide, diethanolamine, monoethanolamine, glycine, methionine, guar gum, and monosodium glutamate.

In some embodiments, the pharmaceutical composition comprises a carrier or filler. Illustrative examples of carriers or fillers include lactose, maltodextrin, mannitol, sorbitol, chitosan, stearic acid, xanthan gum, and guar gum.

In some embodiments, the pharmaceutical composition comprises a surfactant. Illustrative examples of surfactants include d-alpha tocopherol, benzalkonium chloride, benzethonium chloride, cetrimide, cetylpyridinium chloride, docusate sodium, glyceryl behenate, glyceryl monooleate, lauric acid, macrogol 15 hydroxystearate, myristyl alcohol, phospholipids, polyoxyethylene alkyl ethers, polyoxyethylene sorbitan fatty acid esters, polyoxyethylene stearates, polyoxylglycerides, sodium lauryl sulfate, sorbitan esters, and vitamin E polyethylene(glycol) succinate.

In some embodiments, the pharmaceutical composition comprises an anti-caking agent. Illustrative examples of anti-caking agents include calcium phosphate (tribasic), hydroxymethyl cellulose, hydroxypropyl cellulose, and magnesium oxide.

Other excipients that may be used with the pharmaceutical compositions include, for example, albumin, antioxidants, antibacterial agents, antifungal agents, bioabsorbable polymers, chelating agents, controlled release agents, diluents, dispersing agents, dissolution enhancers, emulsifying agents, gelling agents, ointment bases, penetration enhancers, preservatives, solubilizing agents, solvents, stabilizing agents, and sugars. Specific examples of each of these agents are described, for example, in the *Handbook of Pharmaceutical Excipients*, Rowe et al. (Eds.) 6th Ed. (2009), The Pharmaceutical Press, incorporated by reference in its entirety.

In some embodiments, the pharmaceutical composition comprises a solvent. In some aspects, the solvent is saline solution, such as a sterile isotonic saline solution or dextrose solution. In some aspects, the solvent is water for injection.

In some embodiments, the pharmaceutical compositions are in a particulate form, such as a microparticle or a nanoparticle. Microparticles and nanoparticles may be formed from any suitable material, such as a polymer or a lipid. In some aspects, the microparticles or nanoparticles are micelles, liposomes, or polymersomes.

Further provided herein are anhydrous pharmaceutical compositions and dosage forms comprising an antibody conjugate, since, in some embodiments, water can facilitate the degradation of some antibodies.

Anhydrous pharmaceutical compositions and dosage forms provided herein can be prepared using anhydrous or low moisture containing ingredients and low moisture or low humidity conditions. Pharmaceutical compositions and dosage forms that comprise lactose and at least one active ingredient that comprises a primary or secondary amine can be anhydrous if substantial contact with moisture and/or humidity during manufacturing, packaging, and/or storage is expected.

An anhydrous pharmaceutical composition can be prepared and stored such that its anhydrous nature is maintained. Accordingly, anhydrous compositions can be packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Lactose-free compositions provided herein can comprise excipients that are well known in the art and are listed, for example, in the U.S. Pharmacopia (USP) SP (XXI)/NF (XVI). In general, lactose-free compositions comprise an active ingredient, a binder/filler, and a lubricant in pharmaceutically compatible and pharmaceutically acceptable amounts. Exemplary lactose-free dosage forms comprise an active ingredient, microcrystalline cellulose, pre gelatinized starch, and magnesium stearate.

Also provided are pharmaceutical compositions and dosage forms that comprise one or more excipients that reduce the rate by which an antibody or antibody-conjugate will decompose. Such excipients, which are referred to herein as "stabilizers," include, but are not limited to, antioxidants such as ascorbic acid, pH buffers, or salt buffers.

11.1. Parenteral Dosage Forms

In certain embodiments, provided are parenteral dosage forms. Parenteral dosage forms can be administered to subjects by various routes including, but not limited to, subcutaneous, intravenous (including bolus injection), intramuscular, intratumoral and intraperotineal, and intraarterial. For example, the antibody conjugates of the invention may be administered to a human intravenously as a bolus or by continuous infusion over a period of time, by intramuscular, intraperitoneal, intra-cerebrospinal, subcutaneous, intra-articular, intrasynovial, intrathecal, or intratumoral routes. The antibody conjugates also are suitably administered by peritumoral, intralesional, or perilesional routes, to exert local as well as systemic therapeutic effects. Because their administration typically bypasses subjects' natural defenses against contaminants, parenteral dosage forms are typically, sterile or capable of being sterilized prior to administration to a subject. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms are well known to those skilled in the art. Examples include, but are not limited to: Water for Injection USP; phosphate buffered saline (PBS), aqueous vehicles such as, but not limited to, Sodium Chloride Injection, Ringer's Injection, Dextrose Injection, Dextrose and Sodium Chloride Injection, and Lactated Ringer's Injection; water miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Excipients that increase the solubility of one or more of the antibodies disclosed herein can also be incorporated into the parenteral dosage forms.

11.2. Dosage and Unit Dosage Forms

In human therapeutics, the doctor will determine the posology which he considers most appropriate according to a preventive or curative treatment and according to the age, weight, condition and other factors specific to the subject to be treated.

In certain embodiments, a composition provided herein is a pharmaceutical composition or a single unit dosage form. Pharmaceutical compositions and single unit dosage forms provided herein comprise a prophylactically or therapeutically effective amount of one or more prophylactic or therapeutic antibodies.

The amount of the antibody conjugate or composition which will be effective in the prevention or treatment of a disorder or one or more symptoms thereof will vary with the nature and severity of the disease or condition, and the route by which the antibody is administered. The frequency and dosage will also vary according to factors specific for each subject depending on the specific therapy (e.g., therapeutic or prophylactic agents) administered, the severity of the disorder, disease, or condition, the route of administration, as well as age, body, weight, response, and the past medical history of the subject. Effective doses may be extrapolated from dose-response curves derived from in vitro or animal model test systems.

In certain embodiments, exemplary doses of a composition include milligram or microgram amounts of the antibody per kilogram of subject or sample weight (e.g., about 10 micrograms per kilogram to about 50 milligrams per kilogram, about 100 micrograms per kilogram to about 25 milligrams per kilogram, or about 100 microgram per kilogram to about 10 milligrams per kilogram). In certain embodiment, the dosage of the antibody conjugate provided herein, based on weight of the antibody, administered to prevent, treat, manage, or ameliorate a disorder, or one or more symptoms thereof in a subject is 0.1 mg/kg, 1 mg/kg, 2 mg/kg, 3 mg/kg, 4 mg/kg, 5 mg/kg, 6 mg/kg, 10 mg/kg, or 15 mg/kg or more of a subject's body weight. In another embodiment, the dosage of the composition or a composition provided herein administered to prevent, treat, manage, or ameliorate a disorder, or one or more symptoms thereof in a subject is 0.1 mg to 200 mg, 0.1 mg to 100 mg, 0.1 mg to 50 mg, 0.1 mg to 25 mg, 0.1 mg to 20 mg, 0.1 mg to 15 mg, 0.1 mg to 10 mg, 0.1 mg to 7.5 mg, 0.1 mg to 5 mg, 0.1 to 2.5 mg, 0.25 mg to 20 mg, 0.25 to 15 mg, 0.25 to 12 mg, 0.25 to 10 mg, 0.25 mg to 7.5 mg, 0.25 mg to 5 mg, 0.25 mg to 2.5 mg, 0.5 mg to 20 mg, 0.5 to 15 mg, 0.5 to 12 mg, 0.5 to 10 mg, 0.5 mg to 7.5 mg, 0.5 mg to 5 mg, 0.5 mg to 2.5 mg, 1 mg to 20 mg, 1 mg to 15 mg, 1 mg to 12 mg, 1 mg to 10 mg, 1 mg to 7.5 mg, 1 mg to 5 mg, or 1 mg to 2.5 mg.

The dose can be administered according to a suitable schedule, for example, once, two times, three times, or for times weekly. It may be necessary to use dosages of the antibody conjugate outside the ranges disclosed herein in some cases, as will be apparent to those of ordinary skill in the art. Furthermore, it is noted that the clinician or treating physician will know how and when to interrupt, adjust, or terminate therapy in conjunction with subject response.

Different therapeutically effective amounts may be applicable for different diseases and conditions, as will be readily known by those of ordinary skill in the art. Similarly, amounts sufficient to prevent, manage, treat or ameliorate such disorders, but insufficient to cause, or sufficient to reduce, adverse effects associated with the antibodies provided herein are also encompassed by the herein described dosage amounts and dose frequency schedules. Further, when a subject is administered multiple dosages of a composition provided herein, not all of the dosages need be the same. For example, the dosage administered to the subject may be increased to improve the prophylactic or therapeutic effect of the composition or it may be decreased to reduce one or more side effects that a particular subject is experiencing.

In certain embodiments, treatment or prevention can be initiated with one or more loading doses of an antibody conjugate or composition provided herein followed by one or more maintenance doses.

In certain embodiments, a dose of an antibody conjugate or composition provided herein can be administered to achieve a steady-state concentration of the antibody in blood or serum of the subject. The steady-state concentration can be determined by measurement according to techniques available to those of skill or can be based on the physical characteristics of the subject such as height, weight and age.

In certain embodiments, administration of the same composition may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same prophylactic or therapeutic agent may be repeated and the administration may be separated by at least 1 day, 2 days, 3 days, 5 days, 10 days, 15 days, 30 days, 45 days, 2 months, 75 days, 3 months, or 6 months.

11.3. Combination Therapies and Formulations

In certain embodiments, provided are compositions, therapeutic formulations, and methods of treatment or uses comprising any of the antibody conjugates provided herein in combination with one or more chemotherapeutic agents disclosed herein, and methods of treatment comprising administering such combinations to subjects in need thereof. Examples of chemotherapeutic agents include, but are not limited to, Bendamustine (TREANDA®, Cephalon), Venetoclax (VENCLEXTA®, Abbvie, Genentech), Denosumab (XGEVA®, Amgen; PROLIA®, Amgen), Carfilzomib (KYPROLIS®, Amgen), Ixazomib (NINLARO®, Takeda), Erlotinib (TARCEVA®, Genentech/OSI Pharm.), Bortezomib (VELCADE®, Millennium Pharm.), Fulvestrant (FASLODEX®, AstraZeneca), Sutent (SU11248, Pfizer), Letrozole (FEMARA®, Novartis), Imatinib mesylate (GLEEVEC®, Novartis), PTK787/ZK 222584 (Novartis), Oxaliplatin (Eloxatin®, Sanofi), 5-FU (5-fluorouracil), Leucovorin, Rapamycin (Sirolimus, RAPAMUNE®, Wyeth), Lapatinib (TYKERB®, GSK572016, Glaxo Smith Kline), Lonafamib (SCH 66336), Sorafenib (BAY43-9006, Bayer Labs), and Gefitinib (IRESSA®, AstraZeneca), AG1478, AG1571 (SU 5271; Sugen), alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially uncialamycin, calicheamicin gammall, and calicheamicin omegall (Angew Chem. Intl. Ed. Engl. (1994) 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pladienolide B, pteropterin, trimetrexate; purine analogs such as fludarabine, 6-mercaptopurine, thiamniprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (doxetaxel; Rhone-Poulenc Rorer, Antony, France); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylomithine (DMFO); retinoids such as retinoic acid; and pharmaceutically acceptable salts, acids and derivatives of any of the above.

For therapeutic applications, the antibody conjugates of the invention are administered to a mammal, generally a human, in a pharmaceutically acceptable dosage form such as those known in the art and those discussed above. For example, the antibody conjugates of the invention may be administered to a human intravenously as a bolus or by continuous infusion over a period of time, by intramuscular, intraperitoneal, intra-cerebrospinal, subcutaneous, intra-articular, intrasynovial, intrathecal, or intratumoral routes. The antibody conjugates also are suitably administered by peritumoral, intralesional, or perilesional routes, to exert local as well as systemic therapeutic effects. The intraperitoneal route may be particularly useful, for example, in the treatment of ovarian tumors.

The agents administered in combination with the antibody conjugates disclosed herein can be administered just prior to, concurrent with, or shortly after the administration of the antibody conjugates. In certain embodiments, the antibody conjugates provided herein are administered on a first dosing schedule, and the one or more second agents are administered on their own dosing schedules. For purposes of the present disclosure, such administration regimens are considered the administration of an antibody conjugate "in combination with" an additional therapeutically active component. Embodiments include pharmaceutical compositions in which an antibody conjugate disclosed herein is co-formulated with one or more of the chemotherapeutic agents or immunomodulatory agents disclosed herein.

In some embodiments, the immune checkpoint inhibitor is cytotoxic T-lymphocyte antigen 4 (CTLA4, also known as CD 152), T cell immunoreceptor with Ig and ITIM domains (TIGIT), glucocorticoid-induced TNFR-related protein (GITR, also known as TNFRSF18), inducible T cell costimulatory (ICOS, also known as CD278), CD96, poliovirus receptor-related 2 (PVRL2, also known as CD1 12R, programmed cell death protein 1 (PD-1, also known as CD279), programmed cell death 1 ligand 1 (PD-L1, also known as B7-H3 and CD274), programmed cell death ligand 2 (PD-L2, also known as B7-DC and CD273), lymphocyte activation gene-3 (LAG-3, also known as CD223), B7-H4, killer immunoglobulin receptor (KIR), Tumor Necrosis Factor Receptor superfamily member 4 (TNFRSF4, also known as OX40 and CD134) and its ligand OX40L (CD252), indoleamine 2,3-dioxygenase 1 (IDO-1), indoleamine 2,3-dioxygenase 2 (IDO-2), carcinoembryonic antigen-related cell adhesion molecule 1 (CEACAM1), B and T lymphocyte attenuator (BTLA, also known as CD272), T-cell membrane protein 3 (TIM3), the adenosine A2A receptor (A2Ar), and V-domain Ig suppressor of T cell activation (VISTA protein). In some embodiments, the immune checkpoint inhibitor is an inhibitor of CTLA4, PD-1, or PD-L1.

In certain embodiments, provided are compositions, therapeutic formulations, and methods of treatment or uses comprising any of the antibody conjugates provided herein in combination with one or more PD-1 or PD-L1 inhibitors, and methods of treatment comprising administering such combinations to subjects in need thereof. In some embodiments, the one or more PD-1 or PD-L1 inhibitors comprise a small molecule blocker of the PD-1 or PD-L1 pathway. In some embodiments, the one or more PD-1 or PD-L1 inhibitors comprise an antibody that inhibits PD-1 or PD-L1 activity. In some embodiments, the one or more PD-1 or PD-L1 inhibitors are selected from the group consisting of: CA-170, BMS-8, BMS-202, BMS-936558, CK-301, and AUNP12. In some embodiments, the one or more PD-1 or PD-L1 inhibitors are selected from the group consisting of: avelumab, nivolumab, pembrolizumab, atezolizumab, durvalumab, AMP-224 (GlaxoSmithKline), MED10680/AMP-514 (AstraZeneca), PDR001 (Novartis), cemiplimab, TSR-042 (Tesaro, GlaxoSmithKline), Tizlelizumab/BGB-A317 (Beigene), CK-301 (Checkpoint Therapeutics), BMS-936559 (Bristol-Meyers Squibb), cemiplimab (Regeneron), camrelizumab, sintilimab, toripalimab, genolimzumab, and A167 (Sichuan Kelun-Biotech Biopharmaceutical). In some embodiments, the one or more PD-1 or PD-L1 inhibitors are selected from the group consisting of: MGA012 (Incyte/MacroGenics), PF-06801591 (Pfizer/Merck KGaA), LY3300054 (Eli Lilly), FAZ053 (Novartis), PD-11 (Novartis), CX-072 (CytomX), BGB-A333 (Beigene), BI 754091 (Boehringer Ingelheim), JNJ-63723283 (Johnson and Johnson/Jannsen), AGEN2034 (Agenus), CA-327 (Curis), CX-188 (CytomX), STI-A1110 (Servier), JTX-4014 (Jounce), AM0001 (Armo Biosciences, Eli Lilly), CBT-502 (CBT Pharmaceuticals), FS118 (F-Star/Merck KGaA), XmAb20717 (Xencor), XmAb23104 (Xencor), AB122 (Arcus Biosciences), KY1003 (Kymab), RXI-762 (RXi). In some embodiments, the one or more PD-1 or PD-L1 inhibitors are selected from the group consisting of: PRS-332 (*Pieris* Pharmaceuticals), ALPN-202 (Alpine Immune Science), TSR-075 (Tesaro/Anaptys Bio), MCLA-145 (Merus), MGD013 (Macrogenics), MGD019 (Macrogenics), R07121661 (Hoffman-La Roche), LY3415244 (Eli Lilly). In some embodiments, the one or more PD-1 or PD-L1 inhibitors are selected from an anti-PD1 mono-specific or bi-specific antibody described in, for example, WO 2016/077397, WO 2018/156777, and International Application No. PCT/US2013/034213, filed May 23, 2018.

In certain embodiments, provided are compositions, therapeutic formulations, and methods of treatment or uses comprising any of the antibody conjugates provided herein in combination with one or more LAG3 inhibitors, and methods of treatment comprising administering such combinations to subjects in need thereof. In some embodiments, the one or more LAG3 inhibitors comprise a small molecule blocker of the LAG3 pathway. In some embodiments, the one or more LAG3 inhibitors comprise an antibody that inhibits LAG3 activity. In some embodiments, the one or more LAG3 inhibitors are independently selected from the group consisting of: IMP321 (Eftilagimod alpha, Immutep), relatilimab (Brisol-Myers Squibb), LAG525 (Novartis), MK4280 (Merck), BI 754111 (Boehringer Ingelheim), REGN3767 (Regeneron/Sanofi), Sym022 (Symphogen) and TSR-033 (Tesaro/GSK).

In certain embodiments, provided are compositions, therapeutic formulations, and methods of treatment or uses comprising any of the antibody conjugates provided herein in combination with one or more TIM3 inhibitors, and methods of treatment comprising administering such combinations to subjects in need thereof. In some embodiments, the one or more TIM3 inhibitors comprise a small molecule blocker of the TIM3 pathway. In some embodiments, the one or more TIM3 inhibitors comprise an antibody that inhibits TIM3 activity. In some embodiments, the one or more TIM3 inhibitors are independently selected from the group consisting of: TSR-022 (Tesaro), LY3321367 (Eli Lilly), Sym023 (Symphogen) and MBG453 (Novartis).

In certain embodiments, provided are compositions, therapeutic formulations, and methods of treatment or uses comprising any of the antibody conjugates provided herein in combination with one or more TIGIT inhibitors, and methods of treatment comprising administering such combinations to subjects in need thereof. In some embodiments, the one or more TIGIT inhibitors comprise a small molecule blocker of the TIGIT pathway. In some embodiments, the one or more TIGIT inhibitors comprise an antibody that inhibits TIGIT activity. In some embodiments, the one or more TIGIT inhibitors are independently selected from the group consisting of: BMS-986207 (BMS), tiragolumab (RG6058, Genentech), ASP-8374 (Potenza Therapeutics), etigilimab, AB-154 (Arcus).

In certain embodiments, provided are compositions, therapeutic formulations, and methods of treatment or uses comprising any of the antibody conjugates provided herein in combination with one or more inhibitors of V-domain Ig suppressor of T cell activation (VISTA), and methods of treatment comprising administering such combinations to subjects in need thereof. In some embodiments, the one or more VISTA inhibitors comprise a small molecule blocker of the VISTA pathway. In some embodiments, the one or more VISTA inhibitors comprise an antibody that inhibits VISTA activity. In some embodiments, the one or more VISTA inhibitors are independently selected from the group consisting of: PMC-309 (PharmaAbcine Inc), HMBD-002 (Hummingbird Bioscience Pte Ltd), JNJ-61610588 (Janssen), CA-170 (Aurigene Discovery Technologies Ltd)

In certain embodiments, provided are compositions, therapeutic formulations, and methods of treatment or uses comprising any of the antibody conjugates provided herein in combination with one or more CSF1R inhibitors, and methods of treatment comprising administering such combinations to subjects in need thereof. In some embodiments, the one or more CSF1R inhibitors comprise a small molecule blocker of the CSF1R pathway. In some embodiments, the one or more CSF1R inhibitors comprise an antibody that inhibits CSF1R activity. In some embodiments, the one or more CSF1R inhibitors are independently selected from the group consisting of: AMG 820 (Amgen), Emactuzumab (Roche), IMC-CS4 (LY3022855) (Eli Lilly), MCS110 (Novartis), cabiralizumab (FPA008) (Five Prime Therapeutics), JNJ-40346527 (Johnson and Johnson), BLZ945 (Novartis), ARRY-382 (Array Biopharma), PLX7486 (Plexxicon) and Pexidartinib (Plexxicon).

In certain embodiments, provided are compositions, therapeutic formulations, and methods of treatment or uses comprising any of the antibody conjugates provided herein in combination with one or more CD73 inhibitors, and methods of treatment comprising administering such combinations to subjects in need thereof. In some embodiments, the one or more CD73 inhibitors comprise a small molecule blocker of the CD73 pathway. In some embodiments, the one or more CD73 inhibitors comprise an antibody that inhibits CD73 activity. In some embodiments, the one or more CD73 inhibitors are independently selected from the group consisting of: MED19447 (Medimmune), IPH-5301 (Innate Pharma), AB680 (Arcus), and BMS-986179 (Bristol-Myers Squibb).

In certain embodiments, provided are compositions, therapeutic formulations, and methods of treatment or uses comprising any of the antibody conjugates provided herein in combination with one or more CD39 inhibitors, and methods of treatment comprising administering such combinations to subjects in need thereof. In some embodiments, the one or more CD39 inhibitors comprise a small molecule blocker of the CD39 pathway. In some embodiments, the one or more CD39 inhibitors comprise an antibody that inhibits CD39 activity. In some embodiments, the one or more CD39 inhibitors are independently selected from the group consisting of: CPI-444 (Corvus), PBF-509 (Pablobio, Novartis), MK-3814 (Merck), and AZD4635 (AstraZeneca), TTX-030 (Tizona Therapeutics), IPH-5201 (Innate Pharma), SRF-617 (Surface Oncology).

In certain embodiments, provided are compositions, therapeutic formulations, and methods of treatment or uses comprising any of the antibody conjugates provided herein in combination with one or more inhibitors of the A2a receptor (A2aR), and methods of treatment comprising administering such combinations to subjects in need thereof. In some embodiments, the one or more A2aR inhibitors comprise a small molecule blocker of the A2aR signaling pathway. In some embodiments, the one or more A2aR inhibitors comprise an antibody that inhibits activity of A2a receptor. In some embodiments, the one or more A2AR inhibitors are independently selected from the group consisting of: CPI-444 (Corvus), PBF-509 (Pablobio, Novartis), MK-3814 (Merck), and AZD4635 (AstraZeneca).

In certain embodiments, provided are compositions, therapeutic formulations, and methods of treatment or uses comprising any of the antibody conjugates provided herein in combination with one or more inhibitors of transforming growth factor-O (TGF-β), and methods of treatment comprising administering such combinations to subjects in need thereof. In some embodiments, the one or more TGF-β inhibitors comprise a small molecule blocker of the TGF-β signaling pathway. In some embodiments, the one or more TGF-β inhibitors comprise an antibody that inhibits activity of TGF-β receptor. In some embodiments, the one or more TGF-β inhibitors are independently selected from the group consisting of: AVID200 (Formation Biologics), LY3200882 (Eli Lilly), M7824 (Merck KGaA).

In certain embodiments, provided are compositions, therapeutic formulations, and methods of treatment or uses comprising any of the antibody conjugates provided herein in combination with one or more B7-H4 inhibitors, and methods of treatment comprising administering such combinations to subjects in need thereof. In some embodiments, the one or more B7-H4 inhibitors comprise a small molecule blocker of the B7-H4 pathway. In some embodiments, the one or more B7-H4 inhibitors comprise an antibody that inhibits B7-H4 activity. In some embodiments, the one or more B7-H4 inhibitors are independently selected from the group consisting of FPA-150 (Five Prime Therapeutics).

In certain embodiments, provided are compositions, therapeutic formulations, and methods of treatment or uses comprising any of the antibody conjugates provided herein in combination with one or more KIR inhibitors, and methods of treatment comprising administering such combinations to subjects in need thereof. In some embodiments, the one or more KIR inhibitors comprise a small molecule blocker of the KIR pathway. In some embodiments, the one or more KIR inhibitors comprise an antibody that inhibits KIR activity. In some embodiments, the one or more KIR inhibitors are independently selected from the group consisting of Lirilunab (IPH-2102, BMS-986015) (Bristol Myers Squibb), TRL-8605) (Trellis Bioscience Inc), IPH-41 (IPH 4101) (Innate Pharma S. A.).

In certain embodiments, provided are compositions, therapeutic formulations, and methods of treatment or uses comprising any of the antibody conjugates provided herein in combination with one or more inhibitors of Tumor Necrosis Factor Receptor superfamily member 4 (TNFRSF4, also known as OX40 and CD134) and its ligand OX40L (CD252), and methods of treatment comprising administering such combinations to subjects in need thereof In some embodiments, the one or more inhibitors of TNFRSF4/OX40 or OX40L comprise a small molecule blocker of the TNFRSF4/OX40 pathway. In some embodiments, the one or more inhibitors of TNFRSF4/OX40 or OX40L comprise an antibody that inhibits TNFRSF4/OX40 activity. In some embodiments, the immune checkpoint inhibitor reduces the interaction between TNFRSF4/OX40 and OX40L. In some embodiments, the one or more inhibitors of TNFRSF4/OX40 or OX40L are independently selected from the group consisting of INCAGN-1949 (Incyte Corp), GSK-3174998 (Glaxo Smith Kline), PF-04518600 (PF-8600) (Pfizer Inc)

In certain embodiments, provided are compositions, therapeutic formulations, and methods of treatment or uses comprising any of the antibody conjugates provided herein in combination with one or more inhibitors of the indoleamine 2,3-dioxygenase (IDO) pathway, and methods of treatment comprising administering such combinations to subjects in need thereof. In some embodiments, the immune checkpoint inhibitor is an inhibitor of IDO-1. In some embodiments, the immune checkpoint inhibitor is an inhibitor of IDO-2. In some embodiments, the one or more IDO pathway inhibitors comprise a small molecule blocker of the IDO pathway. In some embodiments, the one or more IDO pathway inhibitors comprise an antibody that inhibits IDO-1 or IDO-2. In some embodiments, the one or more IDO1 or IDO-2 inhibitors are independently selected from the group consisting of LY-3381916 (Eli Lilly), BMS-986205 (Bristol-Myers Squibb, KHK2455 (Kyowa Kirin Pharmaceutical Development, Inc.), Indoximod (NewLink Genetics), Epacadostat (INCB24360) (Incyte Corp), GDC-0919 (navoximod) (NewLink Genetics).

In some embodiments, the immune checkpoint inhibitor is an inhibitor of IDO-2. In some embodiments, the immune checkpoint inhibitor is an antibody against IDO-2. In some embodiments, the immune checkpoint inhibitor is a monoclonal antibody against IDO-2. In some embodiments, the immune checkpoint inhibitor is a human or humanized antibody against IDO-2. In some embodiments, the immune checkpoint inhibitor reduces the expression or activity of one or more immune checkpoint proteins, such as IDO-2.

In certain embodiments, provided are compositions, therapeutic formulations, and methods of treatment or uses comprising any of the antibody conjugates provided herein in combination with one or more CEACAM1 inhibitors, and methods of treatment comprising administering such combinations to subjects in need thereof. In some embodiments, the one or more CEACAM1 inhibitors comprise a small molecule blocker of the CEACAM1 pathway. In some embodiments, the one or more CEACAM1 inhibitors comprise an antibody that inhibits CEACAM1. In some embodiments, the one or more independently CEACAM1 inhibitors are selected from the group consisting of PB-04123 (Pangaea Oncology S. A), CM-24 (MK-6018) (Merck Sharpe Dohme).

In certain embodiments, provided are compositions, therapeutic formulations, and methods of treatment or uses comprising any of the antibody conjugates provided herein in combination with one or more activators/agonists of glucocorticoid-induced TNFR-related protein (GITR, also known as TNFRSF18), and methods of treatment comprising administering such combinations to subjects in need thereof. In some embodiments, the one or more GITR agonists comprise a small molecule agonist of the GITR pathway. In some embodiments, the one or more GITR agonists comprise an antibody that activates GITR activity. In some embodiments, the one or more GITR agonists comprise recombinant protein that activates GITR activity. In some embodiments, the one or more GITR agonists are independently selected from the group consisting of BMS-986156 (Bristol Myers Squibb), TRX-518 (Leap Therapeutics), INCAGN-1876 (Incyte Corp), MK-1248 (Merck and Co Inc), MK-4166 (Merck and co) GWN-323 (Novartis).

In certain embodiments, provided are compositions, therapeutic formulations, and methods of treatment or uses comprising any of the antibody conjugates provided herein in combination with one or more activators/agonists of inducible T cell costimulatory (ICOS, also known as CD278), and methods of treatment comprising administering such combinations to subjects in need thereof. In some embodiments, the one or more ICOS agonists comprise a small molecule agonist of the ICOS pathway. In some embodiments, the one or more ICOS agonists comprise an antibody that activates ICOS activity. In some embodiments, the one or more ICOS agonists comprise recombinant protein that activates ICOS activity. In some embodiments, the one or more ICOS agonists are independently selected from the group consisting of Vopratelimab (JTX-2011) (Jounce Therapeutics), GSK-3359609 (GSK), BMS-986226 (BMS), KY-1044 (Kymab Ltd).

In certain embodiments, provided are compositions, therapeutic formulations, and methods of treatment or uses comprising any of the antibody conjugates provided herein in combination with one or more activators/agonists of tumor necrosis factor receptor superfamily member 5 (CD40), and methods of treatment comprising administering such combinations to subjects in need thereof. In some embodiments, the one or more CD40 agonists comprise a small molecule agonist of the CD40 pathway. In some embodiments, the one or more CD40 agonists comprise an antibody that activates CD40 activity. In some embodiments, the one or more CD40 agonists comprise recombinant protein that activates CD40 activity. In some embodiments, the one or more CD40 agonists are independently selected from the group consisting of APX005M (Apexigen), CP-870,893 (Pfizer), ABBV-927 (Abbvie), SEA-CD40 (Seattle Genetics).

In certain embodiments, provided are compositions, therapeutic formulations, and methods of treatment or uses comprising any of the antibody conjugates provided herein in combination with one or more activators/agonists of STING (stimulator of interferon genes) pathway, and methods of treatment comprising administering such combinations to subjects in need thereof. In some embodiments, the one or more STING agonists comprise a small molecule agonist of the STING pathway. In some embodiments, the one or more STING agonists comprise an antibody that activates STING activity. In some embodiments, the one or more STING agonists comprise recombinant protein that activates STING activity. In some embodiments, the one or more STING agonists are independently selected from the group consisting of MK-1454 (Merck), ADU-S100 (Aduro), and SB11285 (Springbank Pharmaceuticals)

In certain embodiments, provided are compositions, therapeutic formulations, and methods of treatment or uses comprising any of the antibody conjugates provided herein in combination with one or more activators/agonists of RIG-I signaling, and methods of treatment comprising administering such combinations to subjects in need thereof. In some embodiments, the one or more RIG-I agonists comprise a small molecule agonist of the RIG-I pathway. In some embodiments, the one or more RIG-I agonists comprise an antibody that activates RIG-I activity. In some embodiments, the one or more RIG-I agonists comprise recombinant protein that activates RIG-I activity. In some embodiments, the one or more RIG-I agonists are independently selected from the group consisting of RGT100 (MK4621, Merck), and KIN1148 (Kineta Inc).

In certain embodiments, the antibody conjugates provided herein are administered in combination with VELCADE® (bortezomib), KYPROLIS® (Carfilzomib), NINLARO® (Ixazomib). In certain embodiments, the antibody conjugates provided herein are administered in combination with FARYDAK® (panobinostat). In certain embodiments, the antibody conjugates provided herein are administered in combination with DARALEX® (daratumumab). In certain embodiments, the antibody conjugates provided herein are administered in combination with EMPLICITI® (elotuzumab). In certain embodiments, the antibody conjugates provided herein are administered in combination with AREDIA® (pamidronate) or ZOMETA® (zolendronic acid). In certain embodiments, the antibody conjugates provided herein are administered in combination with XGEVA® (denosumab) or PROLIA® (denosumab).

In some embodiments, the antibody conjugates described herein are administered in combination with radiotherapy and/or photodynamic therapy (PDT).

12. Therapeutic Applications

For therapeutic applications, the antibody conjugates of the invention are administered to a mammal, generally a human, in a pharmaceutically acceptable dosage form such as those known in the art and those discussed above. For example, the antibody conjugates of the invention may be administered to a human intravenously as a bolus or by continuous infusion over a period of time, by intramuscular, intraperitoneal, intra-cerebrospinal, subcutaneous, intra-articular, intrasynovial, intrathecal, or intratumoral routes. The antibody conjugates also are suitably administered by peritumoral, intralesional, or perilesional routes, to exert local as well as systemic therapeutic effects. The intraperitoneal route may be particularly useful, for example, in the treatment of ovarian tumors.

The antibody conjugates provided herein may be useful for the treatment of any disease or condition described herein (e.g., inflammatory and/or proliferative disease or condition). In some embodiments, the disease or condition is a disease or condition that can be diagnosed by overexpression of an antigen. In some embodiments, the disease or condition is a disease or condition that can benefit from treatment with an antibody. In some embodiments, the disease or condition is a cancer.

Any suitable cancer may be treated with the antibody conjugates provided herein. Illustrative suitable cancers include, for example, acute lymphoblastic leukemia (ALL), acute myeloid leukemia (AML), adrenocortical carcinoma, anal cancer, appendix cancer, astrocytoma, basal cell carcinoma, brain tumor, bile duct cancer, bladder cancer, bone cancer, breast cancer, bronchial tumor, carcinoma of unknown primary origin, cardiac tumor, cervical cancer, chordoma, colon cancer, colorectal cancer, craniopharyngioma, ductal carcinoma, embryonal tumor, endometrial cancer, ependymoma, esophageal cancer, esthesioneuroblastoma, fibrous histiocytoma, Ewing sarcoma, eye cancer, germ cell tumor, gallbladder cancer, gastric cancer, gastrointestinal carcinoid tumor, gastrointestinal stromal tumor, gestational trophoblastic disease, glioma, head and neck cancer, hepatocellular cancer, histiocytosis, Hodgkin lymphoma, hypopharyngeal cancer, intraocular melanoma, islet cell tumor, Kaposi sarcoma, kidney cancer, Langerhans cell histiocytosis, laryngeal cancer, lip and oral cavity cancer, liver cancer, lobular carcinoma in situ, lung cancer, macroglobulinemia, malignant fibrous histiocytoma, melanoma, Merkel cell carcinoma, mesothelioma, metastatic squamous neck cancer with occult primary, midline tract carcinoma involving NUT gene, mouth cancer, multiple endocrine neoplasia syndrome, multiple myeloma, mycosis fungoides, myelodysplastic syndrome, myelodysplastic/myeloproliferative neoplasm, nasal cavity and par nasal sinus cancer, nasopharyngeal cancer, neuroblastoma, non-small cell lung cancer, oropharyngeal cancer, osteosarcoma, ovarian cancer, pancreatic cancer, papillomatosis, paraganglioma, parathyroid cancer, penile cancer, pharyngeal cancer, pheochromocytomas, pituitary tumor, pleuropulmonary blastoma, primary central nervous system lymphoma, prostate cancer, rectal cancer, renal cell cancer, renal pelvis and ureter cancer, retinoblastoma, rhabdoid tumor, salivary gland cancer, Sezary syndrome, skin cancer, small cell lung cancer, small intestine cancer, soft tissue sarcoma, spinal cord tumor, stomach cancer, T-cell lymphoma, teratoid tumor, testicular cancer, throat cancer, thymoma and thymic carcinoma, thyroid cancer, urethral cancer, uterine cancer, vaginal cancer, vulvar cancer, and Wilms tumor.

In some embodiments, the disease to be treated with the antibody conjugates provided herein is gastric cancer, colorectal cancer, renal cell carcinoma, cervical cancer, non-small cell lung carcinoma, ovarian cancer, uterine cancer, endometrial carcinoma, prostate cancer, breast cancer, head and neck cancer, brain carcinoma, liver cancer, pancreatic cancer, mesothelioma, and/or a cancer of epithelial origin. In particular embodiments, the disease is colorectal cancer. In some embodiments, the disease is ovarian cancer. In some embodiments, the disease is breast cancer. In some embodiments, the disease is lung cancer. In some embodiments, the disease is head and neck cancer. In some embodiments, the disease is renal cell carcinoma. In some embodiments, the disease is brain carcinoma. In some embodiments, the disease is endometrial carcinoma. In particular embodiments, the disease is non-hodgkins lymphoma, pancreatic cancer, multiple myeloma, colorectal cancer, renal and mammary carcinomas, skin cancer and/or cervical intraepithelial neoplasia.

In certain embodiments, provided herein are methods for the treatment of cancer that includes the administration of an effective amount of antibody conjugates provided herein, or a pharmaceutically acceptable salt thereof. In certain embodiments, provided herein are methods for treating cancer in a subject. In certain embodiments, the methods encompass the step of administering to the subject in need thereof an amount of an antibody conjugate described herein effective for the treatment of cancer in combination with a second agent effective for the treatment or prevention of the infection. In certain embodiments, the antibody conjugate is in the form of a pharmaceutical composition or dosage form, as described elsewhere herein.

In certain embodiments, the subject is a treatment naïve subject. In further embodiments, the subject has previously received therapy for a cancer. For instance, in certain embodiments, the subject has not responded to a single agent treatment regimen.

In certain embodiments, the subject is a subject that discontinued some other therapy because of one or more adverse events associated with the therapy.

In certain embodiments, the subject has received some other anti-cancer therapy and discontinued that therapy prior to administration of a method provided herein. In further embodiments, the subject has received therapy and continues to receive that therapy along with administration of an antibody conjugate provided herein. The antibody conjugates described herein can be co-administered with other therapy for treatment of cancer according to the judgment of one of skill in the art. In certain embodiments, the methods or compositions provided herein can be co-administered with a reduced dose of the other therapy for the treatment of cancer.

In certain embodiments, provided are methods of treating a subject that is refractory to treatment with some other anti-cancer agent. In some embodiments, the subject can be a subject that has responded poorly to some other anti-cancer treatment.

16. Diagnostic Applications

In some embodiments, the antibody conjugates provided herein are used in diagnostic applications. These assays may be useful, for example, in making a diagnosis and/or prognosis for a disease, such as a cancer.

In some diagnostic and prognostic applications, the antibody conjugate may be labeled with a detectable moiety. Suitable detectable moieties include, but are not limited to radioisotopes, fluorescent labels, and enzyme-substrate labels. In another embodiment, the antibody conjugate need not be labeled, and the presence of the antibody conjugate can be detected using a labeled antibody which specifically binds to the antibody conjugate.

13. Affinity Purification Reagents

The antibody conjugates provided herein may be used as affinity purification agents. In this process, the antibody conjugates may be immobilized on a solid phase such a resin or filter paper, using methods well known in the art. The immobilized antibody conjugate is contacted with a sample containing the antigen (or fragment thereof) to be purified, and thereafter the support is washed with a suitable solvent that will remove substantially all the material in the sample except the protein of interest, which is bound to the immobilized antibody. Finally, the support is washed with another suitable solvent, such as glycine buffer, pH 5.0 that will release the protein from the antibody.

14. Kits

In some embodiments, an antibody conjugate provided herein is provided in the form of a kit, i.e., a packaged combination of reagents in predetermined amounts with instructions for performing a procedure. In some embodiments, the procedure is a diagnostic assay. In other embodiments, the procedure is a therapeutic procedure.

In some embodiments, the kit further comprises a solvent for the reconstitution of the antibody conjugate. In some embodiments, the antibody conjugate is provided in the form of a pharmaceutical composition.

In some embodiments, the kits can include an antibody conjugate or composition provided herein, an optional second agent or composition, and instructions providing information to a health care provider regarding usage for treating the disorder. Instructions may be provided in printed form or in the form of an electronic medium such as a floppy disc, CD, or DVD, or in the form of a website address where such instructions may be obtained. A unit dose of an antibody conjugate or a composition provided herein, or a second agent or composition, can include a dosage such that when administered to a subject, a therapeutically or prophylactically effective plasma level of the compound or composition can be maintained in the subject for at least 1 days. In some embodiments, a compound or composition can be included as a sterile aqueous pharmaceutical composition or dry powder (e.g., lyophilized) composition.

In some embodiments, suitable packaging is provided. As used herein, "packaging" includes a solid matrix or material customarily used in a system and capable of holding within fixed limits a compound provided herein and/or a second agent suitable for administration to a subject. Such materials include glass and plastic (e.g., polyethylene, polypropylene, and polycarbonate) bottles, vials, paper, plastic, and plastic-foil laminated envelopes and the like. If e-beam sterilization techniques are employed, the packaging should have sufficiently low density to permit sterilization of the contents.

EXAMPLES

As used herein, the symbols and conventions used in these processes, schemes and examples, regardless of whether a particular abbreviation is specifically defined, are consistent with those used in the contemporary scientific literature, for example, the Journal of the American Chemical Society or the Journal of Biological Chemistry. Specifically, but without limitation, the following abbreviations may be used in the examples and throughout the specification: aq (aqueous); atm (atmospheres); DIBAL (diisobutylaluminium hydride); DIPEA (diisopropylethylamine); g (grams); mg (milligrams); mL (milliliters); L (microliters); mM (millimolar); M (micromolar); mmol (millimoles); h, hr or hrs (hours); min (minutes); MTBE (methyl tert-butyl ether); MS (mass spectrometry); eq (equivalents); NMP (N-methylpyridine); ESI (electrospray ionization); RB (round-bottom); rt (room temperature); HPLC (high pressure liquid chromatography); LAH (lithium aluminum hydride); LCMS (Liquid chromatography-Mass spectrometry); THF (tetrahydrofuran); AcOH (acetic acid); DBCO (dibenzocyclooctyne-amine); DCM (dichloromethane); DMF (dimethyformamide); Boc (tert-butyloxycarbonyl); DMSO (dimethylsulfoxide); DMSO-$d_6$ (deuterated dimethylsulfoxide); EtOAc (ethyl acetate); MeOH (methanol); and BOC (t-butyloxycarbonyl).

For all of the following examples, standard work-up and purification methods known to those skilled in the art can be utilized. Unless otherwise indicated, all temperatures are expressed in ° C. (degrees Centigrade). All reactions are conducted at room temperature unless otherwise noted. Synthetic methodologies illustrated herein are intended to exemplify the applicable chemistry through the use of specific examples and are not indicative of the scope of the disclosure. FOLR1, as used herein, is also known as FolRa, or FolRα.
Preparation of Compounds
Example 1
Synthesis of Compounds 2, 3, 4, 5 and 6
compound 2
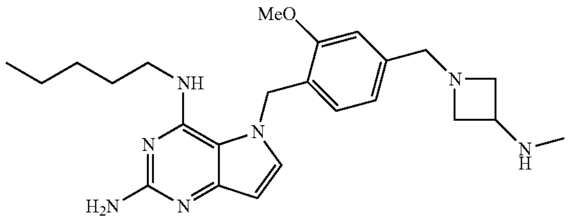
compound 3
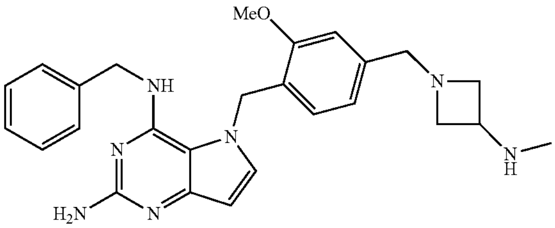
compound 4
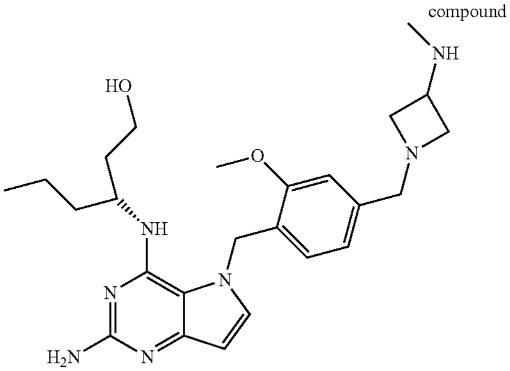
compound 5
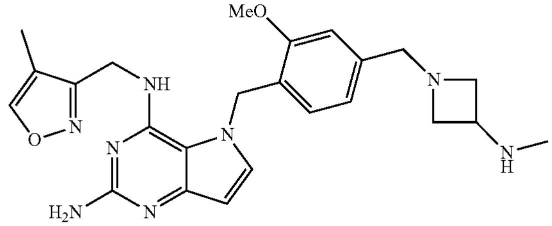
compound 6
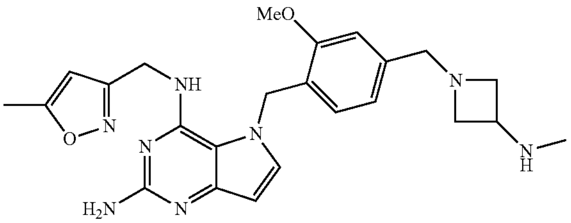
Scheme 2 shows the synthesis of compounds 2, 3, 4, 5, and 6
SCHEME 2
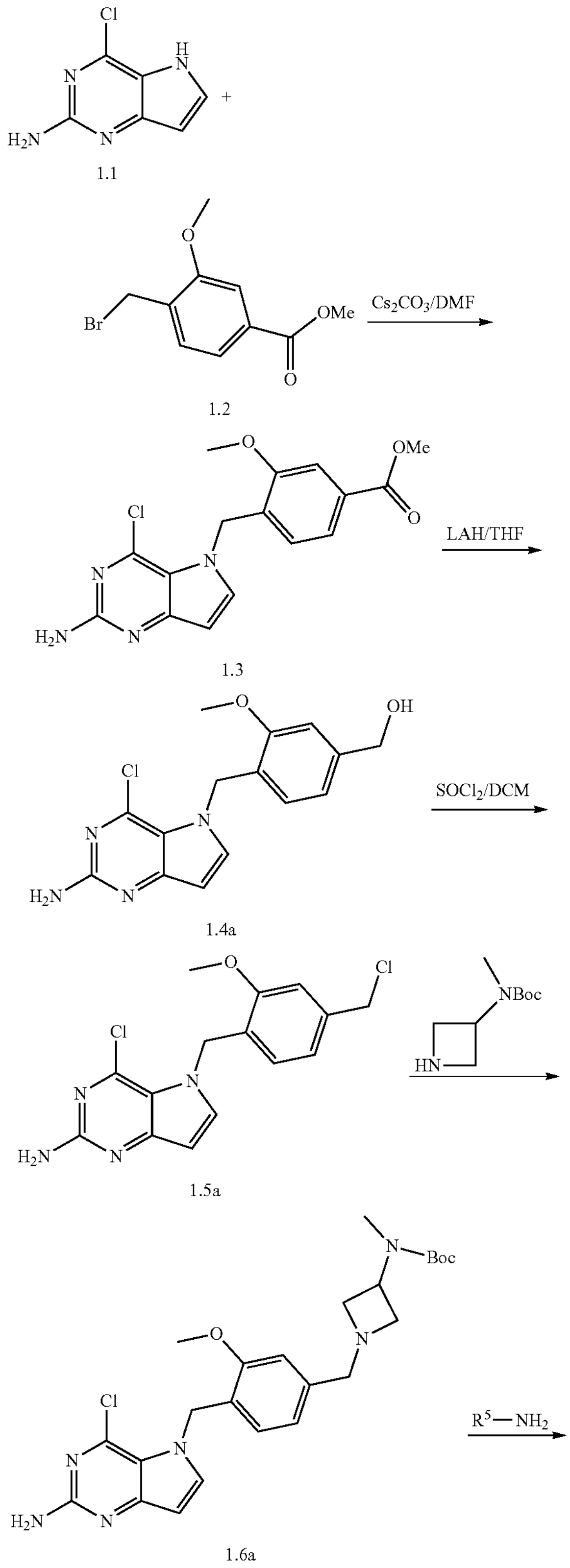

-continued

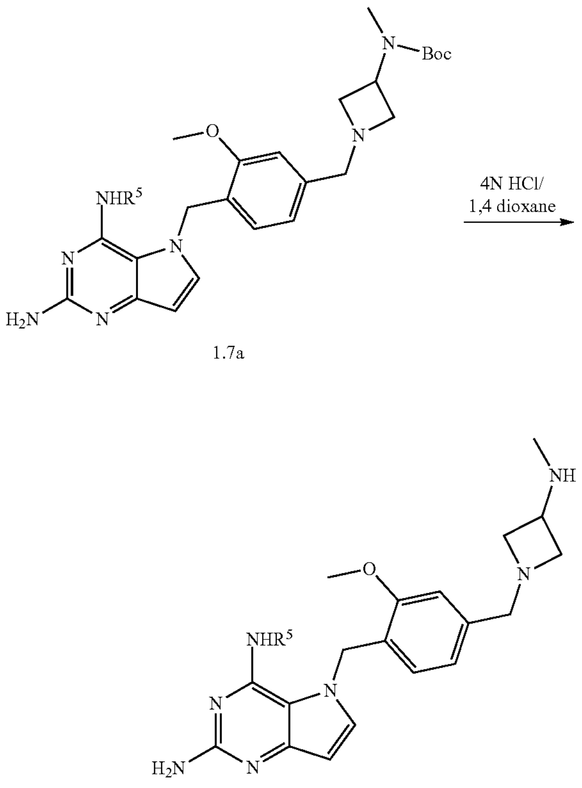

1.7a compounds 3-6

Preparation of ethyl 4-((2-amino-4-chloro-5H-pyrrolo[3,2-d]pyrimidin-5-yl)methyl)-3-methoxybenzoate (1.3)

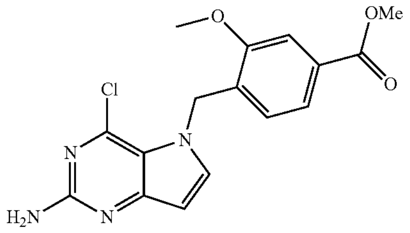 [SMILES: COC(=O)c1ccc(Cn2ccc3nc(N)nc(Cl)c32)c(OC)c1]

An oven dried 250 mL round bottom flask was equipped with magnetic stir bar, to which were added 4-chloro-5H-pyrrolo[3,2-d]pyrimidin-2-amine (commercially available (1.1) (5.5 g, 33 mmol), methyl 4-(bromomethyl)-3-methoxy-benzoate (1.2) (8.45 g, 32.6 mmol), anhydrous DMF (35 mL), cesium carbonate (10.63 g, 32.63 mmol). The mixture was flushed with argon and then stirred at rt for overnight under $N_2$ atm. LCMS showed completion of the reaction; reaction mixture was slowly poured in 500 mL of $H_2O$; solids were formed; the solids removed by filtration; and the crude material was triturated in MTBE, filtered, and dried in vacuum to obtain the compound methyl 4-[(2-amino-4-chloro-pyrrolo[3,2-d]pyrimidin-5-yl)methyl]-3-methoxy-benzoate (1.3) (11.3 g, 32.6, 99% yield). LCMS (ESI) m/z 347 (M+H).

Synthesis of (4-((2-amino-4-chloro-5H-pyrrolo[3,2-d]pyrimidin-5-yl)methyl)-3-methoxyphenyl)methanol 1.4a

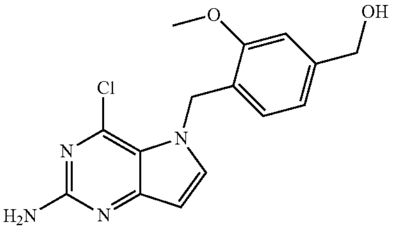 [SMILES: COc1cc(CO)ccc1Cn1ccc2nc(N)nc(Cl)c21]

An oven dried 250 mL round bottom flask was equipped with a magnetic stir bar, to which were added methyl 4-[(2-amino-4-chloro-pyrrolo[3,2-d]pyrimidin-5-yl)methyl]-3-methoxy-benzoate (1.3) (5.1 g, 15 mmol), anhydrous THF (30 mL). The slurry was cooled to 0° C., and LAH (0.56 g, 15 mmol) was added portion wise. The ice bath was removed, and the reaction was stirred at rt for 4 h under $N_2$ atm. LCMS showed completion of the reaction. The reaction was cooled back to 0° C., and satd. aqueous $Na_2SO_4$ was added dropwise. The solids were filtered, and washed with THF. The filtrates were concentrated, and dried under vacuum. LCMS (ESI) m/z 319.1 (M+H).

Synthesis of 4-chloro-5-(4-(chloromethyl)-2-methoxybenzyl)-5H-pyrrolo[3,2-d]pyrimidin-2-amine 1.5a

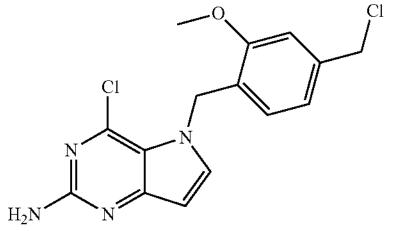 [SMILES: COc1cc(CCl)ccc1Cn1ccc2nc(N)nc(Cl)c21]

An oven dried 250 mL flask was equipped with a magnetic stir bar, to which were added [4-[(2-amino-4-chloro-pyrrolo[3,2-d]pyrimidin-5-yl)methyl]-3-methoxy-phenyl]methanol 1.4a (3 g, 9 mmol), and DCM (25 mL). The slurry was cooled to 0° C., and Thionyl chloride (6.87 mL, 94.1 mmol) was added dropwise. The reaction was bought to rt (reaction became clear solution) and stirred for 3 h. LCMS showed completion of the reaction. The reaction was cooled to 0° C., and carefully quenched by the addition of 1N NaOH. The DCM layer was separated and washed with aq $NaHCO_3$, brine, and dried over $Na_2SO_4$. The solution was concentrated to obtain 4-chloro-5-[[4-(chloromethyl)-2-methoxy-phenyl]methyl]pyrrolo[3,2-d]pyrimidin-2-amine (1.5a) (3 g, 9 mmol, 95% yield). LCMS (ESI) 337.05 (M+H).

Synthesis of tert-butyl (1-(4-((2-amino-4-chloro-5H-pyrrolo[3,2-d]pyrimidin-5-yl)methyl)-3-methoxy-benzyl)azetidin-3-yl)(methyl)carbamate 1.6a

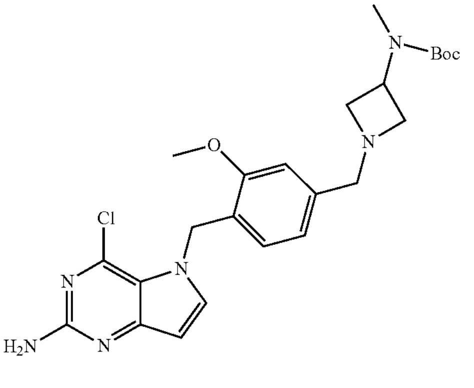 [SMILES: COc1cc(CN2CC(N(C)C(=O)OC(C)(C)C)C2)ccc1Cn1ccc2nc(N)nc(Cl)c21]

An oven-dried 25 mL vial was equipped with a magnetic stir bar, to which were added 4-chloro-5-[[4-(chloromethyl)-2-methoxy-phenyl]methyl]pyrrolo[3,2-d]pyrimidin-2-amine (1.5a) (460 mg, 1.36 mmol), tert-butyl N-(azetidin-3-yl)carbamate (234.94 mg, 1.36 mmol), DMF (5.3667 mL), and DIPEA (0.29 mL, 1.6 mmol). The clear solution was stirred at rt for overnight. LCMS showed completion of the reaction. The crude material was purified by reverse phase HPLC to obtain the compound 1.6a. LCMS (ESI) m/z 487.3 (M+H).

Synthesis of tert-butyl (1-(4-((2-amino-4-(((5-methylisoxazol-3-yl)methyl)amino)-5H-pyrrolo[3,2-d]pyrimidin-5-yl)methyl)-3-methoxybenzyl)azetidin-3-yl)(methyl)carbamate 1.7a

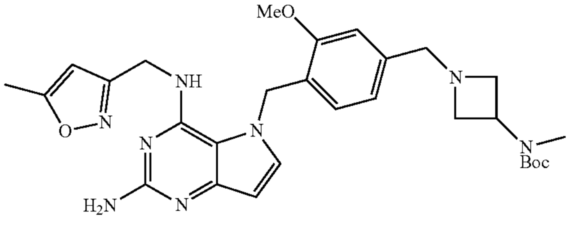

An oven-dried 20 mL vial was equipped with a magnetic stir bar, to which were added tert-butyl N-[1-[[4-[(2-amino-4-chloro-pyrrolo[3,2-d]pyrimidin-5-yl)methyl]-3-methoxy-phenyl]methyl]azetidin-3-yl]-N-methyl-carbamate 1.6a (100 mg, 0.21 mmol), (5-methylisoxazol-3-yl)methanamine (7.04 mL, 0.31 mmol), NMP (2 mL) and DIPEA (0.05 mL, 0.27 mmol). The mixture was flushed with Argon, and the reaction was heated to 40° C. and was stirred at 40° C. for 5 h under $N_2$ atm. LCMS showed completion of the reaction. The solution was concentrated and purified by reverse phase HPLC to obtain the tert-butyl (1-(4-((2-amino-4-(((5-methylisoxazol-3-yl)methyl)amino)-5H-pyrrolo[3,2-d]pyrimidin-5-yl)methyl)-3-methoxybenzyl)azetidin-3-yl)(methyl) carbamate. LCMS (ESI) m/z 563.3 (M+H).

Synthesis of 5-(2-methoxy-4-((3-(methylamino) azetidin-1-yl)methyl)benzyl)-$N_4$-((5-methylisoxazol-3-yl)methyl)-5H-pyrrolo[3,2-d]pyrimidine-2,4-diamine (compound 6)

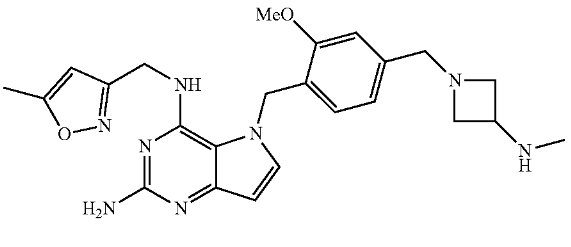

An oven-dried 20 mL vial was equipped with a magnetic stir bar, to which were added tert-butyl N-[1-[[4-[[2-amino-4-[(5-methylisoxazol-3-yl)methylamino]pyrrolo[3,2-d]pyrimidin-5-yl]methyl]-3-methoxy-phenyl]methyl]azetidin-3-yl]-N-methyl-carbamate (30 mg, 0.05 mmol), and DCM (1 mL). The mixture was cooled to 0° C., and 4 M HCl dioxane (0.05 mL, 0.21 mmol) was added. The reaction was stirred at rt for 2 h, after which LCMS showed completion of the reaction. The solution was concentrated and purified by prep HPLC (method 10% ACN in Water to 90% ACN in water in 20 min), and pure fractions were collected and lyophilized to obtain compound 6. LCMS (ESI) m/z 463.5 (M+H).

Compounds 2, 3, 4 and 5 were synthesized by using the methods described above and herein and using suitable amines $R^5$—$NH_2$.

For instance Compound 2 is prepared as follows.

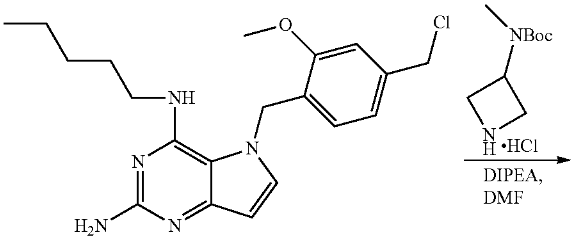

1.6

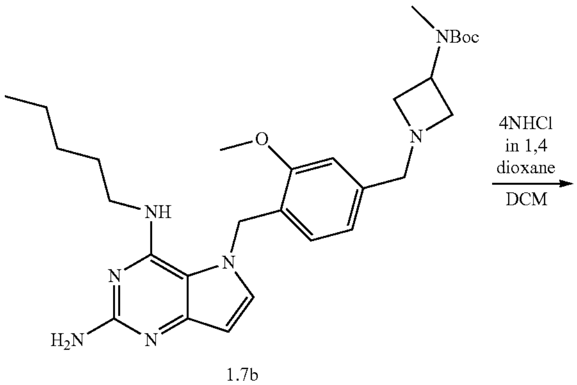

1.7b

-continued

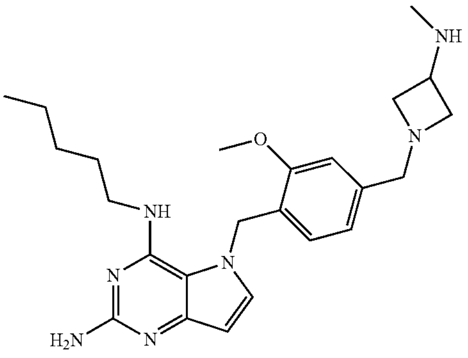

compound 2

The synthesis of compound 1.6 is provided in Example 2 below.

tert-butyl (1-(4-((2-amino-4-(pentylamino)-5H-pyrrolo[3,2-d]pyrimidin-5-yl)methyl)-3-methoxybenzyl)azetidin-3-yl)(methyl)carbamate (1.7b)

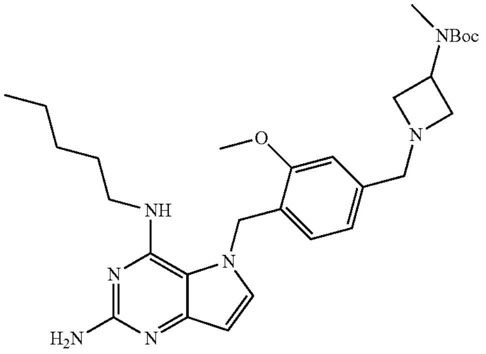 [SMILES: CCCCCNc1nc(N)nc2ccn(Cc3ccc(CN4CC(N(C)C(=O)OC(C)(C)C)C4)cc3OC)c12]

To an oven-dried 250 mL RB flask was equipped with magnetic stir bar, to which were added 5-[[4-(chloromethyl)-2-methoxy-phenyl]methyl]-N4-pentyl-pyrrolo[3,2-d]pyrimidine-2,4-diamine (100 mg, 0.26 mmol) (compound 1.6), tert-butyl N-(azetidin-3-yl)-N-methyl-carbamate hydrochloride (commercially available 60 mg), and DMF (2 mL). To the clear solution was added DIPEA (0.05 mL). The reaction was stirred at rt for 5 h. After LCMS showed completion of the reaction, the crude material was purified by reverse phase HPLC to obtain the compound 1.7b. LCMS (ESI) m/z 538.8 (M+H).

An oven-dried 20 mL vial was equipped with a magnetic stir bar, to which were added tert-butyl N-[1-[[4-[[2-amino-4-(pentylamino)pyrrolo[3,2-d]pyrimidin-5-yl]methyl]-3-methoxy-phenyl]methyl]azetidin-3-yl]-N-methyl-carbamate 1.7b (70 mg, 0.13 mmol), and DCM (2 mL). The clear solution was cooled to 0° C. and 4 M HCl dioxane (0.17 mL, 0.67 mmol) was added to the reaction and was stirred at rt for 2-3 h. After which LCMS showed completion of the reaction, the reaction was concentrated and purified by prep HPLC (method 10% ACN in Water to 90% ACN in water in 20 min), and pure fractions were collected and lyophilized to obtain compound 2. LCMS(ESI) m/z 438.8 (M+H).

Example 2

Preparation of 5-(4-((5-oxa-2,8-diazaspiro[3.5]nonan-2-yl)methyl)-2-methoxybenzyl)-$N_4$-pentyl-5H-pyrrolo[3,2-d]pyrimidine-2,4-diamine (compound 10)

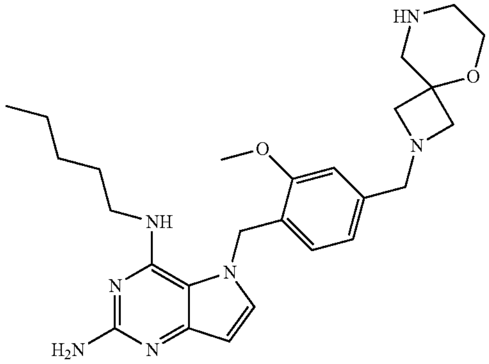 [SMILES: CCCCCNc1nc(N)nc2ccn(Cc3ccc(CN4CC5(CNCCO5)C4)cc3OC)c12]

Compound 10 was prepared according to SCHEME 3 below.

SCHEME 3

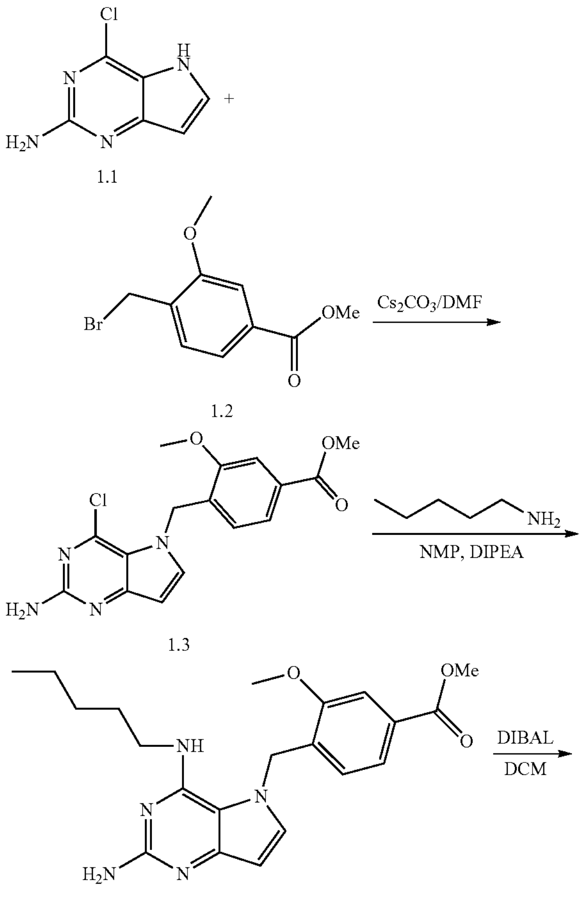

-continued

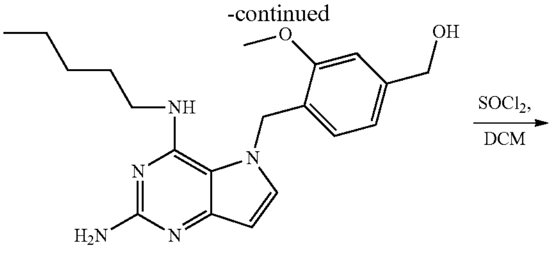

1.5

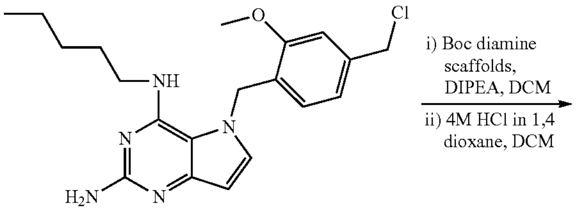

1.6

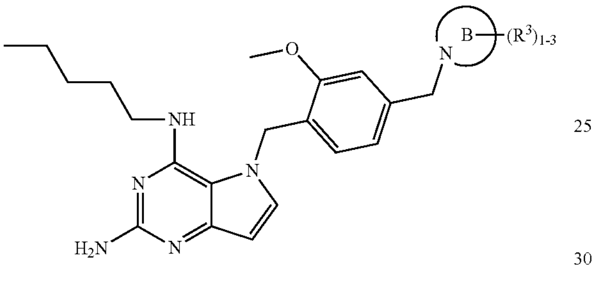

Preparation of methyl 4-((2-amino-4-(pentylamino)-5H-pyrrolo[3,2-d]pyrimidin-5-yl)methyl)-3-methoxybenzoate (1.4b)

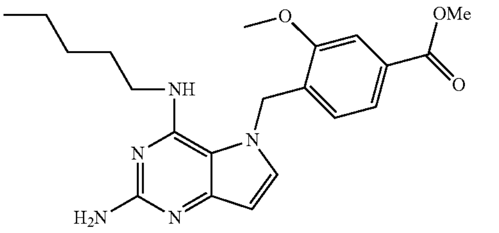 [SMILES: CCCCCNc1nc(N)nc2ccn(Cc3ccc(C(=O)OC)cc3OC)c12]

An oven-dried 250 mL round bottom flask was equipped with magnetic stir bar to which were added methyl 4-[(2-amino-4-chloro-pyrrolo[3,2-d]pyrimidin-5-yl)methyl]-3-methoxy-benzoate (1.3) (7 g, 20 mmol), anhydrous NMP (20 mL), pentan-1-amine (7.04 mL, 60.5 mmol), and DIPEA (2 eq). The reaction was heated to 50° C. and stirred at that temperature for 2 days under $N_2$ atm. LCMS showed the desired product peak. Solvent was removed to dryness, and the crude material was purified by ISCO (DCM to 10% MeOH/DCM) to obtain methyl 4-[[2-amino-4-(pentylamino)pyrrolo[3,2-d]pyrimidin-5-yl]methyl]-3-methoxy-benzoate (1.4b) (6.5 g, 16 mmol, 82% yield). LCMS (ESI) m/z 398.2 (M+H). $^1$HNMR (DMSO-$d_6$): δ 7.53 (d, 1H), 7.51 (d, 1H), 7.48 (dd, 1H), 7.40 (br s, 2H), 7.34 (t, 1H), 6.45 (d, 1H), 6.27 (d, 1H), 5.67 (s, 2H), 3.92 (s, 3H), 3.83 (s, 3H), 3.40 (q, 2H), 1.41-1.32 (m, 2H), 1.17-1.07 (m, 2H), 0.97-0.87 (m, 2H), 0.73 (t, 3H).

Preparation of (4-((2-amino-4-(pentylamino)-5H-pyrrolo[3,2-d]pyrimidin-5-yl)methyl)-3-methoxyphenyl)methanol (1.5)

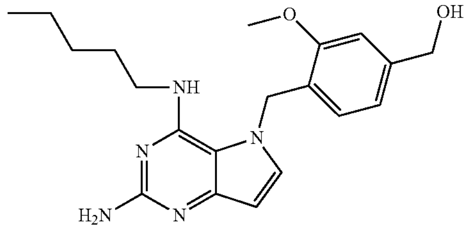 [SMILES: CCCCCNc1nc(N)nc2ccn(Cc3ccc(CO)cc3OC)c12]

An oven-dried 250 mL round bottom flask was equipped with magnetic stir bar, to which were added methyl 4-[[2-amino-4-(pentylamino)pyrrolo[3,2-d]pyrimidin-5-yl]methyl]-3-methoxy-benzoate (1.4) (3.5 g, 8.8 mmol), and THF (40 mL). The mixture was cooled to 0° C. and then DIBAL (35.22 mL, 1M in THF, 35.22 mmol) was added dropwise under argon atm. The reaction was slowly bought to rt and stirred for 2 h, after which reaction was cooled back to 0° C. and then quenched with saturated aq $Na_2SO_4$ until a fine white solid was formed. Excess solid $Na_2SO_4$ was added and the reaction mixture was filtered through a pad of celite and washed with DCM/MeOH and few mL of DMF. The filtrate was concentrated under vacuum to afford compound 1.5 (60% yield). LCMS (ESI) m/z 370.2 (M+H).

Preparation of 5-(4-(chloromethyl)-2-methoxybenzyl)-$N_4$-pentyl-5H-pyrrolo[3,2-d]pyrimidine-2,4-diamine (1.6)

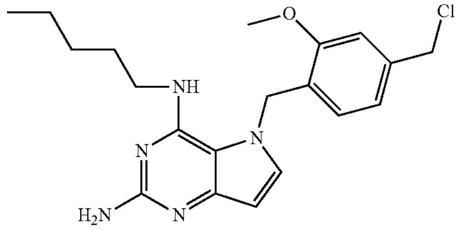 [SMILES: CCCCCNc1nc(N)nc2ccn(Cc3ccc(CCl)cc3OC)c12]

An oven-dried 250 mL round bottom flask was equipped with magnetic stir bar, to which were added [4-[[2-amino-4-(pentylamino)pyrrolo[3,2-d]pyrimidin-5-yl]methyl]-3-methoxy-phenyl]methanol (5) (1.7 g, 4.6 mmol), and anhydrous Chloroform (15 mL). The mixture was cooled to 0° C. and then Thionyl Chloride (2 mL, 28 mmol) was added dropwise under argon atm. The reaction was slowly bought to rt and stirred for 2 h. After which, LCMS showed completion of the reaction. The solution was concentrated to remove DCM and $SOCl_2$, and was cooled to 0° C. and then carefully quenched by the addition of sat $NaHCO_3$. The solution was extracted with DCM. The organic layer was washed with brine, and dried over $Na_2SO_4$, filtered to remove solids, concentrated, and dried in vacuum to afford compound 1.6. LCMS (ESI) m/z 388.1 (M+H).

General Procedure for Boc Diamine Scaffold Coupling to Compound 1.6 to Prepare Boc-Protected Compounds:

An oven-dried 25 mL round bottom flask was equipped with a magnetic stir bar, to which was added 5-[[4-(chloromethyl)-2-methoxy-phenyl]methyl]-N4-pentyl-pyrrolo[3,2-d]pyrimidine-2,4-diamine (1.6) (100 mg, 0.26 mmol), and Boc protected diamine scaffold as described above (1 eq), and anhydrous DMF (2 mL). The clear solution was flushed with argon and then DIPEA (3 eq) was added. The reaction was stirred at rt for 5 h under $N_2$ atm. After LCMS showed completion of the reaction, the crude material was purified by reverse phase HPLC to obtain the Boc protected scaffold.

Deprotection to obtain 5-(4-((5-oxa-2,8-diazaspiro[3.5]nonan-2-yl)methyl)-2-methoxybenzyl)-$N_4$-pentyl-5H-pyrrolo[3,2-d]pyrimidine-2,4-diamine (compound 10)

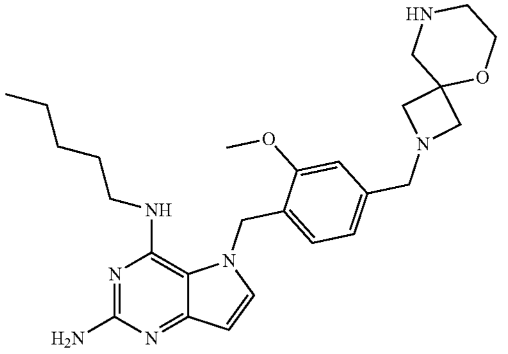 [SMILES: CCCCCNc1nc(N)nc2ccn(Cc3ccc(CN4CC5(CNCCO5)C4)cc3OC)c12]

An oven-dried 250 mL round bottom flask was equipped with a magnetic stir bar, to which were added 5-[[4-(chloromethyl)-2-methoxy-phenyl]methyl]-N4-pentyl-pyrrolo[3,2-d]pyrimidine-2,4-diamine (100 mg, 0.26 mmol) (compound 1.6), tert-butyl 5-oxa-2,8-diazaspiro[3.5]nonane-8-carboxylate hydrochloride (commercially available 102.38 mg), and DMF (2 mL). To the clear solution was added DIPEA (0.05 mL). The reaction was stirred at rt for 5 h. After LCMS showed completion of the reaction, the crude material was purified by reverse phase HPLC to obtain the compound 1.7. LCMS (ESI) m/z 580.7 (M+H).

An oven-dried 20 mL vial was equipped with a magnetic stir bar, to which were added tert-butyl 2-[[4-[[2-amino-4-(pentylamino)pyrrolo[3,2-d]pyrimidin-5-yl]methyl]-3-methoxy-phenyl]methyl]-5-oxa-2,8-diazaspiro[3.5]nonane-8-carboxylate (1.7) (70 mg, 0.12 mmol), and DCM (0.94 mL). The clear solution was cooled to 0° C. and then added 4M HCl dioxane (0.15 mL, 0.60 mmol) was added. The reaction was stirred at rt for 2 h. After LCMS showed completion of the reaction, the reaction mixture was concentrated and purified by prep HPLC (method 10% ACN in Water to 90% ACN in water in 20 min), and pure fractions were collected and lyophilized to obtain compound 10. LCMS(ESI) m/z 480.3 (M+H).

Example 3

Synthesis of 5-(4-((3-aminoazetidin-1-yl)methyl)-2-methoxybenzyl)-N4-pentyl-5H-pyrrolo[3,2-d]pyrimidine-2,4-diamine (compound 13)

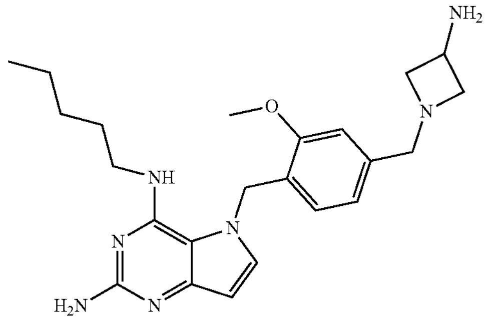 [SMILES: CCCCCNc1nc(N)nc2ccn(Cc3ccc(CN4CC(N)C4)cc3OC)c12]

Synthesis of tert-butyl N-[1-[[4-[[2-amino-4-(pentylamino)pyrrolo[3,2-d]pyrimidin-5-yl]methyl]-3-methoxy-phenyl]methyl]azetidin-3-yl]carbamate (1.8)

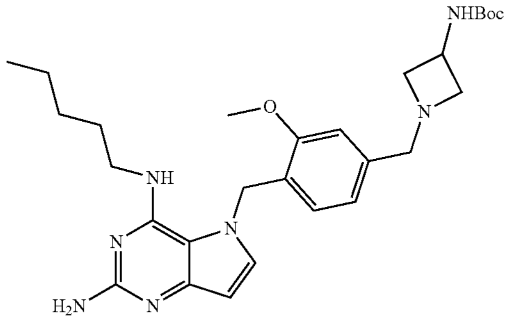 [SMILES: CCCCCNc1nc(N)nc2ccn(Cc3ccc(CN4CC(NC(=O)OC(C)(C)C)C4)cc3OC)c12]

An oven-dried 250 mL round bottom flask was equipped with magnetic stir bar, to which were added 5-[[4-(chloromethyl)-2-methoxy-phenyl]methyl]-N4-pentyl-pyrrolo[3,2-d]pyrimidine-2,4-diamine (100 mg, 0.26 mmol) (compound 1.6), tert-butyl N-(azetidin-3-yl)carbamate hydrochloride (commercially available, 60 mg), and DMF (2 mL). To the clear solution was added DIPEA (0.05 mL), and the reaction was stirred at rt for 5 h. After LCMS showed completion of the reaction, the crude material was purified by reverse phase HPLC to obtain the compound 1.8. LCMS (ESI) m/z 524.7 (M+H).

An oven-dried 20 mL vial was equipped with a magnetic stir bar, to which were added tert-butyl N-[1-[[4-[[2-amino-4-(pentylamino)pyrrolo[3,2-d]pyrimidin-5-yl]methyl]-3-methoxy-phenyl]methyl]azetidin-3-yl]carbamate (1.8) (70 mg, 0.13 mmol), DCM (2 mL). The clear solution was cooled to 0° C. and 4 M HCl dioxane (0.17 mL, 0.67 mmol) were added. The reaction was stirred at rt for 2-3 h. After which LCMS showed completion of the reaction, the reaction was concentrated and purified by prep HPLC (method 10% ACN in Water to 90% ACN in water in 20 min), and pure fractions were collected and lyophilized to obtain compound 13. LCMS(ESI) m/z 424.3 (M+H).

Example 4
Synthesis of Linker Payload-Compound 10
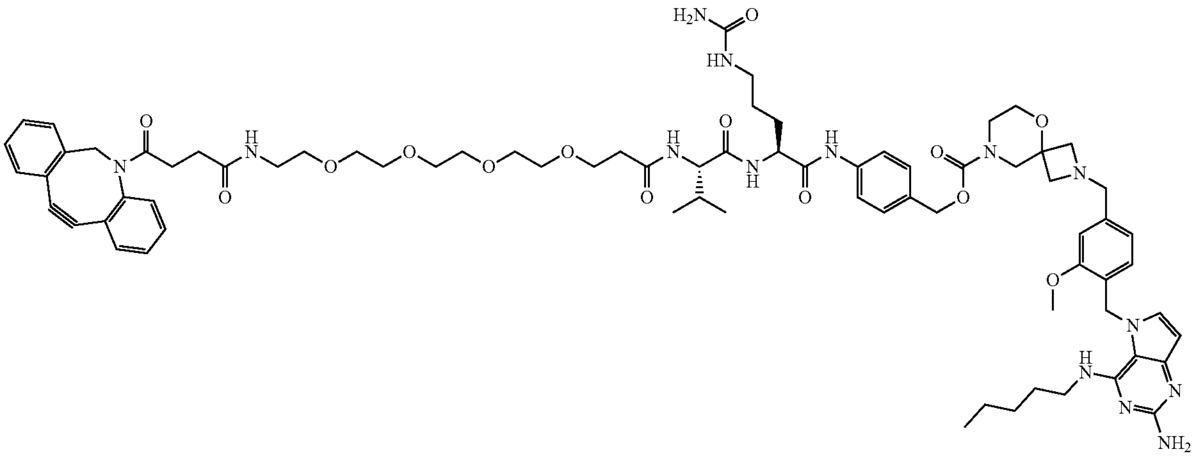
linker payload-compound 10
Scheme 4 shows the synthesis of linker payload-compound 10
SCHEME 4
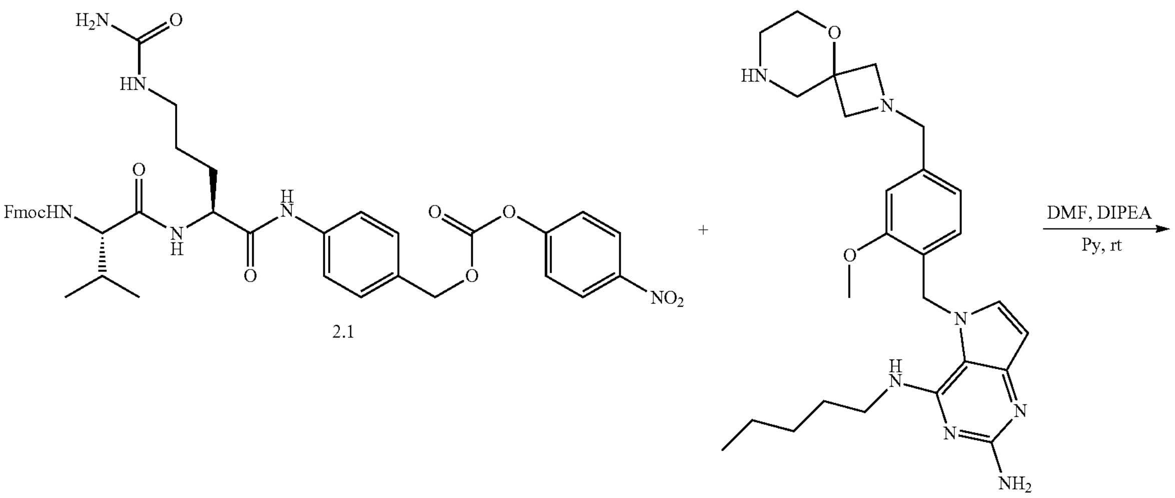
2.1
compound 10

-continued

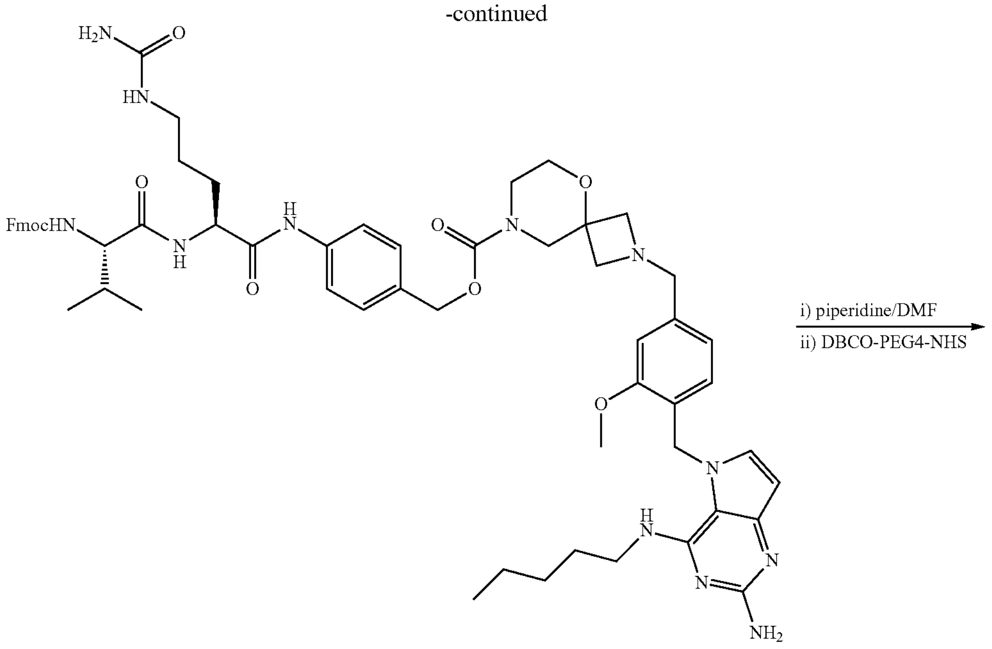

2.2

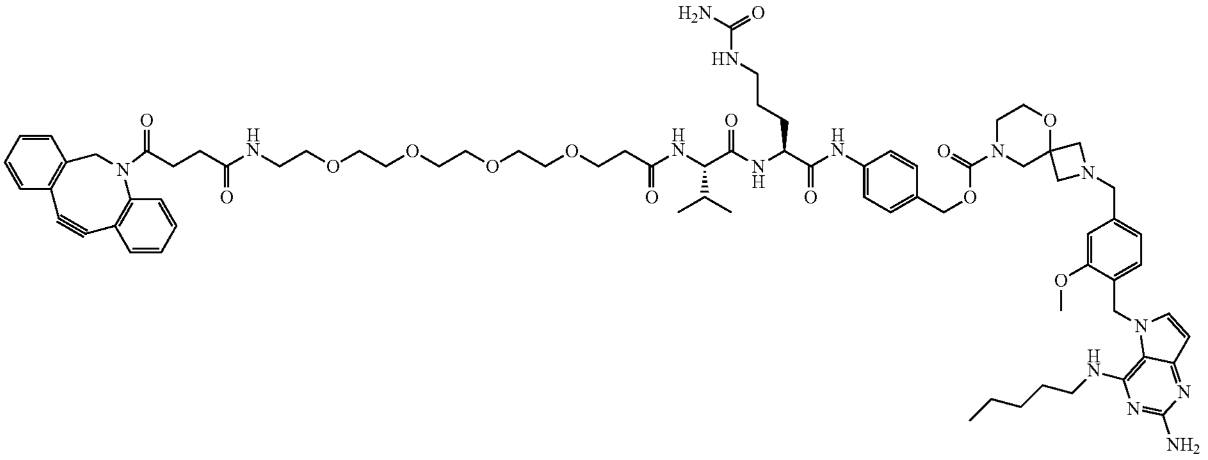

linker payload-compound 10

Synthesis of [4-[[rac-(2S)-2-[[rac-(2S)-2-amino-3-methyl-butanoyl]amino]-5-ureido-pentanoyl]amino]phenyl]methyl 2-[[4-[[2-amino-4-(pentylamino)pyrrolo[3,2-d]pyrimidin-5-yl]methyl]-3-methoxy-phenyl]methyl]-5-oxa-2,8-diazaspiro[3.5]nonane-8-carboxylate (2.2)

An oven-dried 100 mL flask was equipped with a magnetic stir bar, to which were added 5-[[2-methoxy-4-(5-oxa-2,8-diazaspiro[3.5]nonan-2-ylmethyl)phenyl]methyl]-N4-pentyl-pyrrolo[3,2-d]pyrimidine-2,4-diamine (compound 10) (180 mg, 0.38 mmol), (4-nitrophenyl) [4-[[rac-(2S)-2-[[rac-(2S)-2-(9H-fluoren-9-ylmethoxycarbonylamino)-3-methyl-butanoyl]amino]-5-ureido-pentanoyl]amino]phenyl] methyl carbonate (2.1) (345.33 mg, 0.45 mmol), and DMF (2 mL). The clear solution was flushed with argon and then DIPEA (0.2 mL, 1 mmol) was added, and the reaction was stirred at rt for overnight. LCMS showed completion of the reaction. Solvent was removed to dryness, and the residue was purified by flash chromatography to obtain compound 2.2. LC-MS (ESI) m/z+H 1108.3.

An oven-dried 100 mL flask was equipped with magnetic stir bar, to which were added [4-[[rac-(2S)-2-[[rac-(2S)-2-amino-3-methyl-butanoyl]amino]-5-ureido-pentanoyl]amino]phenyl]methyl 2-[[4-[[2-amino-4-(pentylamino)pyrrolo[3,2-d]pyrimidin-5-yl]methyl]-3-methoxy-phenyl]methyl]-5-oxa-2,8-diazaspiro[3.5]nonane-8-carboxylate (2.2) (200 mg, 0.18 mmol) which was dissolved in DMF (2 mL) and piperidine (5 eq) was added. The clear solution was stirred at rt for 30 min, LCMS showed deprotection of Fmoc, and the crude compound 2.2a was purified by prep HPLC.

An oven-dried 100 mL flask was equipped with magnetic stir bar, to which were added compound (2.2a) (150 mg, 0.17 mmol), DBCO-PEG4-NHS Ester (122 mg, 0.19 mmol), and DMF (2 mL). The clear solution was flushed with argon and then DIPEA (60 μL, 0.34 mmol) was added. The reaction was stirred at rt for 2 h under $N_2$ atm. After LCMS showed completion of the reaction, the material was purified by prep HPLC (method 10% ACN to 90% ACN in 20 min), and pure fractions were collected and lyophilized to obtain linker payload-compound 10. HPLC MS data showed the desired product in 98% purity. LC-MS (ESI) m/z+H 1420.8

Preparation of Linker Payloads
Example 5
Synthesis of Linker Payload-Compound 2
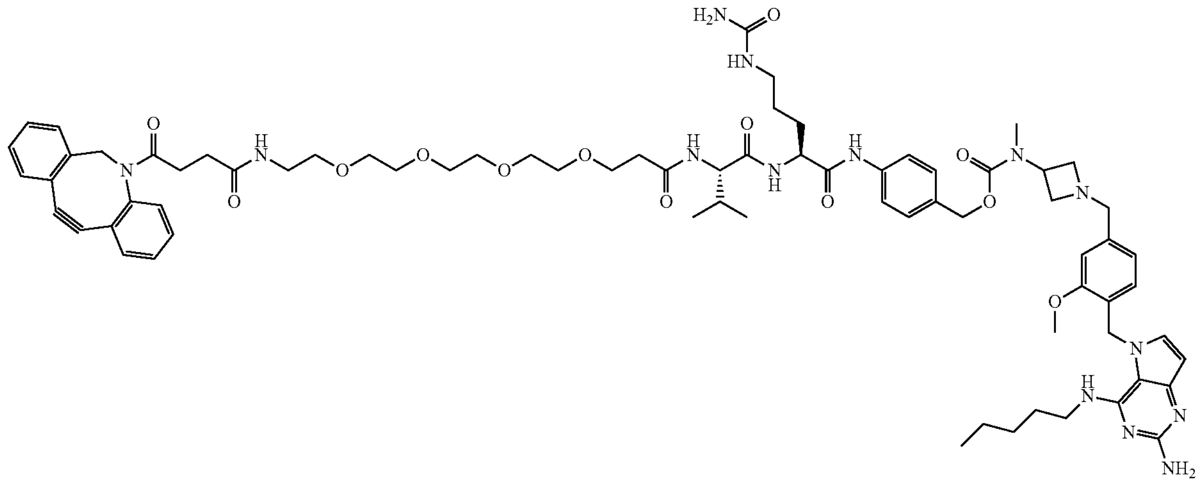
linker payload-compound 2
Scheme 5 shows the synthesis of linker payload-compound 2
SCHEME 5
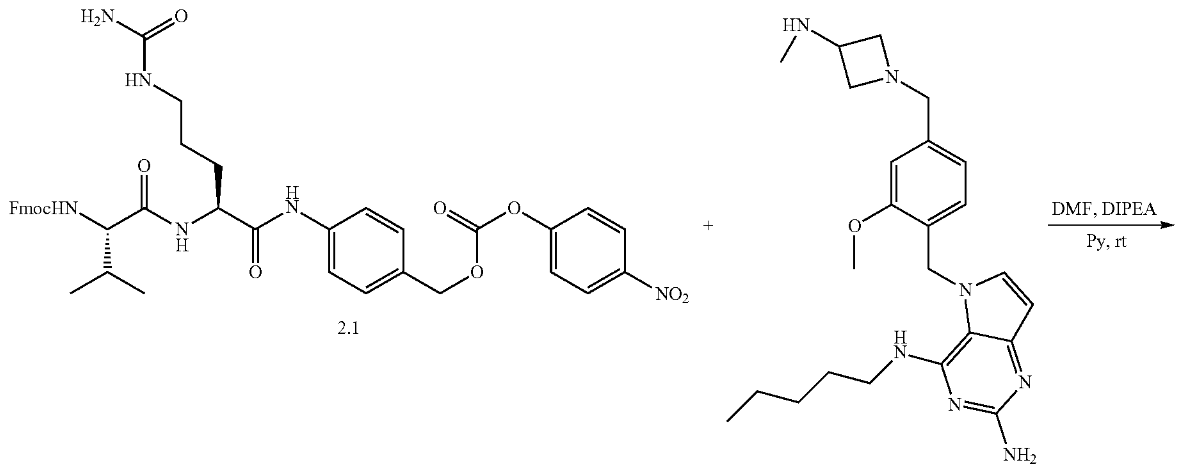
2.1
compound 2

-continued

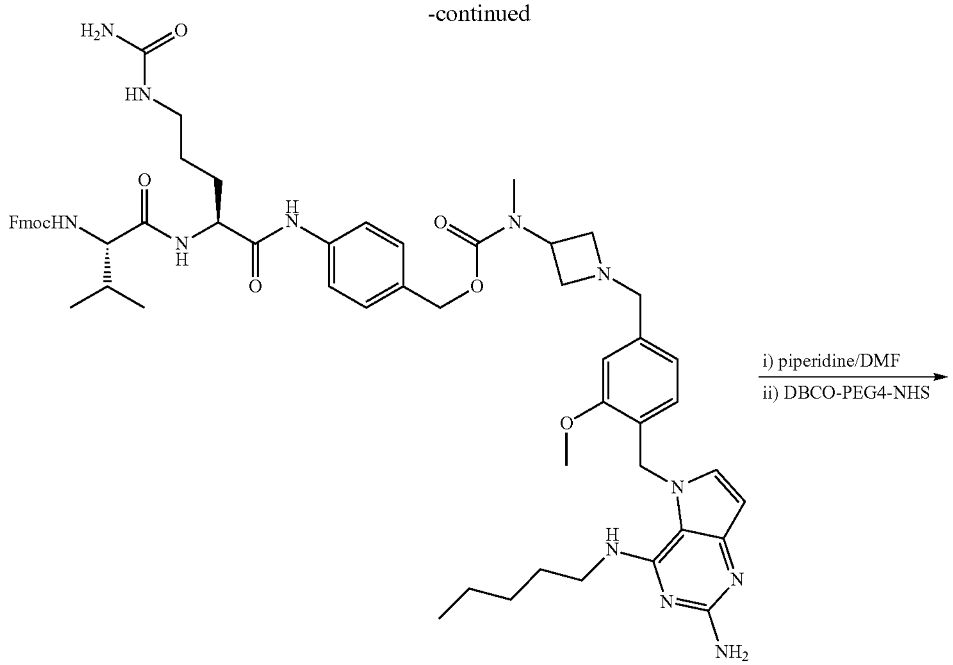

2.3

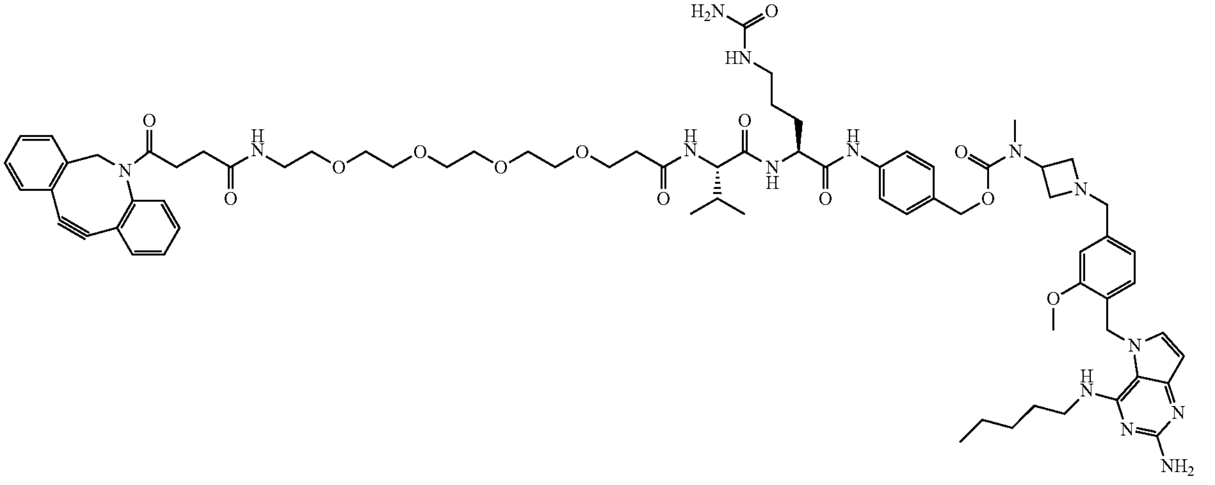

linker payload-compound 2

Synthesis of Linker Payload Compound 2:

An oven-dried 100 mL flask was equipped with a magnetic stir bar, to which were added 5-(2-methoxy-4-((3-(methylamino)azetidin-1-yl)methyl)benzyl)-$N_4$-pentyl-5H-pyrrolo[3,2-d]pyrimidine-2,4-diamine (compound 2) (200 mg, 0.45 mmol), (4-nitrophenyl) [4-[[rac-(2S)-2-[[rac-(2S)-2-(9H-fluoren-9-ylmethoxycarbonylamino)-3-methyl-butanoyl]amino]-5-ureido-pentanoyl]amino]phenyl]methyl carbonate (2.1) (385 mg, 0.50 mmol), and DMF (2 mL). The clear solution was flushed with argon and then DIPEA (0.2 mL, 1 mmol) was added, and the reaction was stirred at rt for overnight. LCMS showed completion of the reaction. Solvent was removed to dryness and the residue was purified by flash chromatography to obtain compound 2.3. LC-MS (ESI) m/z+H 1065.8.

Compound 2.3 (200 mg, 0.18 mmol) was dissolved in DMF (2 mL), added piperidine (5 eq) and the clear solution was stirred at rt for 30 min, LCMS showed deprotection of Fmoc, the crude compound 2.3a was purified by prep HPLC.

An oven-dried 100 mL flask was equipped with magnetic stir bar, to which were added the above prepared compound (2.3a) (150 mg, 0.17 mmol), DBCO-PEG4-NHS Ester (138 mg, 0.21 mmol), and DMF (2 mL). The clear solution was flushed with argon and then added DIPEA (0.05 mL, 0.31 mmol) added. The reaction was stirred at rt for 2 h under $N_2$ atm. After LCMS showed completion of the reaction, the material was purified by prep HPLC (method 10% ACN to 90% ACN in 20 min) and pure fractions were collected and lyophilized to obtain Linker payload-compound 2. HPLC MS data showed the desired product in 98% purity. LC-MS (ESI) m/z+H 1377.9

Example 6
Synthesis of Linker Payload-Compound 13
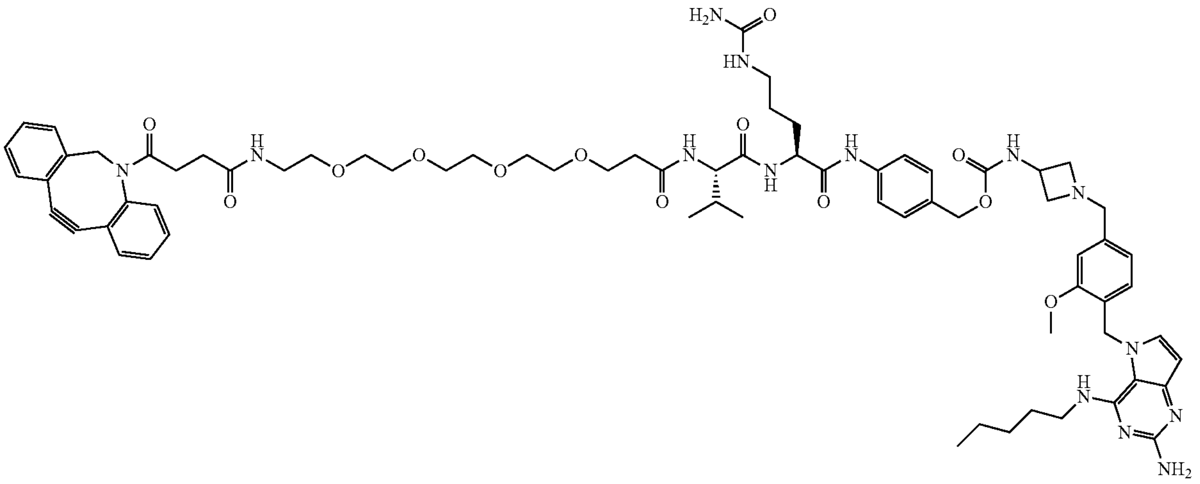
linker payload-compound 13
Scheme 6 shows the synthesis of linker payload-compound 13
SCHEME 6
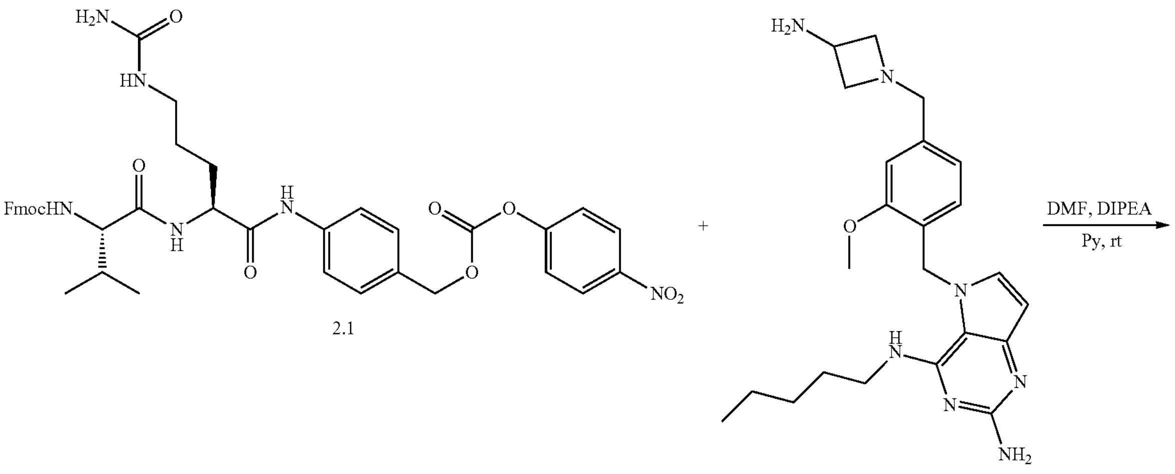
compound 13

-continued

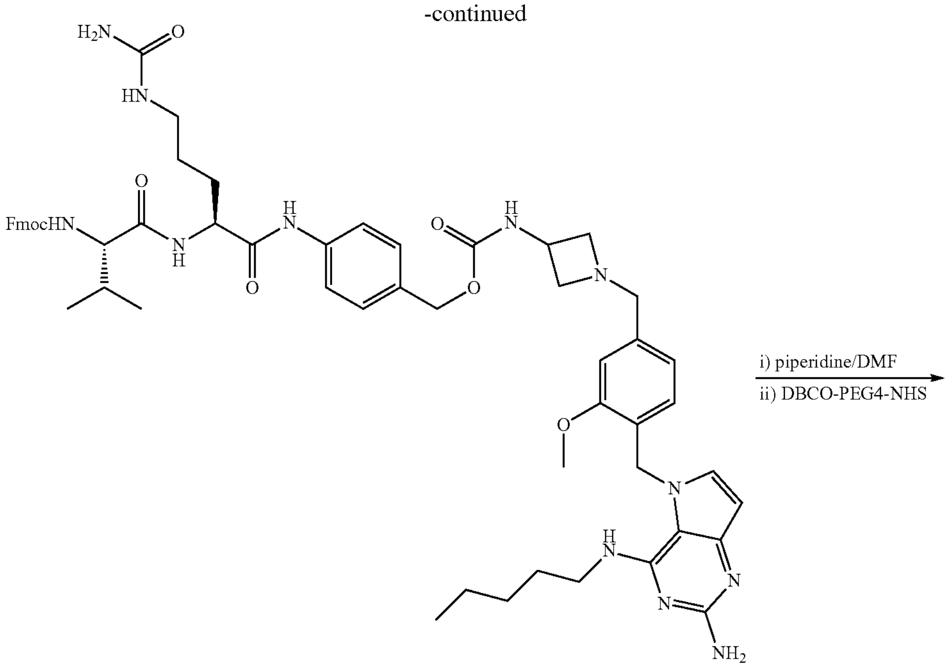

2.4

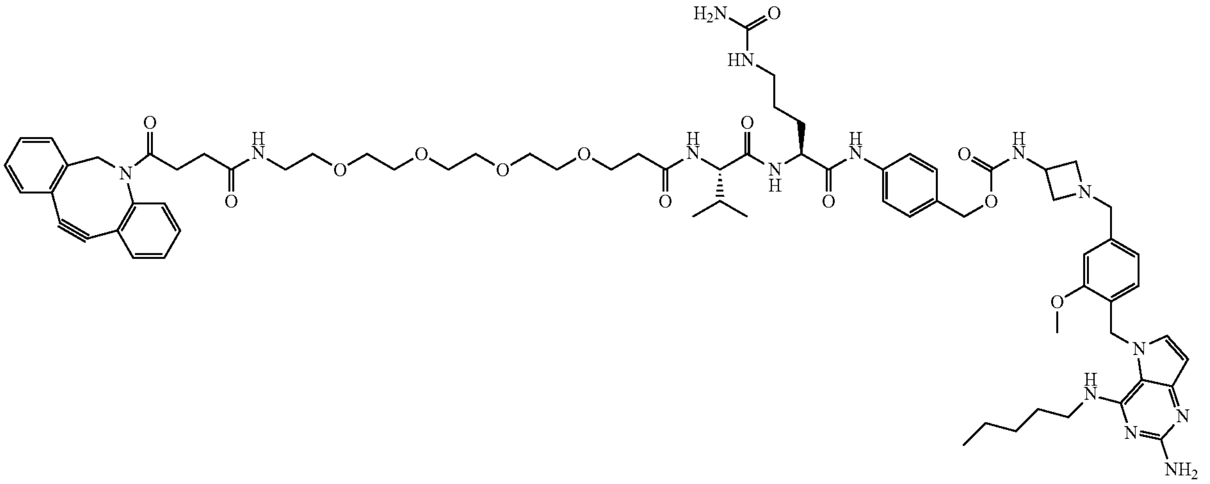

linker payload-compound 13

Synthesis of Linker Payload Compound 13:

An oven-dried 100 mL flask was equipped with a magnetic stir bar, to which were added 5-(4-((3-aminoazetidin-1-yl)methyl)-2-methoxybenzyl)-$N_4$-pentyl-5H-pyrrolo[3,2-d]pyrimidine-2,4-diamine (compound 13) (250 mg, 0.59 mmol), (4-nitrophenyl) [4-[[rac-(2S)-2-[[rac-(2S)-2-(9H-fluoren-9-ylmethoxycarbonylamino)-3-methyl-butanoyl]amino]-5-ureido-pentanoyl]amino]phenyl]methyl carbonate (2.1) (497 mg, 0.64 mmol), and DMF (10 mL). The clear solution was flushed with argon and then DIPEA (0.2 mL, 1 mmol) was added, and the reaction was stirred at rt for overnight. LCMS showed completion of the reaction. Solvent was removed to dryness and the residue was purified by flash chromatography to obtain compound 2.4. LC-MS (ESI) m/z+H 1051.8.

Compound 2.4 (250 mg, 0.23 mmol) was dissolved in DMF (5 mL), and piperidine (5 eq) was added. The clear solution was stirred at rt for 30 min. LCMS showed deprotection of Fmoc, and the crude compound 2.4a was purified by prep HPLC.

An oven-dried 100 mL flask was equipped with magnetic stir bar, to which were added the above prepared compound (2.4a) (200 mg, 0.24 mmol), DBCO-PEG4-NHS Ester (188 mg, 0.29 mmol), and DMF (5 mL). The clear solution was flushed with argon and then DIPEA (60 μL, 0.31 mmol) was added. The reaction was stirred at rt for 2 h under $N_2$ atm. After LCMS showed completion of the reaction, the material was purified by prep HPLC (method 10% ACN to 90% ACN in 20 min) and pure fractions were collected and lyophilized to obtain Linker payload-compound 13. HPLC MS data showed the desired product in 98% purity. LC-MS (ESI) m/z+H 1363.9

Example 7

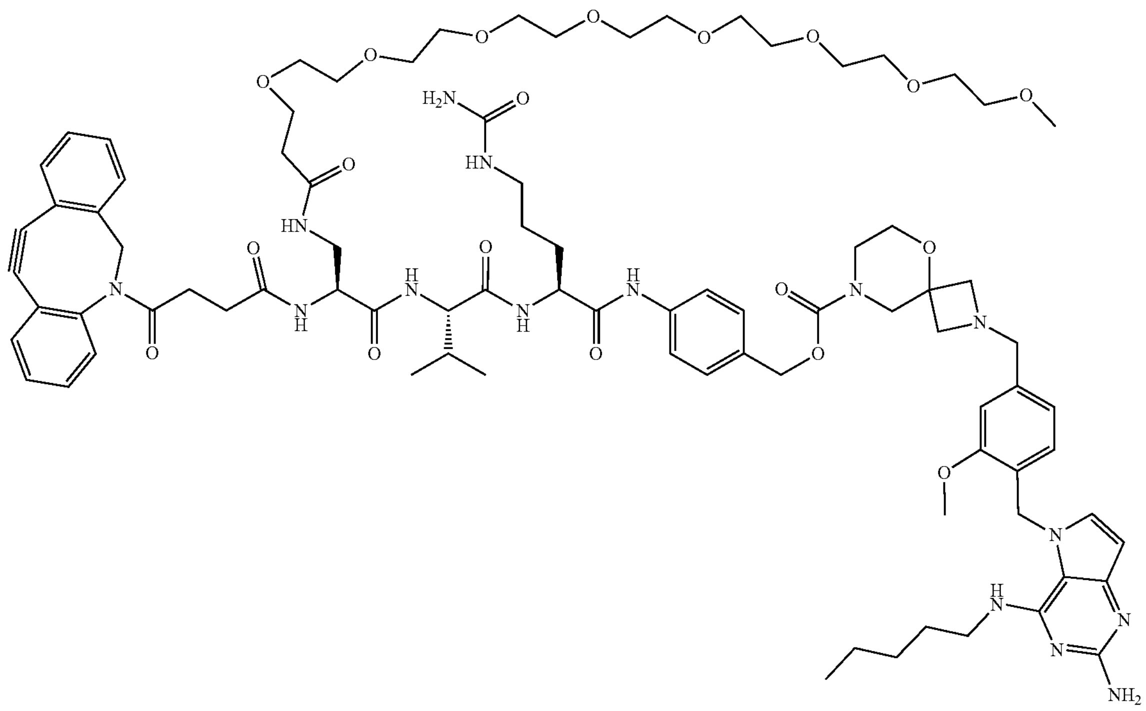 [SMILES: CCCCCNc1nc(N)nc2ccn(Cc3ccc(CN4CC5(C4)CN(C(=O)OCc4ccc(NC(=O)[C@H](CCCNC(N)=O)NC(=O)[C@@H](NC(=O)[C@H](CNC(=O)CCOCCOCCOCCOCCOCCOCCOCCOC)NC(=O)CCC(=O)N6Cc7ccccc7C#Cc7ccccc76)C(C)C)cc4)CCO5)cc3OC)c12]

The linker payload-compound 10 shown above is prepared using a similar procedure as described in Example 4 above. Na-Fmoc-L-2,3-diaminopropionic acid, non-natural amino acid (Dap-OH), is purchased from Sigma Aldrich (cat #47552-1G-F). m-PEG8-NHS is purchased from Broadpharm (cat #BP-21103).

Biological Activity of Compounds

Example 8

In this example, the in vitro activity of compounds to activate human TLR7 (or human TLR8 or mouse TLR7) pathway was evaluated on HEK293 reporter cells transfected with human TLR7 (or human TLR8 or mouse TLR7) and an inducible SEAP (secreted embryonic alkaline phosphatase) reporter gene. The SEAP reporter gene is placed under the control of the IFN-β minimal promoter fused to five NF-κB and AP-1-binding sites. Stimulation with a TLR7 agonist activates NF-κB and AP-1 which induces the production of SEAP. Levels of SEAP were determined by HEK-Blue Detection medium.

The in vitro activity of compounds on TLR7 (human and mouse) and TLR8 (human only) reporter cell lines was assessed as follows. 5-(2-methoxy-4-(piperazin-1-ylmethyl)benzyl)-N4-pentyl-5H-pyrrolo[3,2-d]pyrimidine-2,4-diamine (Compound 1) is a compound used for comparison and has the structure shown below:

Compound 1

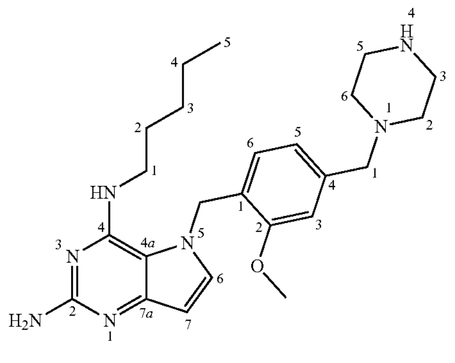

HEK293-humanTLR7 (hTLR7), HEK293-mouseTLR7 (mTLR7) and HEK293-humanTLR8 (hTLR8) reporter cell lines were purchased from Invivogen and cell lines were maintained in the manufacturer's recommended culture medium with required supplemental antibiotics. On the day of assay, the cells were harvested with Accutase and counted by the Vi-CELL Cell Viability Analyzers. Cells were resuspended in HEK blue detection medium and a total of 10,000 cells were seeded in each well of a 384-well flat bottom plate. Serial dilutions of test compounds (1:4 serial dilution starting from 5 μM) were added into treatment wells and assay plates were cultured at 37° C. in a $CO_2$ incubator for 24 hrs. The plates were then read by spectrophotometry at 640 nm. Data was fitted with non-linear regression analysis, using a log(inhibitor) vs. response-variable slope, 3-parameter fit with GraphPad Prism. There result was reported in Table 1 as $EC_{50}$ (the midpoint of the curve, or concentration at which 50% of the maximum effect was observed). The data in Table 1 shows that certain compounds described herein are potent TLR7 agonists and are selective over TLR8.

TABLE 1

| Compound No. | hTLR7 EC50(nM) | hTLR8 EC50(nM) | mTLR7 EC50(nM) |
|---|---|---|---|
| 1 (comparator compound) | 1.9 | 337.9 | 4.6 |
| 1.7 | 0.1 | NA | 6.7 |
| 2 | 1.6 | 367.5 | 10.2 |
| 3 | NA | NA | NA |
| 4 | 493.1 | NC | NC |
| 5 | 1013 | NA | NC |
| 6 | NA | NA | NA |
| 7 | 48.8 | NA | 111.7 |
| 8 | 16.5 | NA | 17.6 |
| 9 | 13.4 | 1140.3 | 16.2 |
| 10 | 1.5 | 341.7 | 3.7 |
| 11 | 92.3 | NA | 222.2 |
| 12 | 370.4 | NA | NC |
| 13 | 0.5 | 374.4 | 2.7 |
| 14 | 108.3 | NA | 321.7 |
| 15 | 4.8 | NA | 24.6 |

NA = Not Active
NC = Active, but EC50 Not Calculable due to incomplete dilution curve

Example 9

In Vitro Cytotoxicity of Compound 10

The cytotoxicity of compound 10 was tested in a cell proliferation assay on KB cells. KB cells were obtained from ATCC and were maintained in Ham's F-12: high glucose DMEM (50:50) (Corning) supplemented with 10% heat-inactivated fetal bovine serum (Corning), 1% Penicillin/Streptomycin (Corning) and 2 mmol/L-glutamax (Thermo Fisher Scientific). One day before the assay, KB cells were harvested with Acutase and a total of 625 cells were seeded in each well of a 384-well flat bottom white polystyrene plate. Compound 10 was formulated at 2-fold starting concentration in the cell culture medium. Serial dilutions of Compound 10 (1:4 serial dilution starting from 1000 nM) was added into treatment wells. Assay plates were cultured at 37° C. in a $CO_2$ incubator for 120 hrs. For cell viability measurement, 30 μL of Cell Titer-Glo® reagent (Promega Corp) was added into each well, and plates were processed as per product instructions. Relative luminescence was measured on an ENVISION® plate reader (Perkin-Elmer). Relative luminescence readings were converted to percent viability using untreated cells as controls.

Compound 10 did not show any cytotoxicity on KB cells even at a concentration up to 1 μM.

Example 10

Compound 10 Activity to Stimulate Other TLRs

In this example, the activity of the compound 10 to stimulate different human and mouse TLR pathways was investigated on HEK293 cells transfected with inducible SEAP (secreted embryonic alkaline phosphatase) reporter genes and also expressing different human TLRs (TLR2, TLR3, TLR4, TLR5, TLR7, TLR8, TLR9) or mouse TLRs (TLR2, TLR3, TLR4, TLR5, TLR7, TLR8, TLR13).

HEK293 reporter cell lines were purchased from Invivogen and cell lines were maintained in manufacture recommended culture medium with required supplemental antibiotics. On the day of assay, the cells were harvested with Accutase and counted by the Vi-CELL Cell Viability Analyzers. Cells were resuspended in HEK blue detection medium and a total of 10000 cells were seeded in each well of a 384-well flat bottom plate. Serial dilutions of compound 10 and compound 1 was added into treatment wells. Assay plates were cultured at 37° C. in a $CO_2$ incubator for 16 hrs. HEK-Blue™ Detection medium changes to a purple/blue color in the presence of secreted SEAP, which can be detected by spectrophotometry at 620-655 nm. Data was fitted with non-linear regression analysis, using a log(inhibitor) vs. response-variable slope, 3-parameter fit with GraphPad Prism.

Compound 10 is very specific to human and mouse TLR7, only slightly activity to human TLR8 was observed. No activity on other human or mouse TLRs was observed. The result was reported in Table 2 as $EC_{50}$ (the midpoint of the curve, or concentration at which 50% of the maximum effect was observed).

TABLE 2

Summary of HEK293 reporter assay $EC_{50}$

| TLR expressed | Compound 10 $EC_{50}$ (nM) | Compound 1 $EC_{50}$ (nM) |
|---|---|---|
| human TLR2 | NA | NA |
| human TLR3 | NA | NA |
| human TLR4 | NA | NA |
| human TLR5 | NA | NA |
| human TLR7 | 11.04 | 2.17 |
| human TLR8 | NC | NC |
| human TLR9 | NA | NA |
| mouse TLR2 | NA | NA |
| mouse TLR3 | NA | NA |
| mouse TLR4 | NA | NA |
| mouse TLR5 | NA | NA |
| mouse TLR7 | 22.9 | 2.6 |
| mouse TLR8 | NA | NA |
| mouse TLR13 | NA | NA |

NA = Not Active
NC = Active but $EC_{50}$ not Calculable due to incomplete dilution curve

Example 11

Compound 10 Induced Immune Cell Activation

This example evaluates the ability of Compound 10 to stimulate the activation of different immune cells populations (monocyte, B cell, and DCs), in human PBMCs (Peripheral blood mononuclear cells), cyno PBMCs and mouse splenocytes.

Peripheral blood mononuclear cells (PBMCs) were isolated from fresh collected blood from two healthy human donors and two cynomolgus monkey donors using Leukosep tube and Nycoprep 1.077 buffer according to the manufacture's recommendation. Mouse splenocytes were isolated from C57/BL6 mouse spleens by macerating and straining over a 70 μm cell strainer. Isolated PBMCs or splenocytes were then frozen down using frozen medium. On the day of the assay, PBMCs or splenocytes were thawed and cultured in PBMC culture medium (RPMI supplemented with 10% heat-inactivated fetal bovine serum from Hyclone, 1% Penicillin/Streptomycin and 2 mmol/L-glutamax). 300 k of PBMC or splenocytes in 50 μl of culture medium were seeded in 96-well cell culture plates. 50 μl of the test articles (formulated at 2× of starting concentration) were then added into the well. The cell mixtures were co-cultured in the presence of test articles and 10 μg/ml LPS-RS for 48 hr. The cells were collected by Accutase and then stained with antibodies to different cell population markers and activation markers. Cells were washed, fixed with 2% PFA overnight, and read on the Attune N×T cytometer (Thermo Fisher). Monocyte activation was indicated as increase of CD86 expression on CD14+ cells. B cell activation was indicated as increase of CD86 expression on CD14−/Lin+/HLA-DR+ cells. Dendritic cells (DC) activation was indicated as increase of CD86 expression on CD14−/Lin−/HLA-DR+/CD123+ cells.

Figure 2:
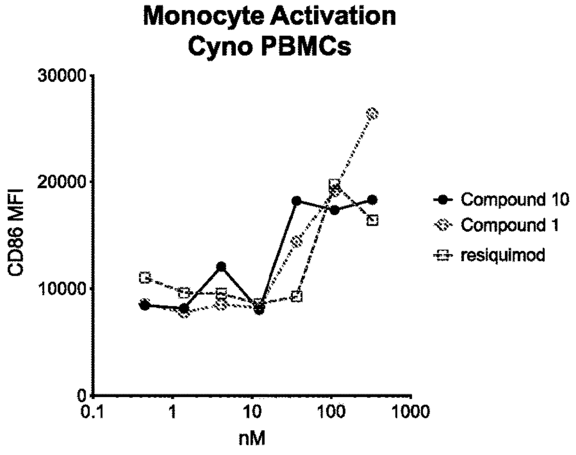
FIG. 2 provides in vitro data demonstrating the ability of Compound 10 to stimulate activation of several immune cell types from cyno PBMCs—monocytes (FIG. 2A), B cells (FIG. 2B), and cDCs (FIG. 2C).
Figure 2:
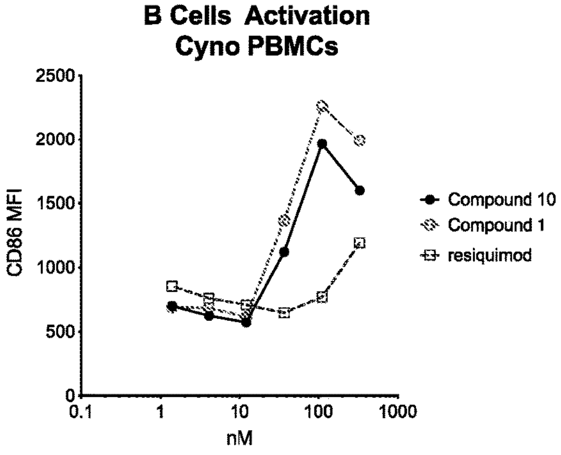
Figure 2:
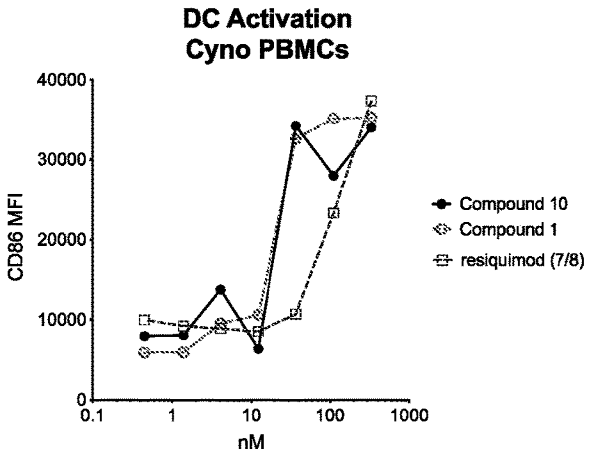
Figure 3:
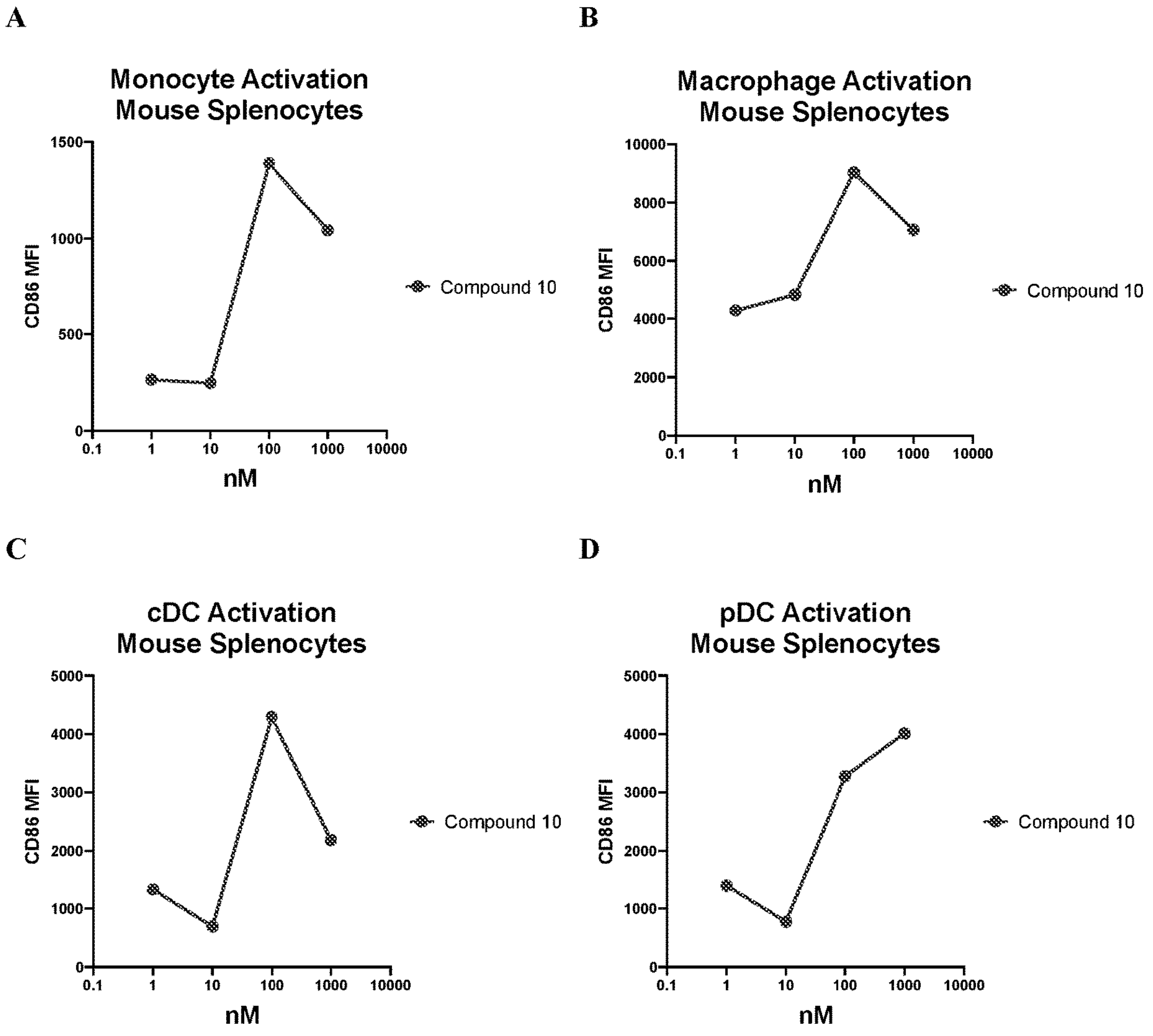
FIG. 3 provides in vitro data demonstrating the ability of Compound 10 to stimulate activation of several immune cell types from mouse splenocytes—monocytes (FIG. 3A), macrophages (FIG. 3B), cDCs (FIG. 3C), and pDCs (FIG. 3D).

TLR7 agonist Compound 10 was very potent in activating monocytes (FIG. 1A), B cells (FIG. 1B), cDCs (FIG. 1C) and pDCs (FIG. 1D) in human PBMCs. Similar immune cell activation was also observed for monocytes (FIG. 2A), B cells (FIG. 2B) and DCs (FIG. 2C) from cyno PBMCs and monocytes (FIG. 3A), macrophages (FIG. 3B), cDC cells (FIG. 3C) and pDCs (FIG. 3D) from mouse splenocytes.

Example 12

Compound 10 Induced Cytokine Release

This example evaluates the ability of Compound 10 to induce cytokine release in human PBMCs, cyno PBMCs and mouse splenocytes. Compound 1 and resiquimod:

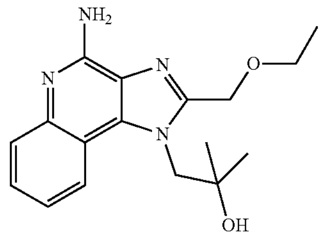

Resiquimod were used as controls in the assays.

Human and cyno PBMCs, mouse splenocytes were isolated as described in previous example. The day of the assay, 300 k of PBMC or splenocytes in 50 μL of culture medium were seeded in 96-well cell culture plates. 50 μl of the test articles (formulated at 2× of starting concentration) were then added into the well. The cell mixtures were co-cultured in the presence of test articles and 10 μg/mL LPS-RS for 24 hr (human PBMCs) or 48 hr (cyno PBMCs and mouse splenocytes). Cytokines released were measured by ELISA using cell culture medium.

Figure 4:
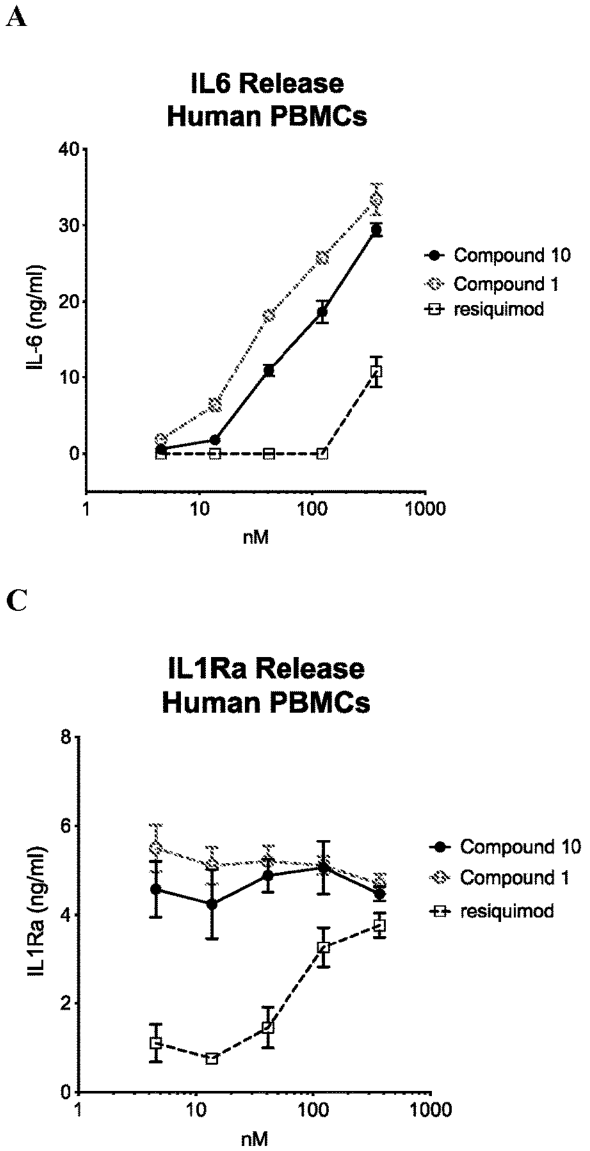
FIG. 4 provides in vitro data demonstrating the ability of Compound 10 to produce cytokine release from human PBMCs—IL-6 (FIG. 4A), MCP-1 (FIG. 4B), and IL1Ra (FIG. 4C).
Figure 5:
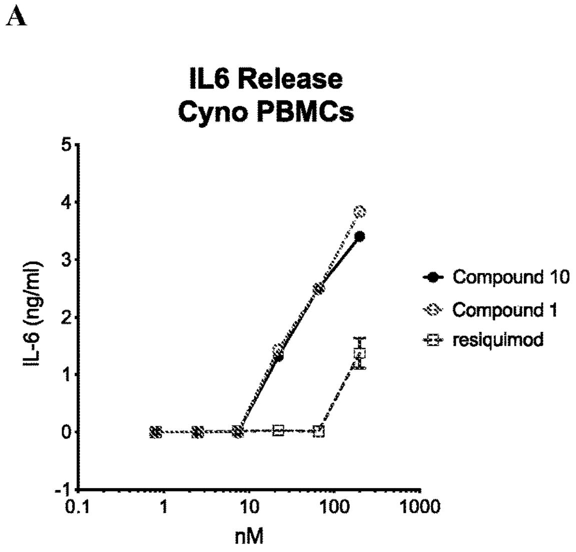
FIG. 5 provides in vitro data demonstrating the ability of Compound 10 to produce cytokine release from cyno PBMCs—IL-6 (FIG. 5A) and MCP-1 (FIG. 5B).
Figure 5:
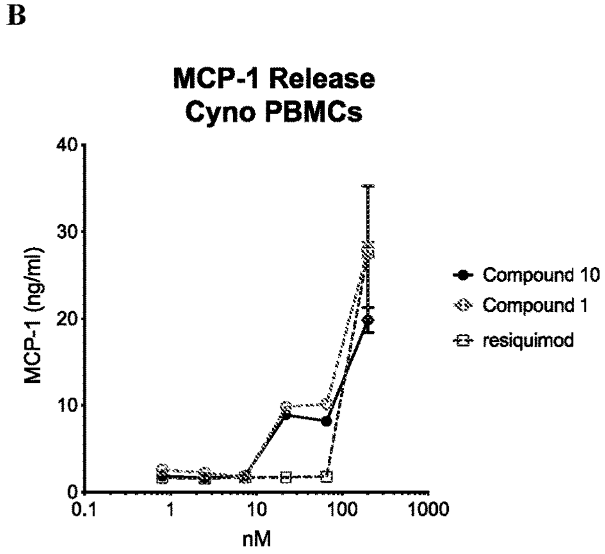
Figure 6:
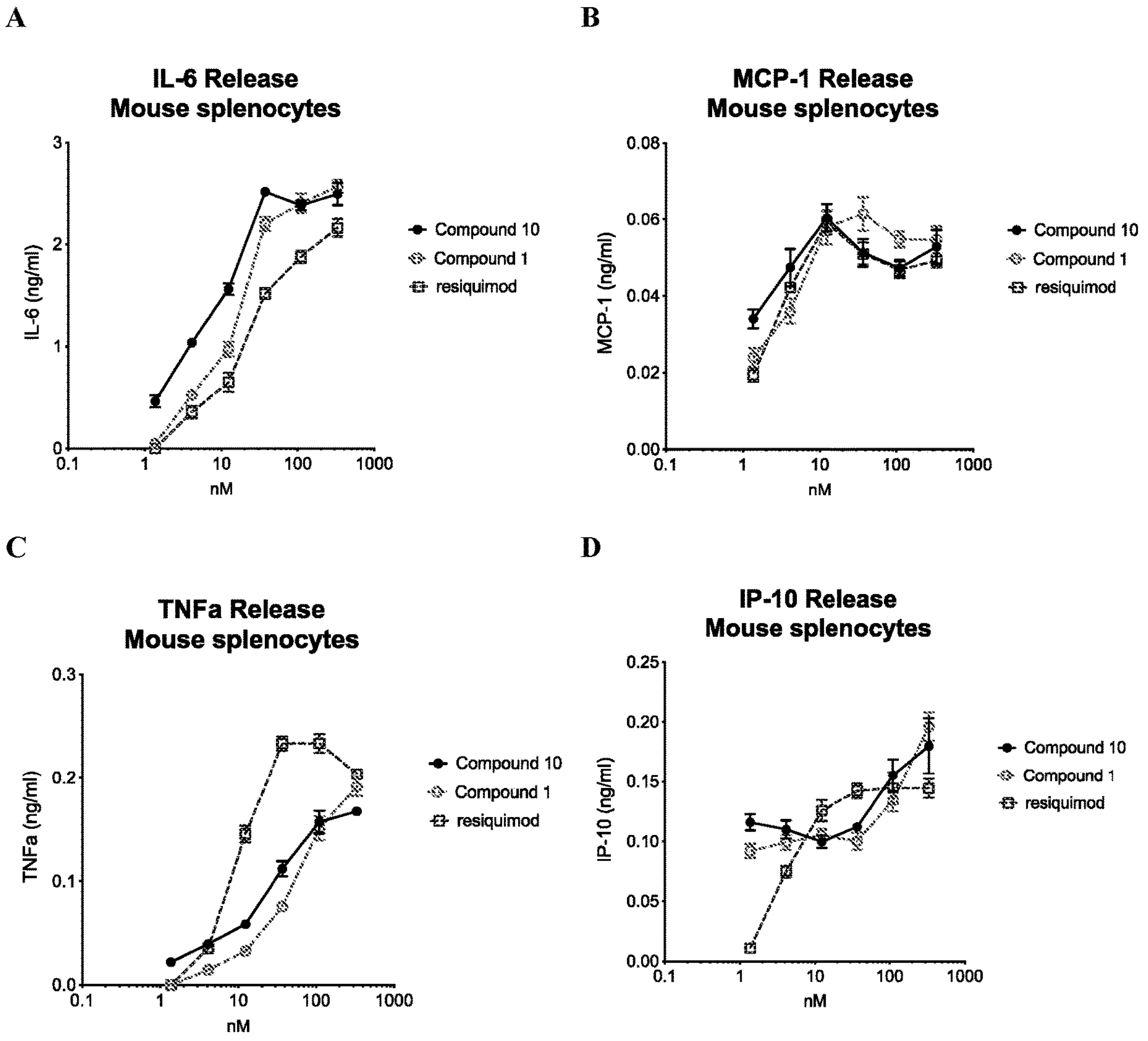
FIG. 6 provides in vitro data demonstrating the ability of Compound 10 to produce cytokine release from mouse splenocytes—IL-6 (FIG. 6A), MCP-1 (FIG. 6B), TNFa (FIG. 6C) and IP-10 (FIG. 6D).

TLR7 agonist Compound 10 stimulated strong IL-6 (FIG. 4A), MCP-1 (FIG. 4B), and IL1Ra (FIG. 4C) release from human PBMCs, IL-6 (FIG. 5A) and MCP-1 (FIG. 5B) release from cyno PBMCs, as well as IL-6 (FIG. 6A), MCP-1 (FIG. 6B), TNFa (FIG. 6C) and IP-10 (FIG. 6D) release from mouse splenocytes, similar to activity observed for Compound 1.

Example 13

Evaluation of In Vivo Activity of Compound 2

This example evaluates the response of MC38-hFolRα tumors to treatment with Compound 2, a TLR 7 agonist.

Female C57BL/6 mice at 9-10 weeks of age were anesthetized with isoflurane and implanted subcutaneously into the right hind flank with 1×10$^6$ MC38-hFolRα (murine colon adenocarcinoma cells engineered to express hFolRα). Randomization and start of treatment was initiated when the average tumor size was approximately 150 mm$^3$ (designated as Day 0 post-treatment). Animals received intratumoral (IT) injections of Compound 2 on Day 0 and Day 4 (q4d×2). Table 3 provides the list of treatment groups for this study. Compound 2 was dissolved in DMSO and dosing solutions were formulated in PBS. Body weight and tumor size were monitored 3×/week. The primary study endpoint was reached when the mean tumor size of the vehicle control group was >1,200 mm$^3$.

TABLE 3

| Group | Treatment | Dose (mg/kg) | Dosing frequency | Route | N |
|---|---|---|---|---|---|
| 1 | Vehicle (PBS) | — | Day 0 and 4 | IT | 8 |
| 2 | Compound 2 | 0.1 | Day 0 and 4 | IT | 8 |
| 3 | Compound 2 | 0.5 | Day 0 and 4 | IT | 8 |
| 4 | Compound 2 | 2 | Day 0 and 4 | IT | 8 |

Figure 7:
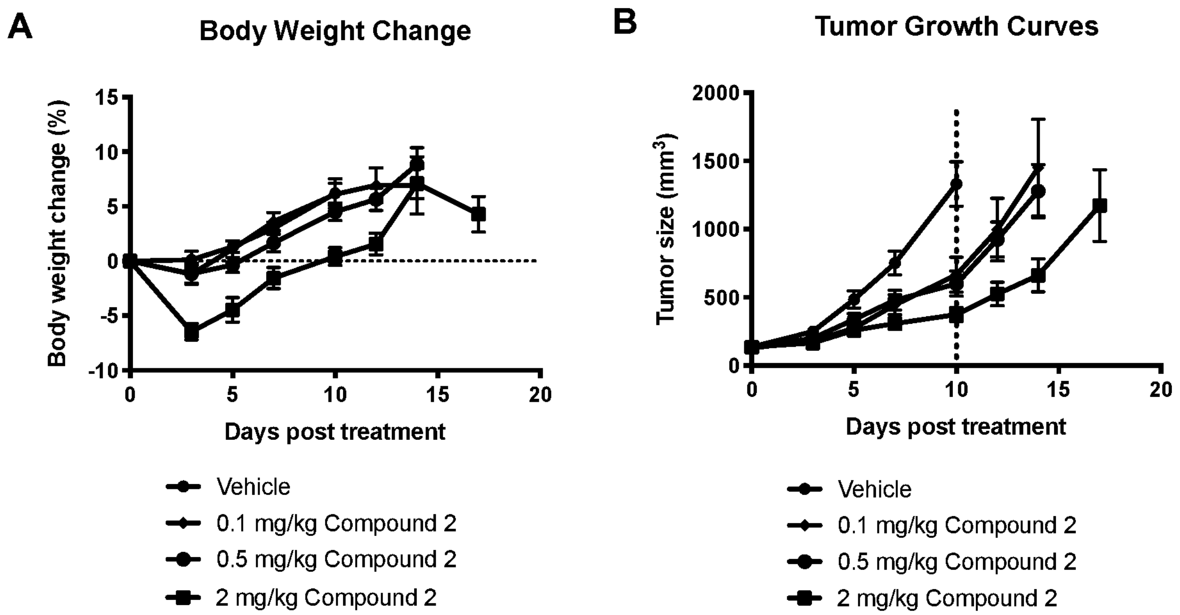
FIG. 7 provides in vivo data for anti-tumor activity of certain compounds in mice bearing established MC38-hFolRα tumors.

Animals bearing established MC38-hFolRα tumors were treated intratumorally with Compound 2 at the doses indicated above. FIG. 7A shows that doses >0.5 mg/kg resulted in minimal body weight loss (approximately 5%) with recovery by approximately Day 7. No weight loss was observed after administration of the second dose.

The effect of treatment on MC38-hFolRα on tumor growth is illustrated in FIG. 7B. Compound 2 exhibited significant efficacy (p<0.0001) at 0.1, 0.5. and 2 mg/kg resulting in 55%, 61%, and 80% tumor growth inhibition (TGI), respectively, compared to vehicle control on day 10 when the mean of the vehicle control group was >1,200 mm$^3$.

This study showed that Compound 2, a TLR 7 agonist, was well tolerated and significantly delayed MC38-hFolRα tumor growth.

Example 14

Antibody-Drug Conjugation and DAR Ratio Determination

Antibody-drug conjugation is described in Zimmerman E S, et al. 2014, *Bioconjugate Chem.*, 25 (2), pp 351-361. Briefly, purified antibodies or antigen-binding fragments thereof were conjugated to a TLR7 agonist described herein. Stock drug was dissolved in DMSO to a final concentration of 5 mM. The linker-payload was diluted with PBS to 1 mM and then added to the purified protein sample to a final drug concentration of 100 μM. The mixture was incubated at RT (20° C.) for 17 hours. Unincorporated drug was removed by passing the reaction sample through a 7000 MWCO resin in Zeba plates (Thermo Scientific) equilibrated in formulation buffer. Filtrate was then passed through a MUSTANG® Q plate (Pall Corp.) to remove endotoxin.

Following purification, the purified antibody or antibody drug conjugate samples were quantified on a Caliper GXII system by comparing with by mass standards of HERCEPTIN® run on the same Protein Express LabChip (Caliper Life Sciences #760499). Samples were prepared for analysis as specified in the Protein Express Reagent Kit (Caliper Life Sciences #760328) with the exception that the samples (mixed in sample buffer+50 mM NEM) were heated at 65° C. for 10 minutes prior to analysis on the Caliper system.

Antibody drug conjugates were reduced with 10 mM TCEP (Pierce) for 10 min at 37° C. Add 30 μL of TA30 (30% Acetonitrile, 70% of 0.1% Trifluoroacetic acid) to the reduced sample. Dissolve 20 mg of super-DHB (Sigma, part No. 50862) into TA50 (50% acetonitrile, 50% of 0.1% trifluoroacetic acid) to generate a sample matrix. Next add 0.5 μL of sample in TA30 to 0.8 μL of super-DHB matrix in TA50 and deposit onto MALDI sample plate. Spectra were acquired on a Bruker Autoflex Speed MALDI instrument with the following initial settings: Mass range 7000-70000 Da, sample rate and digitizer settings of 0.05, 0.1, 0.5, 1, 2, with realtime smoothing set at High and no baseline offset adjustment. High voltage switched On and Ion source 1 adjusted to 20 kV. Pulse ion extraction at 200 ns, matrix suppression on deflection and suppress up to 6000 Da. Peak detection algorithm is centroid with signal to noise threshold at 20, peak width at 150 m/z height at 80% with baseline subtraction TopHat. Smoothing algorithm is SavtzkyGolay with width of 10 m/z and cycles of 10. The DAR for all samples was determined as a weighted average of the deconvoluted mass spectrum area under the curve for each conjugate.

Example 15

Linker payload Compound 2 conjugation method: linker payload Compound 2 was dissolved in DMSO to a final concentration of 5 mM. The conjugation was carried out in 1×PBS at antibody concentration of 1 mg/mL, Compound 2 to pAMF in a ratio of 3:1, and with 25% of DMSO. The reaction mixture was incubated at room temperature for overnight. The conjugation efficiency was measured by LC/MS. Unconjugated linker payload Compound 2 was removed by cation exchange. The conjugate was formulated in 10 mM $Na_3PO_4$ (pH7.4) buffer supplemented with 9% sucrose.

Linker payload Compound 10 conjugation method: linker payload Compd 10 was dissolved in DMSO to a final concentration of 5 mM. The conjugation was carried out in 1×PBS at antibody concentration of 1 mg/mL, Compound 10 to pAMF in a ratio of 3:1, and with 25% of DMSO. The reaction mixture was incubated at room temperature for overnight. The conjugation efficiency was measured by LC/MS.

| | mAbs | | DAR |
|---|---|---|---|
| 1 | Anti FolR1 H01 Y180F404 | Linker payload Compound 2 | 3.9 |
| 2 | Anti GFP Y180F404 | Linker payload Compound 2 | 3.8 |
| 3 | Anti FolR1 B10 F404 | Linker payload Compound 2 | 1.9 |
| 4 | Anti FolR1 H01 Y180F404 | Linker payload Compound 10 | 3.9 |

EQUIVALENTS

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in this application, in applications claiming priority from this application, or in related applications. Such claims, whether directed to a different invention or to the same invention, and whether broader, narrower, equal, or different in scope in comparison to the original claims, also are regarded as included within the subject matter of the inventions of the present disclosure.

One or more features from any embodiments described herein or in the figures may be combined with one or more features of any other embodiments described herein or in the figures without departing from the scope of the invention.

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A compound of Formula (I):

Formula (I)

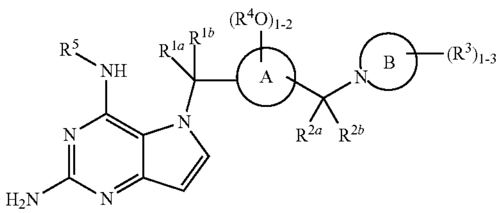

or a pharmaceutically acceptable salt, solvate or N-oxide thereof;

wherein $R^{1a}$, $R^{1b}$, $R^{2a}$, and $R^{2b}$ are independently, at each occurrence, selected from hydrogen, and $C_{1-6}$alkyl;

ring A is cycloalkyl, heterocycloalkyl, monocyclic aryl, monocyclic heteroaryl, fused bicyclic aryl, or fused bicyclic heteroaryl, where heterocycloalkyl and each heteroaryl comprise 1, 2, 3 or 4 heteroatoms independently selected from N, S, and O;

ring B is a 4-membered N-linked heterocycloalkyl, which is substituted with 1-2 $R^3$; wherein the heterocycloalkyl includes 1 or 2 heteroatoms independently selected from N, S, and O;

and wherein $R^3$ is, independently, at each occurrence, —$N(R^{3a})_2$, —$OR^{3b}$, —$C(R^{3c})_2NH_2$, $C_{1-6}$alkyl, heterocycloalkyl, heteroaryl, or partially saturated heteroaryl, or two $R^3$ attached to the same carbon, together with the carbon atom to which they are attached, form a spiro-heterocycloalkyl; wherein heterocycloalkyl, spiro-heterocycloalkyl, heteroaryl, and partially saturated heteroaryl in $R^3$ include 1, 2, 3 or 4 heteroatoms independently selected from N, S, and O, and are optionally substituted with 1-2 $C_{1-3}$alkyl; or ring B is a 5-6 membered N-linked heterocycloalkyl, which is substituted with 1-3 $R^3$, or a 5-6 membered N-linked heteroaryl, which is substituted with 1-3 $R^3$; wherein the heterocycloalkyl includes 1 or 2 heteroatoms independently selected from N, S, and O; and wherein $R^3$ is, independently, at each occurrence, —$N(R^{3a})_2$, —$OR^{3b}$, —$C(R^{3c})_2NH_2$ heterocycloalkyl, heteroaryl, or partially saturated heteroaryl, or two $R^3$ attached to the same carbon, together with the carbon atom to which they are attached, form a spiro-heterocycloalkyl; wherein heterocycloalkyl, spiro-heterocycloalkyl, heteroaryl, and partially saturated heteroaryl in $R^3$ include 1, 2, 3 or 4 heteroatoms independently selected from N, S, and O, and are optionally substituted with 1-2 $C_{1-3}$alkyl; or ring B is a 7-10 membered N-linked heterocycloalkyl, which is substituted with 1-3 $R^3$, or a 5-10 membered N-linked heteroaryl which is substituted with 1-3 $R^3$; wherein $R^3$ is, independently, at each occurrence, —$N(R^{3a})_2$, —$OR^{3b}$, —$C(R^{3c})_2NH_2$, $C_{1-6}$alkyl, heterocycloalkyl, heteroaryl, or partially saturated heteroaryl, or two $R^3$ attached to the same carbon, together with the carbon atom to which they are attached, form a spiro-heterocycloalkyl; wherein heterocycloalkyl, spiro-heterocycloalkyl, heteroaryl, and partially saturated heteroaryl in $R^3$ include 1, 2, 3 or 4 heteroatoms independently selected from N, S, and O, and are optionally substituted with 1-2 $C_{1-3}$alkyl;

or ring B is unsubstituted 2,5-diazabicyclo[2.2.2]octanyl or 3,9-diazabicyclo[3.3.2]decanyl;

$R^{3a}$ is independently, at each occurrence, selected from hydrogen, $C_{1-6}$alkyl, —C(═O)—$CH_2NH_2$, and cycloalkyl;

$R^{3b}$ is independently, at each occurrence, selected from hydrogen,

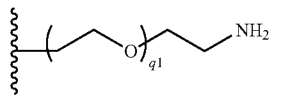

where q1 is 1, 2, or 3, and —$CH_2$-aryl-$CH_2NH_2$;

$R^{3c}$ is independently, at each occurrence, selected from hydrogen, and $C_{1-6}$alkyl, or two $R^{3c}$, together with the carbon atom to which they are attached, form a cycloalkyl;

$R^4$ is $C_{1-6}$alkyl; and $R^5$ is $C_{3-6}$cycloalkyl, or $C_{1-6}$alkyl, each of which is optionally substituted with 1, 2, or 3 $R^{5a}$ groups independently selected from halo, hydroxy, alkoxy, amino, $C_{1-6}$alkylamino, $C_{1-6}$ dialkylamino, $C_{3-6}$cycloalkyl, aryl, and heteroaryl, wherein heteroaryl includes 1, 2, 3 or 4 heteroatoms independently selected from N, S, and O, and wherein any of the $R^{5a}$ $C_{3-6}$cycloalkyl, aryl, and heteroaryl groups are optionally further substituted with 1, 2, or 3 groups independently selected from halo, hydroxy, alkyl, and haloalkyl.

2. The compound of claim 1, wherein ring A is cycloalkyl, heterocycloalkyl, monocyclic aryl, monocyclic heteroaryl, fused bicyclic aryl, or fused bicyclic heteroaryl, where heterocycloalkyl and each heteroaryl comprise 1, 2, 3 or 4 heteroatoms selected from N, S, and O;

ring B is a 4-membered N-linked heterocycloalkyl, which is further substituted with 1-2 $R^3$;

wherein $R^3$ is, independently, at each occurrence, —$N(R^{3a})_2$, —$OR^{3b}$, —$C(R^{3c})_2NH_2$, $C_{1-6}$alkyl, heterocycloalkyl, heteroaryl, or partially saturated heteroaryl, or two $R^3$ attached to the same carbon, together with the carbon atom to which they are attached, form a spiro-heterocycloalkyl; wherein heterocycloalkyl, spiro-heterocycloalkyl, heteroaryl, and partially saturated heteroaryl include 1, 2, 3 or 4 heteroatoms selected from N, S, and O, and are optionally further substituted with 1-2 $C_{1-3}$alkyl;

or ring B is a 5-6 membered N-linked heterocycloalkyl, which is further substituted with 1-3 $R^3$; wherein $R^3$ is, independently, at each occurrence, —$N(R^{3a})_2$, —$OR^{3b}$, —$C(R^{3c})_2NH_2$ heterocycloalkyl, heteroaryl, or partially saturated heteroaryl, or two $R^3$ attached to the same carbon, together with the carbon atom to which they are attached, form a spiro-heterocycloalkyl; wherein heterocycloalkyl, spiro-heterocycloalkyl, heteroaryl, and partially saturated heteroaryl include 1, 2, 3 or 4 heteroatoms selected from N, S, and O, and are optionally further substituted with 1-2 $C_{1-3}$alkyl;

or ring B is a 7-10 membered N-linked heterocycloalkyl, which is further substituted with 1-3 $R^3$, or a 5-10 membered N-linked heteroaryl which is further substituted with 1-3 $R^3$; wherein $R^3$ is, independently, at each occurrence, —$N(R^{3a})_2$, —$OR^{3b}$, —$C(R^{3c})_2NH_2$, $C_{1-6}$alkyl, heterocycloalkyl, heteroaryl, or partially saturated heteroaryl, or two $R^3$ attached to the same carbon, together with the carbon atom to which they are attached, form a spiro-heterocycloalkyl; wherein heterocycloalkyl, spiro-heterocycloalkyl, heteroaryl, and partially saturated heteroaryl include 1, 2, 3 or 4 heteroatoms selected from N, S, and O, and are optionally further substituted with 1-2 $C_{1-3}$alkyl;

$R^{3b}$ is independently, at each occurrence, selected from hydrogen,

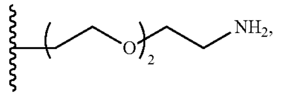

and —$CH_2$-aryl-$CH_2NH_2$;

$R^5$ is $C_{1-6}$cycloalkyl, or $C_{1-6}$alkyl optionally substituted with halo, hydroxy, alkoxy, amino, $C_{1-6}$alkylamino, $C_{1-6}$dialkylamino, $C_{1-6}$cycloalkyl, aryl or heteroaryl, wherein heteroaryl includes 1, 2, 3 or 4 heteroatoms selected from N, S, and O, and wherein cycloalkyl, aryl, and heteroaryl are optionally further substituted with halo, hydroxy, alkyl, or haloalkyl.

3. The compound of claim 1, according to the structure of Formula (II):

Formula (II)

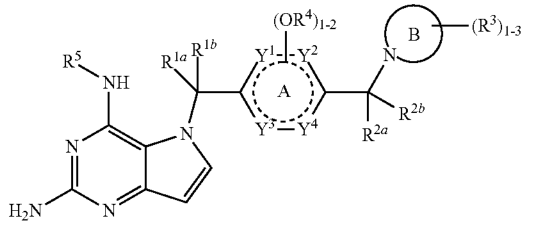

or a pharmaceutically acceptable salt, solvate or N-oxide thereof;

wherein $R^{1a}$, $R^{1b}$, $R^{2a}$, and $R^{2b}$ are independently, at each occurrence, selected from hydrogen, and $C_{1-6}$alkyl;

ring A is a six-membered aryl or six-membered heteroaryl ring, where $Y^1$, $Y^2$, $Y^3$, and $Y^4$ are independently selected from C and N;

ring B is a 4-membered N-linked heterocycloalkyl, which is substituted with 1-2 $R^3$; wherein $R^3$ is, independently, at each occurrence, —$N(R^{3a})_2$, —$OR^{3b}$, —$C(R^{3c})_2NH_2$, $C_{1-6}$alkyl, heterocycloalkyl, heteroaryl, or partially saturated heteroaryl, or two $R^3$ attached to the same carbon, together with the carbon atom to which they are attached, form a spiro-heterocycloalkyl; wherein heterocycloalkyl, spiro-heterocycloalkyl, heteroaryl, and partially saturated heteroaryl in $R^3$ include 1, 2, 3 or 4 heteroatoms independently selected from N, S, and O, and are optionally substituted with 1-2 $C_{1-3}$alkyl;

or ring B is a 5-6 membered N-linked heterocycloalkyl, which is further substituted with 1-3 $R^3$, or a 5-6 membered N-linked heteroaryl, which is substituted with 1-3 $R^3$; wherein $R^3$ is, independently, at each occurrence, $—N(R^{3a})_2$, $—OR^{3b}$, $—C(R^{3c})_2NH_2$, heterocycloalkyl, heteroaryl, or partially saturated heteroaryl, or two $R^3$ attached to the same carbon, together with the carbon atom to which they are attached, form a spiro-heterocycloalkyl; wherein heterocycloalkyl, spiro-heterocycloalkyl, heteroaryl, and partially saturated heteroaryl in $R^3$ include 1, 2, 3 or 4 heteroatoms independently selected from N, S, and O, and are optionally further substituted with 1-2 $C_{1-3}$alkyl;

or ring B is a 7-10 membered N-linked heterocycloalkyl, which is substituted with 1-3 $R^3$, or a 5-10 membered N-linked heteroaryl which is substituted with 1-3 $R^3$; wherein $R^3$ is, independently, at each occurrence, $—N(R^{3a})_2$, $—OR^3$, $—C(R^{3c})_2NH_2$, $C_{1-6}$alkyl, heterocycloalkyl, heteroaryl, or partially saturated heteroaryl, or two $R^3$ attached to the same carbon, together with the carbon atom to which they are attached, form a spiro-heterocycloalkyl; wherein heterocycloalkyl, spiro-heterocycloalkyl, heteroaryl, and partially saturated heteroaryl in $R^3$ include 1, 2, 3 or 4 heteroatoms independently selected from N, S, and O, and are optionally substituted with 1-2 $C_{1-3}$alkyl;

$R^{3a}$ is independently, at each occurrence, selected from hydrogen, $C_{1-6}$alkyl, $—C(═O)—CH_2NH_2$, and cycloalkyl;

$R^{3b}$ is independently, at each occurrence, selected from hydrogen,

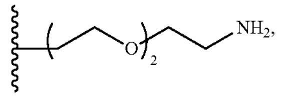

and $—CH_2$-aryl-$CH_2NH_2$;

$R^{3c}$ is independently, at each occurrence, selected from hydrogen, and $C_{1-6}$alkyl, or two $R^{3c}$, together with the carbon atom to which they are attached, form a cycloalkyl;

$R^4$ is $C_{1-6}$alkyl; and $R^5$ is $C_{3-6}$cycloalkyl, or $C_{1-6}$alkyl, each of which is optionally substituted with 1, 2, or 3 $R^{5a}$ groups independently selected from halo, hydroxy, alkoxy, amino, $C_{1-6}$alkylamino, $C_{1-6}$ dialkylamino, $C_{3-6}$cycloalkyl, aryl, and heteroaryl, wherein heteroaryl includes 1, 2, 3 or 4 heteroatoms independently selected from N, S, and O, and wherein any of the $R^{5a}$ $C_{3-6}$cycloalkyl, aryl, and heteroaryl groups are optionally further substituted with one or two groups independently selected from halo, hydroxy, alkyl, and haloalkyl.

4. The compound of claim 1, wherein ring A is a phenyl ring.

5. The compound of claim 1, wherein ring A is a heteroaryl ring.

6. The compound of claim 1, wherein ring A is a monocyclic heteroaryl ring.

7. The compound of claim 1, wherein, on ring A, at least one $—OR^4$ is in an ortho-position relative to the group

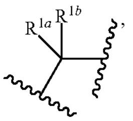

wherein each

indicates a point of attachment to the rest of the formula.

8. The compound of claim 1, according to the structure of Formula (III):

Formula (III)

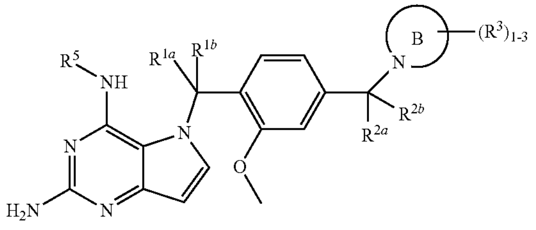

wherein $R^{1a}$, $R^{1b}$, $R^{2a}$, and $R^{2b}$ are independently, at each occurrence, selected from hydrogen, and $C_{1-6}$alkyl;

ring B is an N-linked azetidinyl ring which is substituted with 1-2 $R^3$; wherein $R^3$ is, independently, at each occurrence, $—N(R^{3a})_2$, $—OR^{3b}$, $—C(R^{3c})_2NH_2$, $C_{1-6}$alkyl, heterocycloalkyl, heteroaryl, or partially saturated heteroaryl, or two $R^3$ attached to the same carbon, together with the carbon atom to which they are attached, form a spiro-heterocycloalkyl; wherein heterocycloalkyl, spiro-heterocycloalkyl, heteroaryl, and partially saturated heteroaryl in $R^3$ include 1, 2, 3 or 4 heteroatoms independently selected from N, S, and O, and are optionally substituted with 1-2 $C_{1-3}$alkyl; or ring B is an N-linked piperidinyl, piperazinyl, morpholinyl, or triazolyl ring which is further substituted with 1-3 $R^3$; wherein $R^3$ is, independently, at each occurrence, $—N(R^{3a})_2$, $—OR^{3b}$, $—C(R^{3c})_2NH_2$, heterocycloalkyl, heteroaryl, or partially saturated heteroaryl, or two $R^3$ attached to the same carbon, together with the carbon atom to which they are attached, form a spiro-heterocycloalkyl; wherein heterocycloalkyl, spiro-heterocycloalkyl, heteroaryl, and partially saturated heteroaryl in $R^3$ include 1, 2, 3 or 4 heteroatoms independently selected from N, S, and O, and are optionally substituted with 1-2 $C_{1-3}$alkyl;

or ring B is unsubstituted 2,5-diazabicyclo[2.2.2]octanyl, or 3,9-diazabicyclo[3.3.2]decanyl;

or ring B is a 5-10 membered N-linked heteroaryl which is substituted with 1-3 $R^3$; wherein the heteroaryl includes 1, 2, 3 or 4 heteroatoms independently selected from N, S, and O; and wherein $R^3$ is, independently, at each occurrence, —$N(R^{3a})_2$, —$OR^{3b}$, —$C(R^{3c})_2NH_2$, $C_{1-6}$alkyl, heterocycloalkyl, heteroaryl, or partially saturated heteroaryl, or two $R^3$ attached to the same carbon, together with the carbon atom to which they are attached, form a spiro-heterocycloalkyl; wherein heterocycloalkyl, spiro-heterocycloalkyl, heteroaryl, and partially saturated heteroaryl in $R^3$ include 1, 2, 3 or 4 heteroatoms independently selected from N, S, and O, and are optionally substituted with 1-2 $C_{1-3}$alkyl;

$R^{3a}$ is independently, at each occurrence, selected from hydrogen, $C_{1-6}$alkyl, —C(═O)—$CH_2NH_2$, and cycloalkyl;

$R^{3b}$ is independently, at each occurrence, selected from hydrogen,

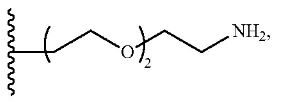

and —$CH_2$-aryl-$CH_2NH_2$;

$R^{3c}$ is independently, at each occurrence, selected from hydrogen and $C_{1-3}$alkyl, or two $R^{3c}$, together with the carbon atom to which they are attached, form a cyclopropyl; and $R^5$ is $C_{3-6}$cycloalkyl, or $C_{1-6}$alkyl, each of which is optionally substituted with 1, 2, or 3 $R^{5a}$ groups independently selected from halo, hydroxy, alkoxy, amino, $C_{1-6}$alkylamino, $C_{1-6}$ dialkylamino, $C_{3-6}$cycloalkyl, aryl, and heteroaryl, wherein heteroaryl includes 1, 2, 3 or 4 heteroatoms independently selected from N, S, and O, and wherein any of the $R^{5a}$ $C_{3-6}$cycloalkyl, aryl, and heteroaryl groups are optionally substituted with halo, hydroxy, alkyl, or haloalkyl.

9. The compound of claim 1, wherein $R^{1a}$ and $R^{1b}$ are each hydrogen.

10. The compound of claim 1, wherein $R^{2a}$ and $R^{2b}$ are each hydrogen.

11. The compound of claim 1, wherein $R^{1a}$, $R^{1b}$, $R^{2a}$, and $R^{2b}$ are each hydrogen.

12. The compound of claim 1, wherein $R^4$ is methyl, ethyl, propyl or isopropyl.

13. The compound of claim 1, wherein $R^4$ is methyl.

14. The compound of claim 1, wherein $R^5$ is $C_{1-6}$alkyl optionally substituted with one or two $R^{5a}$ groups independently selected from halo, hydroxy, alkoxy, amino, $C_{1-6}$alkylamino, and $C_{1-6}$dialkylamino.

15. The compound of claim 1, wherein $R^5$ is $C_{1-6}$alkyl optionally substituted with hydroxy or alkoxy.

16. The compound of claim 15, wherein $R^5$ is

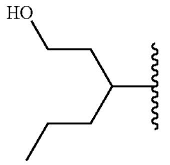

or

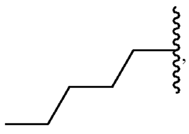

, wherein each

indicates a point of attachment to the rest of the formula.

17. The compound of claim 1, wherein $R^5$ is $C_{1-6}$alkyl optionally substituted with one aryl or heteroaryl, wherein heteroaryl includes 1, 2, 3 or 4 heteroatoms independently selected from N, S, and O, and wherein aryl and heteroaryl are optionally further substituted with halo, alkyl, or haloalkyl.

18. The compound of claim 17, wherein $R^5$ is

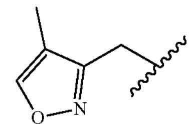

or

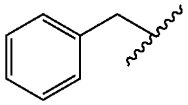

wherein each

indicates a point of attachment to the rest of the formula.

19. The compound of claim 1, wherein ring B in

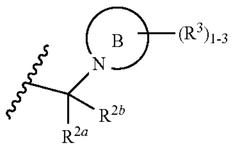

is a 4, 5, or 6-membered fully saturated heterocycloalkyl ring substituted with 1-3 $R^3$.

20. The compound of claim 1, wherein ring B in

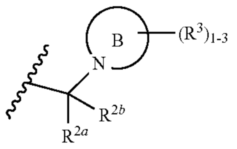

is a 4, 5, or 6-membered fully saturated heterocycloalkyl ring substituted with two $R^3$ attached to the same carbon, which together with the carbon atom to which they are attached, form a spiro-heterocycloalkyl; wherein spiro-heterocycloalkyl includes 1, 2, 3 or 4 heteroatoms independently selected from N, S, and O, and is optionally substituted with 1-2 $C_{1-3}$alkyl.

21. The compound of claim 1, wherein
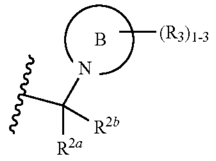
is
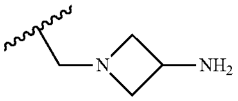,
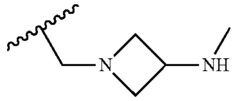,
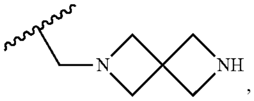,
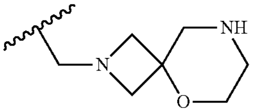,
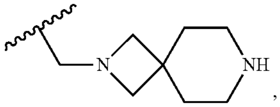,
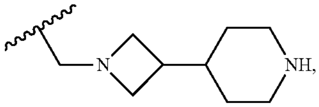
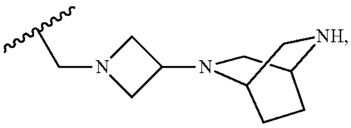
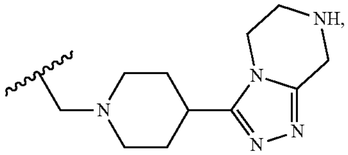
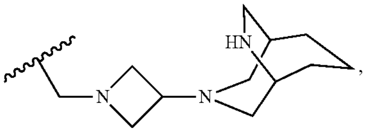,
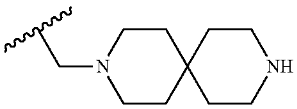,
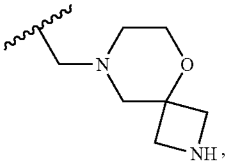,
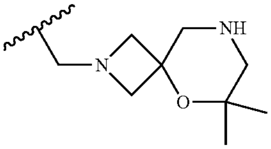,
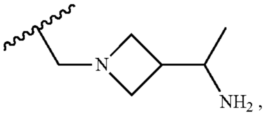,
-continued
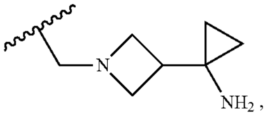,
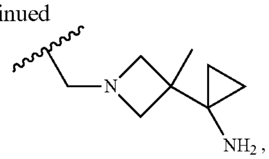,
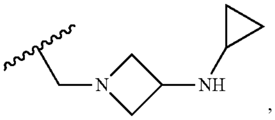,
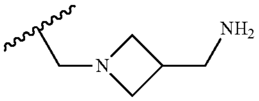,
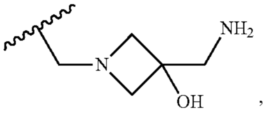,
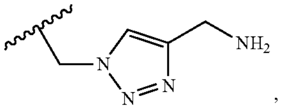,
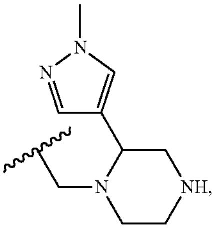
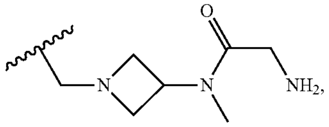
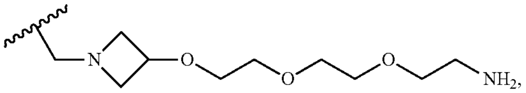
or
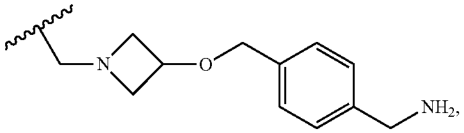
wherein each
indicates a point of attachment to the rest of the formula.
22. The compound or a pharmaceutically acceptable salt, solvate or N-oxide thereof, of claim 1 selected from the group consisting of:
2
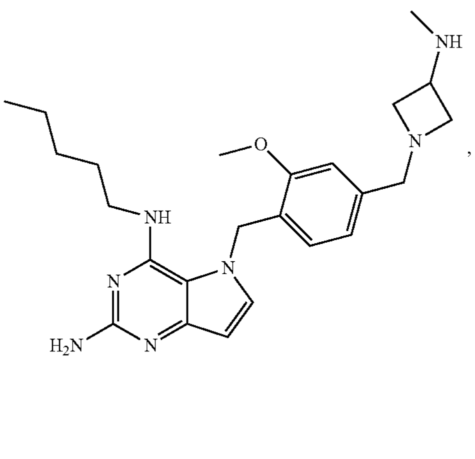,
3
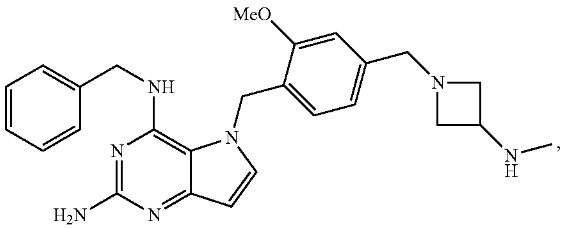, -continued
4
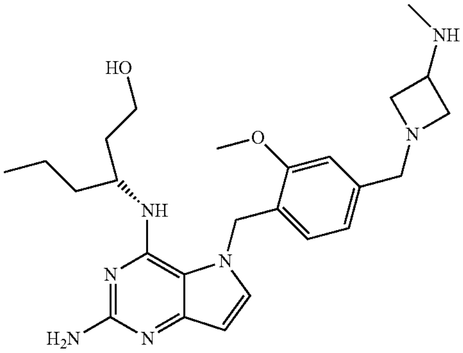
,
5
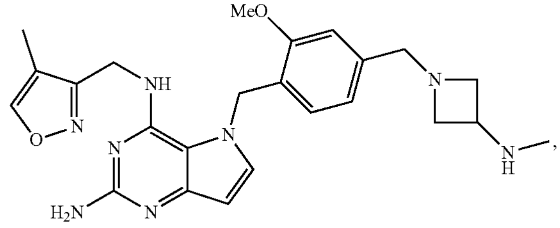
,
6
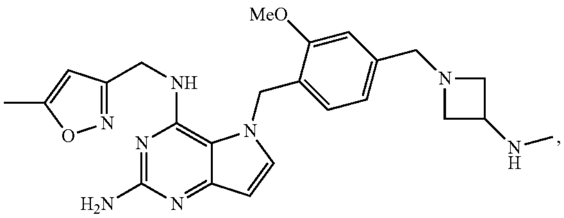
,
7
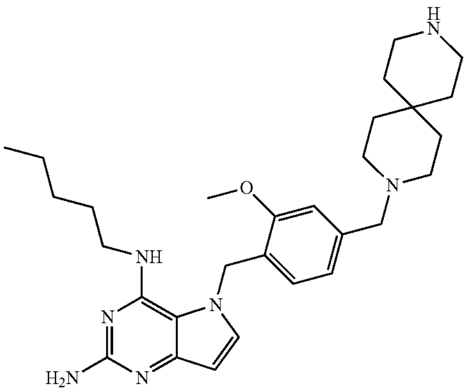
,
8
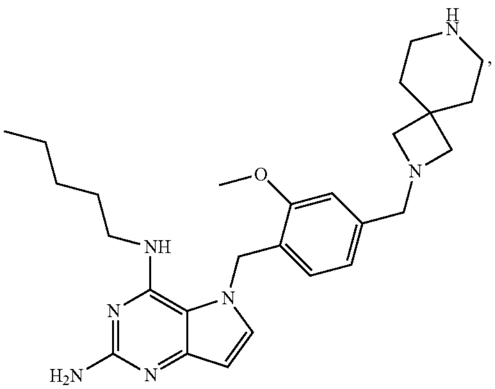
,
9
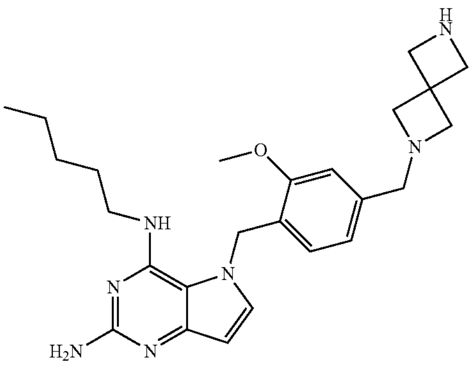
,
10
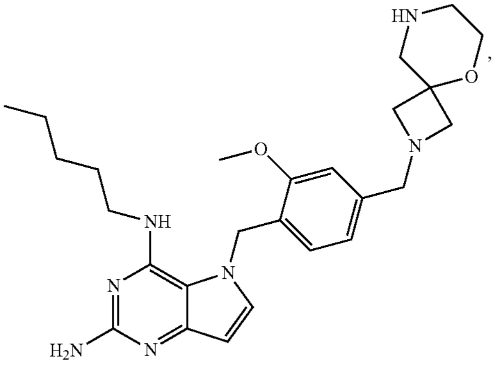
,
11
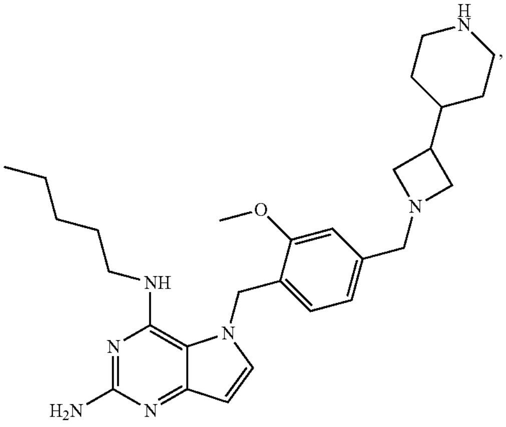
, -continued
12
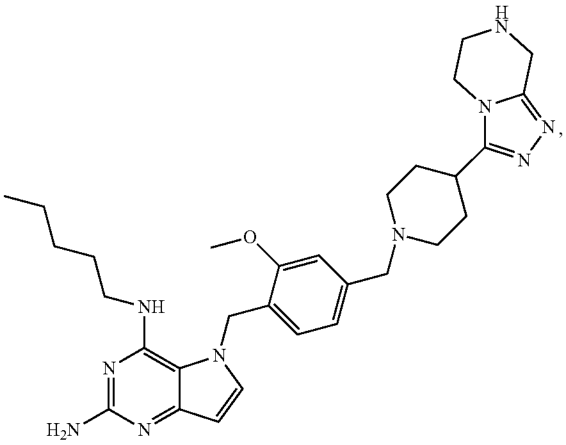
,
13
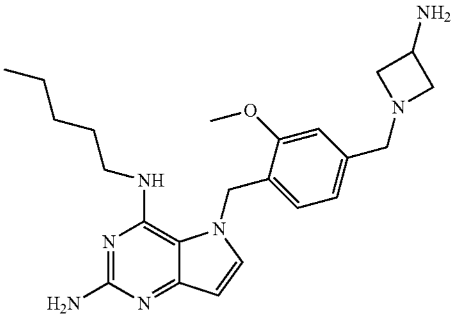
,
14
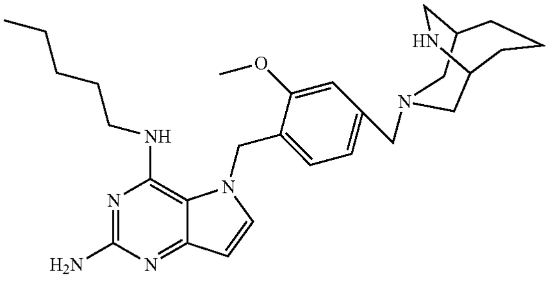
,
15
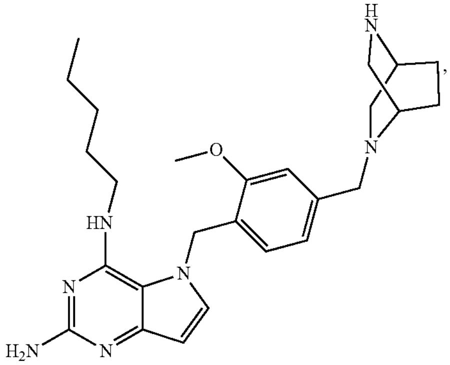
,
16
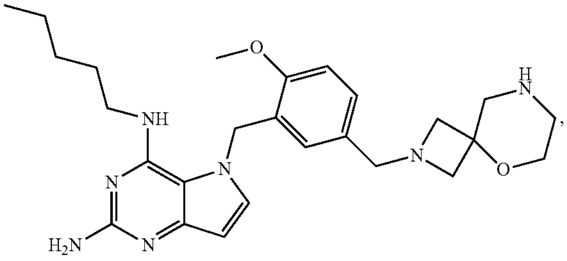
,
17
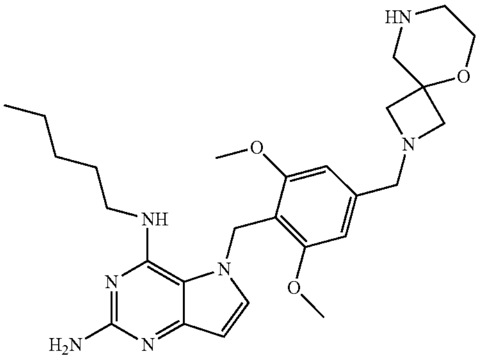
,
18
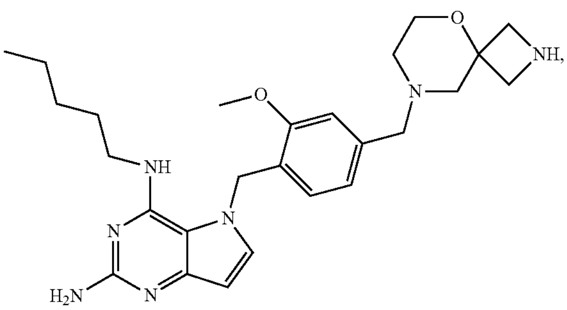
,
19
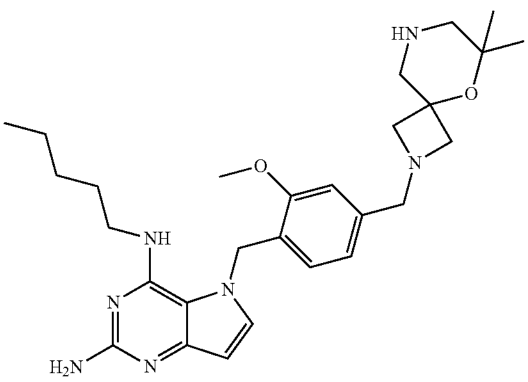

-continued
20
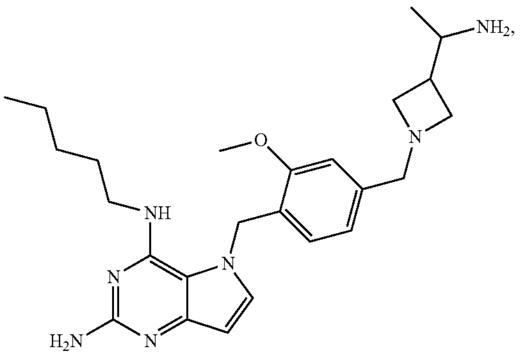
21
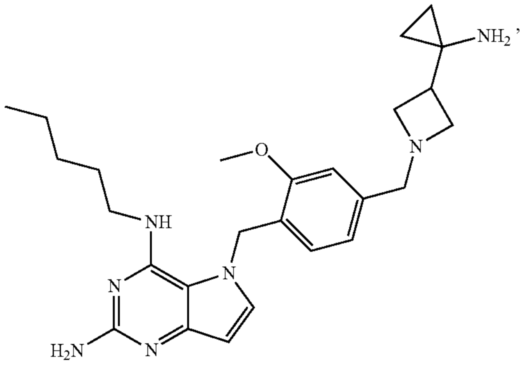
22
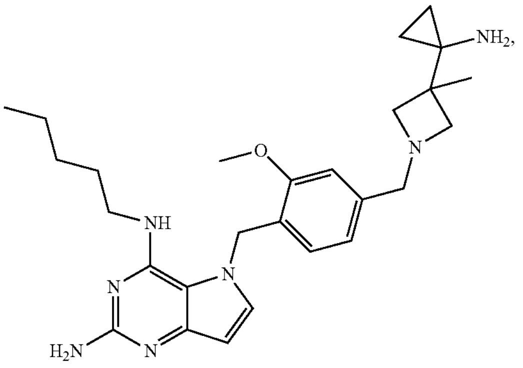
23
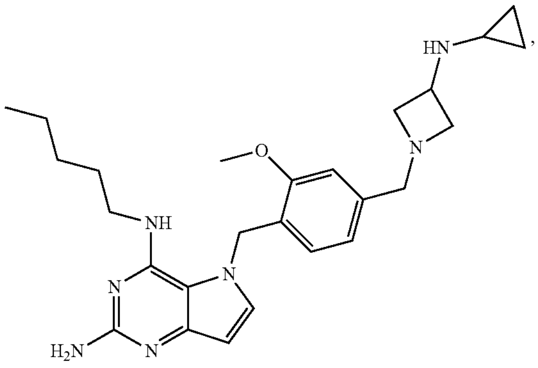
24
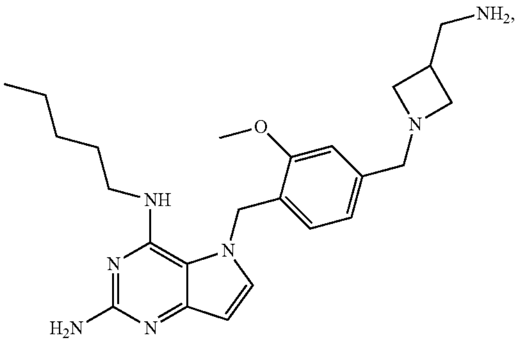
25
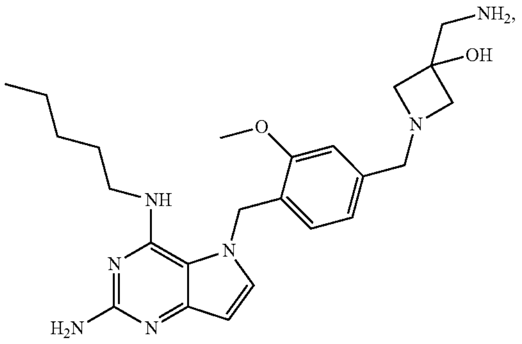
26
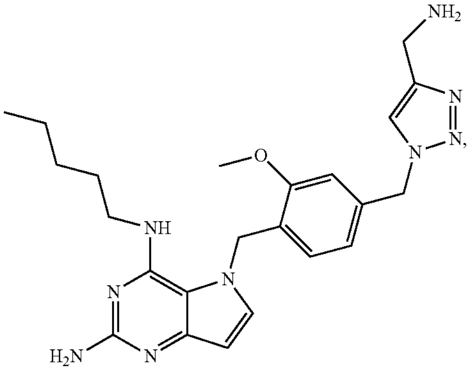

-continued

27

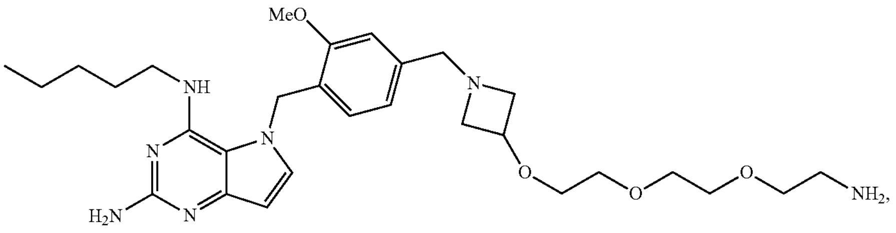

28

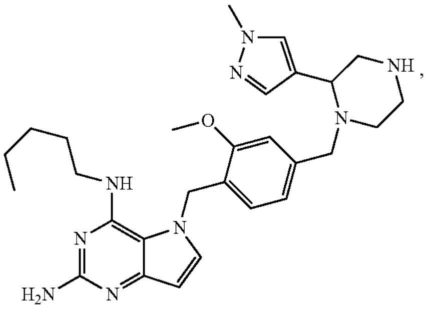

, and

30

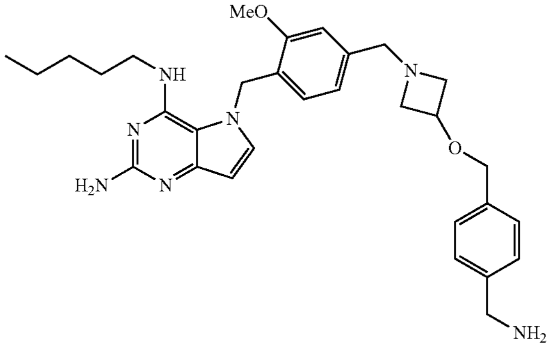

.

23. A pharmaceutical composition comprising the compound of claim 1, and a pharmaceutically acceptable carrier.

24. A method for treating colon cancer, renal cancer, mammary carcinomas, skin cancer, or cervical intraepithelial neoplasia in a subject in need thereof comprising administering to the subject an effective amount of a compound of claim 1.

25. A compound according to Formula (IV):

Formula (IV)

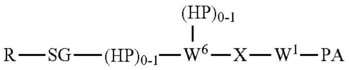

or a pharmaceutically acceptable salt, solvate, stereoisomer, tautomer, or mixture of regioisomers thereof, wherein:

$W^1$ is a single bond, absent or a divalent attaching group;

X is absent,

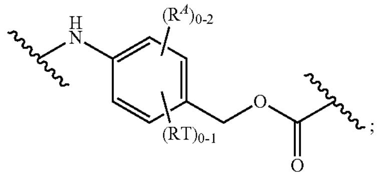

; or

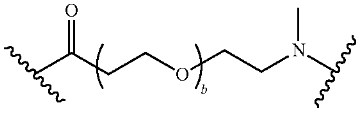

;

subscript b is an integer selected from 1 to 10;

$R^A$, when present, is independently, at each occurrence, selected from $C_{1-3}$alkyl;

each RT, when present, is a release trigger group;

HP, when present, is a hydrophilic group;

$W^6$ is a residue of a peptide, or absent;

SG is absent, or a divalent spacer group;

R is hydrogen, or a terminal conjugating group; and

PA is a residue of Formula (I):

Formula (I)

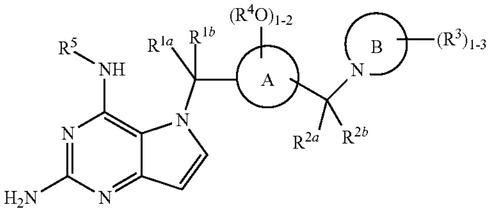

or a pharmaceutically acceptable salt, solvate or N-oxide thereof;

wherein $R^{1a}$, $R^{1b}$, $R^{2a}$, and $R^{2b}$ are independently, at each occurrence, selected from hydrogen, and $C_{1-6}$alkyl;

ring A is cycloalkyl, heterocycloalkyl, monocyclic aryl, monocyclic heteroaryl, fused bicyclic aryl, or fused bicyclic heteroaryl, where heterocycloalkyl and each heteroaryl comprise 1, 2, 3 or 4 heteroatoms independently selected from N, S, and O;

ring B is a 4-membered N-linked heterocycloalkyl, which is substituted with 1-2 $R^3$; wherein the heterocycloalkyl includes 1 or 2 heteroatoms independently selected from N, S, and O; and wherein $R^3$ is, independently, at each occurrence, —$N(R^{3a})_2$, —$OR^{3b}$, —$C(R^{3c})_2NH_2$, $C_{1-6}$alkyl, heterocycloalkyl, heteroaryl, or partially saturated heteroaryl, or two $R^3$ attached to the same carbon, together with the carbon atom to which they are attached, form a spiro-heterocycloalkyl; wherein heterocycloalkyl, spiro-heterocycloalkyl, heteroaryl, and partially saturated heteroaryl in $R^3$ include 1, 2, 3 or 4 heteroatoms independently selected from N, S, and O, and are optionally substituted with 1-2 $C_{1-3}$alkyl;

or ring B is a 5-6 membered N-linked heterocycloalkyl, which is substituted with 1-3 $R^3$, or a 5-6 membered N-linked heteroaryl, which is substituted with 1-3 $R^3$; wherein the heterocycloalkyl includes 1 or 2 heteroatoms independently selected from N, S, and O; and $R^3$ is, independently, at each occurrence, $—N(R^{3a})_2$, $—OR^{3b}$, $—C(R^{3c})_2NH_2$, heterocycloalkyl, heteroaryl, or partially saturated heteroaryl, or two $R^3$ attached to the same carbon, together with the carbon atom to which they are attached, form a spiro-heterocycloalkyl; wherein heterocycloalkyl, spiro-heterocycloalkyl, heteroaryl, and partially saturated heteroaryl in $R^3$ include 1, 2, 3 or 4 heteroatoms independently selected from N, S, and O, and are optionally substituted with 1-2 $C_{1-3}$alkyl;

or ring B is a 7-10 membered N-linked heterocycloalkyl, which is substituted with 1-3 $R^3$, or a 5-10 membered N-linked heteroaryl which is substituted with 1-3 $R^3$; wherein $R^3$ is, independently, at each occurrence, $—N(R^{3a})_2$, $—OR^3$, $—C(R^{3c})_2NH_2$, $C_{1-6}$alkyl, heterocycloalkyl, heteroaryl, or partially saturated heteroaryl, or two $R^3$ attached to the same carbon, together with the carbon atom to which they are attached, form a spiro-heterocycloalkyl; wherein heterocycloalkyl, spiro-heterocycloalkyl, heteroaryl, and partially saturated heteroaryl in $R^3$ include 1, 2, 3 or 4 heteroatoms independently selected from N, S, and O, and are optionally substituted with 1-2 $C_{1-3}$alkyl;

or ring B is unsubstituted 2,5-diazabicyclo[2.2.2]octanyl or 3,9-diazabicyclo[3.3.2]decanyl;

$R^{3a}$ is independently, at each occurrence, selected from hydrogen, $C_{1-6}$alkyl, $—C(=O)—CH_2NH_2$, and cycloalkyl;

$R^{3b}$ is independently, at each occurrence, selected from hydrogen, $NH_2$,

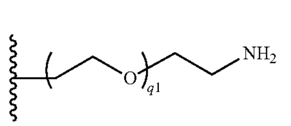

where q1 is 1, 2, or 3, and $—CH_2$-aryl-$CH_2NH_2$;

$R^{3c}$ is independently, at each occurrence, selected from hydrogen, and $C_{1-6}$alkyl, or two $R^{3c}$, together with the carbon atom to which they are attached, form a cycloalkyl;

$R^4$ is $C_{1-6}$alkyl; and $R^5$ is $C_{3-6}$cycloalkyl, or $C_{1-6}$alkyl, each of which is optionally substituted with 1, 2, or 3 $R^{5a}$ groups independently selected from halo, hydroxy, alkoxy, amino, $C_{1-6}$alkylamino, $C_{1-6}$dialkylamino, $C_{3-6}$cycloalkyl, aryl and heteroaryl, wherein heteroaryl includes 1, 2, 3 or 4 heteroatoms independently selected from N, S, and O, and wherein any of the $R^{5a}$ $C_{3-6}$cycloalkyl, aryl, and heteroaryl groups are optionally further substituted with 1, 2, or 3 groups independently selected from halo, hydroxy, alkyl, and haloalkyl; and wherein PA is bonded to the rest of the molecule via $—NR^{3a}—$, the —NH— of $—C(R^{3c})_2NH—$, the nitrogen of an $R^3$ heterocycloalkyl, the nitrogen of an $R^3$ partially saturated heteroaryl, the —NH— of $—O—CH_2$-(phenyl)-$CH_2—NH—$, or a nitrogen of ring B.

26. The compound of claim 25, according to Formula (IVa), (IVb), (IVc), (IVd), or (IVe):

Formula (IVa)

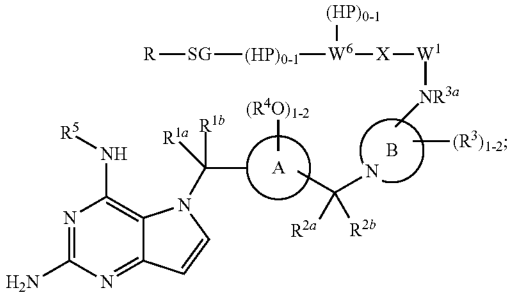

Formula (IVb)

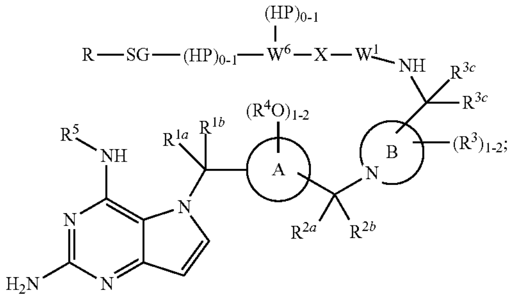

Formula (IVc)

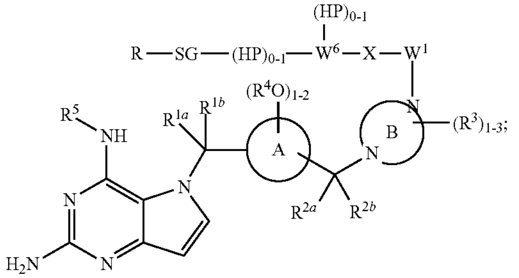

Formula (IVd)

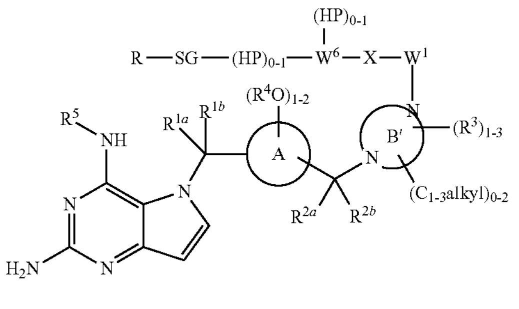

wherein B' is spiro-heterocycloalkyl which includes 1, 2, 3 or 4 heteroatoms independently selected from N, S, and O; or Formula (IVe)

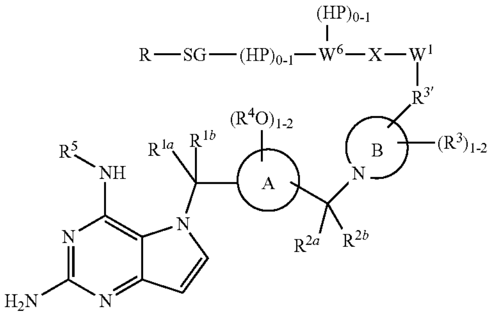

wherein $R^{3'}$ is heterocycloalkyl or partially saturated heteroaryl, each of which includes 1, 2, 3 or 4 heteroatoms independently selected from N, S, and O, provided that at least one nitrogen is present in the $R^{3'}$ ring and is attached to $W^1$; or $R^{3'}$ is —O—$CH_2$-(phenyl)-$CH_2$—NH— where the NH is attached to $W^1$.

27. The compound of claim 25, wherein SG is absent,

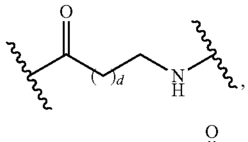,
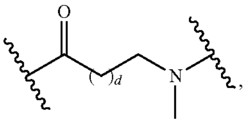, or
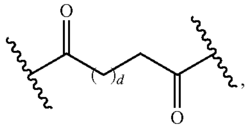, wherein subscript d is an integer selected from 1 to 10, wherein each

indicates a point of attachment to the rest of the formula.

28. The compound of claim 25, wherein SG is

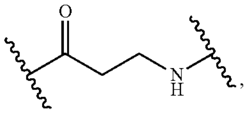,
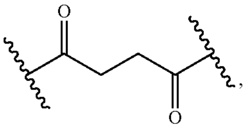,
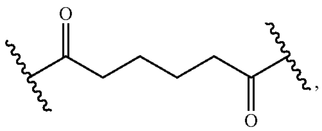, or
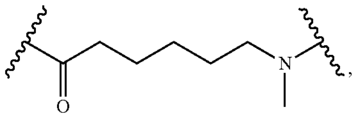, wherein each

indicates a point of attachment to the rest of the formula.

29. The compound of claim 25, wherein $W^1$, when present, is

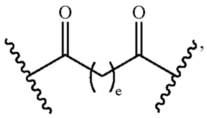,
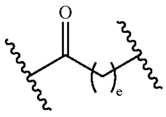 or
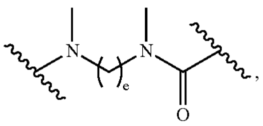, wherein subscript e is an integer selected from 1 to 10, wherein each

indicates a point of attachment to the rest of the formula.

30. The compound of claim 25, wherein $W^1$, when present, is

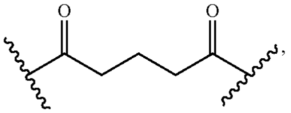,
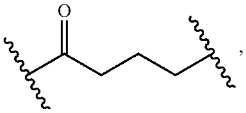, or
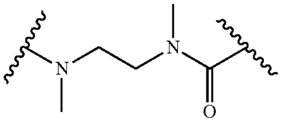

wherein each

indicates a point of attachment to the rest of the formula.

31. The compound of claim 25, wherein $W^6$, when present, is a tripeptide residue.

32. The compound of claim 25, wherein, $W^6$, when present, is

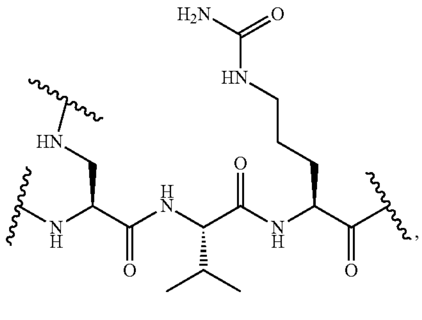 [SMILES: *NC[C@H](N*)C(=O)N[C@H](C(=O)N[C@@H](CCCNC(N)=O)C(*)=O)C(C)C]

wherein each

indicates a point of attachment to the rest of the formula.

33. The compound of claim 25, wherein $W^6$, when present, is a dipeptide residue.

34. The compound of claim 25, wherein, $W^6$, when present, is

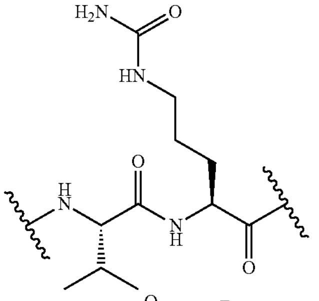

or

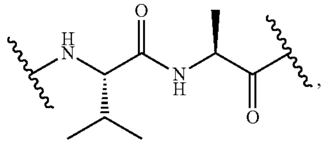

wherein each

indicates a point of attachment to the rest of the formula.

35. The compound of claim 25, wherein RT is

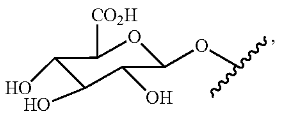

wherein

indicates a point of attachment to the rest of the formula.

36. The compound of claim 25, wherein HP, when present, is

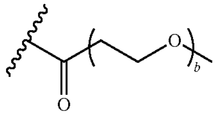

or

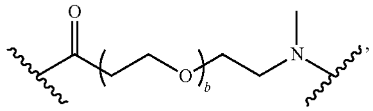

wherein subscript b is an integer selected from 1 to 10, and

indicates a point of attachment to the rest of the formula.

37. The compound of claim 25, wherein R is a conjugating group.

38. The compound of claim 3, wherein R is:

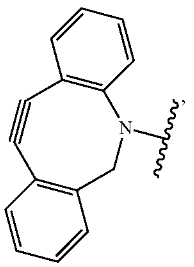

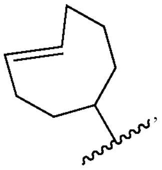

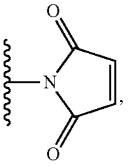

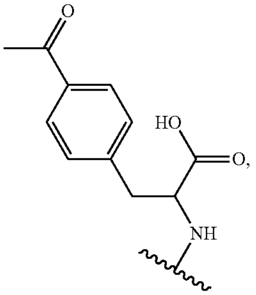

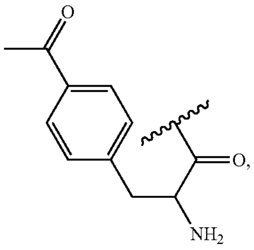

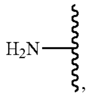

-continued
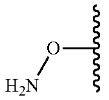 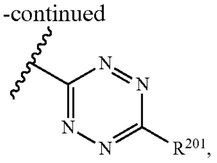
—$N_3$, or —SH; wherein $R^{201}$ is $C_{1-6}$alkyl, and each
indicates a point of attachment to the rest of the formula.
39. The compound of claim 25, wherein PA is selected from the group consisting of:
2
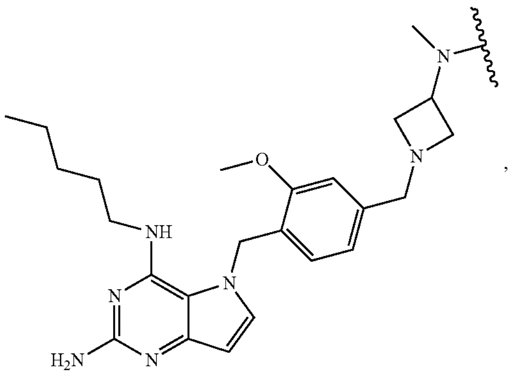
3
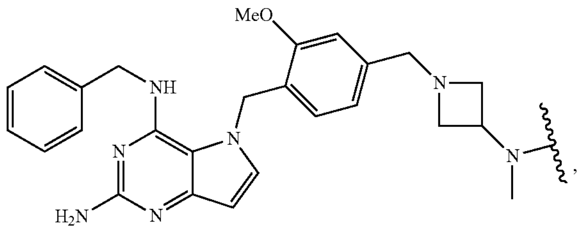
4
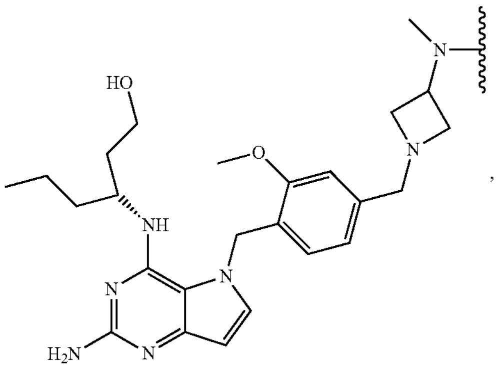
5
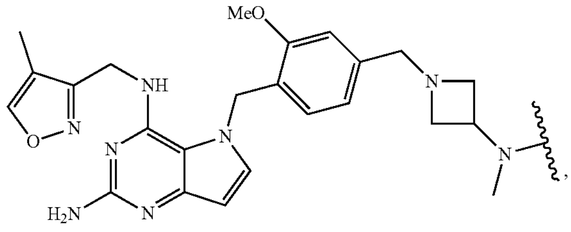

-continued
6
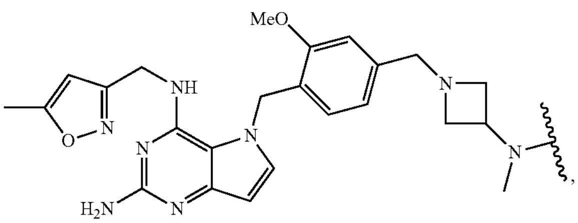
,
7
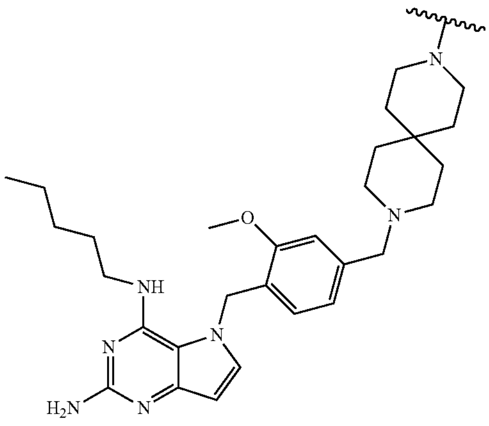
,
8
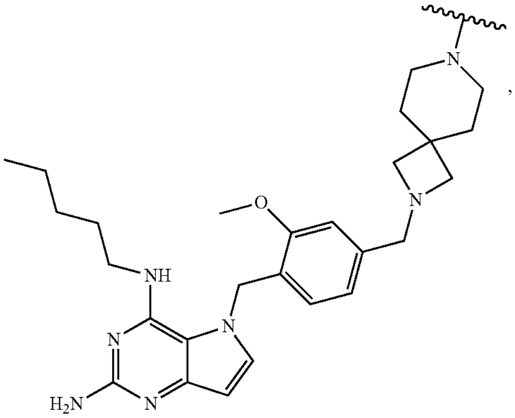
,
9
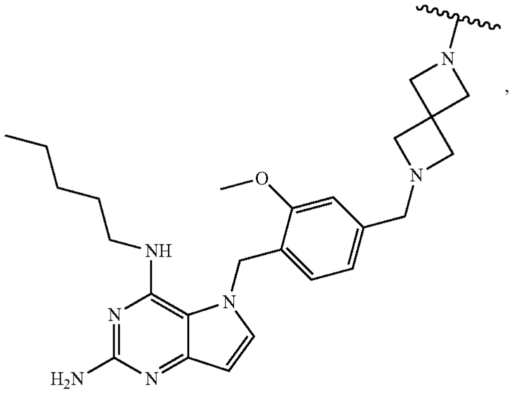
,
10
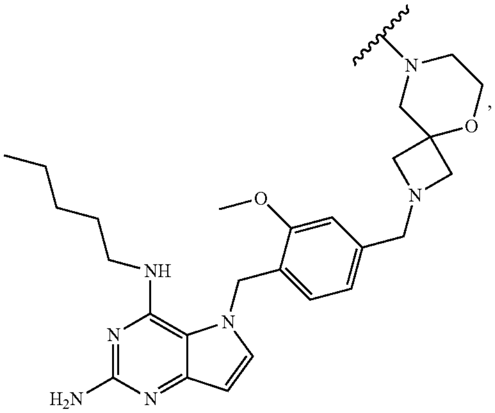
,
11
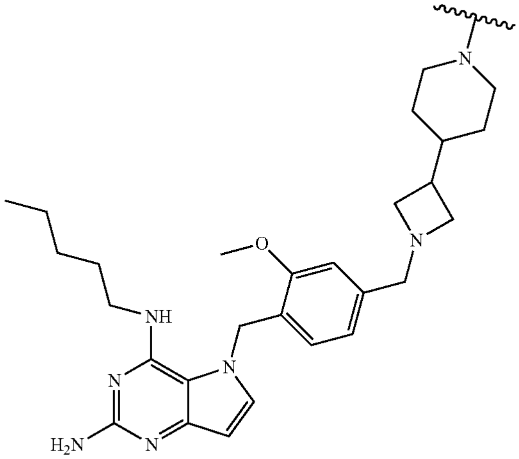
, -continued
12
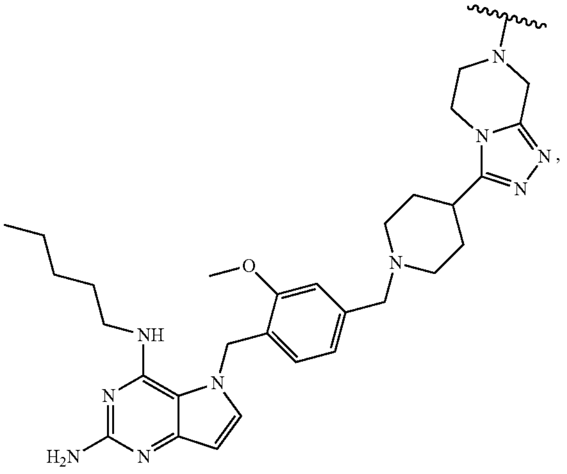
13
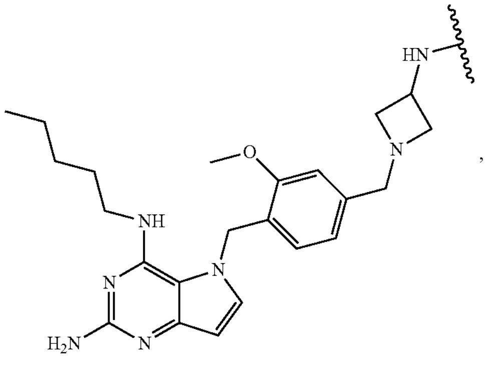
14
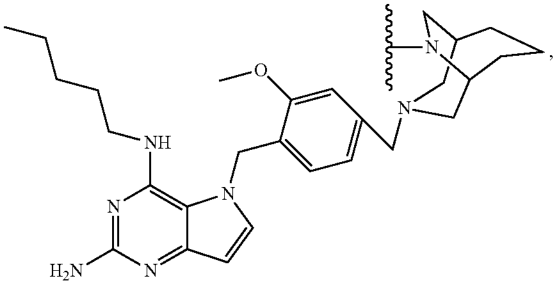
15
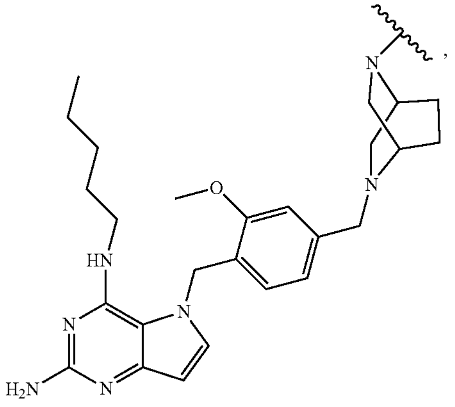
16
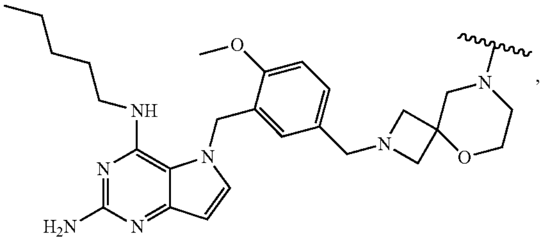
17
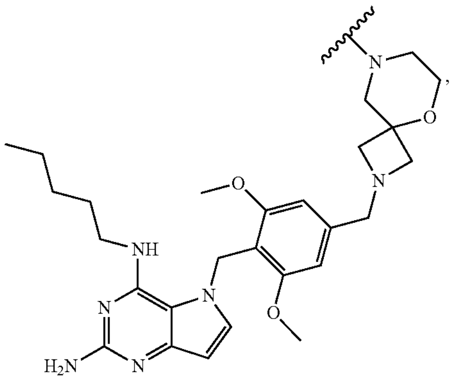

-continued
18
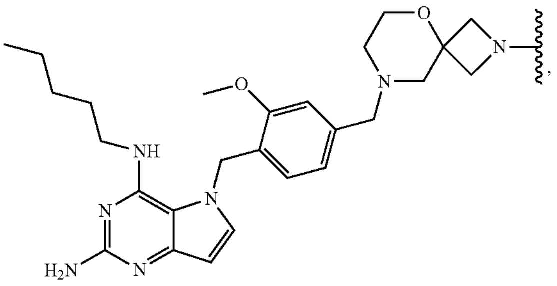
19
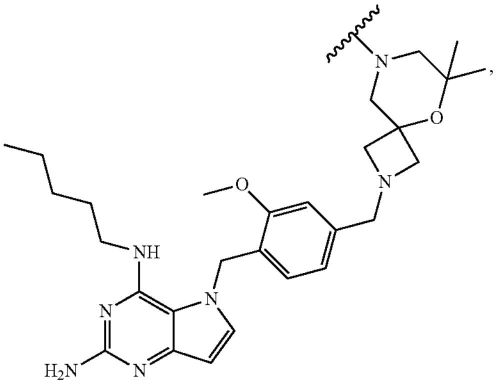
20
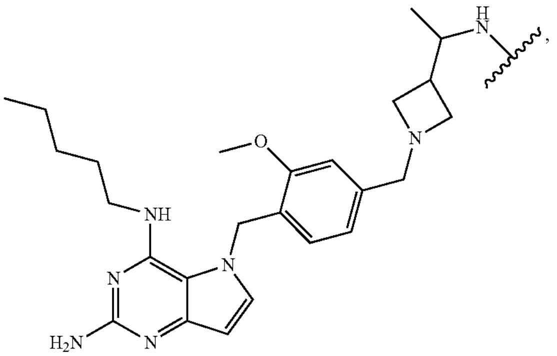
21
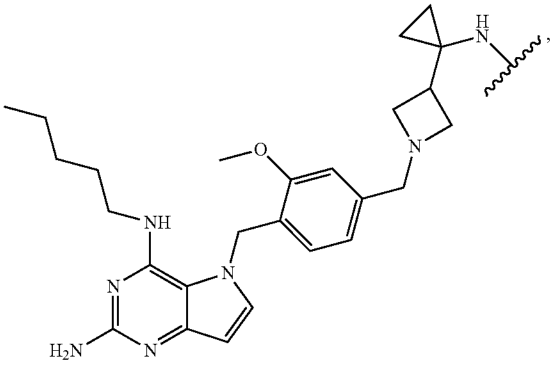
22
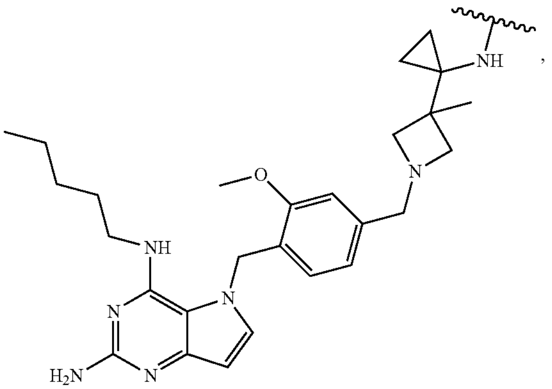
23
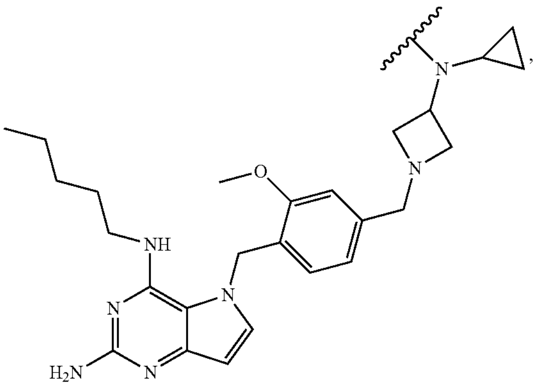
24
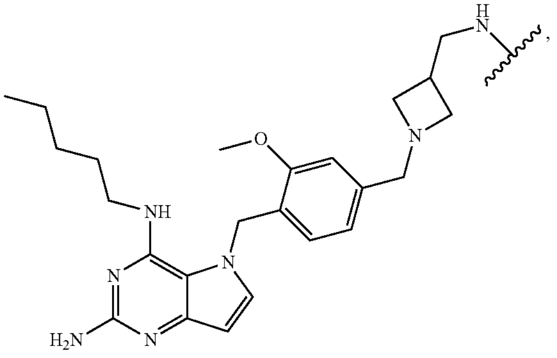
25
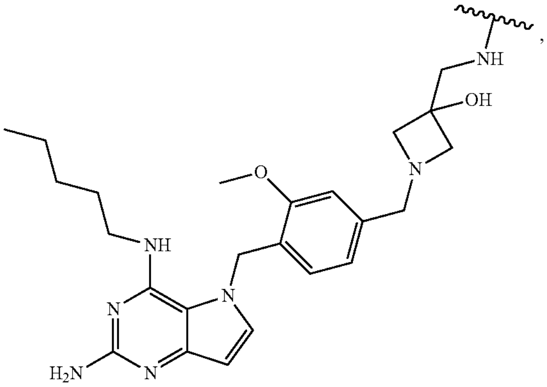

-continued
26
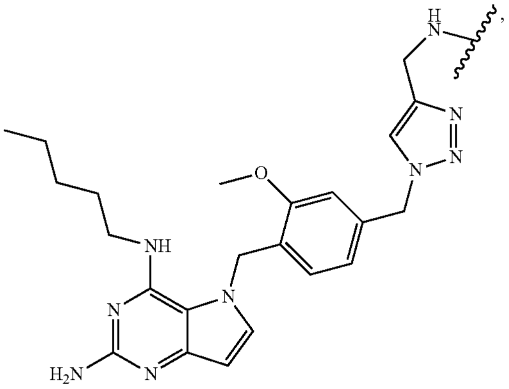
27
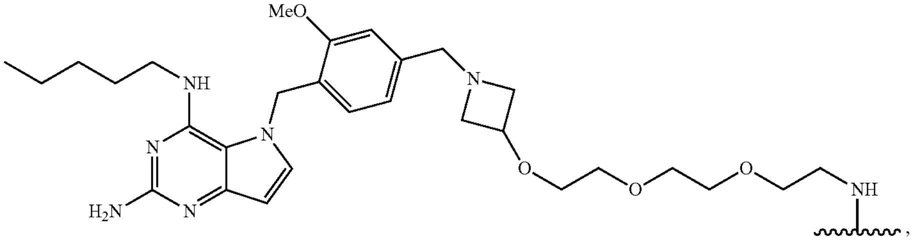
28
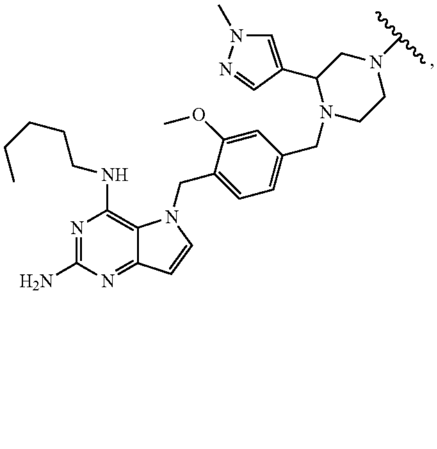
, and
30
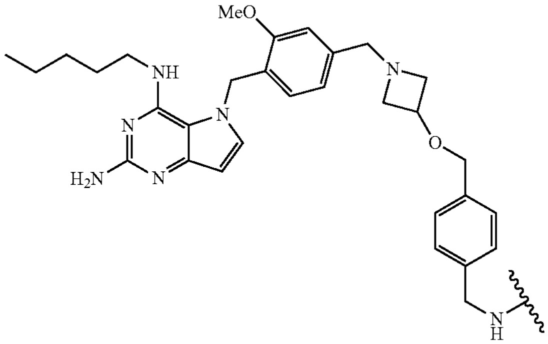
, wherein each
indicates a point of attachment to the rest of the formula.
40. The compound of claim 25, selected from the group consisting of:
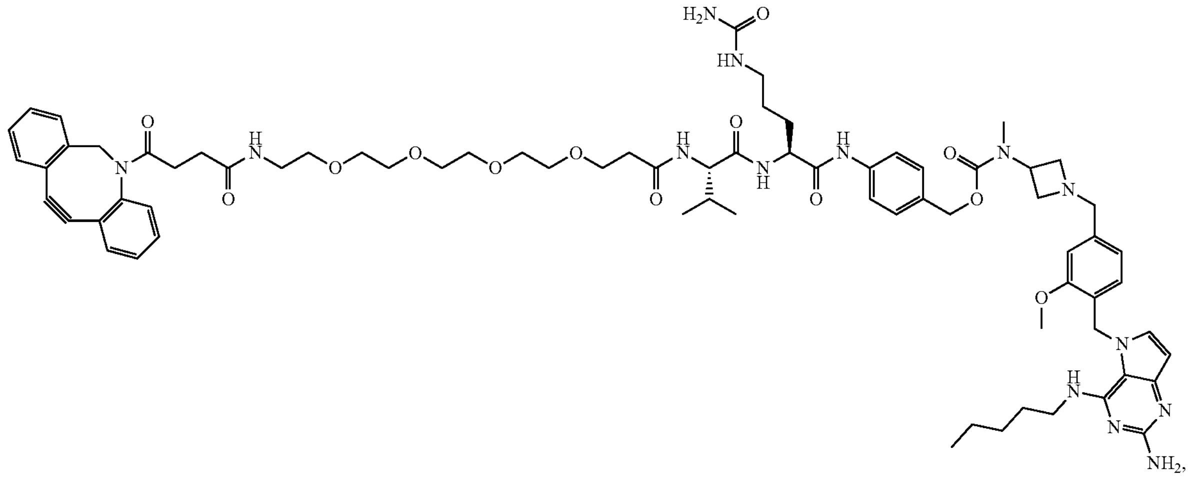
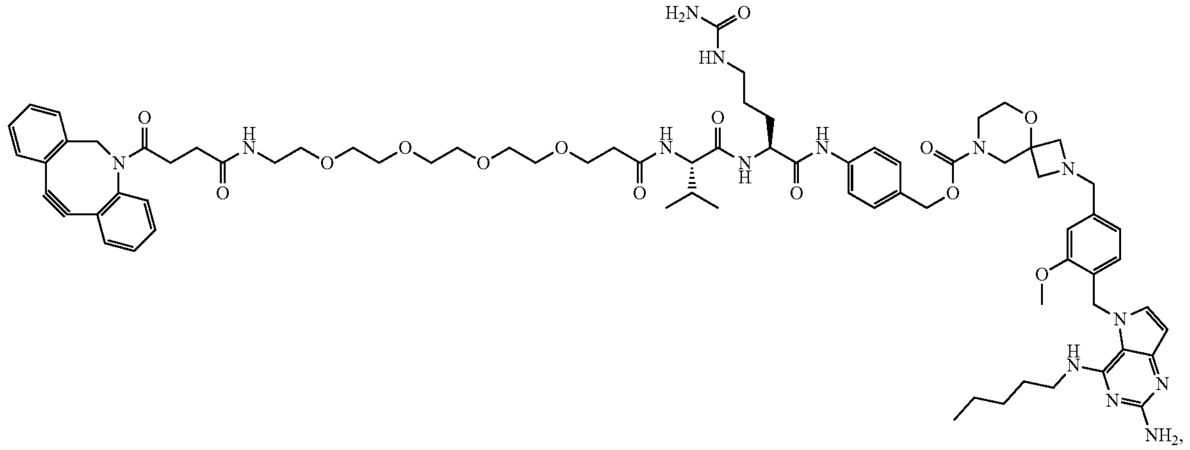
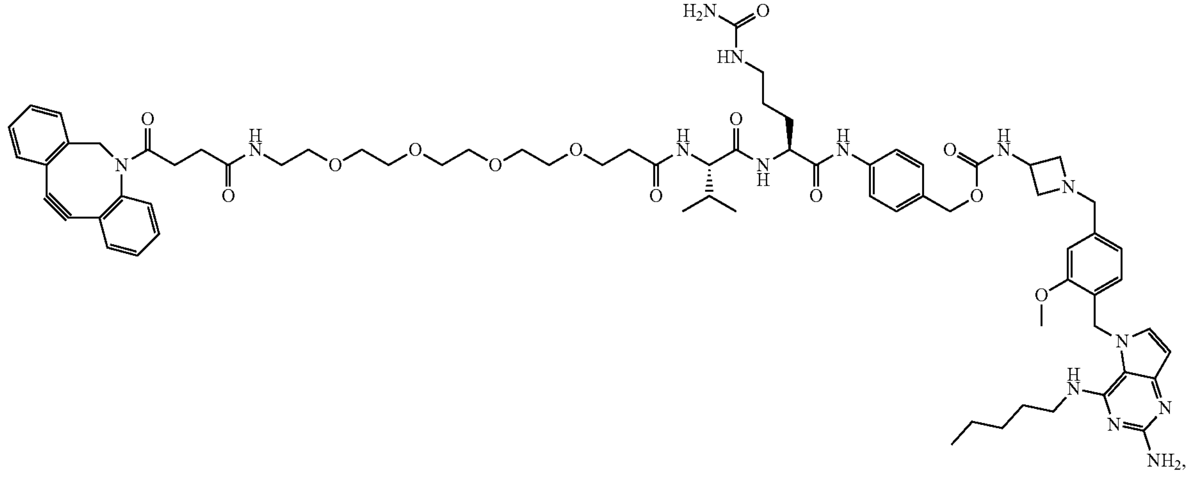

-continued
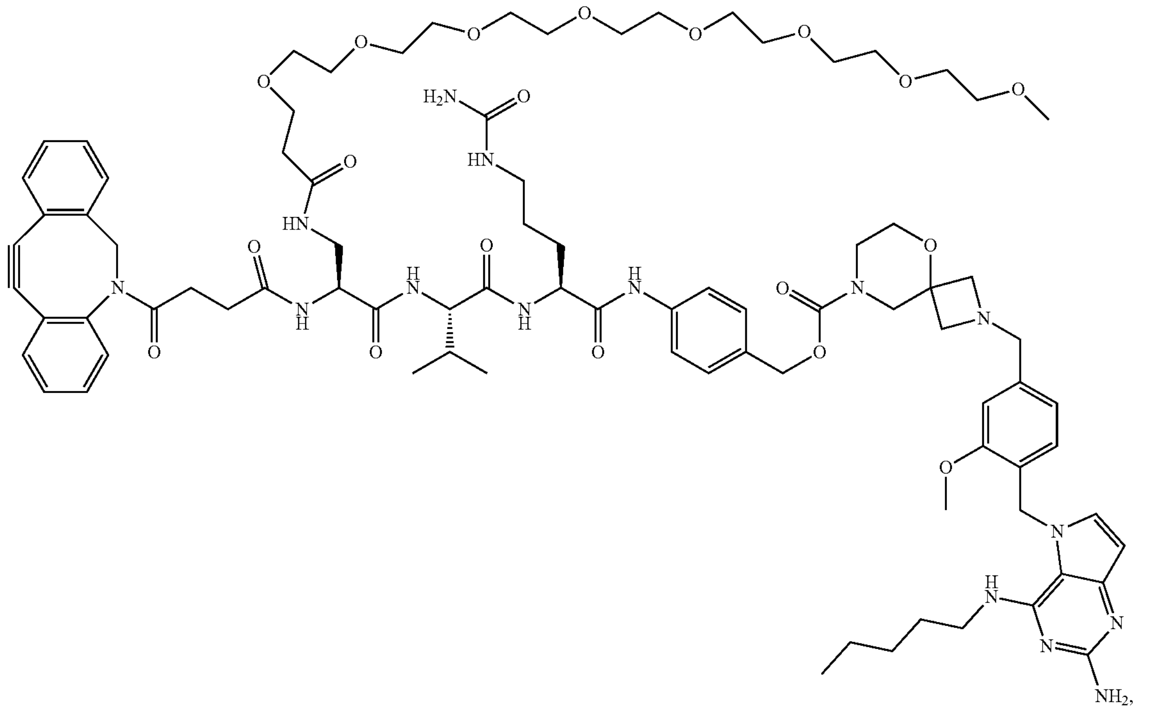
NH2, and
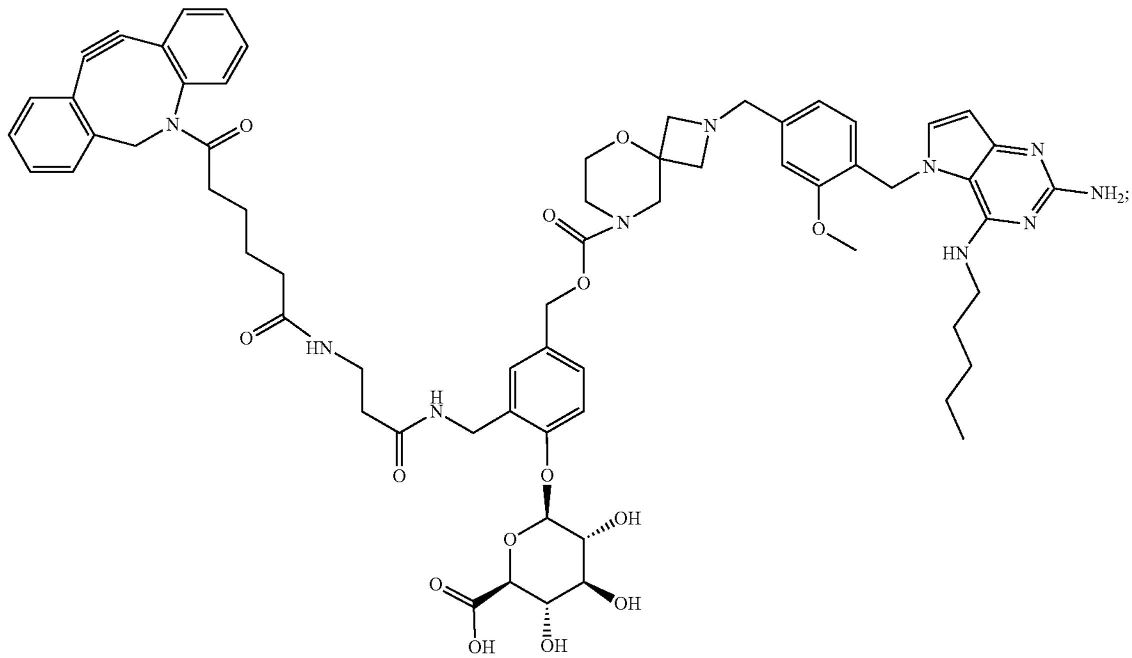
NH2;

or a pharmaceutically acceptable salt, solvate, stereoisomer, tautomer or mixture of regioisomers thereof.

41. An antibody drug conjugate according to Formula (V):

Formula (V)

$$Ab-[L-PA]_n$$

or a pharmaceutically acceptable salt, solvate, stereoisomer, tautomer, or mixture of regioisomers thereof, wherein Ab is an antibody or an antigen binding fragment thereof, L is a linker;

PA is a residue of Formula (I); and subscript n is an integer selected from 1 to 30.

42. The antibody drug conjugate of claim 41, according to Formula (VI):

Formula (VI)

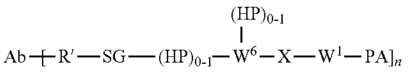

or a pharmaceutically acceptable salt, solvate, stereoisomer, tautomer, or mixture of regioisomers thereof, wherein:

each $W^1$ is independently a single bond, absent or a divalent attaching group;

each X is independently, at each occurrence, absent,

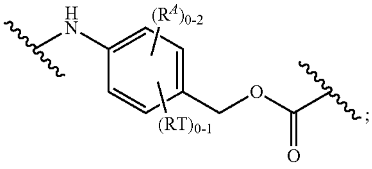

; or

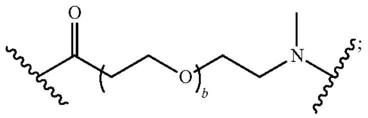

;

subscript b is an integer from 1 to 10;

each $R^A$, when present, is independently, at each occurrence, selected from $C_{1-3}$alkyl;

each RT, when present, is independently, at each occurrence, a release trigger group;

each HP, when present, is independently a hydrophilic group;

each $W^6$ is independently a residue of a peptide, or absent;

each SG is independently, at each occurrence, absent, or a divalent spacer group;

each R' is independently, at each occurrence, a divalent residue of a conjugated group;

subscript n is an integer selected from 1 to 30;

Ab is an antibody or an antigen binding fragment thereof, and each PA is a residue of Formula (I):

Formula (I)

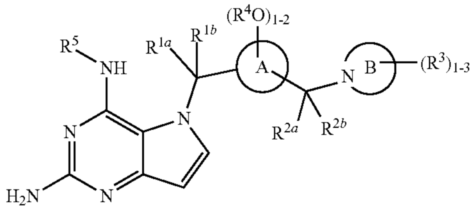

or a pharmaceutically acceptable salt, solvate or N-oxide thereof;

wherein $R^{1a}$, $R^{1b}$, $R^{2a}$, and $R^{2b}$ are independently, at each occurrence, selected from hydrogen, and $C_{1-6}$alkyl;

ring A is cycloalkyl, heterocycloalkyl, monocyclic aryl, monocyclic heteroaryl, fused bicyclic aryl, or fused bicyclic heteroaryl, where heterocycloalkyl and each heteroaryl comprise 1, 2, 3 or 4 heteroatoms independently selected from N, S, and O;

ring B is a 4-membered N-linked heterocycloalkyl, which is substituted with 1-2 $R^3$; wherein the heterocycloalkyl includes 1 or 2 heteroatoms independently selected from N, S, and O;

and wherein $R^3$ is, independently, at each occurrence, $—N(R^{3a})_2$, $—OR^{3b}$, $—C(R^{3c})_2NH_2$, $C_{1-6}$alkyl, heterocycloalkyl, heteroaryl, or partially saturated heteroaryl, or two $R^3$ attached to the same carbon, together with the carbon atom to which they are attached, form a spiro-heterocycloalkyl; wherein heterocycloalkyl, spiro-heterocycloalkyl, heteroaryl, and partially saturated heteroaryl in $R^3$ include 1, 2, 3 or 4 heteroatoms independently selected from N, S, and O, and are optionally substituted with 1-2 $C_{1-3}$alkyl;

or ring B is a 5-6 membered N-linked heterocycloalkyl, which is substituted with 1-3 $R^3$, or a 5-6 membered N-linked heteroaryl, which is substituted with 1-3 $R^3$; wherein the heterocycloalkyl includes 1 or 2 heteroatoms independently selected from N, S, and O; and wherein $R^3$ is, independently, at each occurrence, $—N(R^{3a})_2$, $—OR^{3b}$, $—C(R^{3c})_2NH_2$ heterocycloalkyl, heteroaryl, or partially saturated heteroaryl, or two $R^3$ attached to the same carbon, together with the carbon atom to which they are attached, form a spiro-heterocycloalkyl; wherein heterocycloalkyl, spiro-heterocycloalkyl, heteroaryl, and partially saturated heteroaryl in $R^3$ include 1, 2, 3 or 4 heteroatoms independently selected from N, S, and O, and are optionally substituted with 1-2 $C_{1-3}$alkyl;

or ring B is a 7-10 membered N-linked heterocycloalkyl, which is substituted with 1-3 $R^3$, or a 5-10 membered N-linked heteroaryl which is substituted with 1-3 $R^3$; wherein $R^3$ is, independently, at each occurrence, $—N(R^{3a})_2$, $—OR^3$, $—C(R^{3c})_2NH_2$, $C_{1-6}$alkyl, heterocycloalkyl, heteroaryl, or partially saturated heteroaryl, or two $R^3$ attached to the same carbon, together with the carbon atom to which they are attached, form a spiro-heterocycloalkyl; wherein heterocycloalkyl, spiro-heterocycloalkyl, heteroaryl, and partially saturated heteroaryl in $R^3$ include 1, 2, 3 or 4 heteroatoms independently selected from N, S, and O, and are optionally substituted with 1-2 $C_{1-3}$alkyl;

or ring B is unsubstituted 2,5-diazabicyclo[2.2.2]octanyl or 3,9-diazabicyclo[3.3.2]decanyl;

$R^{3a}$ is independently, at each occurrence, selected from hydrogen, $C_{1-6}$alkyl, —C(=O)—$CH_2NH_2$, and cycloalkyl;

$R^{3b}$ is independently, at each occurrence, selected from hydrogen,

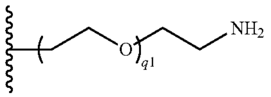

where q1 is 1, 2, or 3, and —$CH_2$-aryl-$CH_2NH_2$;

$R^{3c}$ is independently, at each occurrence, selected from hydrogen, and $C_{1-6}$alkyl, or two $R^{3c}$, together with the carbon atom to which they are attached, form a cycloalkyl;

$R^4$ is $C_{1-6}$alkyl; and $R^5$ is $C_{3-6}$cycloalkyl, or $C_{1-6}$alkyl, each of which is optionally substituted with 1, 2, or 3 $R^{5a}$ groups independently selected from halo, hydroxy, alkoxy, amino, $C_{1-6}$alkylamino, $C_{1-6}$ dialkylamino, $C_{3-6}$cycloalkyl, aryl or heteroaryl, wherein heteroaryl includes 1, 2, 3 or 4 heteroatoms independently selected from N, S, and O, and wherein any of the $R^{5a}$ $C_{3-6}$cycloalkyl, aryl and heteroaryl groups are optionally further substituted with 1, 2, or 3 groups independently selected from halo, hydroxy, alkyl, and haloalkyl; and wherein PA is bonded to the rest of the molecule via —$NR^{3a}$—, the —NH— of —$C(R^{3c})_2NH$—, the nitrogen of an $R^3$ heterocycloalkyl, the nitrogen of an $R^3$ partially saturated heteroaryl, the —NH— of —O—$CH_2$-(phenyl)-$CH_2$—NH—, or a nitrogen of ring B.

43. The antibody drug conjugate of claim 42, wherein SG is absent,

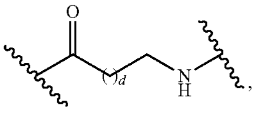,
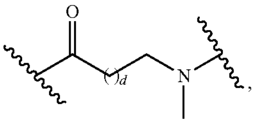, or
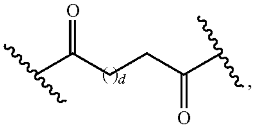, wherein subscript d is an integer selected from 1 to 10, wherein each

indicates a point of attachment to the rest of the formula.

44. The antibody drug conjugate of claim 42, wherein SG is

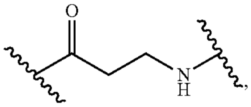,
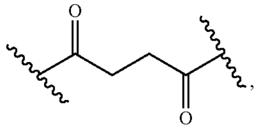,
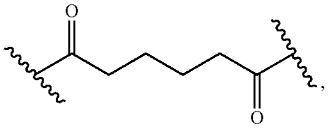, or
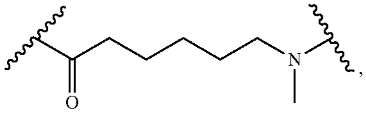, wherein each

indicates a point of attachment to the rest of the formula.

45. The antibody drug conjugate of claim 42, wherein $W^1$, when present, is

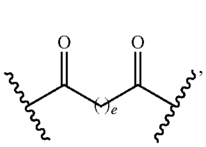,
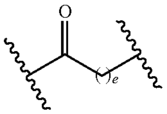 or
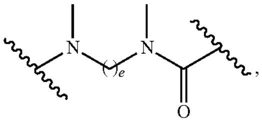, wherein subscript e is an integer selected from 1 to 10, wherein each

indicates a point of attachment to the rest of the formula.

46. The antibody drug conjugate of claim 42, wherein $W^1$, when present, is

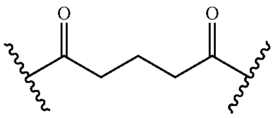,
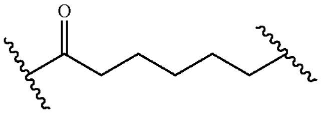, or

-continued

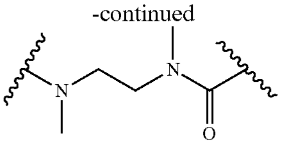

wherein each

indicates a point of attachment to the rest of the formula.

47. The antibody drug conjugate of claim 42, wherein $W^6$, when present, is a tripeptide residue.

48. The antibody drug conjugate of claim 42, wherein, $W^6$, when present, is

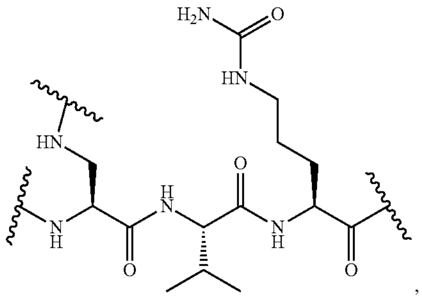 [SMILES: *NC[C@H](N*)C(=O)N[C@H](C(=O)N[C@@H](CCCNC(N)=O)C(*)=O)C(C)C]

wherein each

indicates a point of attachment to the rest of the formula.

49. The antibody drug conjugate of claim 42, wherein $W^6$, when present, is a dipeptide residue.

50. The antibody drug conjugate of claim 43, wherein, $W^6$, when present, is

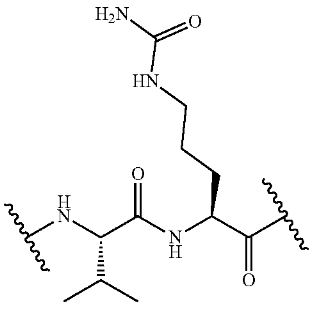

or

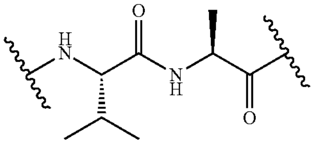

, wherein each

indicates a point of attachment to the rest of the formula.

51. The antibody drug conjugate of claim 42, wherein RT is

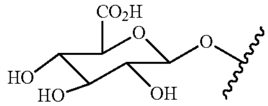

wherein

indicates a point of attachment to the rest of the formula.

52. The antibody drug conjugate of claim 42, wherein HP, when present, is

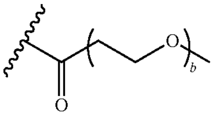

or

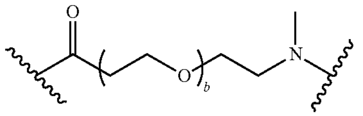

, wherein subscript b is an integer selected from 1 to 10, and

indicates a point of attachment to the rest of the formula.

53. The antibody drug conjugate of claim 42, wherein R' is:

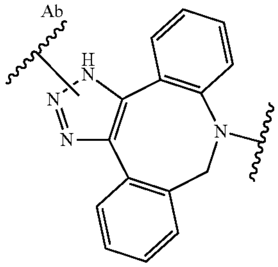

,

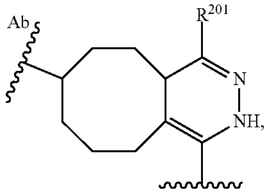

-continued

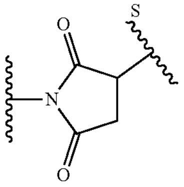
,
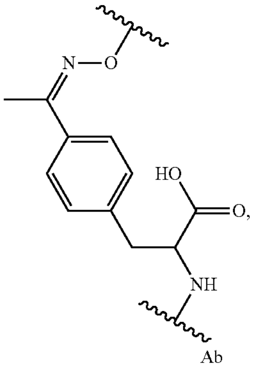

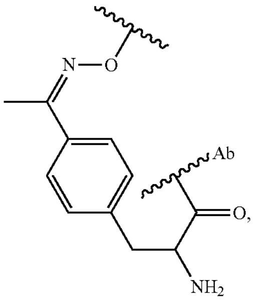
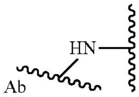
,

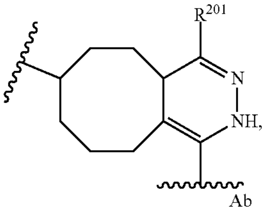
or
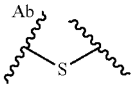
;

wherein $R^{201}$ is $C_{1-6}$alkyl, wherein each

indicates a point of attachment to the rest of the formula,

indicates a point of attachment to the antibody, or an antigen binding fragment thereof, and

indicates a point of attachment to the antibody, or an antigen binding fragment thereof, via a sulfur atom of a cysteine residue.

54. The antibody drug conjugate of claim 42, selected from the group consisting of:

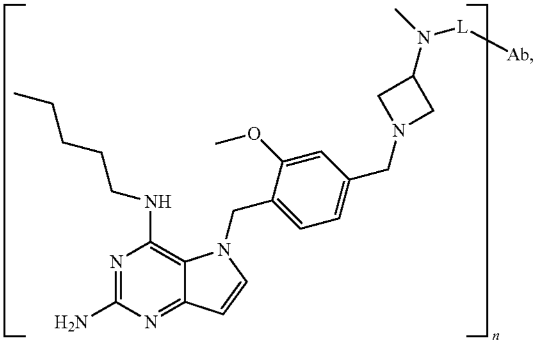
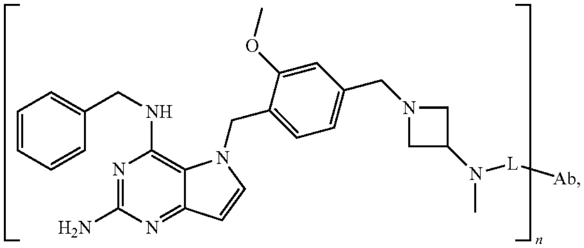

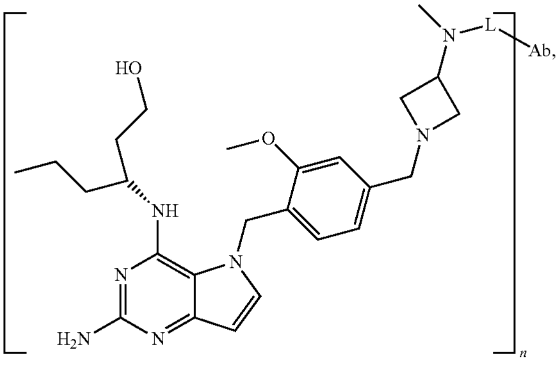
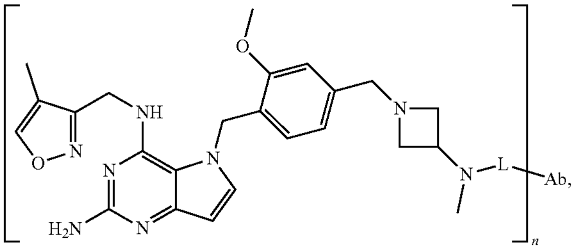

-continued
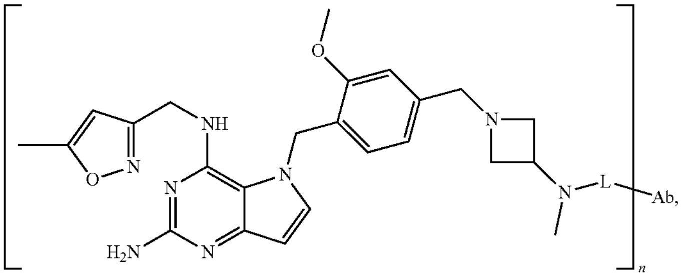
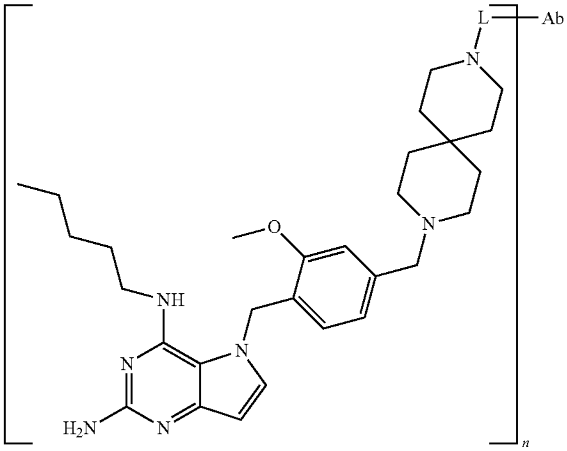
,
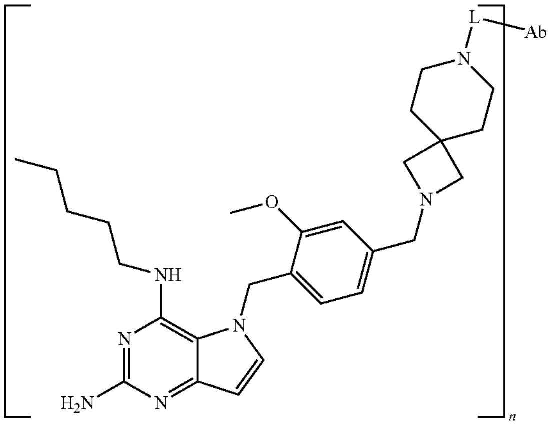
,
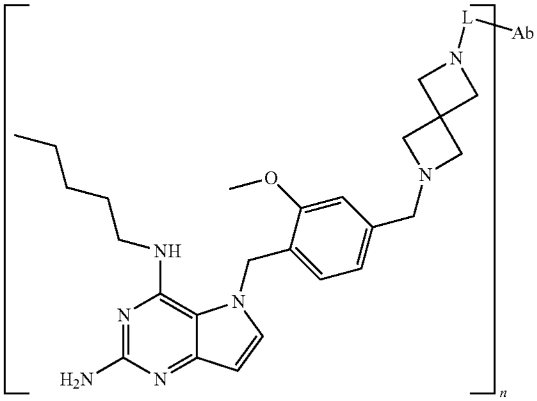
,
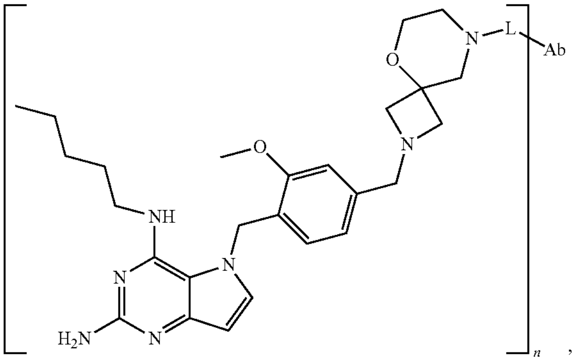
,
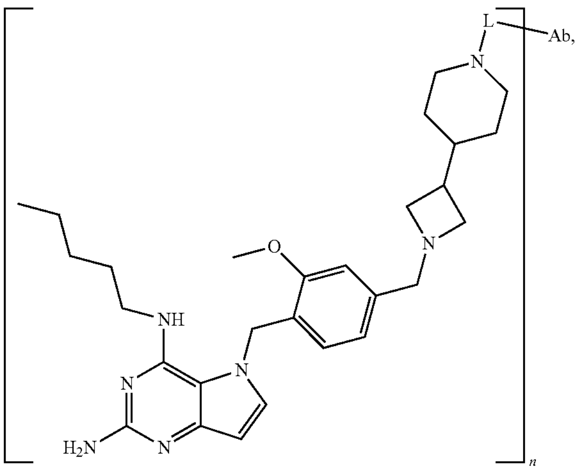
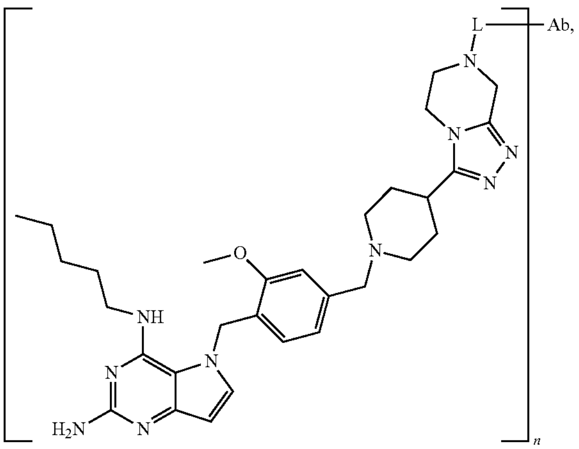

-continued
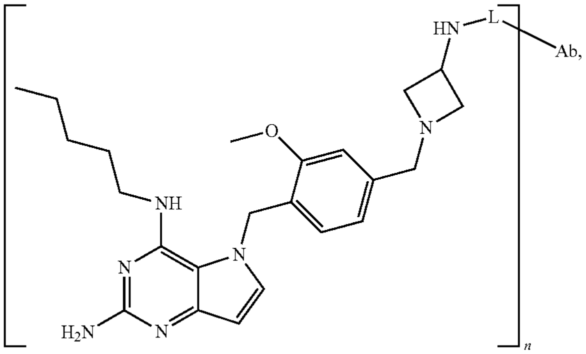
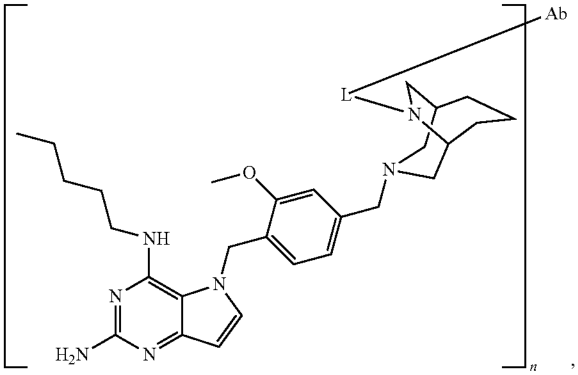
,
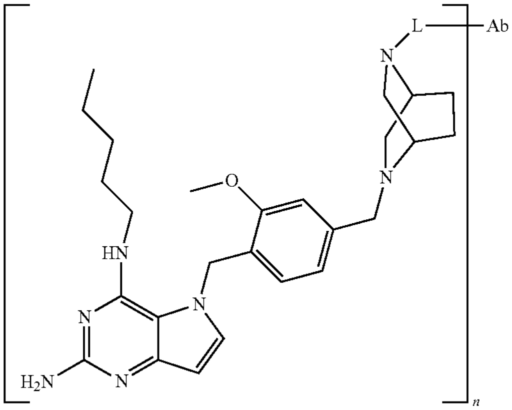
,
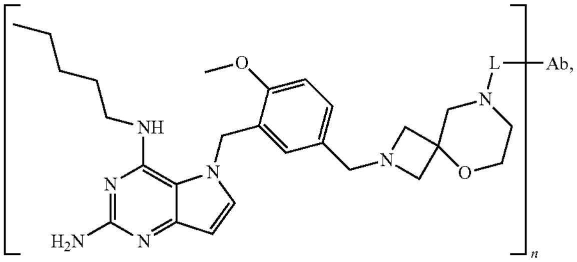
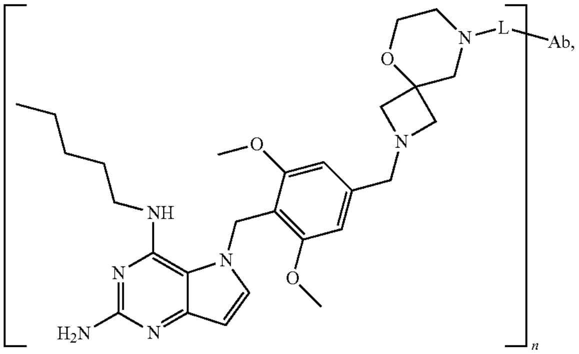
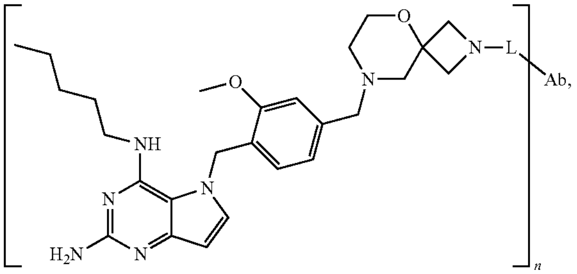
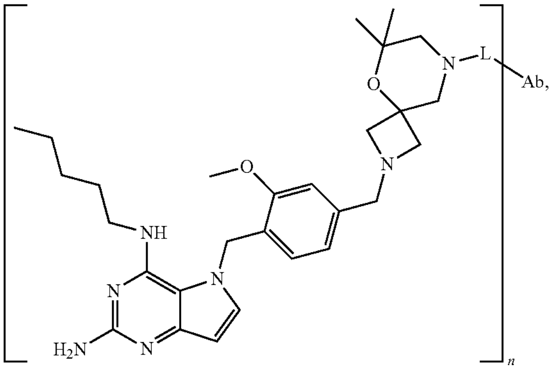

-continued
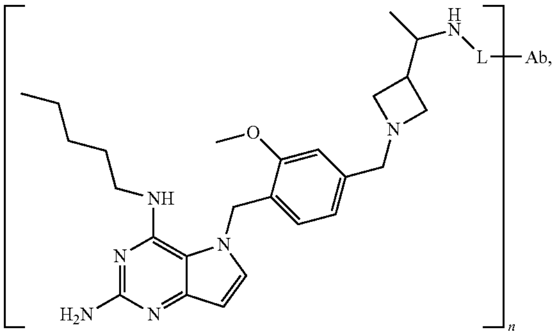
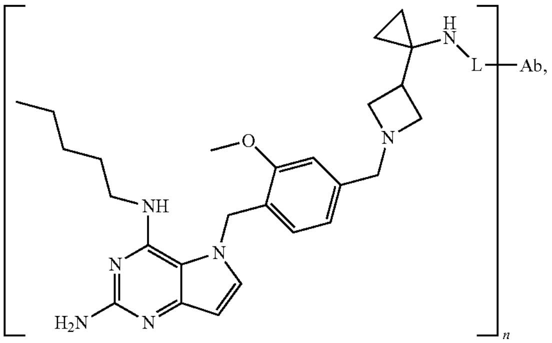
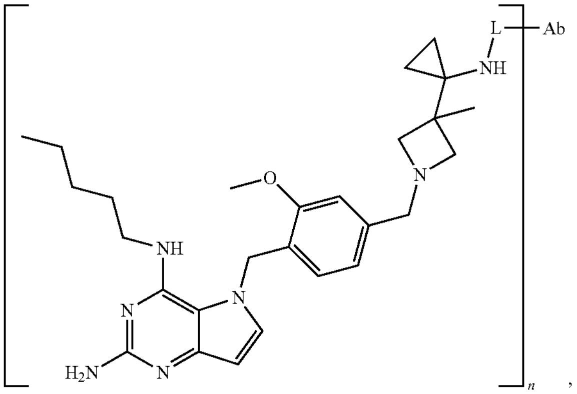
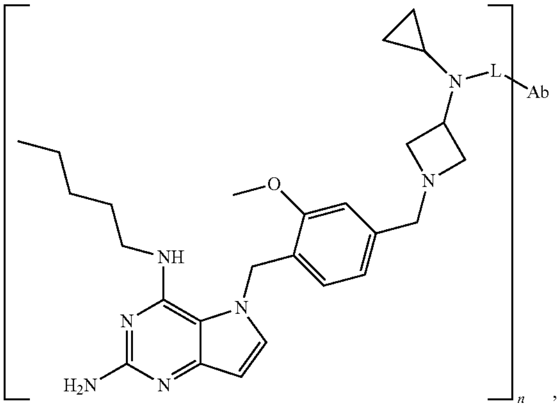
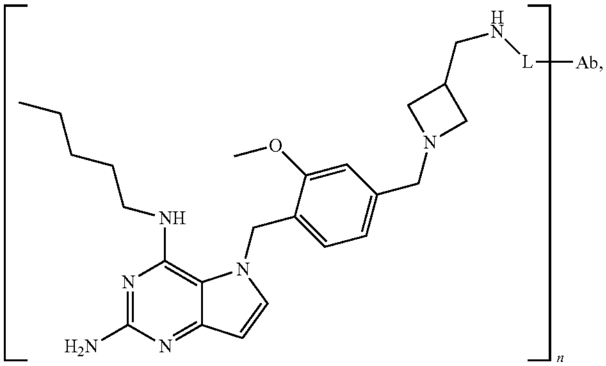
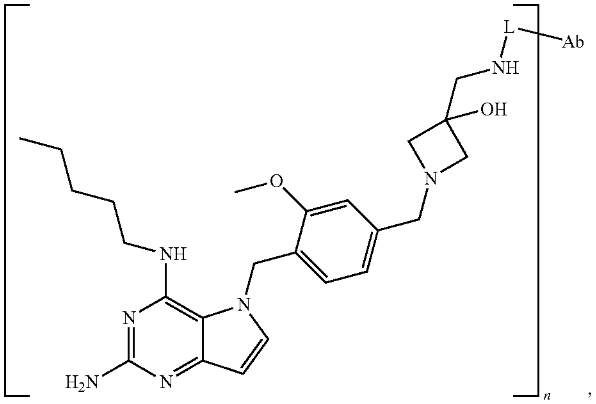
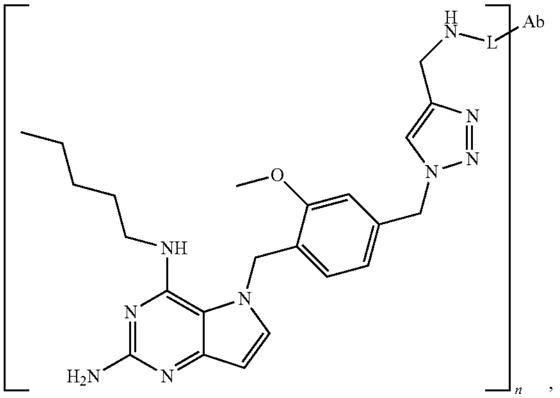

-continued
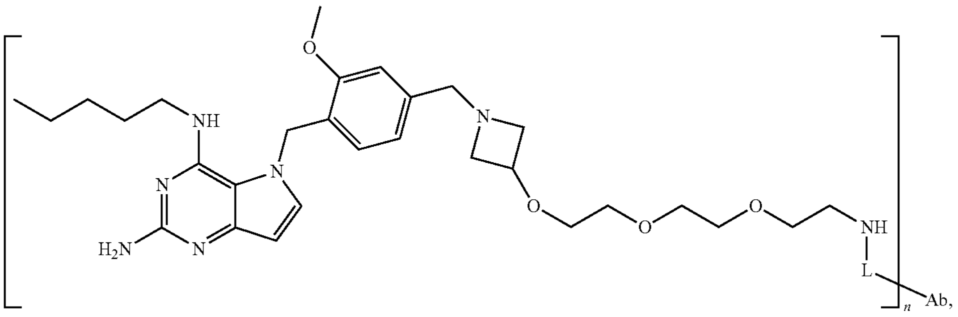
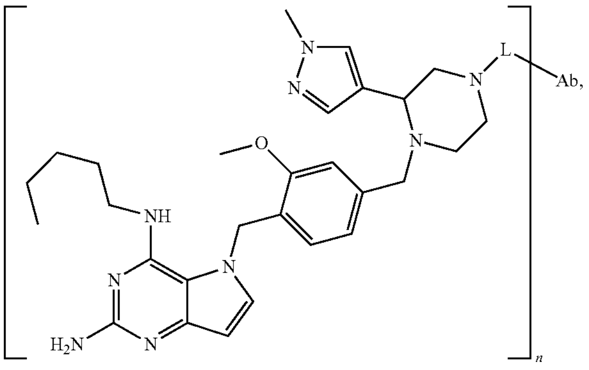
and
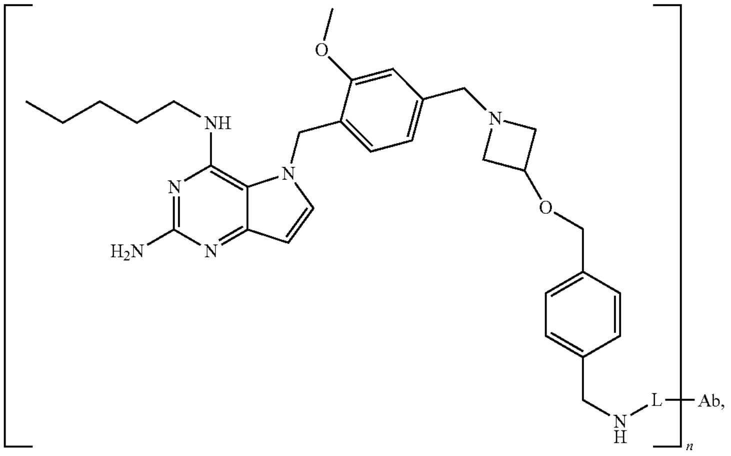

or a pharmaceutically acceptable salt, solvate, stereoisomer, tautomer or mixture of regioisomers thereof, wherein each
indicates a point of attachment to the rest of the formula;
L is a linker; and
Ab is an antibody or an antigen binding fragment thereof.
55. The antibody drug conjugate of claim 42, selected from the group consisting of:
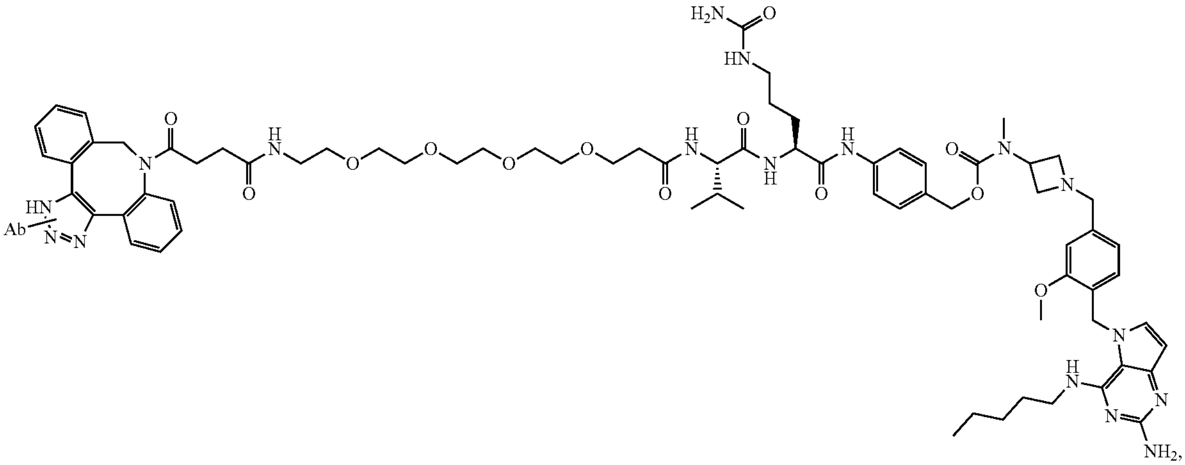
,
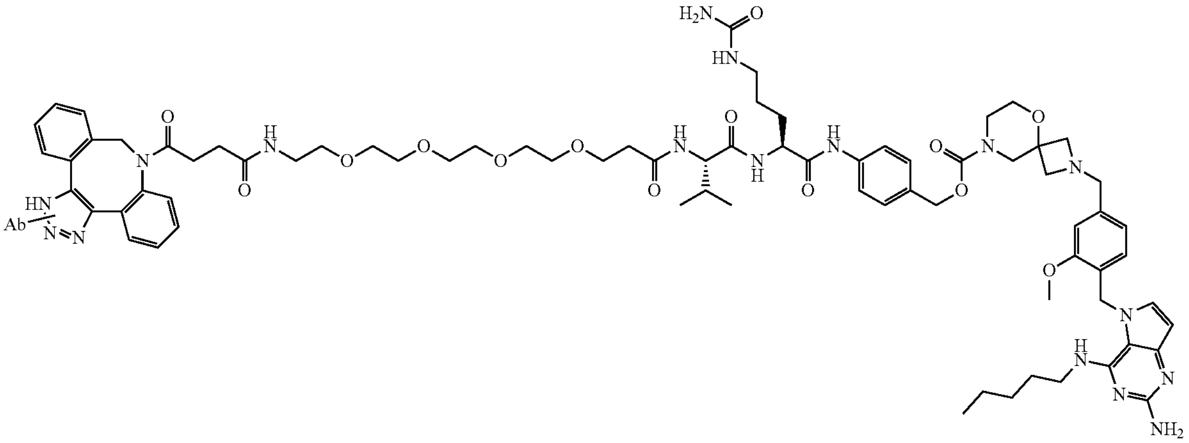
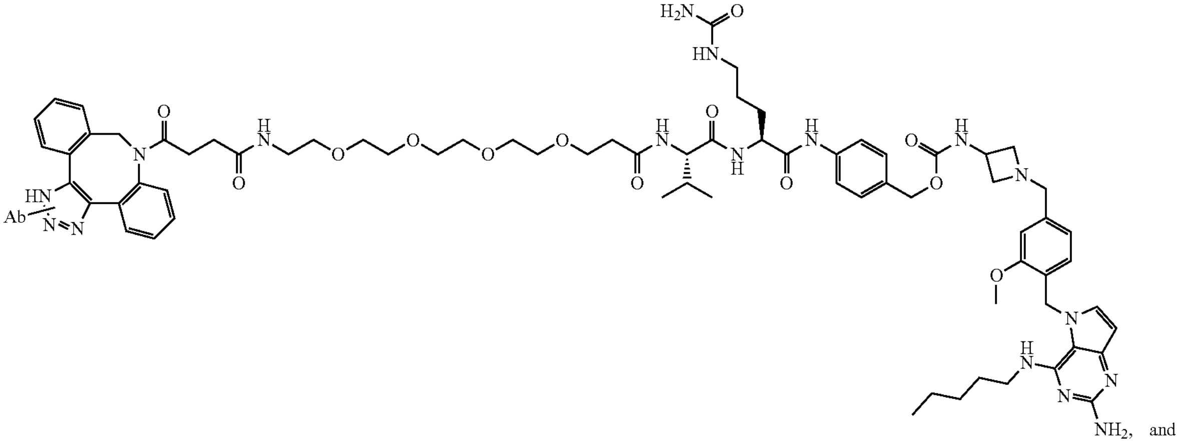
, and -continued

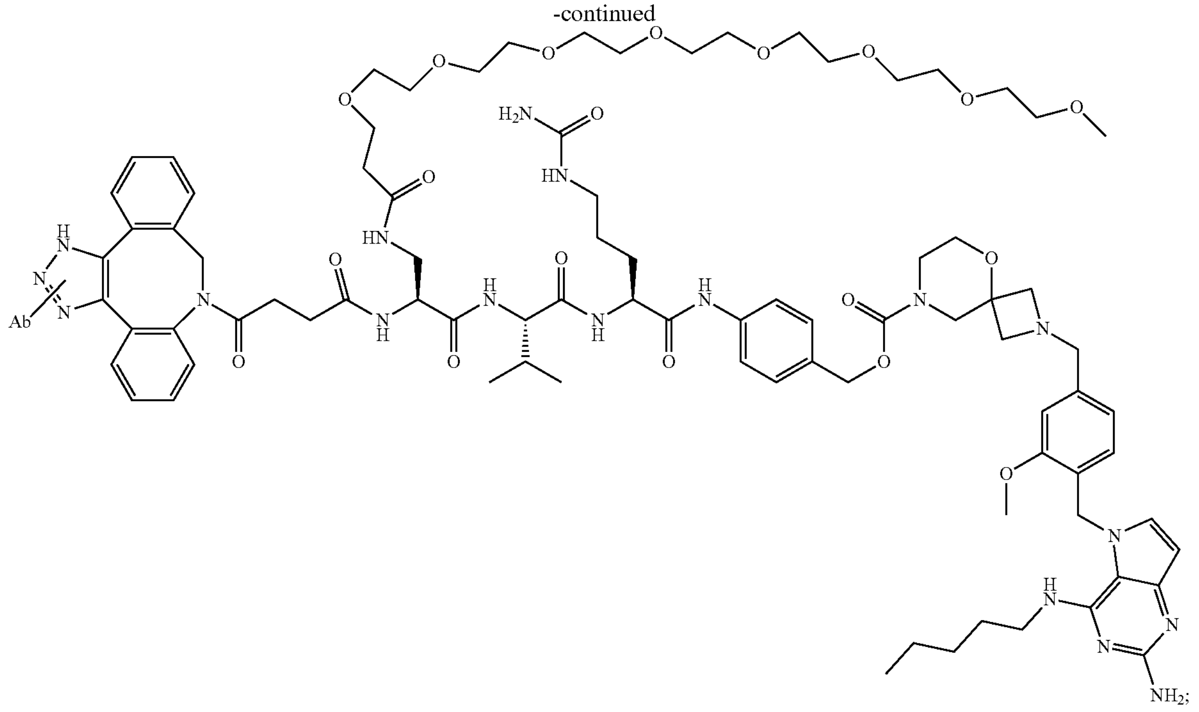

or a pharmaceutically acceptable salt, solvate, stereoisomer, tautomer or mixture of regioisomers thereof.

56. The antibody drug conjugate claim 42, wherein the antibody, or an antigen binding fragment thereof, is selected from the group consisting of anti-BCMA, anti-Muc16, trastuzumab, sofitizumab, anti-GFP, and anti-FolRa, or an antigen binding fragment thereof.

57. The antibody drug conjugate of claim 42, wherein the antibody, or an antigen binding fragment thereof, comprises Y180 pAMF mutations, F404 pAMF mutations, or both.

58. A pharmaceutical composition comprising an antibody drug conjugate of claim 42, and a pharmaceutically acceptable carrier.

59. A method for treating colon cancer, renal cancer, mammary carcinomas, skin cancer, or cervical intraepithelial neoplasia in a subject in need thereof comprising administering to the subject an effective amount of an antibody drug conjugate of claim 42.

* * * * *

SEQUENCE LISTING

```
<160> NUMBER OF SEQ ID NOS: 53

<210> SEQ ID NO 1
<211> LENGTH: 5
<212> TYPE: PRT
<213> ORGANISM: Artificial Sequence
<220> FEATURE:
<223> OTHER INFORMATION: Synthetic

<400> SEQUENCE: 1

Leu Leu Gln Gly Ala
1               5


<210> SEQ ID NO 2
<211> LENGTH: 7
<212> TYPE: PRT
<213> ORGANISM: Artificial Sequence
<220> FEATURE:
```

<223> OTHER INFORMATION: Synthetic

<400> SEQUENCE: 2

Tyr Ala His Gln Ala His Tyr
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic

<400> SEQUENCE: 3

Tyr Arg Tyr Arg Gln
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic

<400> SEQUENCE: 4

Pro Asn Pro Gln Leu Pro Phe
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic

<400> SEQUENCE: 5

Pro Lys Pro Gln Gln Phe Met
1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic

<400> SEQUENCE: 6

Gly Gln Gln Gln Leu Gly
1               5

<210> SEQ ID NO 7
<211> LENGTH: 7
<212> TYPE: PRT
<213> ORGANISM: Artificial Sequence
<220> FEATURE:
<223> OTHER INFORMATION: Synthetic

<400> SEQUENCE: 7

Trp Ala Leu Gln Arg Pro His
1               5

<210> SEQ ID NO 8
<211> LENGTH: 7
<212> TYPE: PRT
<213> ORGANISM: Artificial Sequence
<220> FEATURE:
<223> OTHER INFORMATION: Synthetic

<400> SEQUENCE: 8

Trp Glu Leu Gln Arg Pro Tyr
1 5

<210> SEQ ID NO 9
<211> LENGTH: 7
<212> TYPE: PRT
<213> ORGANISM: Artificial Sequence
<220> FEATURE:
<223> OTHER INFORMATION: Synthetic

<400> SEQUENCE: 9

Tyr Pro Met Gln Gly Trp Phe
1 5

<210> SEQ ID NO 10
<211> LENGTH: 6
<212> TYPE: PRT
<213> ORGANISM: Artificial Sequence
<220> FEATURE:
<223> OTHER INFORMATION: Synthetic

<400> SEQUENCE: 10

Leu Ser Leu Ser Gln Gly
1 5

<210> SEQ ID NO 11
<211> LENGTH: 8
<212> TYPE: PRT
<213> ORGANISM: Artificial Sequence
<220> FEATURE:
<223> OTHER INFORMATION: Synthetic

<400> SEQUENCE: 11

Gly Gly Gly Leu Leu Gln Gly Gly
1 5

<210> SEQ ID NO 12
<211> LENGTH: 5
<212> TYPE: PRT
<213> ORGANISM: Artificial Sequence
<220> FEATURE:
<223> OTHER INFORMATION: Synthetic

<400> SEQUENCE: 12

Gly Leu Leu Gln Gly
1 5

<210> SEQ ID NO 13
<211> LENGTH: 10
<212> TYPE: PRT
<213> ORGANISM: Artificial Sequence
<220> FEATURE:
<223> OTHER INFORMATION: Synthetic

<400> SEQUENCE: 13

Gly Ser Pro Leu Ala Gln Ser His Gly Gly
1 5 10

<210> SEQ ID NO 14
<211> LENGTH: 7
<212> TYPE: PRT
<213> ORGANISM: Artificial Sequence
<220> FEATURE:
<223> OTHER INFORMATION: Synthetic -continued

<400> SEQUENCE: 14

Gly Leu Leu Gln Gly Gly Gly
1 5

<210> SEQ ID NO 15
<211> LENGTH: 6
<212> TYPE: PRT
<213> ORGANISM: Artificial Sequence
<220> FEATURE:
<223> OTHER INFORMATION: Synthetic

<400> SEQUENCE: 15

Gly Leu Leu Gln Gly Gly
1 5

<210> SEQ ID NO 16
<211> LENGTH: 4
<212> TYPE: PRT
<213> ORGANISM: Artificial Sequence
<220> FEATURE:
<223> OTHER INFORMATION: Synthetic

<400> SEQUENCE: 16

Gly Leu Leu Gln
1

<210> SEQ ID NO 17
<211> LENGTH: 8
<212> TYPE: PRT
<213> ORGANISM: Artificial Sequence
<220> FEATURE:
<223> OTHER INFORMATION: Synthetic

<400> SEQUENCE: 17

Leu Leu Gln Leu Leu Gln Gly Ala
1 5

<210> SEQ ID NO 18
<211> LENGTH: 5
<212> TYPE: PRT
<213> ORGANISM: Artificial Sequence
<220> FEATURE:
<223> OTHER INFORMATION: Synthetic

<400> SEQUENCE: 18

Leu Leu Gln Gly Ala
1 5

<210> SEQ ID NO 19
<211> LENGTH: 7
<212> TYPE: PRT
<213> ORGANISM: Artificial Sequence
<220> FEATURE:
<223> OTHER INFORMATION: Synthetic

<400> SEQUENCE: 19

Leu Leu Gln Tyr Gln Gly Ala
1 5

<210> SEQ ID NO 20
<211> LENGTH: 6
<212> TYPE: PRT
<213> ORGANISM: Artificial Sequence
<220> FEATURE:
<223> OTHER INFORMATION: Synthetic

<400> SEQUENCE: 20

```
Leu Leu Gln Gly Ser Gly
1               5


<210> SEQ ID NO 21
<211> LENGTH: 6
<212> TYPE: PRT
<213> ORGANISM: Artificial Sequence
<220> FEATURE:
<223> OTHER INFORMATION: Synthetic

<400> SEQUENCE: 21

Leu Leu Gln Tyr Gln Gly
1               5


<210> SEQ ID NO 22
<211> LENGTH: 7
<212> TYPE: PRT
<213> ORGANISM: Artificial Sequence
<220> FEATURE:
<223> OTHER INFORMATION: Synthetic

<400> SEQUENCE: 22

Leu Leu Gln Leu Leu Gln Gly
1               5


<210> SEQ ID NO 23
<211> LENGTH: 5
<212> TYPE: PRT
<213> ORGANISM: Artificial Sequence
<220> FEATURE:
<223> OTHER INFORMATION: Synthetic

<400> SEQUENCE: 23

Ser Leu Leu Gln Gly
1               5


<210> SEQ ID NO 24
<211> LENGTH: 5
<212> TYPE: PRT
<213> ORGANISM: Artificial Sequence
<220> FEATURE:
<223> OTHER INFORMATION: Synthetic

<400> SEQUENCE: 24

Leu Leu Gln Leu Gln
1               5


<210> SEQ ID NO 25
<211> LENGTH: 6
<212> TYPE: PRT
<213> ORGANISM: Artificial Sequence
<220> FEATURE:
<223> OTHER INFORMATION: Synthetic

<400> SEQUENCE: 25

Leu Leu Gln Leu Leu Gln
1               5


<210> SEQ ID NO 26
<211> LENGTH: 5
<212> TYPE: PRT
<213> ORGANISM: Artificial Sequence
<220> FEATURE:
<223> OTHER INFORMATION: Synthetic

<400> SEQUENCE: 26
```

Leu Leu Gln Gly Arg
1 5

<210> SEQ ID NO 27
<211> LENGTH: 6
<212> TYPE: PRT
<213> ORGANISM: Artificial Sequence
<220> FEATURE:
<223> OTHER INFORMATION: Synthetic

<400> SEQUENCE: 27

Leu Leu Gln Gly Pro Ala
1 5

<210> SEQ ID NO 28
<211> LENGTH: 6
<212> TYPE: PRT
<213> ORGANISM: Artificial Sequence
<220> FEATURE:
<223> OTHER INFORMATION: Synthetic

<400> SEQUENCE: 28

Leu Leu Gln Gly Pro Pro
1 5

<210> SEQ ID NO 29
<211> LENGTH: 8
<212> TYPE: PRT
<213> ORGANISM: Artificial Sequence
<220> FEATURE:
<223> OTHER INFORMATION: Synthetic

<400> SEQUENCE: 29

Gly Gly Leu Leu Gln Gly Pro Pro
1 5

<210> SEQ ID NO 30
<211> LENGTH: 5
<212> TYPE: PRT
<213> ORGANISM: Artificial Sequence
<220> FEATURE:
<223> OTHER INFORMATION: Synthetic

<400> SEQUENCE: 30

Leu Leu Gln Gly Gly
1 5

<210> SEQ ID NO 31
<211> LENGTH: 4
<212> TYPE: PRT
<213> ORGANISM: Artificial Sequence
<220> FEATURE:
<223> OTHER INFORMATION: Synthetic

<400> SEQUENCE: 31

Leu Leu Gln Gly
1

<210> SEQ ID NO 32
<211> LENGTH: 6
<212> TYPE: PRT
<213> ORGANISM: Artificial Sequence
<220> FEATURE:
<223> OTHER INFORMATION: Synthetic

<400> SEQUENCE: 32

Leu Ser Leu Ser Gln Gly

-continued

```
1               5


<210> SEQ ID NO 33
<211> LENGTH: 8
<212> TYPE: PRT
<213> ORGANISM: Artificial Sequence
<220> FEATURE:
<223> OTHER INFORMATION: Synthetic

<400> SEQUENCE: 33

Gly Gly Gly Leu Leu Gln Gly Gly
1               5


<210> SEQ ID NO 34
<211> LENGTH: 5
<212> TYPE: PRT
<213> ORGANISM: Artificial Sequence
<220> FEATURE:
<223> OTHER INFORMATION: Synthetic

<400> SEQUENCE: 34

Gly Leu Leu Gln Gly
1               5


<210> SEQ ID NO 35
<211> LENGTH: 10
<212> TYPE: PRT
<213> ORGANISM: Artificial Sequence
<220> FEATURE:
<223> OTHER INFORMATION: Synthetic

<400> SEQUENCE: 35

Gly Ser Pro Leu Ala Gln Ser His Gly Gly
1               5                   10


<210> SEQ ID NO 36
<211> LENGTH: 7
<212> TYPE: PRT
<213> ORGANISM: Artificial Sequence
<220> FEATURE:
<223> OTHER INFORMATION: Synthetic

<400> SEQUENCE: 36

Gly Leu Leu Gln Gly Gly Gly
1               5


<210> SEQ ID NO 37
<211> LENGTH: 6
<212> TYPE: PRT
<213> ORGANISM: Artificial Sequence
<220> FEATURE:
<223> OTHER INFORMATION: Synthetic

<400> SEQUENCE: 37

Gly Leu Leu Gln Gly Gly
1               5


<210> SEQ ID NO 38
<211> LENGTH: 4
<212> TYPE: PRT
<213> ORGANISM: Artificial Sequence
<220> FEATURE:
<223> OTHER INFORMATION: Synthetic

<400> SEQUENCE: 38

Gly Leu Leu Gln
1
```

<210> SEQ ID NO 39
<211> LENGTH: 8
<212> TYPE: PRT
<213> ORGANISM: Artificial Sequence
<220> FEATURE:
<223> OTHER INFORMATION: Synthetic

<400> SEQUENCE: 39

Leu Leu Gln Leu Leu Gln Gly Ala
1 5

<210> SEQ ID NO 40
<211> LENGTH: 5
<212> TYPE: PRT
<213> ORGANISM: Artificial Sequence
<220> FEATURE:
<223> OTHER INFORMATION: Synthetic

<400> SEQUENCE: 40

Leu Leu Gln Gly Ala
1 5

<210> SEQ ID NO 41
<211> LENGTH: 7
<212> TYPE: PRT
<213> ORGANISM: Artificial Sequence
<220> FEATURE:
<223> OTHER INFORMATION: Synthetic

<400> SEQUENCE: 41

Leu Leu Gln Tyr Gln Gly Ala
1 5

<210> SEQ ID NO 42
<211> LENGTH: 6
<212> TYPE: PRT
<213> ORGANISM: Artificial Sequence
<220> FEATURE:
<223> OTHER INFORMATION: Synthetic

<400> SEQUENCE: 42

Leu Leu Gln Gly Ser Gly
1 5

<210> SEQ ID NO 43
<211> LENGTH: 6
<212> TYPE: PRT
<213> ORGANISM: Artificial Sequence
<220> FEATURE:
<223> OTHER INFORMATION: Synthetic

<400> SEQUENCE: 43

Leu Leu Gln Tyr Gln Gly
1 5

<210> SEQ ID NO 44
<211> LENGTH: 7
<212> TYPE: PRT
<213> ORGANISM: Artificial Sequence
<220> FEATURE:
<223> OTHER INFORMATION: Synthetic

<400> SEQUENCE: 44

Leu Leu Gln Leu Leu Gln Gly
1 5

<210> SEQ ID NO 45
<211> LENGTH: 5
<212> TYPE: PRT
<213> ORGANISM: Artificial Sequence
<220> FEATURE:
<223> OTHER INFORMATION: Synthetic

<400> SEQUENCE: 45

Ser Leu Leu Gln Gly
1 5

<210> SEQ ID NO 46
<211> LENGTH: 5
<212> TYPE: PRT
<213> ORGANISM: Artificial Sequence
<220> FEATURE:
<223> OTHER INFORMATION: Synthetic

<400> SEQUENCE: 46

Leu Leu Gln Leu Gln
1 5

<210> SEQ ID NO 47
<211> LENGTH: 6
<212> TYPE: PRT
<213> ORGANISM: Artificial Sequence
<220> FEATURE:
<223> OTHER INFORMATION: Synthetic

<400> SEQUENCE: 47

Leu Leu Gln Leu Leu Gln
1 5

<210> SEQ ID NO 48
<211> LENGTH: 5
<212> TYPE: PRT
<213> ORGANISM: Artificial Sequence
<220> FEATURE:
<223> OTHER INFORMATION: Synthetic

<400> SEQUENCE: 48

Leu Leu Gln Gly Arg
1 5

<210> SEQ ID NO 49
<211> LENGTH: 6
<212> TYPE: PRT
<213> ORGANISM: Artificial Sequence
<220> FEATURE:
<223> OTHER INFORMATION: Synthetic

<400> SEQUENCE: 49

Leu Leu Gln Gly Pro Ala
1 5

<210> SEQ ID NO 50
<211> LENGTH: 6
<212> TYPE: PRT
<213> ORGANISM: Artificial Sequence
<220> FEATURE:
<223> OTHER INFORMATION: Synthetic

<400> SEQUENCE: 50

Leu Leu Gln Gly Pro Pro
1 5

-continued

```
<210> SEQ ID NO 51
<211> LENGTH: 8
<212> TYPE: PRT
<213> ORGANISM: Artificial Sequence
<220> FEATURE:
<223> OTHER INFORMATION: Synthetic

<400> SEQUENCE: 51

Gly Gly Leu Leu Gln Gly Pro Pro
1               5


<210> SEQ ID NO 52
<211> LENGTH: 5
<212> TYPE: PRT
<213> ORGANISM: Artificial Sequence
<220> FEATURE:
<223> OTHER INFORMATION: Synthetic

<400> SEQUENCE: 52

Leu Leu Gln Gly Gly
1               5


<210> SEQ ID NO 53
<211> LENGTH: 5
<212> TYPE: PRT
<213> ORGANISM: Artificial Sequence
<220> FEATURE:
<223> OTHER INFORMATION: Synthetic

<400> SEQUENCE: 53

Leu Leu Gln Gly Ala
1               5
```